US011020397B2

(12) United States Patent
Warrell, Jr. et al.

(10) Patent No.: US 11,020,397 B2
(45) Date of Patent: *Jun. 1, 2021

(54) COMPOUNDS AND THEIR USE FOR REDUCING URIC ACID LEVELS

(71) Applicant: Acquist LLC, Chatham, NJ (US)

(72) Inventors: Raymond P. Warrell, Jr., Chatham, NJ (US); John J. Piwinski, Lebanon, NJ (US); Alexandre Larivée, Montréal (CA); Arshad Siddiqui, Newton, MA (US); Karen Thai, Ottawa (CA)

(73) Assignee: Acquist LLC, Chatham, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/872,629

(22) Filed: May 12, 2020

(65) Prior Publication Data

US 2020/0268757 A1   Aug. 27, 2020

Related U.S. Application Data

(63) Continuation of application No. 16/227,398, filed on Dec. 20, 2018, now Pat. No. 10,688,095, which is a continuation-in-part of application No. PCT/US2017/040836, filed on Jul. 6, 2017.

(60) Provisional application No. 62/732,737, filed on Sep. 18, 2018, provisional application No. 62/358,669, filed on Jul. 6, 2016.

(51) Int. Cl.
| | |
|---|---|
| *C07D 403/14* | (2006.01) |
| *A61K 31/513* | (2006.01) |
| *C07D 403/12* | (2006.01) |
| *C07D 401/14* | (2006.01) |
| *C07D 417/14* | (2006.01) |
| *A61P 19/06* | (2006.01) |

(52) U.S. Cl.
CPC ............ *A61K 31/513* (2013.01); *A61P 19/06* (2018.01); *C07D 401/14* (2013.01); *C07D 403/12* (2013.01); *C07D 403/14* (2013.01); *C07D 417/14* (2013.01)

(58) Field of Classification Search
CPC .. A61K 31/513; C07D 401/14; C07D 403/04; C07D 403/14
USPC .................... 514/252.02, 272; 544/238, 320
See application file for complete search history.

(56) References Cited

U.S. PATENT DOCUMENTS

| | | | |
|---|---|---|---|
| 4,034,093 A | 7/1977 | Klemm et al. | |
| 4,239,762 A | 12/1980 | Kramer et al. | |
| 4,602,912 A | 7/1986 | De Sousa et al. | |
| 4,634,707 A | 1/1987 | Brewer et al. | |
| 4,636,508 A | 1/1987 | Brewer et al. | |
| 4,762,830 A | 8/1988 | Sturm et al. | |
| 4,879,276 A | 11/1989 | Brewer | |
| 4,880,811 A | 11/1989 | Warrell, Jr. | |
| 6,335,332 B1 | 1/2002 | Ambrogio et al. | |
| 7,119,201 B2 | 10/2006 | Reiter et al. | |
| 9,428,466 B2 | 8/2016 | Warrell | |
| 10,093,658 B2 | 10/2018 | Warrell, Jr. et al. | |
| 10,688,095 B2 * | 6/2020 | Warrell, Jr. ............. | A61P 19/06 |
| 10,752,613 B2 | 8/2020 | Piwinski et al. | |
| 10,759,784 B2 * | 9/2020 | Piwinski .............. | C07D 498/04 |
| 2009/0264401 A1 | 10/2009 | Gill et al. | |

FOREIGN PATENT DOCUMENTS

| | | |
|---|---|---|
| JP | S60166669 A | 8/1985 |
| WO | 88/10114 A1 | 12/1988 |
| WO | 91/13623 A1 | 9/1991 |
| WO | 2015/073317 A1 | 5/2015 |
| WO | 2015/123003 A1 | 8/2015 |
| WO | 2016/118611 A1 | 7/2016 |

OTHER PUBLICATIONS

CAS Abstract US4634707 (1987), 2 pages.
CAS Registry No. 1349276-03-4 (2011), 1 page.
International Preliminary Report on Patentability in PCT/US2016/014107, dated Aug. 3, 2017, 7 pages.
International Search Report and Written Opinion in Intl. Appl. No. PCT/US2017/038525, dated Aug. 22, 2017, 16 pgs.
International Search Report and Written Opinion in PCT/US15/12370, dated Apr. 17, 2015, 10 pages.
International Search Report and Written Opinion in PCT/US2016/014107, dated May 17, 2016, 11 pages.
International Search Report and Written Opinion in PCT/US2017/038522, dated Oct. 3, 2017, 20 pages.
International Search Report and Written Opinion in PCT/US2017/040836, dated Sep. 12, 2017, 15 pages.
Non-Final Office Action dated Oct. 5, 2017, in U.S. Appl. No. 15/118,243, 21 pages.
Partial Search Report in PCT Application No. PCT/US2017/038522, dated Aug. 15, 2017, 2 pgs.
Provisional Opinion Accompanying the Partial Search Result in EP 15 748 739.8, May 22, 2017, 5 pages.
Search Opinion in EP Application No. 15 748 739.8, dated Sep. 1, 2017, 5 pgs.
Supplementary Partial European Search Report in EP 15 74 8739, dated May 22, 2017, 4 pages.
Non-Final Office Action in U.S. Appl. No. 16/310,921 dated Mar. 6, 2020, 9 pages.
Non-Final Office Action in U.S. Appl. No. 16/310,950 dated Jan. 15, 2020, 12 pages.

(Continued)

*Primary Examiner* — Jeffrey H Murray
(74) *Attorney, Agent, or Firm* — Servilla Whitney LLC

(57) ABSTRACT

Bifunctional barbiturate-derivative compounds that increase uric acid excretion and reduce uric acid production, and monofunctional barbiturate-derivative compounds that either increase uric acid excretion or reduce uric acid production are provided. Methods of using these compounds for reducing uric acid levels in blood or serum, for treating disorders associated with excess uric acid, and for maintaining normal uric acid levels in blood or serum, or the whole body, are also provided. Pharmaceutical compositions comprising the bifunctional and monofunctional compounds are also provided.

10 Claims, 43 Drawing Sheets

(56) References Cited

OTHER PUBLICATIONS

PCT International Preliminary Report on Patentability in PCT/US2017/038522 dated Jan. 10, 2019, 9 pages.
PCT International Preliminary Report on Patentability in PCT/US2017/038525 dated Jan. 10, 2019, 7 pages.
PCT Preliminary Report on Patentability in PCT/US2015/012370 dated Aug. 25, 2016, 7 pages.
Lebedyeva, Iryna O., et al., "Reaction of barbituric acid with organic azides and phosphonium ylides", Central European Journal of Chemistry, vol. 11, No. 6, 2013, pp. 1019-1022.
Wilson, Walter , "Journal of the Chemical Society (1948) pp. 1157-1161".
Non-Final Office Action in U.S. Appl. No. 16/928,623, dated Feb. 5, 2021, 8 pages.
Non-Final Office Action in U.S. Appl. No. 16/928,629, dated Mar. 12, 2020, 8 pages.

* cited by examiner

COMPOUNDS AND THEIR USE FOR REDUCING URIC ACID LEVELS

CROSS REFERENCE TO RELATED APPLICATIONS

This application is a continuation of U.S. application Ser. No. 16/227,398, filed on Dec. 20, 2018, which claims priority to U.S. Provisional Application Ser. No. 62/732,737, filed Sep. 18, 2018, and which is a continuation-in-part of International Appln. No. PCT/US2017/040836, filed Jul. 6, 2017, which claims priority to U.S. Provisional Appln. Ser. No. 62/358,669, filed Jul. 6, 2016, the disclosures of which are hereby incorporated by reference in their entireties.

TECHNICAL FIELD

This invention relates to pharmaceutical compositions and methods for reducing uric acid in blood or serum of a subject, or in the whole body of a subject, employing bifunctional and monofunctional compounds as active agents.

BACKGROUND

Uric acid (UA) has emerged as a central regulator of inflammation and fat formation in various human illnesses. Gout afflicts more than 8 million U.S. subjects, and is associated with chronic elevation of uric acid (UA) in blood. The incidence of this condition has doubled in the past ten years. When UA exceeds solubility limits, it forms crystals that settle into joints and kidney, causing severe pain, destructive arthritis, and kidney failure. Uric acid itself is known to be directly toxic to a number of other tissues, and the generation of uric acid by xanthine oxidase is also known to be toxic due to oxidative stress induced by release of oxygen free radicals. In addition, nonalcoholic steatohepatitis (NASH) I disease associated by excess production liver fat that triggers hepatitis and leads to cirrhosis—is expected to become the most common global contributor to requisite liver transplantation. Treatment for disorders associated with excess uric acid such as chronic gout and NASH entails extended—if not lifelong—therapy focused on reducing UA production or increasing its excretion. For example, the standard-of-care for initial therapy of gout is allopurinol, a drug that inhibits xanthine oxidase (XO), a key production enzyme. Launched in 2009, Uloric® (febuxostat; Takeda), has similar activity as an XO inhibitor with somewhat higher efficacy and improved safety. Xanthine oxidase inhibitors are used as initial therapy in more than 90% of gout patients; nonetheless, the therapeutic target is achieved in less than one-third of patients, the drugs have multiple side effects, and hypersensitivity (especially to allopurinol) is common. Given that most patients do not actually respond, the continued use of ineffective treatment administered over many months in order to determine the low percentage of patients who might respond represents an important burden to patients as well as substantial costs to global healthcare systems, Moreover, the high proportion of failures causes many patients to become non-compliant with therapy and thus at increased risk for development of chronic complications of gout, especially destructive arthritis and renal insufficiency. Lastly, the U.S. FDA has issued a warning letter to physicians that Uloric® is associated with an increase in cardiac and all-cause mortality.

Since 2000, rapid advances in the biology of proteins known as transporters have presented an array of new drug targets. The enzyme URAT1 is a high capacity renal transporter that reabsorbs most of the UA that is initially filtered into the urine from the blood by the kidney. Inhibitors of certain urate transporters may prevent such reabsorption and thereby increase UA excretion. Several drugs are now known to inhibit URAT1, including benzbromarone (approved but withdrawn in the US by Sanofi in 2003), and lesinurad (Zurampic®, AstraZeneca), which was approved in the U.S. and EU in 2016.

These drugs are all mono-functional. That is, they inhibit only one of the two equilibrium paths that reduce the levels of UA in blood (i.e., decreased production or increased excretion). Allopurinol is an example of a drug that decreases UA production by inhibiting xanthine oxidase, but it has no effect on renal excretion. As expected, allopurinol does not affect the activity of URAT1 or other renal urate transporters. Benzbromarone and lesinurad increase UA excretion (i.e., they promote uricosuria) primarily via inhibition of URAT1, but these agents have no effect on UA production, since they have no substantial effect on xanthine oxidase. Since xanthine oxidase inhibition is the principal, preferred, and primary $1^{st}$-line form of treatment for hyperuricemia, agents that promote uricosuria are used second-line and are commonly employed only in combination with xanthine oxidase inhibitors rather than as single-agents. However, because of structural similarities, other transporter enzymes may also be inhibited by URAT1 inhibitors, including but not limited to organic anion transporters such as OAT1, OAT3 and GLUT9a/b.

Non-sedating 5-carboxanilide derivatives of barbiturates, including merbarone (5-(N-phenylcarboxamido)-2-thio-barbituric acid), have been evaluated as potential cytotoxic anticancer drugs. Subsequently, it was discovered that clinical treatment with merbarone was associated with a marked reduction of UA levels in blood. Despite these discoveries, the cytotoxic activity of merbarone completely precluded its use as a treatment for a chronic disorder associated with excess uric acid, since the safety of such use (primarily its genotoxicity) posed a serious risk to other aspects of human health. Such clinical utility would only be possible if the genotoxic activity could be chemically dissociated and eliminated from the hypouricemic activity. The inventors have since described a number of non-genotoxic hypouricemic derivatives of merbarone.

There exists a compelling need for new drugs than can reduce UA levels in blood or the whole body and provide better treatment for patients afflicted by gout. Reduction in UA is universally acknowledged as beneficial for patients with gout, as well as other disorders associated with excess uric acid, and such reduction is directly linked to patient benefit. More specifically, reduction of serum uric acid below a "target" level is accepted by international drug regulatory agencies (e.g., the U.S. Food and Drug Administration [FDA], the European Medicines Agency [EMA], etc.) as an endpoint for commercial drug approval in gout. As previously noted, drugs that can overcome the limited clinical activity of xanthine oxidase inhibitors are available or are currently being investigated, but only as "add-ons" for combination use. The approval of lesinurad [Zurampic®] is the most recent example. The present invention relates to new compounds that can provide alternatives to current therapy for elevated UA levels and treatment of other disorders associated with excess uric acid such as gout. Certain of these compounds have the particular advantage of bifunctional activity (i.e., decreasing UA production by inhibiting xanthine oxidase and increasing UA excretion by inhibiting a renal urate transporter), making them suitable for use as initial therapy and as single agents rather than "add-on" therapies. In addition, certain of the compounds have reduced toxicity compared to prior art drugs such as merbarone.

SUMMARY

In a first aspect, compounds having a structure represented by Formula (I) are provided:

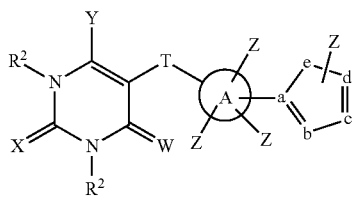

Formula (I)

wherein
W, X, and Y are each independently O, S, $NR^2$ or $N(R^2)_2$;
T is $-CONR^2-$, $-C(NR^2)NH-$, $-C(NOR^2)NH-$, $-C(N-NR^2)NH-$, $-C(SR^2)N-$, or $-NHC(O)-$;
A is phenyl, heteroaryl, C5-C10 branched or unbranched cycloalkyl, C6-C10 bicycloalkyl or C5-C10 spirocycloalkyl;
each Z is independently present or absent and, if present, is independently selected from one or more halogen atoms, $-CN$, $-CF_3$, $-OR^2$, $-C(O)R^2$, $SR^2$, $-S(O)_gR^3$ where g is 1 or 2, $-N(R^2)_2$, $-NO_2$, $-CO_2R^2$, $-OCO_2R^3$, $OC(O)R^2$, $-CON(R^2)_2$, $-NR^2C(O)R^2$, $-SO_2N(R^2)_2$, $-NR^2SO_2R^3$, $-NR^2SO_2N(R^2)_2$ or $-NR^2C(O)N(R^2)_2$, $-C(O)NHOR^2$, alkyl, aryl, alkenyl and alkynyl;
wherein each $R^2$ is independently H, alkyl or aryl;
wherein each $R^3$ is independently alkyl or aryl, optionally substituted with one or more halogen atoms or $OR^2$; and
wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In a second aspect, compounds having a structure represented by Formula (II) are provided:

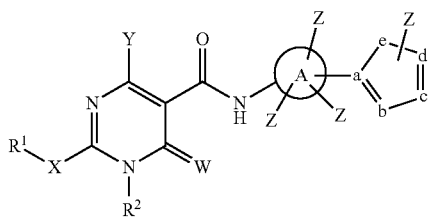

Formula (II)

wherein
W, X, and Y are each independently O, S, $NR^2$ or $N(R^2)_2$;
A is phenyl, heteroaryl, C5-C10 branched or unbranched cycloalkyl, C6-C10 bicycloalkyl or C5-C10 spirocycloalkyl;
each Z is independently present or absent and, if present, is independently selected from one or more halogen atoms, $-CN$, $-CF_3$, $-OCF_3$, $-OCHF_2$, $-OR^2$, $-C(O)R^2$, $SR^2$, $-S(O)_gR^3$ where g is 1 or 2, $-N(R^2)_2$, $-NO_2$, $-CO_2R^2$, $-OCO_2R_3$, $OC(O)R^2$, $-CON(R^2)_2$, $-NR^2C(O)R^2$, $-SO_2N(R^2)_2$, $-NR^2SO_2R_3$, $-NR^2SO_2N(R^2)_2$ or $-NR^2C(O)N(R^2)_2$, $-C(O)NHOR^2$, alkyl, aryl, alkenyl, alkynyl and cycloalkyl;
wherein each $R^1$ is C1-C8 branched or unbranched alkyl, optionally substituted with Z;
wherein each $R^2$ is independently H, alkyl or aryl;
wherein each $R^3$ is independently alkyl or aryl, optionally substituted with one or more halogen atoms or $OR^2$; and
wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

A further aspect relates to methods for reducing uric acid levels in blood or serum of a subject, or preventing elevation of uric acid levels in blood or serum of a subject, comprising administering a compound having a structure represented by Formula (I), Formula (II), or a combination thereof, to a subject in need thereof in an amount effective to reduce blood or serum uric acid levels or prevent elevation of blood or serum uric acid levels. In a modification of this embodiment, the methods comprise administering a compound according to a specific embodiment of the compounds of Formula (I), Formula (II), or a combination thereof, as described above, to a subject in need thereof in an amount effective to reduce blood or serum uric acid levels or prevent elevation of blood or serum uric acid levels.

In certain embodiments of these methods, a compound having a structure represented by Formula (I), Formula (II), or a combination thereof, is administered to a subject with a disorder associated with excess uric acid such as gout, hyperuricemia, kidney disease, arthritis, kidney stones, kidney failure, urolithiasis, plumbism, hyperparathyroidism, psoriasis, inborn genetic errors of metabolism (including but not limited to Lesch-Nyhan syndrome), sarcoidosis, cardiovascular disease (including but not limited to atherosclerosis and hypertension), diabetes or insulin resistance, obesity, metabolic syndrome, or transplantation of blood, bone marrow or solid organs, to reduce uric acid levels.

A further aspect relates to methods for treating a disorder associated with excess uric acid associated with or caused by elevated uric acid in blood or serum comprising administering to a subject in need thereof a compound having a structure represented by Formula (I), Formula (II), or a combination thereof, in an amount effective to reduce blood or serum uric acid levels or prevent elevation of blood or serum uric acid levels, thereby treating the disorder associated with excess uric acid. One such embodiment relates to methods for treating a disorder of excess uric acid associated with or caused by elevated uric acid in blood or serum comprising administering to the subject a compound according to a specific embodiment of the compounds of Formula (I), Formula (II), or a combination, as described above.

A further aspect of the invention provides pharmaceutical compositions comprising a compound having a structure represented by Formula (I), Formula (II), or a combination thereof, and a pharmaceutically acceptable carrier. In a specific embodiment, the pharmaceutical composition comprises a compound according to a specific embodiment of the compounds of Formula (I), Formula (II), or a combination thereof, as described above.

A further aspect provides methods for synthesizing the compounds discussed above, as discussed in more detail below.

DETAILED DESCRIPTION

Figure 1:
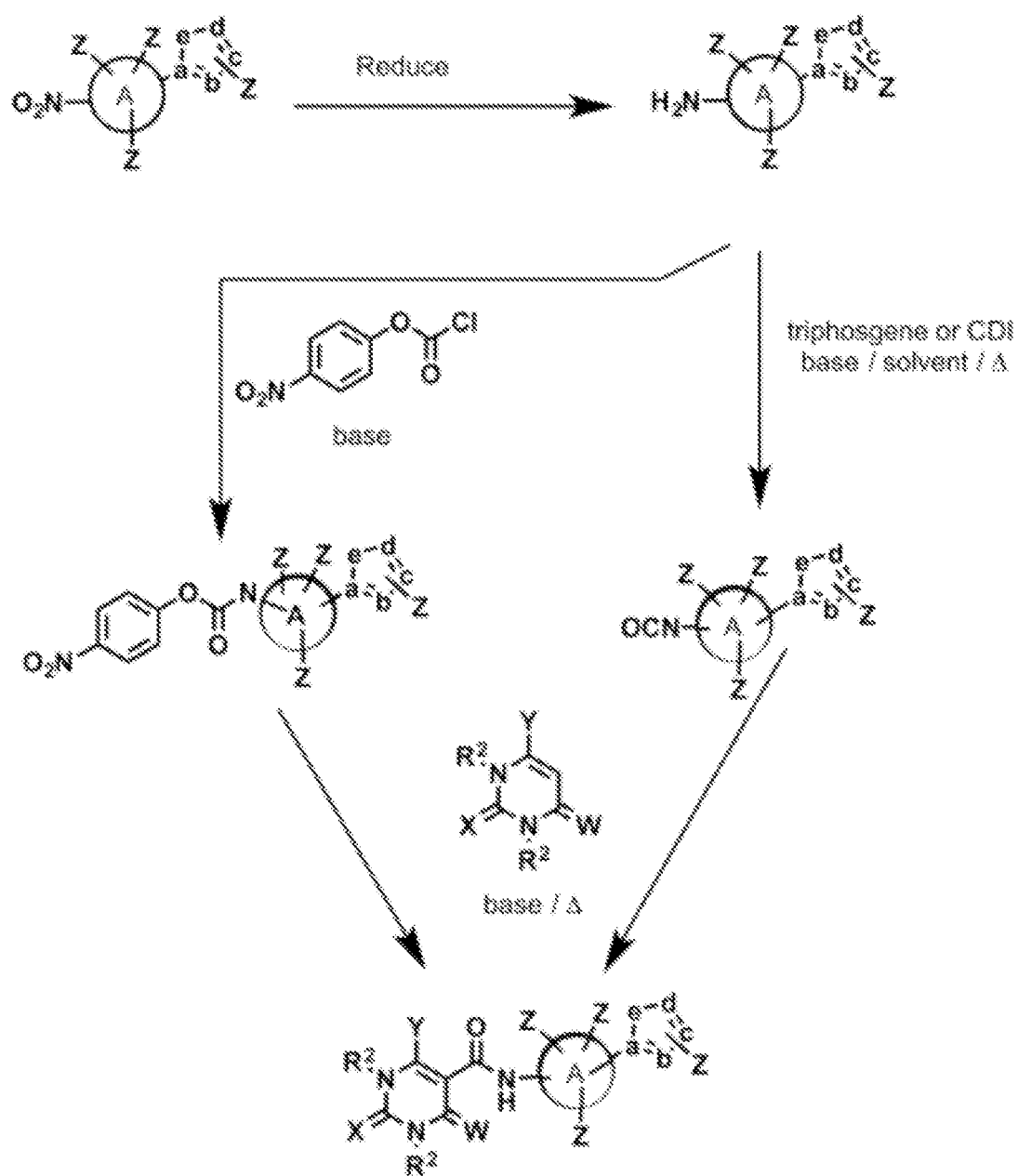
FIG. 1 illustrates a general scheme for synthesis of compounds according to Formula (I).

Before describing several exemplary embodiments provided herein, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used herein, the term "bifunctional" with respect to disclosed compounds means that the compound inhibits both a renal transporter, including but not limited to URAT1, and xanthine oxidase. The potency of inhibition of either target may vary, but in general an IC50 of less than about 100 μM for both xanthine oxidase and a renal transporter such as URAT1 is considered bifunctional. An IC50 of less than about 50 μM for both xanthine oxidase and URAT1 is considered a particularly active bifunctional compound, and an IC50 of less than 10 μM is considered a highly potent bifunctional compound.

As used herein, the term "monofunctional" with respect to disclosed compounds means that the compound inhibits an enzyme in the uric acid metabolic pathway involved in uric acid excretion that is either a renal transporter, including but not limited to URAT1, or an enzyme involved in uric acid production, including but not limited to xanthine oxidase, but not both. The potency of inhibition of single target may vary, but in general an IC50 of greater than about 100 μM for one of xanthine oxidase or URAT1, and an IC50 of less than about 100 μM for the other of xanthine oxidase or URAT1, is considered monofunctional. An IC50 of less than about 50 μM for one of xanthine oxidase or URAT1, and an IC50 of greater than about 100 μM for the other of xanthine oxidase or URAT1, is considered a particularly active monofunctional compound. An IC50 of less than about 1 μM for one of xanthine oxidase or URAT1, and an IC50 of greater than about 100 μM for the other of xanthine oxidase or URAT1, is considered a highly potent monofunctional compound. As previously noted, other transporter enzymes may also be inhibited by "bifunctional" inhibitors or by "monofunctional" URAT1 inhibitors, including but not limited to organic anion transporters such as OAT1, OAT3 and GLUT9a/b.

As used herein, the term "treatment" refers to reducing elevated uric acid levels in blood or serum, preferably by reducing levels to the normal, low-normal or sub-normal range, with an overall goal of relieving symptoms and/or preventing recurrences of active disease. For example, a typical "therapeutic target" for treatment of elevated serum uric acid is a level ≤6.0 mg/dL. "Elevated" uric acid levels generally refer above-normal uric acid levels, as long-term elevated levels can result in conditions that require additional treatment.

As used herein, the term "preventing" elevation of uric acid levels in blood or serum refers to maintaining normal or therapeutically acceptable uric acid levels in blood or serum in a subject who would otherwise experience an increase in uric acid levels, with an overall goal of preventing development or recurrence of symptoms and/or preventing recurrences of active disease. It will be appreciated that prevention of elevation of uric acid levels, or achievement of a sustained reduction in uric acid, is a goal of the long-term maintenance therapy discussed below, as well as certain short-term conditions.

The numbering of the positions on the barbiturate ring used herein follows the convention of Warrell (U.S. Pat. No. 4,880,811). It is also to be understood that although the compounds disclosed herein are generally illustrated by specific chemical structures, the disclosure of the compounds is intended to include their tautomers. Representative examples of tautomers in the barbiturate ring include the structures depicted below, as well as any additional tautomers on the substituents of Formula (I) or Formula (II):

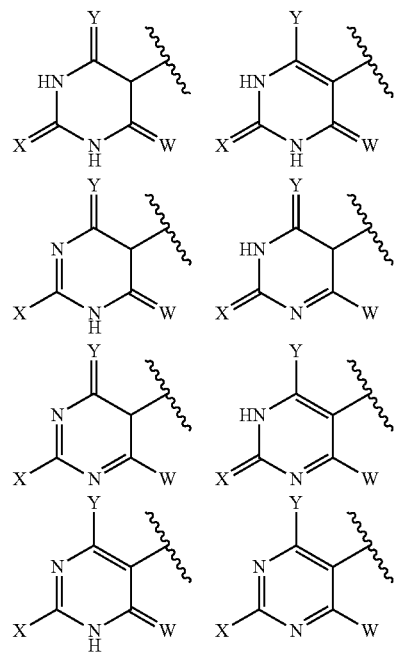

The compounds described herein meet certain needs in the therapeutic field of reduction of uric acid levels in blood and treatment of disorders associated with excess uric acid in blood or serum, or in the whole body. Certain of the compounds are potent monofunctional inhibitors of URAT1 or xanthine oxidase. Certain of the compounds are bifunctional inhibitors of both URAT1 and xanthine oxidase.

The improved biological activity profile of the compounds of the invention and their potency make these compounds useful new drugs for reducing uric acid levels in blood or the whole body, and for treating disorders associated with, or caused by, excess uric acid levels in blood or serum or the whole body, including gout. Of particular significance is the advantage that the bifunctional compounds can be used effectively as monotherapy for reducing uric acid levels in blood, for treating or preventing disorders associated with excess uric acid uric acid, and specifically for treating gout. In certain embodiments, the bifunctional compounds can be used effectively for treating or preventing non-alcoholic fatty liver disease (NAFLD), non-alcoholic steatohepatitis (NASH), and metabolic syndrome, atherosclerosis or other forms of cardiovascular disease, hypertension, chronic kidney disease, obesity, diabetes or insulin resistance, and metabolic syndrome.

In a first aspect, compounds having a structure represented by Formula (I) are provided:

Formula (I)

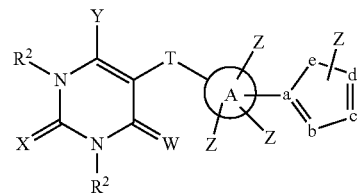

wherein
W, X, and Y are each independently O, S, $NR^2$ or $N(R^2)_2$;
T is —$CONR^2$—, —$C(NR^2)NH$—, —$C(NOR^2)NH$—, —$C(N—NR^2)NH$—, —$C(SR^2)N$—, or —NHC(O)—;
A is phenyl, heteroaryl, C5-C10 branched or unbranched cycloalkyl, C6-C10 bicycloalkyl or C5-C10 spirocycloalkyl;
each Z is independently present or absent and, if present, is independently selected from one or more halogen atoms, —CN, —$CF_3$, —$OR^2$, —$C(O)R^2$, $SR^2$, —$S(O)_gR^3$ where g is 1 or 2, —$N(R^2)_2$, —$NO_2$, —$CO_2R_2$, —$OCO_2R_3$, $OC(O)R^2$, —$CON(R^2)_2$, —$NR^2C(O)R^2$, —$SO_2N(R^2)_2$, —$NR^2SO_2R_3$, —$NR^2SO_2N(R^2)_2$ or —$NR^2C(O)N(R^2)_2$, —$C(O)NHOR^2$, alkyl, aryl, alkenyl and alkynyl;
wherein each $R^2$ is independently H, alkyl or aryl;
wherein each $R^3$ is independently alkyl or aryl, optionally substituted with one or more halogen atoms or $OR^2$; and
wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In one or more embodiments, the compound having a structure represented by Formula (I) is a compound wherein T is —$CONR^2$—.

In one or more embodiments, the compound having a structure represented by Formula (I) is a compound wherein the 5-member heterocyclic ring is a substituted or unsubstituted triazole, or a substituted or unsubstituted tetrazole (i.e., a, b, c, d, and e are each independently carbon or nitrogen, with the proviso that three or four of a, b, c, d and e are nitrogen, and Z is not connected directly to nitrogen).

In one or more embodiments, the compound having a structure represented by Formula (I) is a compound wherein A is heteroaryl having two heteroatoms, for example thiazole or isothiazole.

In a specific non-limiting embodiment, the compound having a structure represented by Formula (I) is a compound wherein X is O or S; Y and W are O; A is substituted or unsubstituted thiazole or isothiazole; each Z is independently present or absent; each $R^2$ is H, and; the 5-member heterocyclic ring is substituted, or unsubstituted triazole or substituted or unsubstituted tetrazole (i.e., a, b, c, d, and e are each independently carbon or nitrogen, with the proviso that three or four of a, b, c, d and e are nitrogen, and Z is not connected directly to nitrogen).

In a further specific non-limiting embodiment, the compound having a structure represented by Formula (I) is a compound wherein W, X and Y are each independently O or S; T is $CONR^2$; A is heteroaryl; Z is absent; $R^2$ is H, and; the 5-member heterocyclic ring is triazole. In one or more of these embodiments, the heteroaryl A is thiazole or isothiazole.

Specific examples of compounds having a structure represented by Formula (I) include the following:

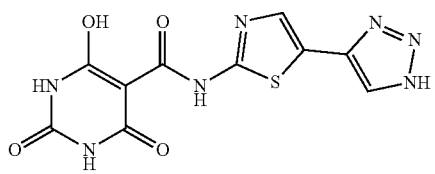

Formula ($I_o$)

In a second aspect, compounds having a structure represented by Formula (II) are provided:

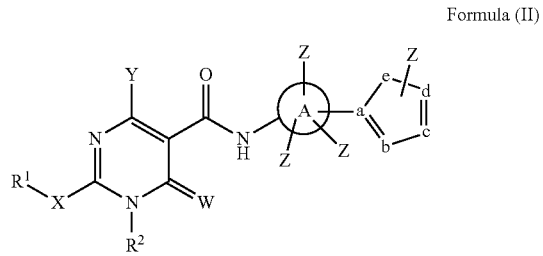

Formula (II)

wherein
W, X, and Y are each independently O, S, $NR^2$ or $N(R^2)_2$;
A is phenyl, heteroaryl, C5-C10 branched or unbranched cycloalkyl, C6-C10 bicycloalkyl or C5-C10 spirocycloalkyl;
each Z is independently present or absent and, if present, is independently selected from one or more halogen atoms, —CN, —$CF_3$, —$OCF_3$, —$OCHF_2$, —$OR^2$, —$C(O)R^2$, $SR^2$, —$S(O)_gR^3$ where g is 1 or 2, —$N(R^2)_2$, —$NO_2$, —$CO_2R^2$, —$OCO_2R^3$, $OC(O)R^2$, —$CON(R^2)_2$, —$NR^2C(O)R^2$, —$SO_2N(R^2)_2$, —$NR^2SO_2R^3$, —$NR^2SO_2N(R^2)_2$ or —$NR^2C(O)N(R^2)_2$, —$C(O)NHOR^2$, alkyl, aryl, alkenyl, alkynyl and cycloalkyl;
wherein each $R^1$ is C1-C8 branched or unbranched alkyl, optionally substituted with Z;
wherein each $R^2$ is independently H, alkyl or aryl;
wherein each $R^3$ is independently alkyl or aryl, optionally substituted with one or more halogen atoms or $OR^2$; and
wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In one or more embodiments, the 5-member heterocyclic ring of the compound having a structure represented by Formula (II) is a substituted or unsubstituted triazole, or substituted or unsubstituted tetrazole (i.e., a, b, c, d, and e are each independently carbon or nitrogen, with the proviso that three or four of a, b, c, d and e are nitrogen, and Z is not connected directly to nitrogen).

In one or more embodiments, the compound having a structure represented by Formula (II) is a compound wherein $R^1$ is —$CH_3$.

In a one or more embodiments, the compound having a structure represented by Formula (II) is a compound wherein —$XR^1$ is —$SCH_3$, —$SC(CH_3)$ or —$OCH_3$.

In a specific non-limiting embodiment, the compound having a structure represented by Formula (II) is a compound wherein X is O, S or $N(R^2)_2$; Y and W are each independently O or S; A is substituted or unsubstituted phenyl, bicycloalkyl, spirocycloalkyl, pyridine or diazine; Z is alkyl, cycloalkyl, halogen, $CF_3$, or $N(R^2)_2$; each $R^1$ is C1-C3 branched or unbranched alkyl, optionally substituted with Z; each $R^2$ is H, and; the 5-member heterocyclic ring is substituted or unsubstituted triazole, or substituted or unsubstituted tetrazole (i.e., a, b, c, d, and e are each independently carbon or nitrogen, with the proviso that three or four of a, b, c, d and e are nitrogen, and Z is not connected directly to nitrogen).

Specific examples of compounds having a structure represented by Formula (II) include the following:

1. A compound wherein the 5-member heterocyclic ring is an unsubstituted triazole or an unsubstituted tetrazole. Representative examples of such compounds include:

The compound wherein A is substituted or unsubstituted phenyl; and X is S; including certain exemplary compounds wherein $R^1$ is —$CH_3$ or —$C(CH_3)_2$; and tautomers thereof, such as a structure represented by Formula (II$_i$):

Formula (II$i$)

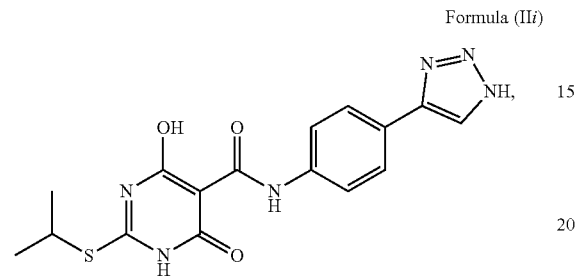

a structure represented by Formula (II$_j$):

Formula II$j$

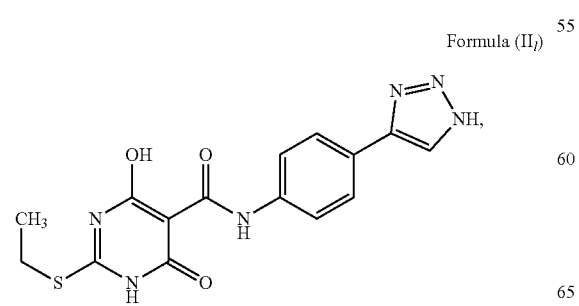

a structure represented by Formula (II$_k$):

Formula (II$_k$)

a structure represented by Formula (II$_l$):

Formula (II$_l$)

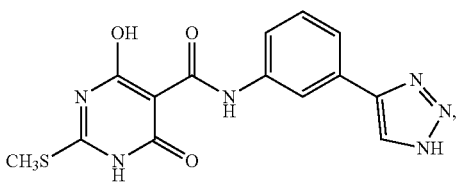

a structure represented by Formula (II$_m$):

Formula (II$_m$)

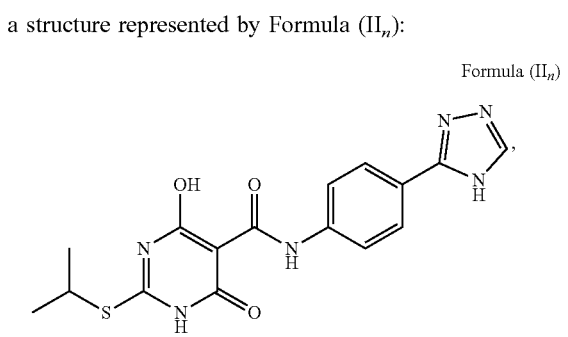

a structure represented by Formula (II$_n$):

Formula (II$_n$)

a structure represented by Formula (II$_o$):

Formula (II$_o$)

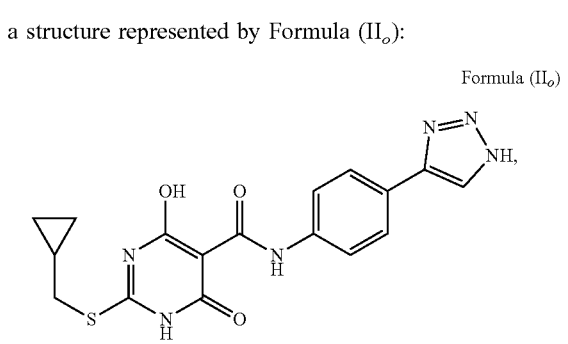

a structure represented by Formula (II$_p$):

Formula (II$_p$)

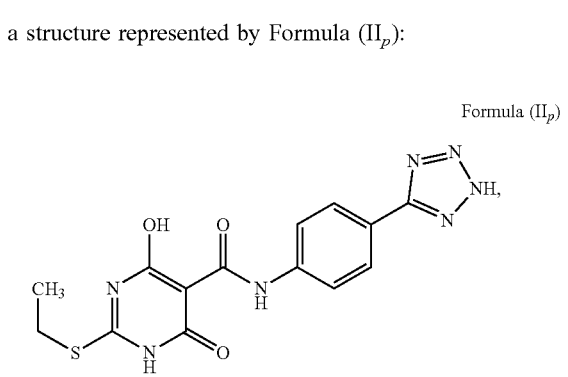

a structure represented by Formula (II$_q$):

Formula (II$_q$)

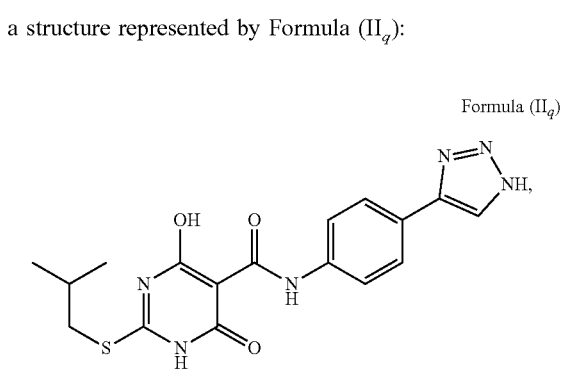

a structure represented by Formula (II$_r$):

Formula (II$_r$)

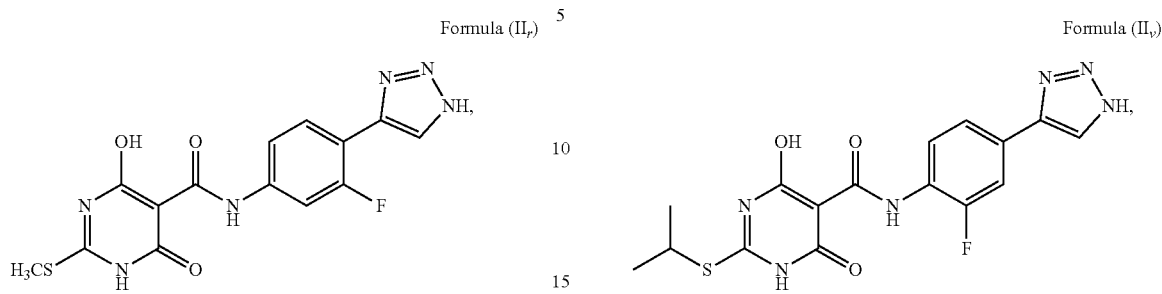

a structure represented by Formula (II$_s$):

Formula (II$_s$)

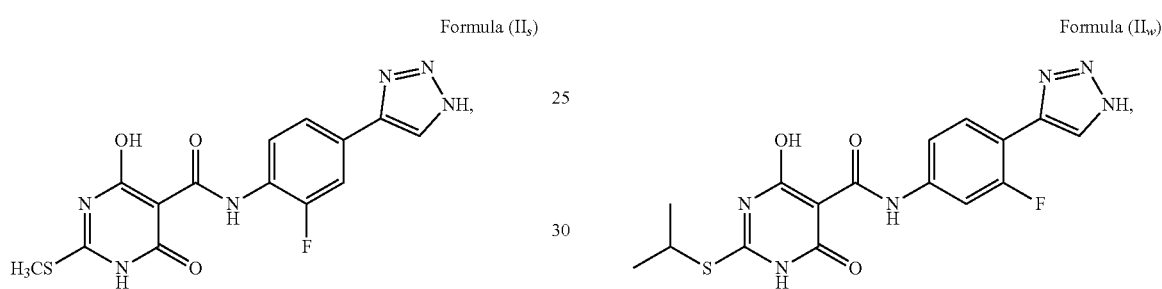

a structure represented by Formula (II$_t$):

Formula (II$_t$)

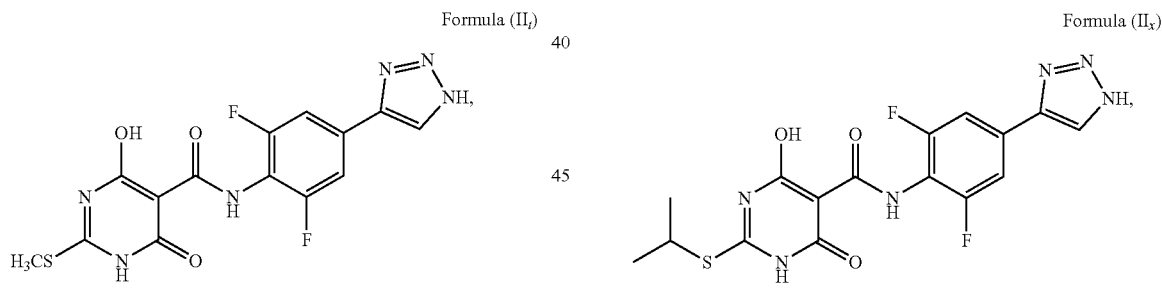

a structure represented by Formula (II$_u$):

Formula (II$_u$)

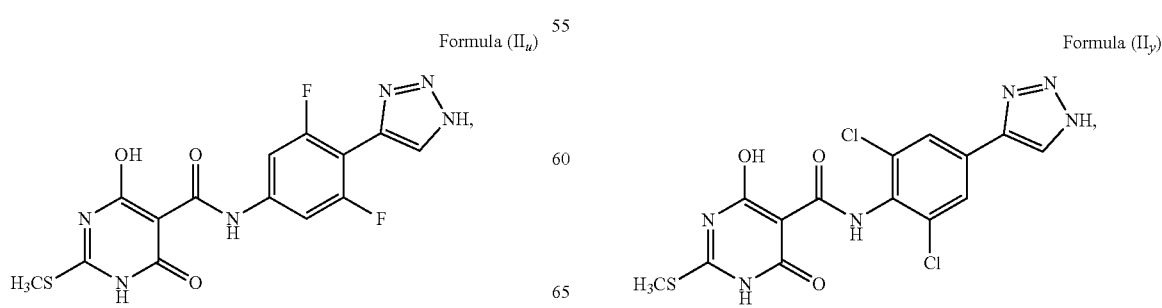

a structure represented by Formula (II$_v$):

Formula (II$_v$)

a structure represented by Formula (II$_w$):

Formula (II$_w$)

a structure represented by Formula (II$_x$):

Formula (II$_x$)

a structure represented by Formula (II$_y$):

Formula (II$_y$)

a structure represented by Formula (II$_z$):

a structure represented by Formula (II$_{dd}$):

a structure represented by Formula (II$_{aa}$):

a structure represented by Formula (II$_{ee}$):

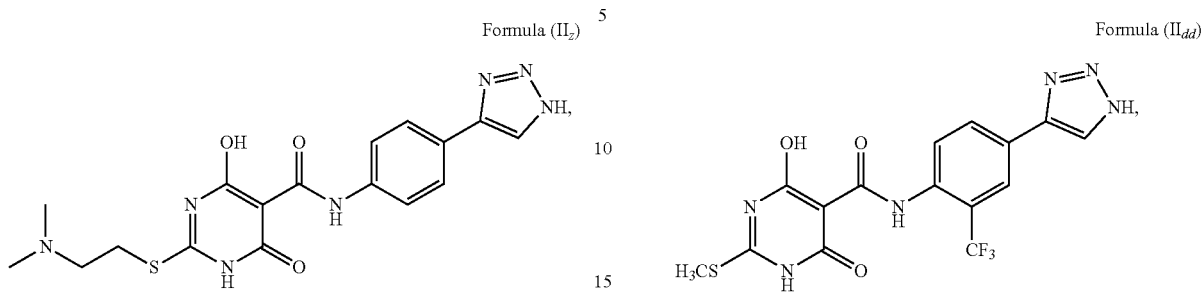

Formula (II$_z$)

Formula (II$_{dd}$)

a structure represented by Formula (II$_{bb}$):

a structure represented by Formula (II$_2$):

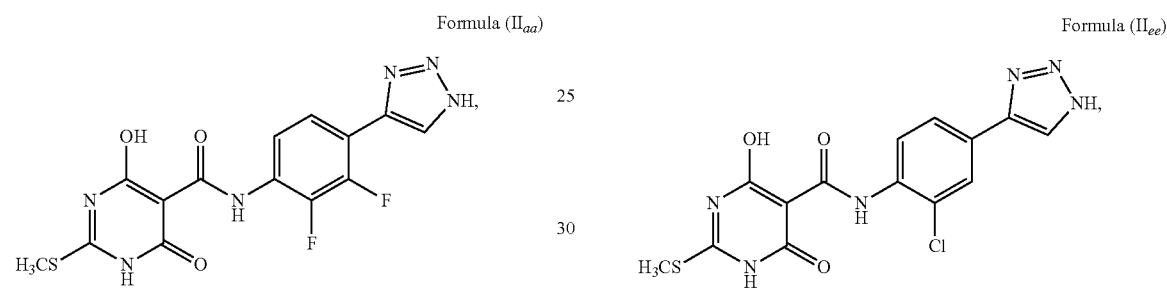

Formula (II$_{aa}$)

Formula (II$_{ee}$)

a structure represented by Formula (II$_{cc}$):

a structure represented by Formula (II$_3$):

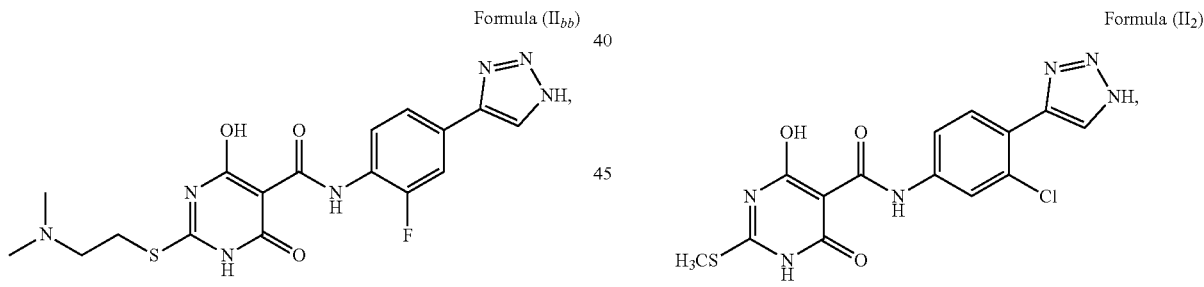

Formula (II$_{bb}$)

Formula (II$_2$)

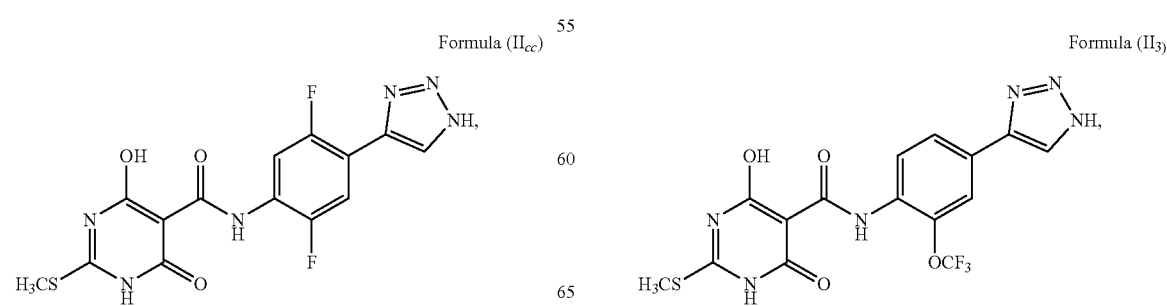

Formula (II$_{cc}$)

Formula (II$_3$)

a structure represented by Formula (II₄):

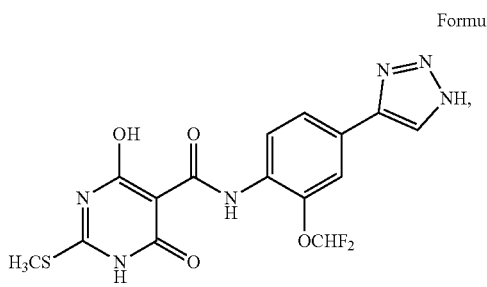

Formula (II₄)

a structure represented by Formula (II₅):

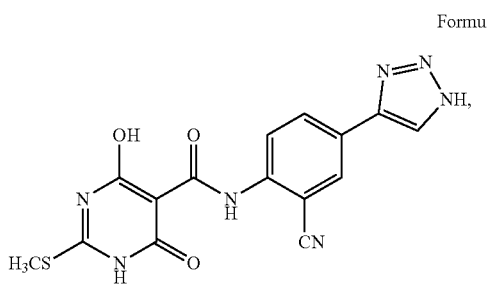

Formula (II₅)

a structure represented by Formula (II₆):

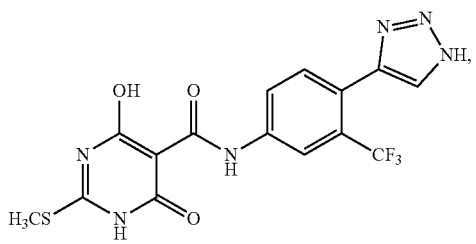

Formula (II₆)

a structure represented by Formula (II₇):

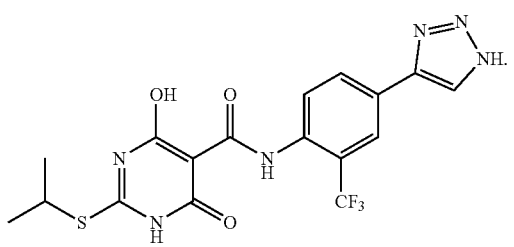

Formula (II₇)

Among the foregoing class of compounds, particularly useful compounds are the compounds wherein A is CF₃-substituted phenyl, X is S and R¹ is —C(CH₃)₂, and tautomers thereof.

The compound wherein A is unsubstituted phenyl; and X is NR² or N(R²)₂; and tautomers thereof, such as a structure represented by Formula (II_ll):

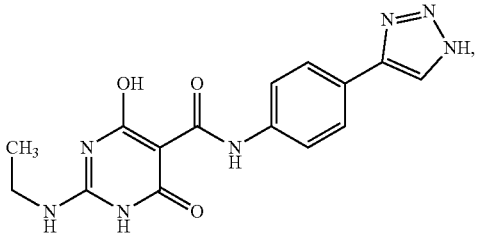

Formula (II_ll)

and
a structure represented by Formula (II_mm):

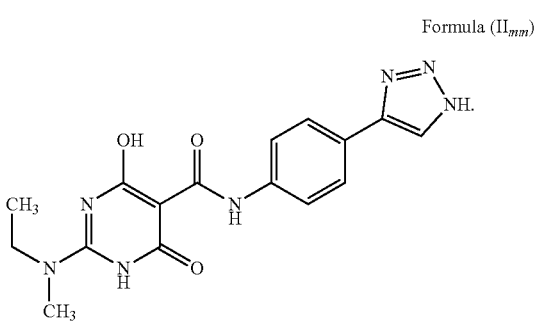 [SMILES: CCN(C)c1nc(O)c(C(=O)Nc2ccc(-c3c[nH]nn3)cc2)c(=O)[nH]1]

Formula (II_mm)

The compound wherein A is heteroaryl such as substituted or unsubstituted pyridine; and X is S; including certain exemplary compounds wherein R¹ is —CH₃; and tautomers thereof, such as a structure represented by Formula (II₈):

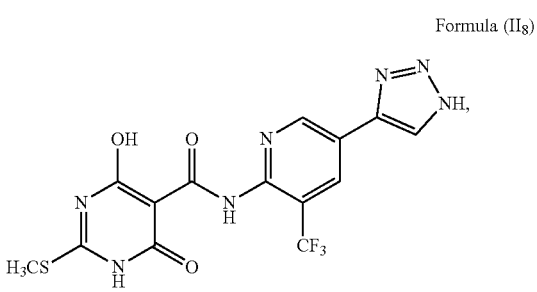

Formula (II₈)

and
a structure represented by Formula (II₉):

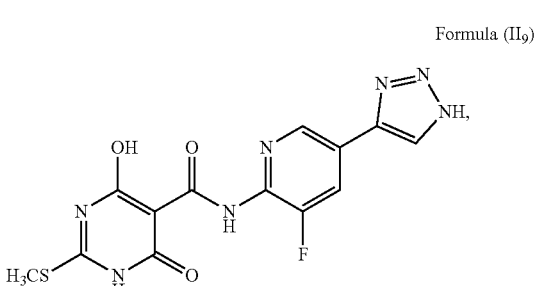

Formula (II₉)

The compound wherein A is heteroaryl such as substituted or unsubstituted quinoline; and X is S; including certain exemplary compounds wherein $R^1$ is —$CH_3$; and tautomers thereof, such as a structure represented by Formula ($II_{10}$):

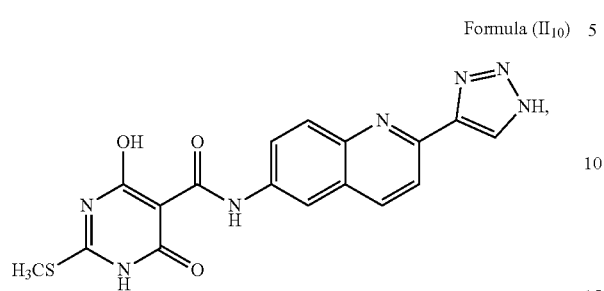

Formula ($II_{10}$)

and
a structure represented by Formula ($II_{11}$):

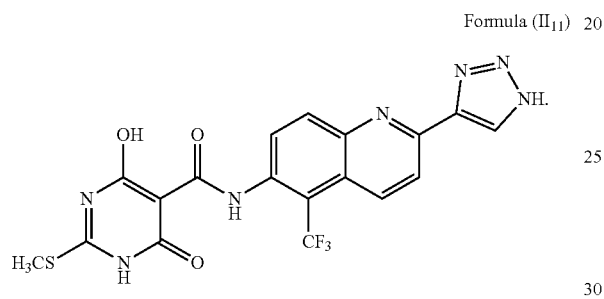

Formula ($II_{11}$)

2. A compound wherein the 5-member heterocyclic ring is a substituted triazole. Representative examples of such compounds include:

The compound wherein A is phenyl; X is O or S; and $R^1$ is methyl ($CH_3$); and tautomers thereof, such as a structure represented by Formula ($II_{ff}$):

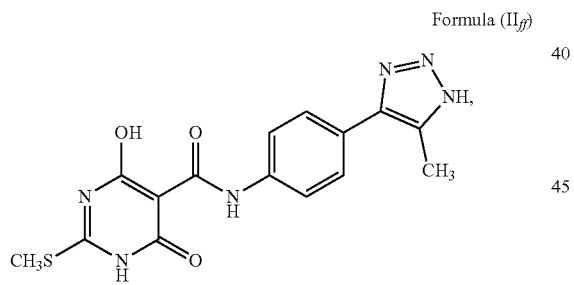

Formula ($II_{ff}$)

and
a structure represented by Formula ($II_{gg}$):

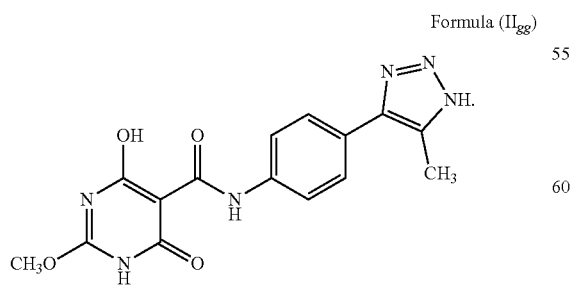

Formula ($II_{gg}$)

3. A compound wherein A is spirocycloalkyl. Representative examples of such compounds include structures represented by Formula ($II_{hh}$):

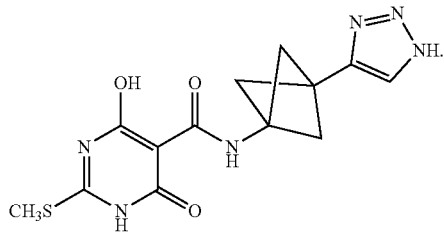

Formula ($II_{hh}$)

4. A compound wherein A is pyridine or diazine. Representative examples of such compounds include a structure represented by Formula ($II_{ii}$):

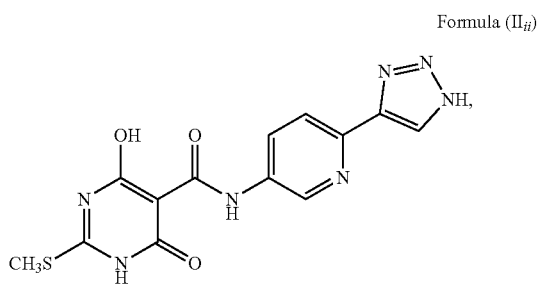

Formula ($II_{ii}$)

a structure represented by Formula (II):

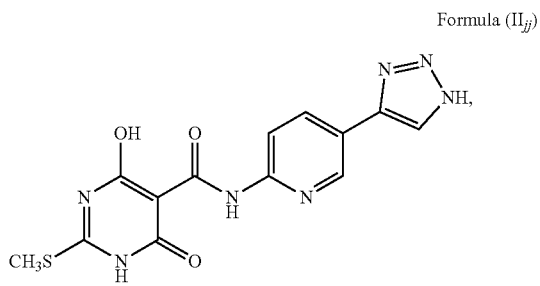

Formula ($II_{jj}$)

and
a structure represented by Formula ($II_{kk}$):

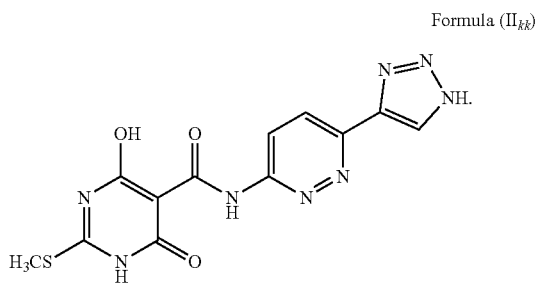

Formula ($II_{kk}$)

As disclosed herein, reference to compounds having a structure represented by Formula (I), Formula II, or a combination thereof, is intended to include all compounds falling within the generic structure, as well as the specific embodiments described and their tautomers.

The compounds disclosed herein can be synthesized various general procedures, for example as depicted in FIGS.

Figure 43A:
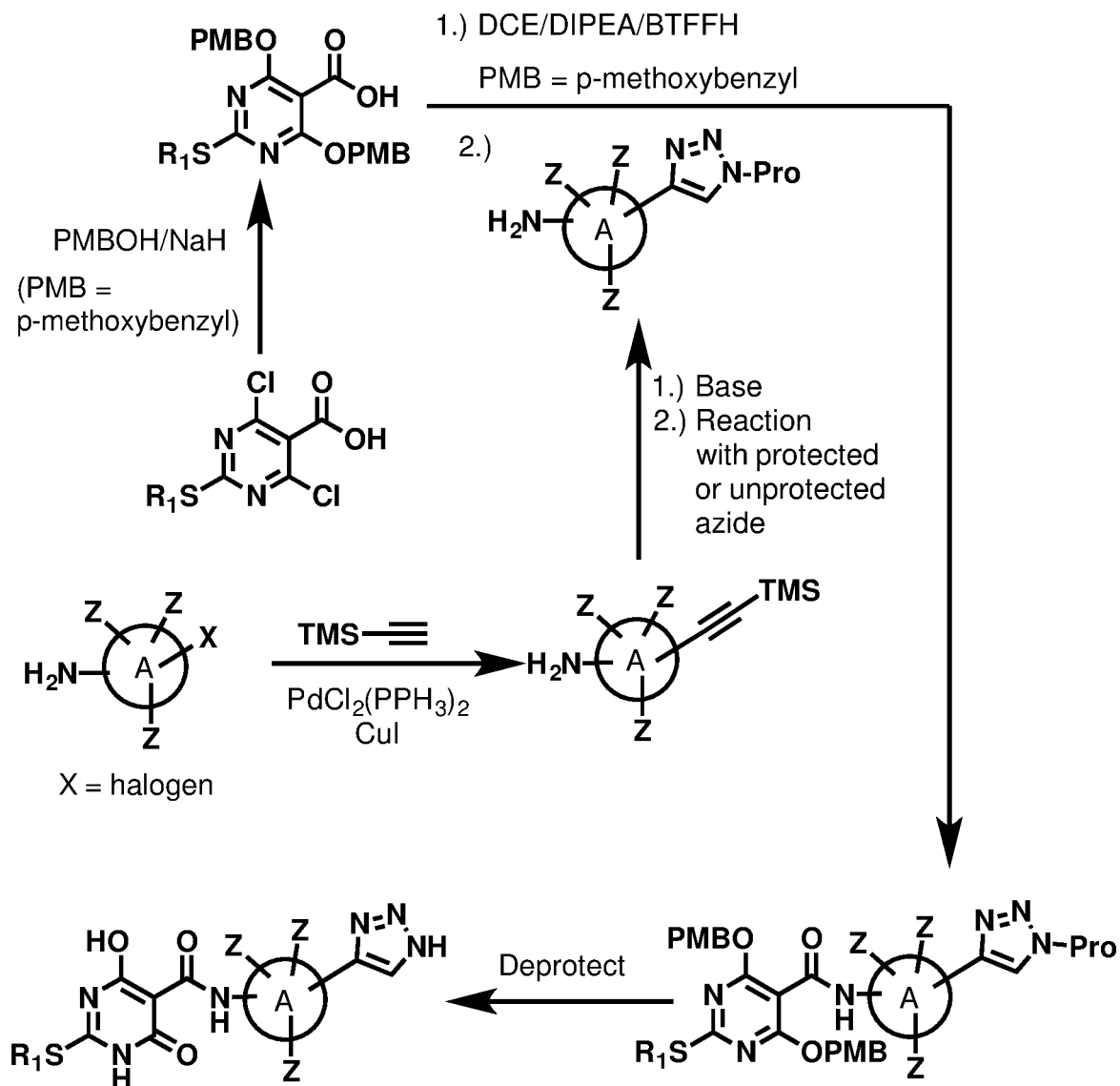
FIG. 43A and FIG. 43B illustrate general schemes for synthesis of compounds according to Formula (II).
Figure 44A:
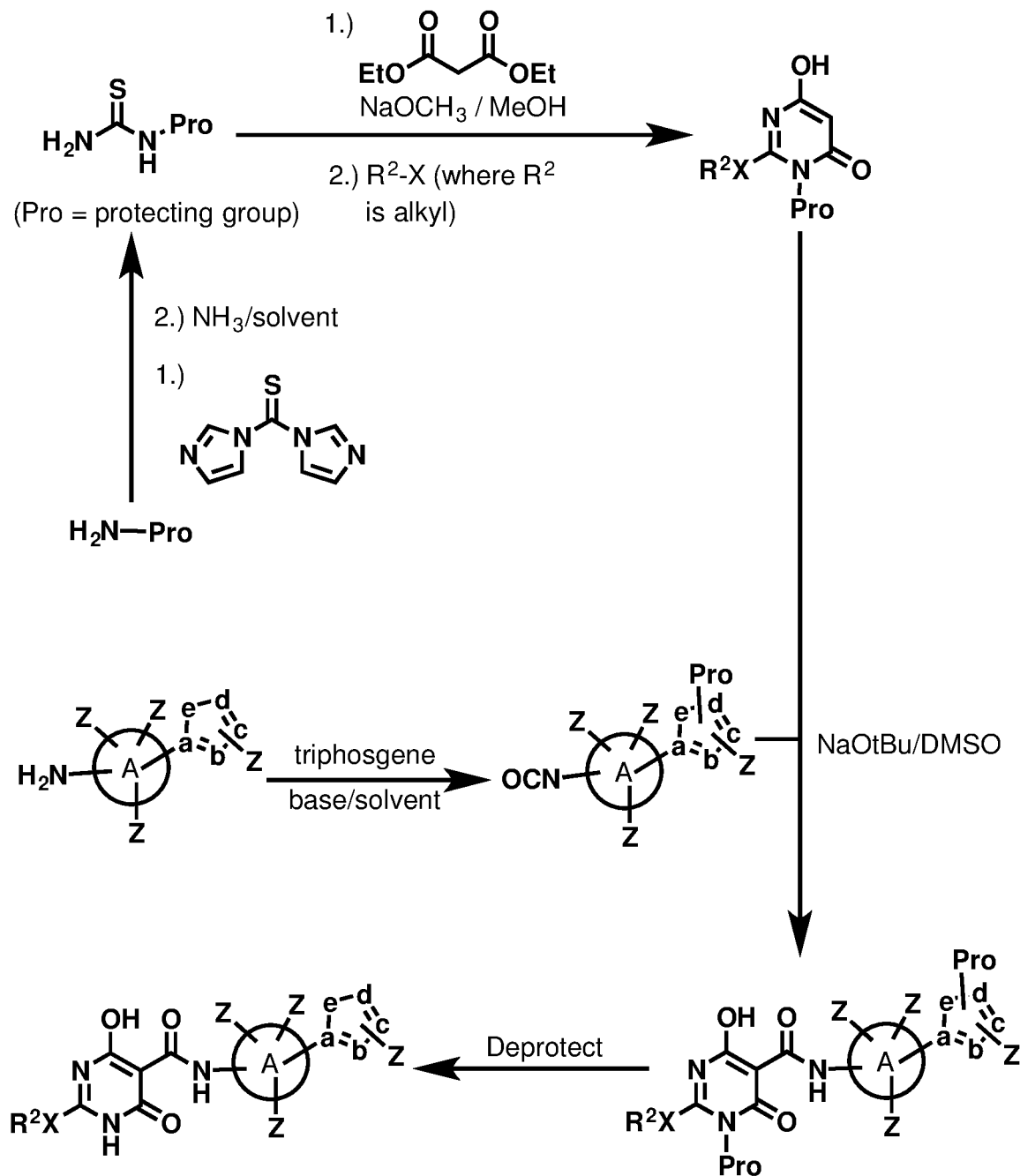
FIG. 44A and FIG. 44B illustrate additional general schemes for synthesis of compounds according to Formula (II).

1-8, FIGS. 43A and B, and FIGS. 44A and B. In general the various synthetic routes center on the coupling of a substituted phenyl, heterocyclic, cycloalkyl or spirocyclic A ring with an appropriately substituted barbiturate ring. Several different coupling agents can be employed in this process. Many of the compounds of Formula (I) can be made as illustrated in FIG. 1 if the appropriately substituted nitro or amino ring A is known in the art.

Figure 2:
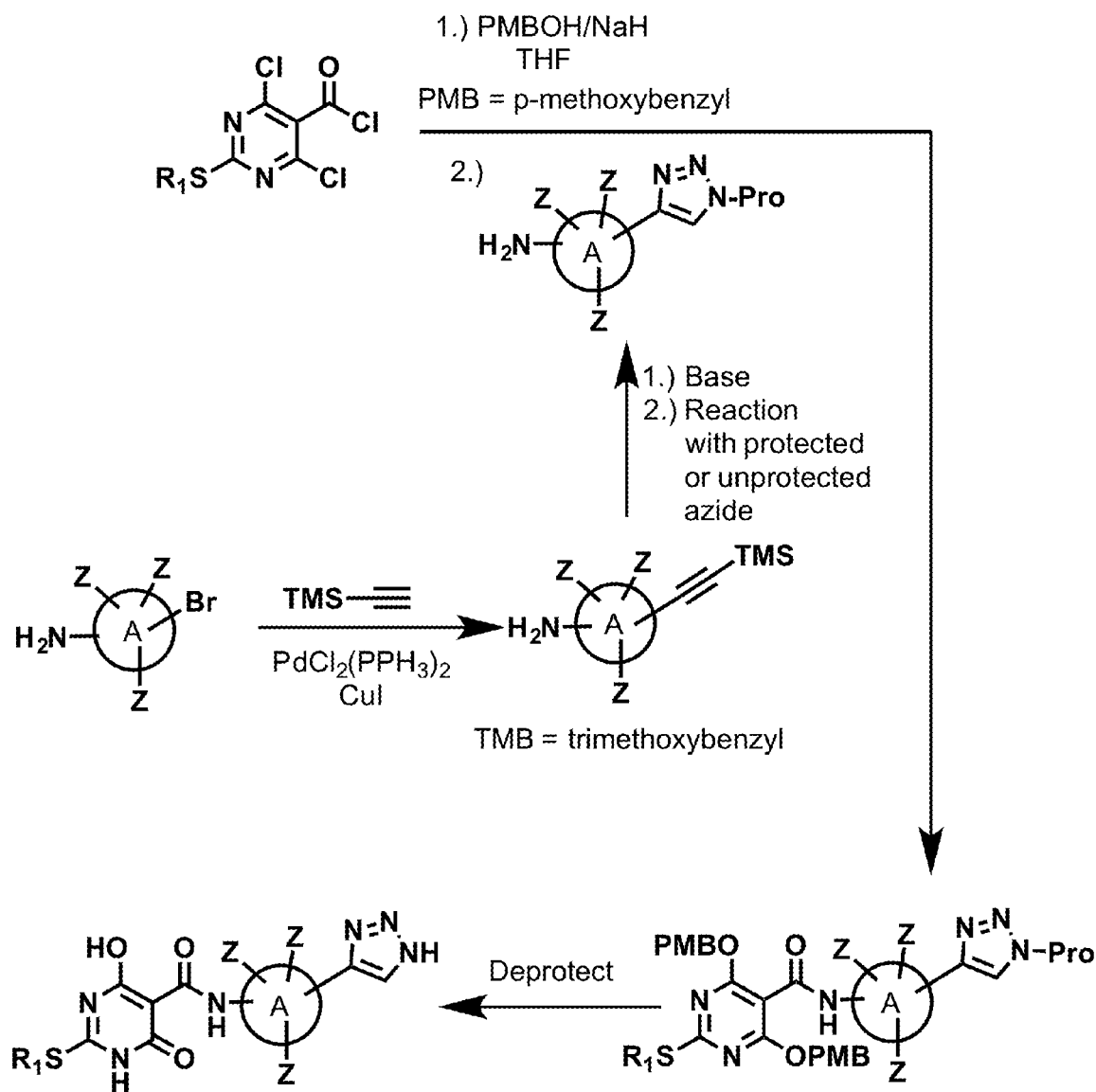
FIG. 2 illustrates a general scheme for synthesis of compounds according to Formula (II).

As shown in FIG. 2, for synthesis of Formula (II) compounds 4,6-dichloro-2-thiopyrimidine-5-carbonyl chloride with the appropriate $R^1$ group already incorporated can be protected with various protecting groups, including with a para-methoxy benzyl group. Other protecting groups are also possible, although para-methoxy benzyl is preferred. This can then be reacted with the appropriate amino derivative attached to ring A containing the desired heterocycle, which is usually a triazine or tetrazole. However, in many cases this moiety needs to be synthesized. This is accomplished by employing a Sonogashira cross-coupling reaction between the appropriately substituted halogen (e.g., bromine) containing amino derivative with an acetylene. This acetylene is best protected with a trimethylsilyl group at one end. The trimethyl silyl group is then removed by base and the resulting acetylene is reacted with the appropriate azide to produce the intermediate that is to be coupled to the 4,6-dichloro-2-alkylthiopyrimidine-5-carbonyl chloride. The azide may or may not be substituted with a protecting group. One such group is azidomethyl pivalate, which can be subsequently removed by base. The resultant coupled product is then deprotected by the appropriate reagents. For example, the PMB groups can be removed by acid and the pivalate group by base to produce the desired final product. However, those skilled in the art will realize that other protecting groups can be employed.

Figure 3:
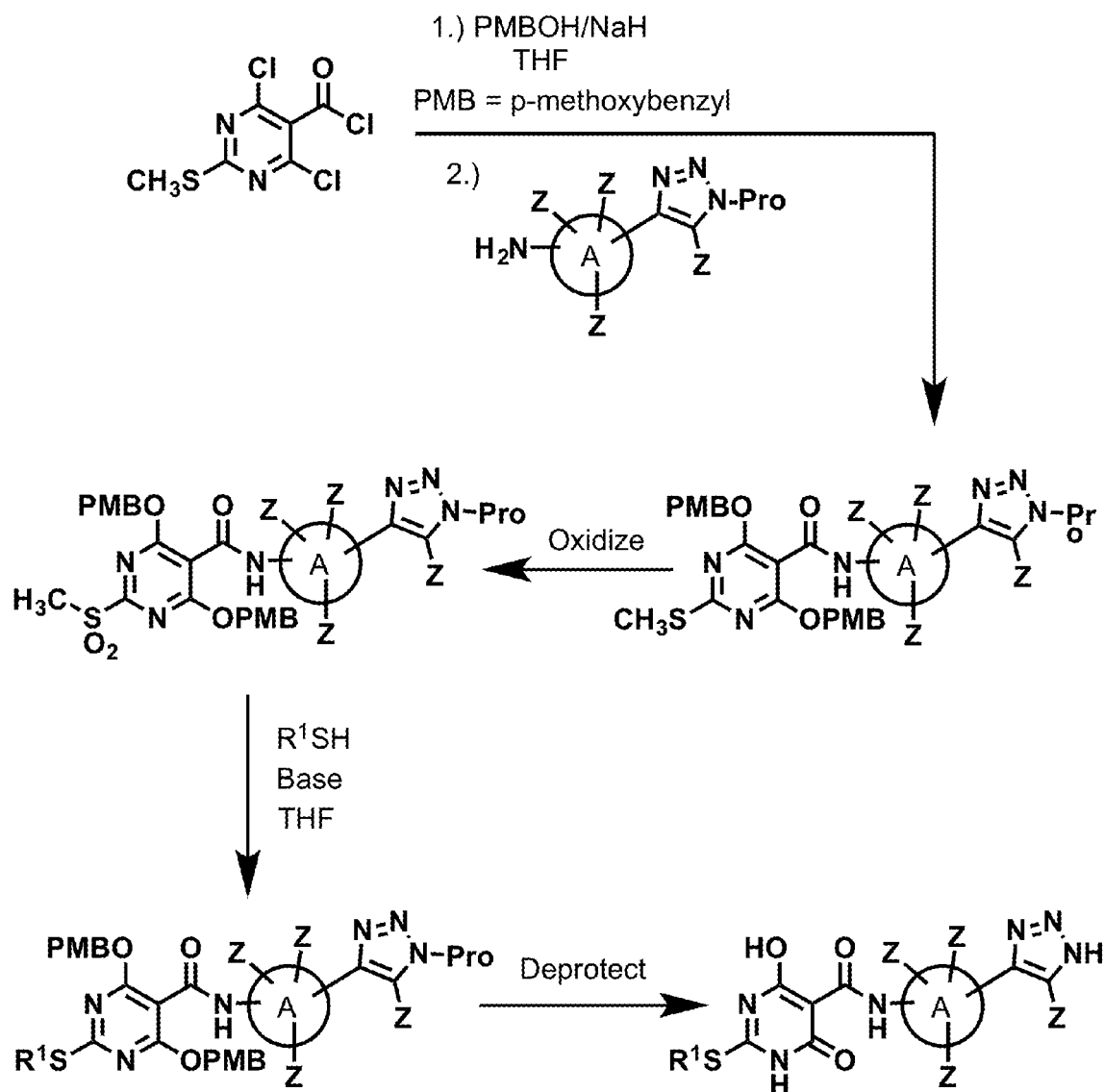
FIG. 3 illustrates an alternative general scheme for synthesis of compounds according to Formula (II).

As shown in FIG. 3, for synthesis of Formula (II) compounds, 4,6-dichloro-2-(methylthio)pyrimidine-5-carbonyl chloride can be protected with various protecting groups, including with a para-methoxy benzyl group. Other protecting groups are also possible, although para-methoxy benzyl is preferred. This can then be reacted with the appropriate amino derivative attached to ring A containing the desired heterocycle, which is usually a triazine or tetrazole. This moiety can be protected with a protecting group or not. In some cases the reactions work without a protecting group. Once the two moieties are coupled together, the thiomethyl group can be oxidized by a variety of agents including mCPBA. This produces the methyl sulfone, which can be displaced by a variety alkylated sulfhydryl agents. Then the protecting groups are removed. The PMB group is usually removed by acid, such as triflic acid. If there is a protecting group on the triazine or similar nitrogen heterocycle, this group is removed by other agents depending on the nature of the group. For example, methyl pivalate is removed by base, trimethoxybenzyl by acid, and [2-(Trimethylsilyl)ethoxy]methyl by fluoride. Those skilled in the art will realize that other protecting groups are possible.

Figure 41:
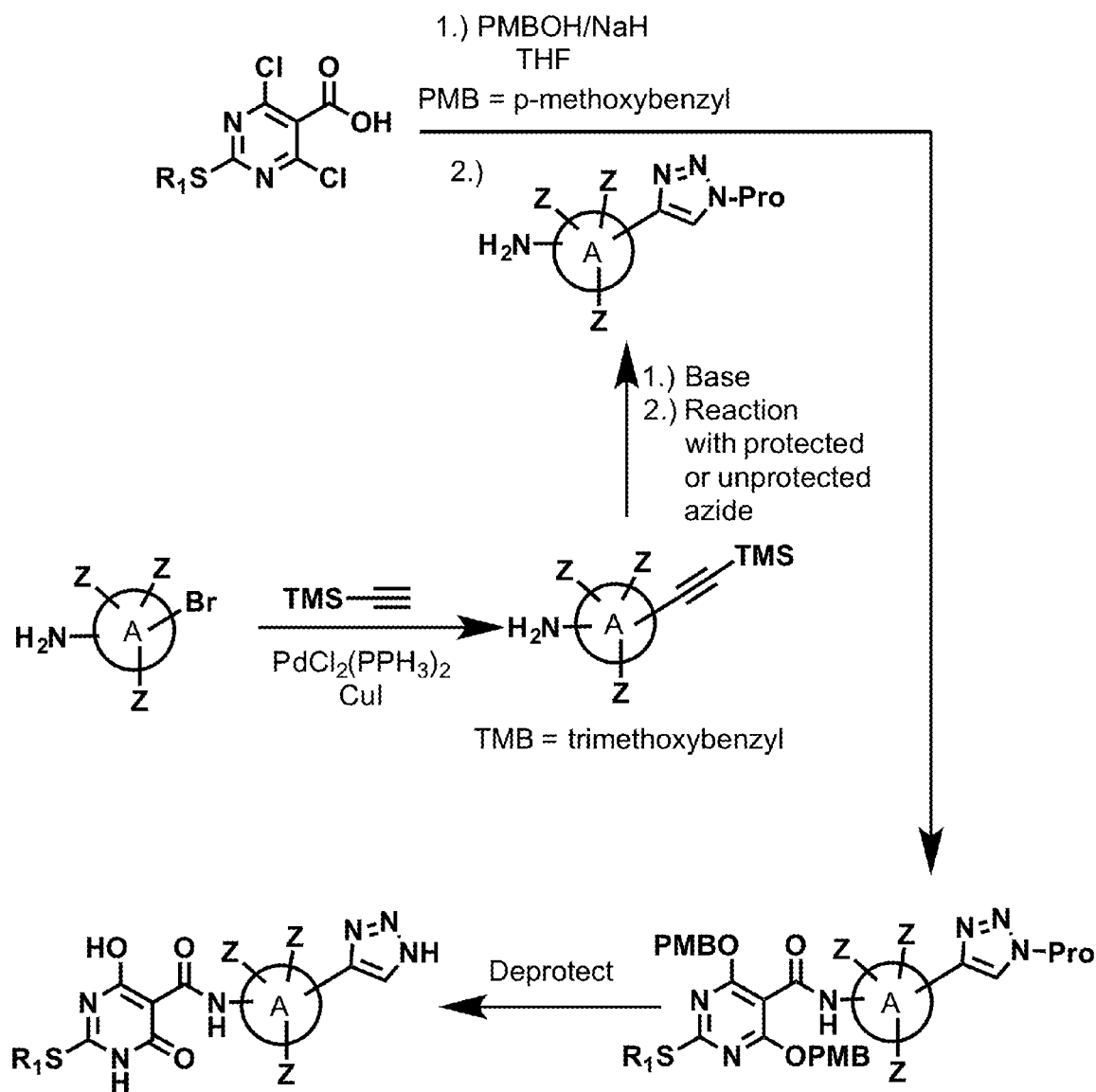
FIG. 41 illustrates an alternative general scheme for synthesis of compounds according to Formula (II).

FIG. 41 illustrates a synthesis scheme that is similar to the schemes described in FIG. 2 and FIG. 3 except that 4,6-dichloro-2-thiopyrimidine-5-carboxylic acid is used in place of the acid chloride. In this case an appropriate coupling agent is employed to form the bond between the amino heterocycle and the barbiturate ring. Such agents include $T_3P/Et_3N$, EDC, DCC and carbonyl di-imidazole, although there are many others that can be employed, as one skilled in the art would know. If other substituents are desired in addition to the methyl group on sulfur, one skilled in the art would employ the scheme described in FIG. 13.

Figure 42:
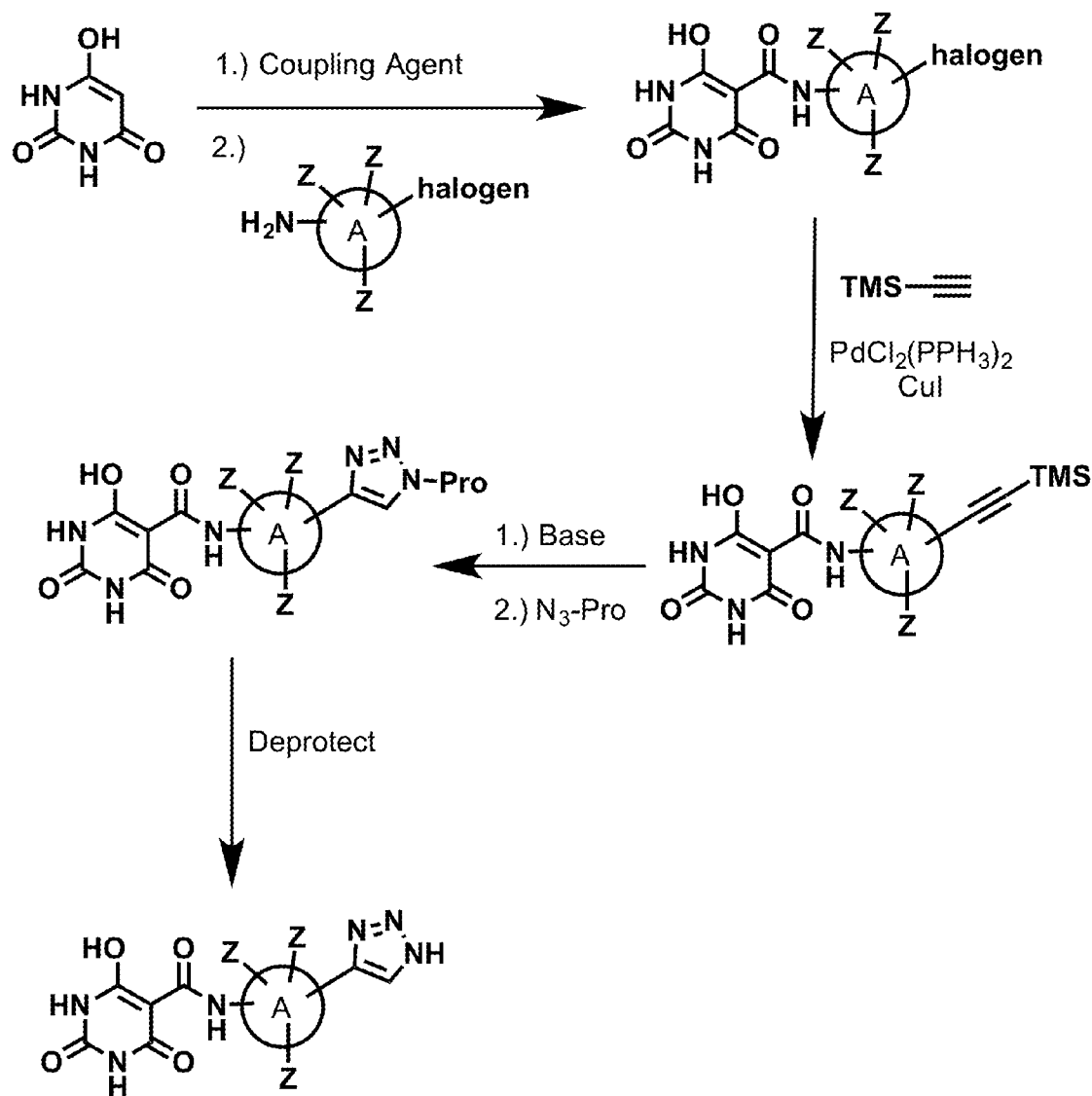
FIG. 42 illustrates an alternative general scheme for synthesis of compounds according to Formula (I).

FIG. 42 illustrates synthesis of a compound of Formula (I), wherein barbiturate acid is activated with an appropriate coupling agent as described in other figures. This can then be reacted with the appropriate amino derivative that contains a halogen, usually bromine. Subsequent Sonogashira cross-coupling reaction with a substituted acetylene then produces the intermediate that can be reacted with the appropriately protected azide. In many cases different protecting groups can be employed, but azidomethyl pivalate is often preferred, in which the pivolate group can often be easily removed by base.

Figure 4:
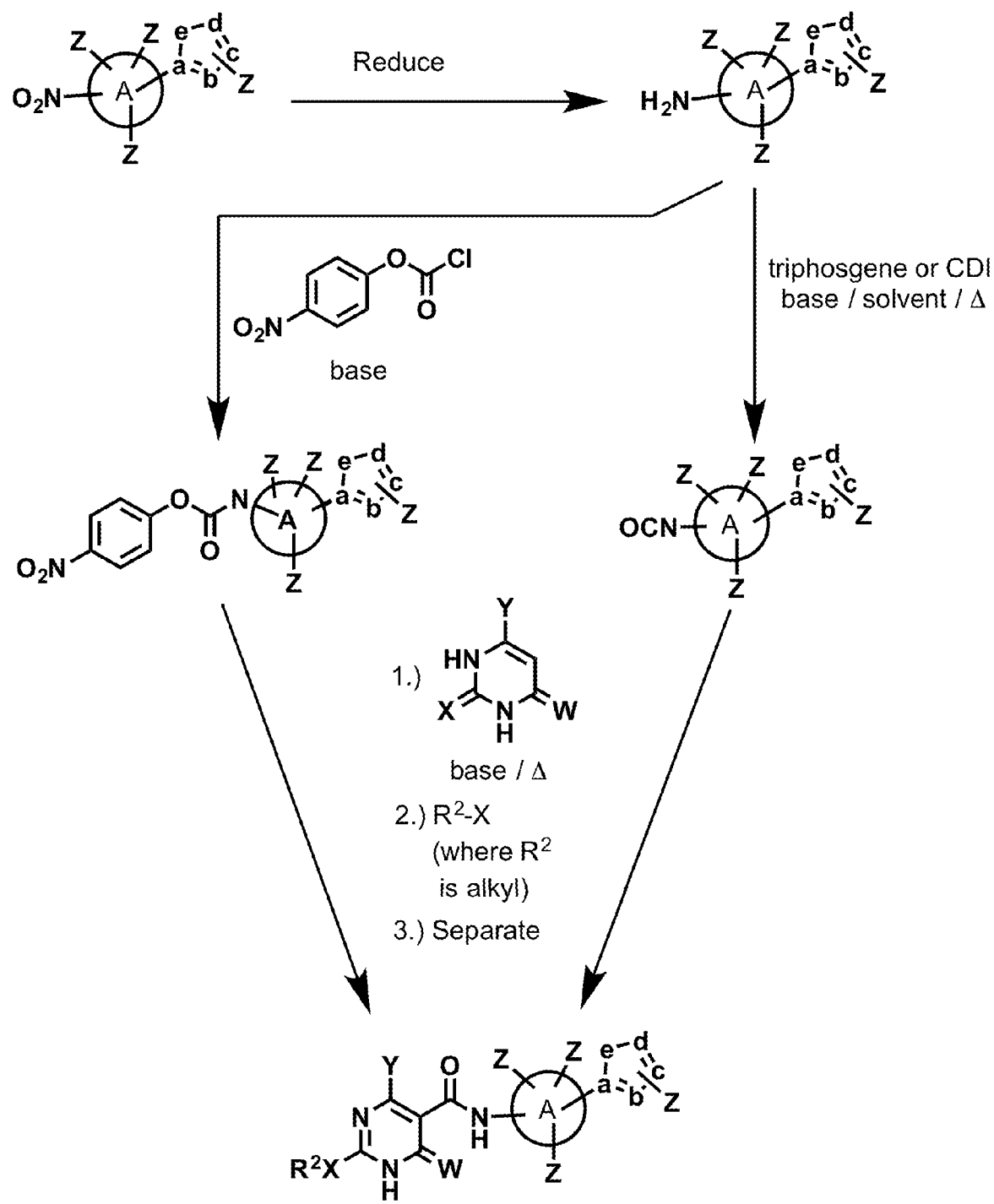
FIG. 4 illustrates a general scheme for synthesis of compounds containing a substituent on X of the barbiturate ring.
Figure 5:
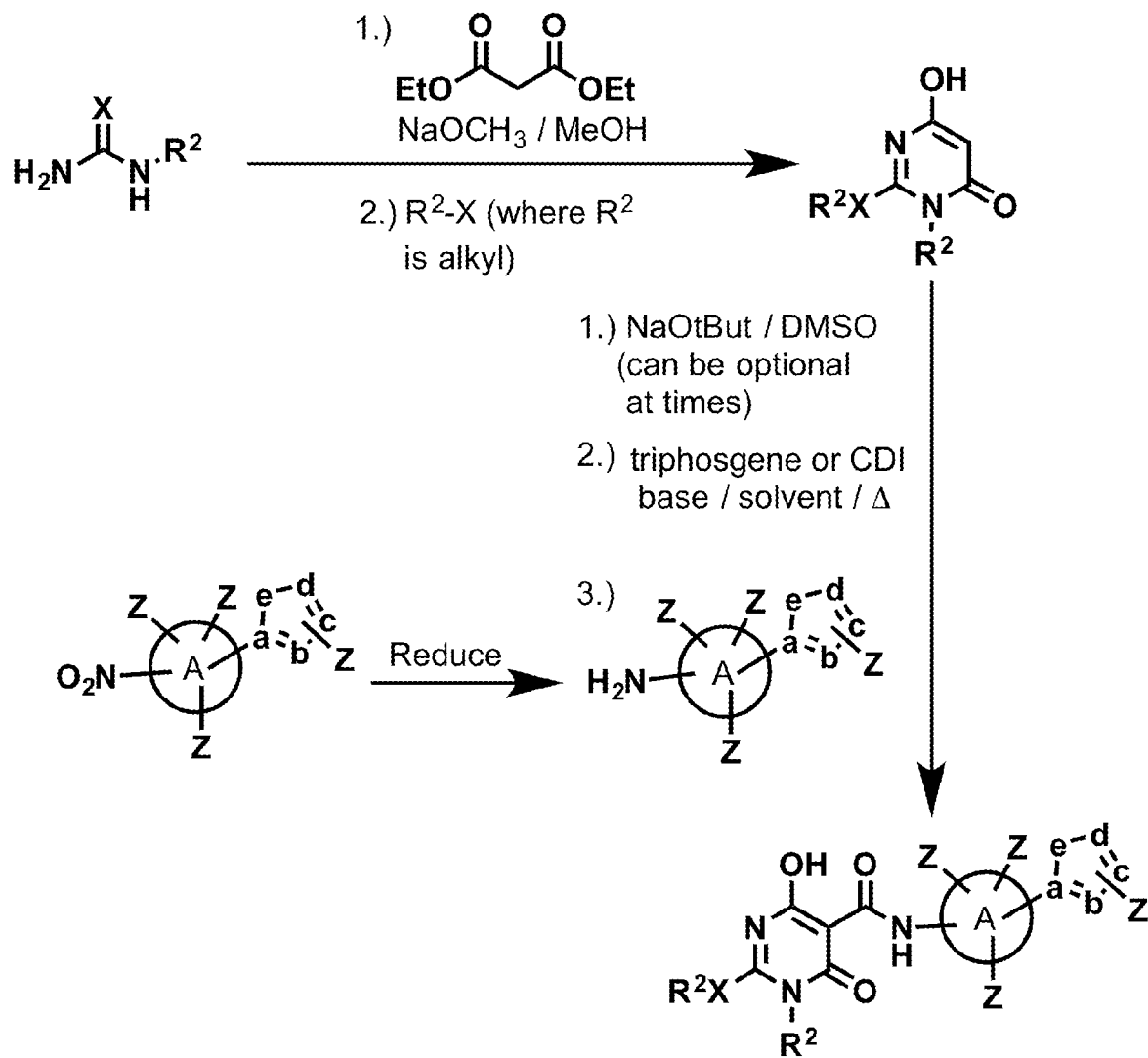
FIG. 5 illustrates an alternative general scheme for synthesis of compounds containing a substituent on X of the barbiturate ring.
Figure 6:
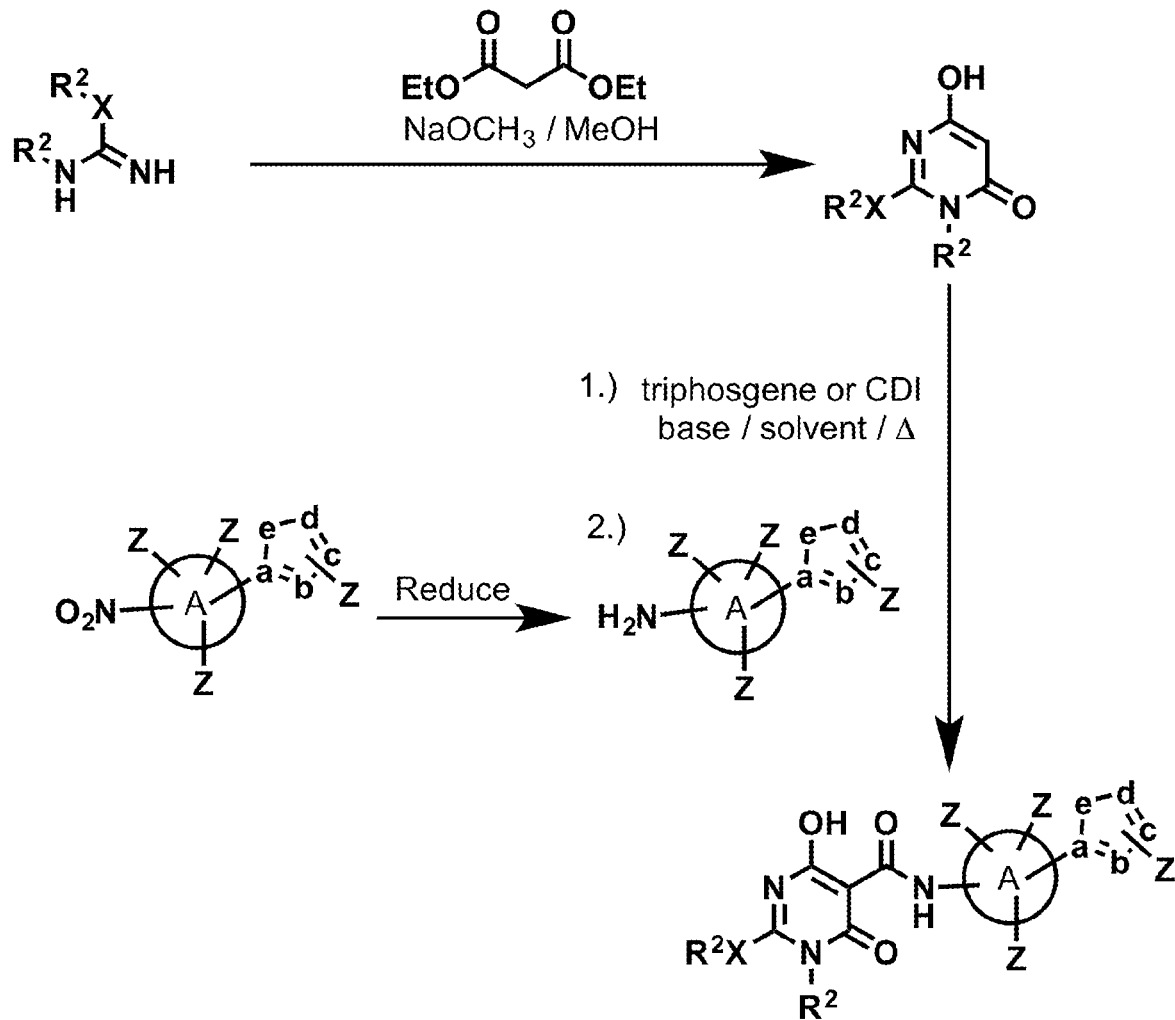
FIG. 6 illustrates a further alternative general scheme for synthesis of compounds containing a substituent on X of the barbiturate ring.

FIGS. 4-6 depict methods of synthesis that result in compounds containing a substituent on X of the barbiturate ring. FIG. 4 is the most straightforward way of making such compounds, as it generally follows the sequence depicted in FIG. 1. However, this method involves a subsequent last step, which involves alkylation of the X group. This is only possible if $R^2$ is an alkyl group, and separation of the various possible isomers obtained may be necessary. The synthesis outlined in FIG. 5 is more direct in that it ensures that the $R^2$ group is attached to the barbiturate ring. This process involves the introduction of the $R^2$ group early in the synthesis, first by condensation of malonate to an appropriately substituted urea, followed by alkylation, which again is conducted with an alkyl halide (i.e., $R^2$ is alkyl). In certain cases, a protecting group may be necessary depending on the nature of the substituents. In another case the $R^2$ group on the X can be introduced in the earliest part of the synthesis. It can be intact on the substituted urea or thiourea. This would allow for compounds that contain an aryl or heterocyclic aryl group on X. This is depicted in FIG. 6 and involves the condensation of the $R^2$ substituted urea or thiourea with malonate. The subsequent barbiturate ring is then coupled to the appropriate amino A ring compound to produce the desired product.

Figure 7:
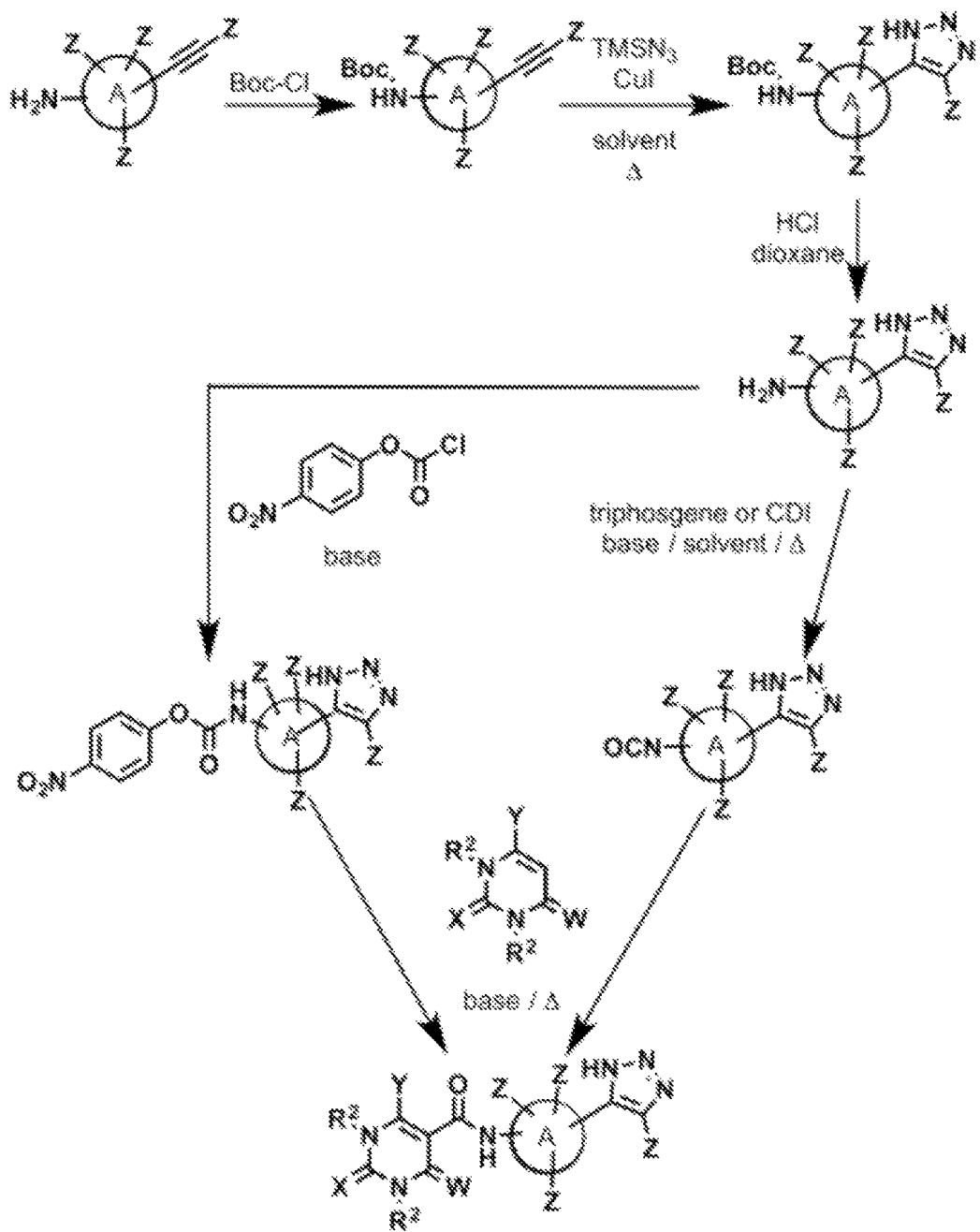
FIG. 7 illustrates a method for forming the triazole heterocyclic ring when it is not known in the art.
Figure 8:
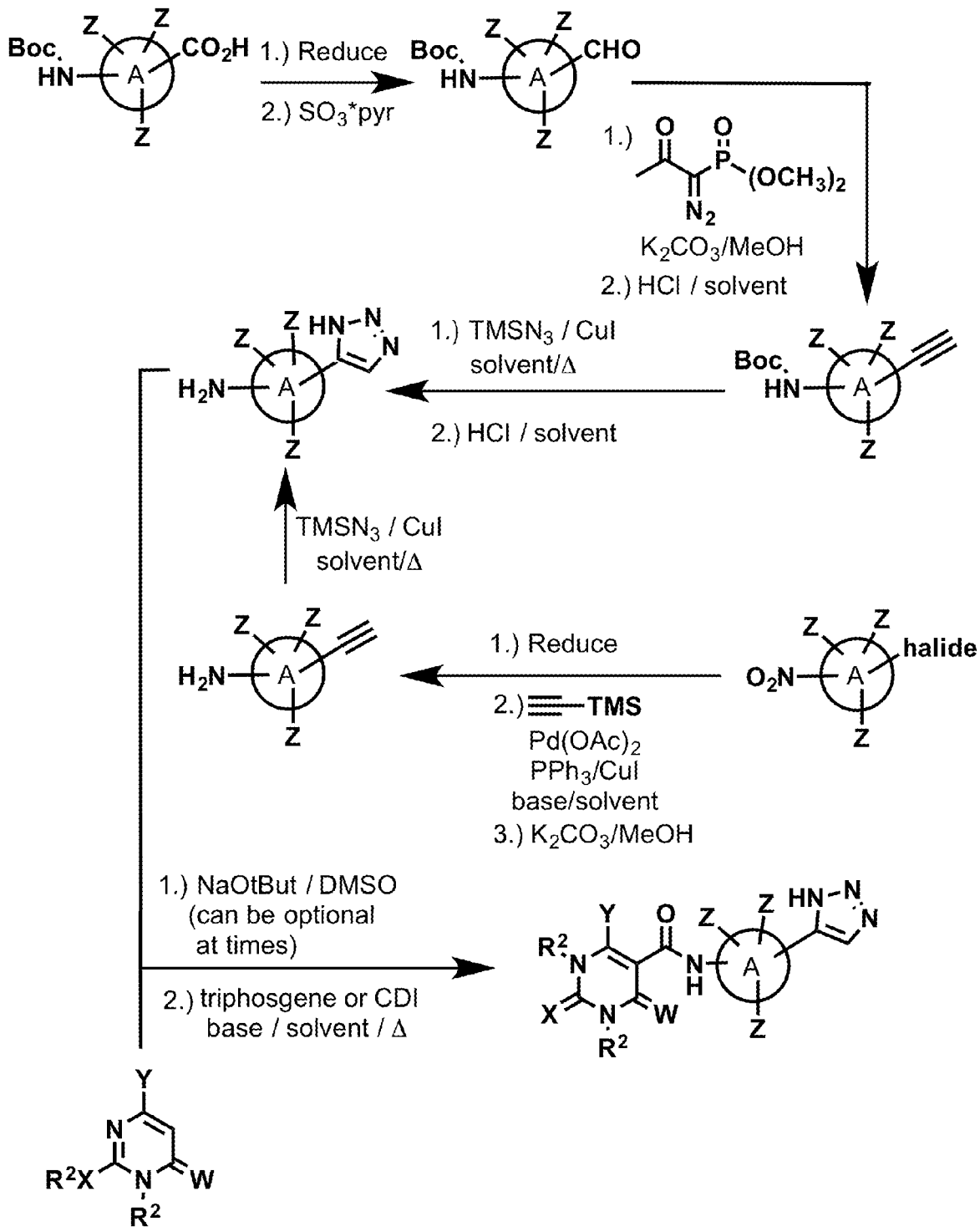
FIG. 8 illustrates alternative general schemes for synthesis of the A ring of the compounds.

FIG. 7 depicts methods for forming the triazole heterocyclic ring when it is not known in the art. Addition of azide to an amino containing A ring can be accomplished via a variety of methods which all involve the addition of azide to the acetylene. Protecting groups as illustrated in the figure may be necessary. Sometimes the acetylene containing A ring may not be known in the art, so it needs to be synthesized. This can be accomplished via a variety of methods as illustrated in FIG. 8. Treatment of the corresponding aldehyde of the ring A compound with 1-diazo-1-((dimethylperoxy)(oxo)-$\lambda^4$-phosphanyl)propan-2-one, which is known in the art, or Sonogashira reaction on the halide of a ring A compound would produce the corresponding acetylenic A ring containing compound. Subsequent addition of azide to the acetylene would produce the triazole. This can then be coupled by the methods described above to produce the desired targeted compound.

As shown in FIG. 43A, for synthesis of Formula (II) compounds 4,6-dichloro-2-mercaptopyrimidine-5-carboxylic acid with the appropriate $R^1$ group already incorporated can be protected with various protecting groups, including with a para-methoxy benzyl group. Other protecting groups are also possible, although para-methoxy benzyl is preferred. This can then be reacted with the appropriate amino derivative attached to ring A containing the desired heterocycle, which is usually a triazine. However, in many cases this moiety needs to be synthesized. This is accomplished by employing a Sonogashira cross-coupling reaction between the appropriately substituted halogen (e.g., bromine) containing amino derivative with an acetylene. This acetylene is best protected with a trimethylsilyl group at one end. The trimethyl silyl group is then removed by base and the resulting acetylene is reacted with the appropriate azide to produce the intermediate that is to be coupled to the 4,6-PMB-protected carboxylic acid, described above. The azide may or may not be substituted with a protecting group. One such group is azidomethyl pivalate, which can be subsequently removed by base or a SEM group which can be removed by fluoride or acid. The resultant coupled product is then deprotected by the appropriate reagents. For example, the PMB groups can be removed by acid and the pivalate or SEM group by base or fluoride (or acid), respectively, to produce the desired final product. However, those skilled in the art will realize that other protecting groups can be employed.

Figure 43B:
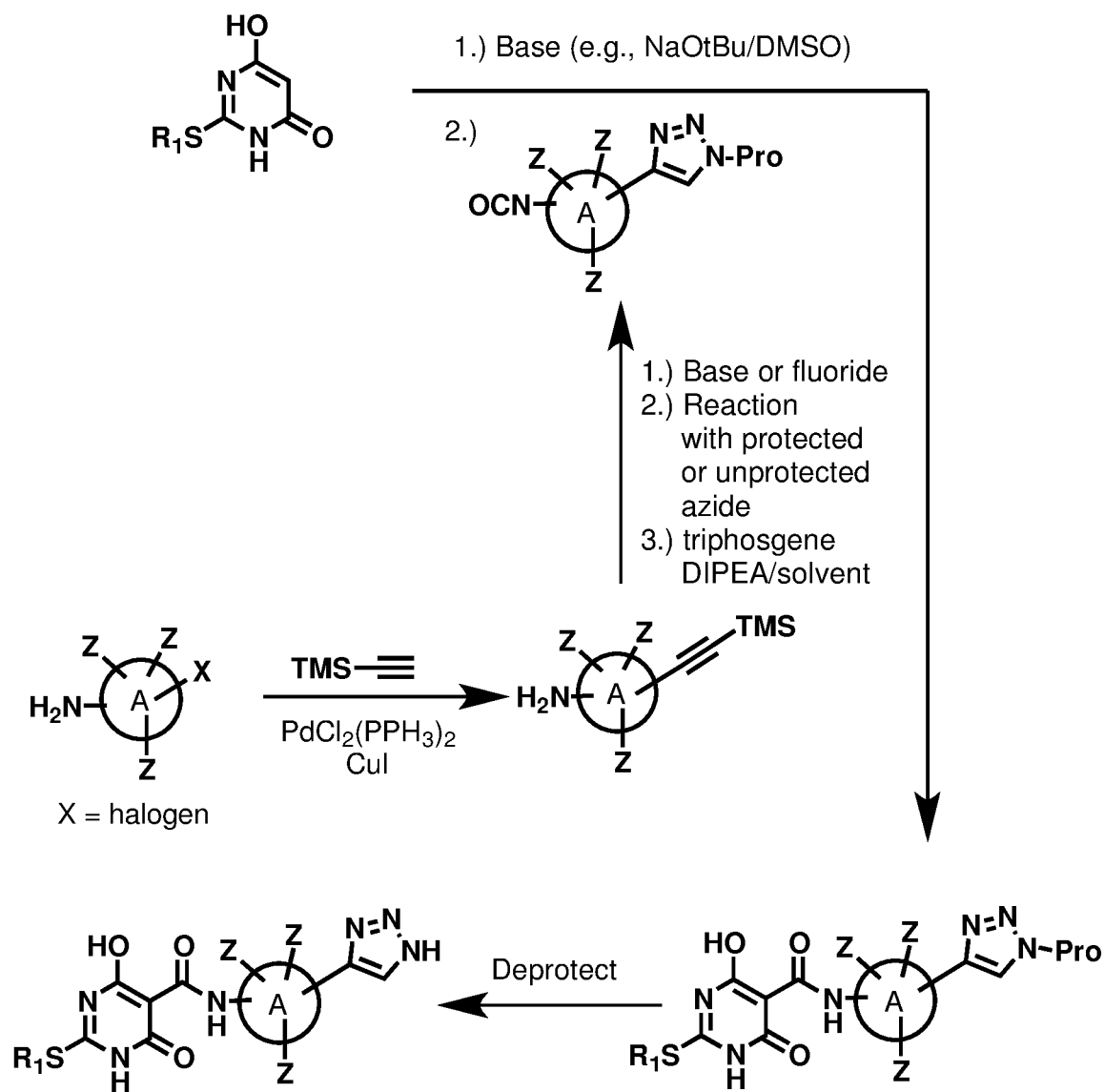

An alternative procedure involves the coupling of the appropriately substituted barbituric acid with an isocyanate attached to ring A containing the heterocycle, in most cases a protected triazine. This sequence is depicted in FIG. 43B. The isocyanate can be synthesized by employing a Sonogashira cross-coupling reaction between the appropriately substituted halogen (e.g., bromine) containing amino derivative with an acetylene. This acetylene is best protected with a trimethylsilyl group at one end. The trimethyl silyl group is then removed by base and the resulting acetylene is reacted with the appropriate azide to produce the intermediate isocyanate. Usually a base such as sodium t-butoxide is employed in the coupling. The resultant coupled product is then deprotected on the azide by the appropriate reagents. For example, the pivalate or SEM groups by base or fluoride (or acid), respectively, to produce the desired final product. However, those skilled in the art will realize that other protecting groups can be employed.

Alternatively, the thio-substituted barbiturate ring can be constructed to allow different R1 groups on the sulfur of the ring, as depicted in FIG. 44A. An appropriately protected amine is reacted with di(1H-imidazol-1-yl)methanethione, followed by ammonia to produce the protected thiourea. This is then condensed with diethyl malonate with base to produce the barbiturate ring. The sulfur atom is then alkylated with the appropriate alkyl halide to provide the R1 group on the sulfur. This is then reacted with the appropriate isocyanate, which is prepared as described in FIG. 43B. The resultant coupled product is then deprotected on the azide by the appropriate reagents. For example, the pivalate or SEM groups by base or fluoride (or acid), respectively, to produce the desired final product. However, those skilled in the art will realize that other protecting groups can be employed.

Figure 44B:
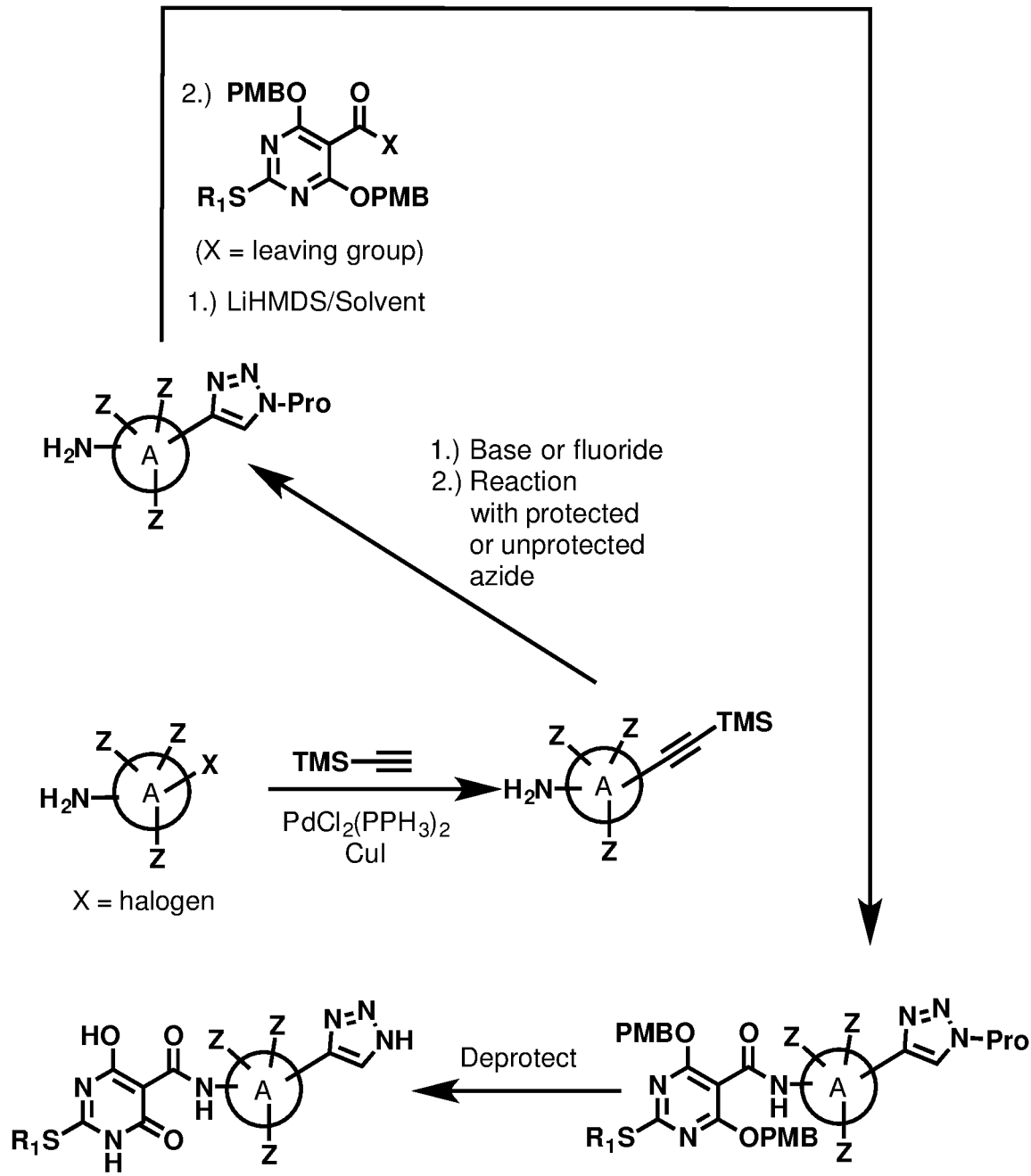

Another sequence that can be utilized to prepare compounds of the invention is depicted in FIG. 44B. The amino derivative containing the A ring substituted with the heterocycle, which is usually a protected triazine is prepared as described in FIG. 43A. This is reacted with the di-substituted PMB-barbiturate, which contains an acid halide or other appropriate leaving group like penta-fluorophenol at the C-5 position. This results in the coupled product protected by PMB groups and a protecting group on the triazine like a pivalate or SEM group. The resultant coupled product is then deprotected by the appropriate reagents. For example, the PMB groups can be removed by acid and the pivalate or SEM group by base or fluoride (or acid), respectively, to produce the desired final product. However, those skilled in the art will realize that other protecting groups can be employed.

In one aspect, the invention provides methods for reducing uric acid levels in the blood or serum, or in the whole body, of a subject comprising administering a compound having a structure represented by Formula (I), Formula (II), or a combination thereof, to the subject in an amount effective to reduce blood or serum uric acid levels. It is to be understood that all such methods for reducing uric acid levels correspond to a compound having a structure represented by any of Formula (I) or Formula (II), or a combination thereof, for use in medicine as well as a compound having a structure represented by Formula (I), Formula (II), or a combination thereof, for use in the treatment of elevated uric acid levels. Typically, the compound having a structure represented by Formula (I), Formula (II), or a combination thereof, will be administered when the level of uric acid in the blood of the subject is elevated, i.e., in the upper range of normal or above normal levels. One skilled in the art would further recognize that continued administration after normal uric acid levels are achieved is also contemplated in order to maintain uric acid levels within the normal range or to reduce the overall body burden of excess uric acid that may have occurred due to a period of previous excess. Accordingly, methods for preventing elevation of uric acid levels in blood or serum, or the whole body, are also an aspect of the invention. It is to be understood that all such methods for preventing elevation of uric acid correspond to a compound having a structure represented by Formula (I), Formula (II), or a combination thereof, for therapeutic use as well as a compound having a structure represented by Formula (I), Formula (II), or a combination thereof, for prevention of elevated uric acid levels.

Normal uric acid levels in serum are generally in the range of 4.3 mg/dL to 8.0 mg/dL. In certain embodiments, a compound having a structure represented by any of Formulae (I), Formula (II), or a combination thereof, is administered to a subject with a serum uric acid level of at least about 6 mg/dL. Administration may continue until a serum uric acid level of about 6.0 mg/dL or less is reached; however, it is generally considered to be beneficial to maintain uric acid levels below this target in patients with disorders associated with excess uric acid.

In certain embodiments, the invention provides methods of treating a disorder associated with excess uric acid in blood or serum or the whole body. The method of treating such disorders comprises administering a compound having a structure represented by Formula (I), Formula (II), or a combination thereof, to a subject in need thereof in an amount effective to reduce serum uric acid levels, thereby treating the disorder associated with excess uric acid in the subject. These disorders are associated with, or caused by, elevated uric acid levels in blood or serum or the whole body which are in the upper range of normal or above normal, and include gout; hyperuricemia; kidney disease; arthritis; kidney stones; kidney failure; urolithiasis; plumbism; hyperparathyroidism; psoriasis; inborn genetic errors of metabolism (such as Lesch-Nyhan syndrome) and sarcoidosis. In certain embodiments, the bifunctional compounds can be used effectively for treating or preventing other disorders associated with excess uric acid including NAFLD, NASH, atherosclerosis or other forms of cardiovascular disease, hypertension, chronic kidney disease, obesity, diabetes, insulin resistance, and metabolic syndrome, and/or transplantation of blood, bone marrow or solid organs.

These drugs are particularly useful for treating gout and kidney disease (including acute uric acid nephropathy, chronic urate nephropathy, uric acid nephrolithiasis, and chronic kidney disease). In addition, treatment of some cancers with chemotherapy leads to the release of large amounts of uric acid into the blood, which can damage the kidneys. Chemotherapy-induced hyperuricemia, particularly the disorder known as "tumor lysis syndrome," may also be treated, prevented or ameliorated according to the methods of the invention. Administration of a compound having a structure represented by Formula (I), Formula (II), or a combination thereof, to a subject with excess uric acid, such as a subject suffering from gout, kidney disease, or a risk of inducing elevated uric acid levels due to chemotherapy, treats, prevents or ameliorates these disorders by reducing uric acid levels in blood, or preventing or controlling their level of increase. In specific embodiments, the disorder associated with excess uric acid treated by administration of a compound having a structure represented by Formula (I), Formula (II), or a combination thereof, is gout. It is to be understood that all such methods for treating disorders associated with excess uric acid or elevated uric acid levels in serum (hyperuricemia) correspond to a compound having a structure represented by Formula (I), Formula (II), or a combination thereof, for therapeutic use as well as a compound having a structure represented by any of Formulae (I), Formula (II), or a combination thereof, for treatment of disorders associated with excess uric acid in blood or serum or the whole body.

The dose of a compound having a structure represented by Formula (I), Formula (II), or a combination thereof, administered to the subject may be any dose sufficient to achieve a desired reduction in uric acid levels in blood or serum over the time-course of administration. In certain embodiments, a daily dose of about 20 to about 1,500 mg/m²/day is administered. In other embodiments, a daily dose of about 20 to about 500 mg/m²/day, about 20 to about 250 mg/m²/day, about 20 to about 150 mg/m²/day or about 20 to about 100 mg/m²/day is administered. In other embodiments, a daily dose of about 50 to about 1,500 mg/m²/day is administered. In other embodiments, a daily dose of about 50 to about 500 mg/m²/day, about 50 to about 150 mg/m²/day, about 50 to about 100 mg/m²/day, or about 20 to about 100 mg/m²/day is administered.

In certain embodiments of any of the foregoing methods, a compound having a structure represented by Formula (I), Formula (II), or a combination thereof, is administered to the subject parenterally, intraperitoneally, intravenously, intranasally, intrarectally, or orally. Particularly useful routes of administration include injection, infusion, or oral administration. The amount of the drug administered per dose is an amount sufficient to achieve a reduction in uric acid levels in blood or serum, or the whole body, to prevent elevation of uric acid levels in blood or serum or the whole body, or to treat or prevent disorders associated with excess uric acid over the course of therapy. One skilled in the art will recognize that individualization of dosage based on a patient's body composition or his/her hypouricemic response to treatment may be medically necessary or desirable.

The drug(s) may be administered to the subject either intermittently or continuously over a period of time in order to achieve the desired reduction in uric acid levels in blood or serum or the whole body, or to treat a disorder associated with excess uric acid. For example, doses may be administered intermittently several times per day, daily, once, twice or three times per week, or at monthly intervals. In a specific example, a compound having a structure represented by Formula (I), Formula (II), or a combination thereof, may be administered to the subject by continuous intravenous infusion over 24 hours for about five days. Alternatively, a compound having a structure represented by Formula (I), Formula (II), or a combination thereof, may be administered to the subject by intravenous infusion over about 1 hour to about 5 hours for about five consecutive days. In a specific example, a compound having a structure represented by Formula (I), Formula (II), or a combination thereof, may be administered to the subject by intramuscular injection or by intravenous infusion over about 10 minutes for about five consecutive days. In further specific embodiments, a compound having a structure represented by Formula (I), Formula (II), or a combination thereof, may be administered to the subject by daily bolus injections for about five days. The period of time of administration in any of the foregoing protocols may be modified to achieve the desired reduction in uric acid levels and UA body burden, including about 2 days, about 3 days, about 4 days, about one week or about two weeks of administration, or for longer periods in repeated treatment cycles, and these treatments may be repeated at intervals of every two to every 10 weeks.

In addition to continuous intravenous infusion or bolus intravenous or subcutaneous injection, a compound having a structure represented by Formula (I), Formula (II), or a combination thereof, may be administered to the subject orally. In this embodiment, an oral dose in amounts as described above may be administered in one, two, three or four administrations per day for 1, 2, 3, 4, or 5 days to achieve the desired reduction in uric acid levels. In further embodiments, the oral dose as described above may be administered once per day, or in one, two, three or four administrations per day for one week or two weeks, to achieve the desired reduction in uric acid levels.

It will be appreciated that a subject in need of reduced levels of uric acid in blood or serum or the whole body, or in need of treatment of a disorder associated with excess uric acid, will be treated more aggressively initially to achieve the desired reduction in uric acid. Following initial therapy and reduction of uric acid to normal or sub-normal levels, the subject may be further treated over a period of time, or over a lifetime, to maintain normal or sub-normal levels of uric acid in blood or serum and prevent elevation of uric acid levels subsequent to the initial treatment. The maintenance or preventive protocol may comprise reduced dosages and/or less frequent administration of a compound having a structure represented by Formula (I), Formula (II), or a combination thereof, as necessary or desired to maintain normal or sub-normal uric acid levels in blood or serum or the whole body. For example, in a maintenance protocol the drug(s) may be administered daily, weekly, monthly, or intermittently as uric acid levels rise between treatment periods. Such maintenance protocols will serve to maintain normal or sub-normal uric acid levels for a prolonged period of time and reduce the subject's lifetime risk of developing a disorder associated with excess uric acid. The initial reduction of uric acid levels from above normal or high normal to normal or sub-normal, and maintenance of normal or sub-normal uric acid levels are both features included in treatment of a disorder associated with excess uric acid. It is anticipated that in certain embodiments, a typical patient will require daily treatment of varying duration, and that such daily treatment may be provided intermittently for life or for extended periods.

In certain embodiments of any of the foregoing methods, blood or serum uric acid levels of the subject are reduced by at least 25% compared to uric acid levels prior to administration of a compound having a structure represented by Formula (I), Formula (II), or a combination thereof. In certain further embodiments, blood or serum uric acid levels of the subject are reduced by 50% or more compared to levels prior to administration. In a specific embodiment, uric acid levels are reduced by about 75% even at daily doses of 500 mg/m²/day or less.

In a second aspect of the invention methods are provided for treating a disorder associated with excess uric acid in blood or serum or the whole body comprising administering to a subject in need thereof a compound having a structure represented by Formula (I), Formula (II), or a combination thereof, in an amount effective to reduce blood or serum uric acid levels, thereby treating the disorder associated with excess uric acid. Specific embodiments of the methods for treating a disorder associated with excess uric acid metabolism relating to dosing, routes of administration, initial therapy and maintenance therapy are as described above for reducing uric acid levels in blood or serum. The initial reduction in uric acid levels is typically rapid, and often occurs within 1-3 days. Upon reduction in uric acid levels to normal or sub-normal levels, continued maintenance or preventive therapy may also result in a detectable improvement in at least one symptom of excess uric acid, such as reduced inflammation, reduced pain, slowing of deformity development, reduction of kidney stones, improvement in kidney function, prevention of tumor lysis syndrome, improved cognition, improvement in (or reduction of actual or risk for) cardiovascular disease and hypertension, reversal of insulin resistance, or improvement in parameters of liver function. One skilled in the art will recognize that prevention of recurrent symptoms or complications of disease due to recurrence of excess uric acid that may necessitate extended treatment, would be highly desirable to maximize patient benefit.

In embodiments corresponding to the foregoing methods, the invention relates to use of a compound disclosed herein, or a combination thereof, for reducing uric acid levels in blood or serum or the whole body of a subject in need thereof, preventing elevation of uric acid levels in blood or serum or the whole body of a subject, or treating a disorder associated with excess uric acid. Each of the methods of treatment or prevention disclosed, including routes of administration, dosage and compounds administered, are also applicable to such uses of the compounds.

A further aspect of the invention provides a pharmaceutical composition comprising a compound having a structure represented by Formula (I), Formula (II), or a combination thereof, and a pharmaceutically acceptable carrier. In certain embodiments of the pharmaceutical compositions, the composition is formulated as a solution or tablet. Solutions or dispersions of the drug(s) can be prepared in water or saline. In certain embodiments of the pharmaceutical compositions, the pharmaceutically acceptable carrier is one or more component selected from the group consisting of one or more of a solvent, a dispersing agent, a coating (e.g., lecithin), a surfactant (e.g., hydroxypropylcellulose), a preservative (e.g., paraben, phenol, thimerosal, sorbic acid, chlorobutanol), an emulsion, an alcohol (e.g., ethanol), a polyol (e.g., glycerol, propylene glycol), and an isotonic agent (e.g., sugars, sodium chloride).

In certain embodiments of the foregoing pharmaceutical compositions, the composition is formulated for controlled release of the compound having a structure represented by Formula (I), Formula (II), or a combination thereof. In certain embodiments of the foregoing methods, a compound having a structure represented by Formula (I), Formula (II), or a combination thereof, is administered in a form for controlled release. The controlled release compositions may include pharmaceutically acceptable carriers or excipients which cause release of the active ingredient more slowly or which extend the duration of its action within the body. Examples of controlled release compositions include pharmaceutically acceptable carriers or excipients which delay absorption of the active ingredient (e.g., aluminum monostearate, gelatin, natural or synthetic hydrophilic gums). Alternatively, controlled release of the pharmaceutical composition may employ a device such as a pump, implant or transdermal patch.

In certain embodiments of the foregoing pharmaceutical compositions, the composition is formulated for improved oral bioavailability or extended release in the body. For example, microemulsions, particle size reduction and complexation technologies may be used to improve dissolution rates or equilibrium solubilities of the compounds. Other suitable chemical and physical means for improving oral bioavailability or extended release will also be known to those skilled in the art.

EXAMPLES

General Procedure for Triphosgene coupling: 2-(Methylthio)pyrimidine-4,6-diol (2 eq) was added to a stirring solution of sodium tert-butoxide (2.0 eq) dissolved in DMSO (0.2 M) at rt for 5 min. In a separate flask, the appropriately substituted amine was dissolved in 1,4-dioxane (0.8 M), to this solution was added triphosgene (0.33 eq) in one-portion. The suspension was stirred vigorously for 2 min at rt, then iPr$_2$NEt (2 eq) was added. The suspension was stirred vigorously at rt for 2 min. Freshly prepared solution of sodium 6-hydroxy-2-(methylthio)pyrimidin-4-olate in DMSO was added to the suspension in one-portion. The reaction was stirred at 90° C. for 30 min, until complete consumption of starting material observed via LCMS. The reaction mixture was loaded directly on C18 column and purified via reverse-phase chromatography.

Example 1

Figure 9:
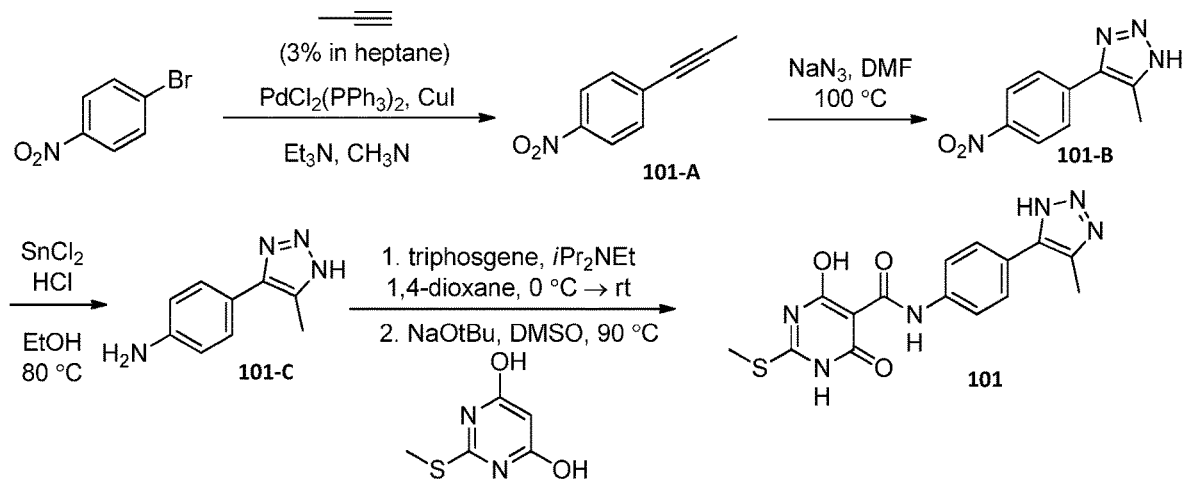
FIG. 9 illustrates the synthesis scheme described in Example 1.

Preparation of 4-hydroxy-N-(4-(4-methyl-H-1,2,3-triazol-5-yl)phenyl)-2-(methylthio)-6-oxo-1,6-dihydropyrimidine-5-carboxamide (101, Formula (II$_{ff}$), with Reference to FIG. 9)

Step One. 1-Nitro-4-(prop-1-yn-1-yl)benzene: A round bottom flask containing 1-bromo-4-nitrobenzene (1.00 g, 4.95 mmol), PdCl$_2$(PPh$_3$)$_2$ (174 mg, 0.248 mmol), and CuI (47 mg, 0.248 mmol) was purged with nitrogen for 15 min. Anhydrous acetonitrile (2.5 mL) was added, followed by propyne in heptane (13.2 mL, 99.0 mmol, 3% in heptane) and Et$_3$N (1.4 mL, 9.90 mmol). The reaction mixture was sealed and allow to stir at rt for 20 h. The reaction mixture was then concentrated, diethyl ether was added, then filtered through a small pad of Celite. The filtrate was concentrated then purified via ISCO (SiO$_2$, gradient eluent from 0 to 25% ethyl acetate in hexanes over 20 CV) to yield the product as a yellow solid (645 mg, >99% purity, 81% yield).

R$_f$: 0.79 (25% ethyl acetate in hexanes).

LCMS: R$_T$=1.73 min; purity=>99%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 5-Methyl-4-(4-nitrophenyl)-1H-1,2,3-triazole (101-B): Sodium azide (111 mg, 1.71 mmol) was added to 101-A (229 mg, 1.42 mmol) dissolved in anhydrous DMF (7.1 mL) at rt. The reaction was sealed in a pressure vessel and heated to 120° C. for 18 h. The reaction mixture was then allowed to warm up to rt, dichloromethane was added, followed by water. The aqueous layer was extracted with dichloromethane (3×20 mL), the combined organic extract was washed with brine, dried over MgSO$_4$, then concentrated under reduced pressure to yield the product as a brown solid (180 mg, >99% purity, 62% yield), without further purification.

LCMS: m/z [M+1]$^+$=205.29; R$_T$=1.29 min; purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. 4-(5-Methyl-1H-1,2,3-triazol-4-yl)aniline (101-C): Tin (II) chloride (938 mg, 4.51 mmol) was added to 101-B (230 mg, 1.13 mmol) in EtOH (3.8 mL) and conc. HCl (710 µL) at rt, the resulting reaction mixture was heated to reflux for 1 h. After complete consumption of the starting material was observed via LCMS, the reaction was allowed to cool to rt, before pouring into a solution of K$_3$PO$_4$ (~1.0 g) in MeOH (10 mL) at rt. The resulting reaction was stirred at rt for 30 min until the pH is not longer acidic. The precipitate was filtered, washed with additional methanol. The filtrate was collected and concentrated under reduced pressure. The crude product was purified via ISCO (SiO$_2$, gradient eluent from 0 to 15% methanol in dichloromethane over 12 CV) to yield the product as a brown oil (69 mg, 35% yield).

LCMS: m/z [M+1]$^+$=175.42; R$_T$=0.83 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. 4-hydroxy-N-(4-(4-methyl-1H-1,2,3-triazol-5-yl)phenyl)-2-(methylthio)-6-oxo-1,6-dihydropyrimidine-5-carboxamide (101): 101 was synthesized following general procedure 2. 2-(Methylthio)pyrimidine-4,6-diol (171 mg, 1.08 mmol) was added to a stirring solution of sodium tert-butoxide (104 mg, 1.08 mmol) dissolved in DMSO (2.7 mL) at rt for 5 min. In a separate flask, aniline 101-C was dissolved in 1,4-dioxane (680 mL), to this solution was added triphosgene (53 mg, 0.178 mmol) in one-portion. The suspension was stirred vigorously for 2 min at rt, then iPr$_2$NEt (190 µL) was added. The suspension was stirred vigorously at rt for 2 min. Freshly prepared solution of sodium 6-hydroxy-2-(methylthio)pyrimidin-4-olate in DMSO was added to the suspension in one-portion. The reaction was stirred at 90° C. for 30 min, until complete consumption of starting material observed via LCMS. The reaction mixture was loaded directly on C18 column and purified via reverse-phase chromatography (gradient eluent from 0 to 100% acetonitrile in water with an ammonium formate buffer 10 mM over 20 CV) to yield the product as brown solid (29.2 mg, 97.7% purity, 15% yield), after lyophilization.

$^1$H NMR (400 MHz, DMSO-d$_6$) δ 7.69 (br s, 4H), 2.44 (s, 3H), 2.37 (s, 3H).

LCMS: m/z [M+1]$^+$=359.0; R$_T$=1.37 min; purity=97.7%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 2

Figure 10:
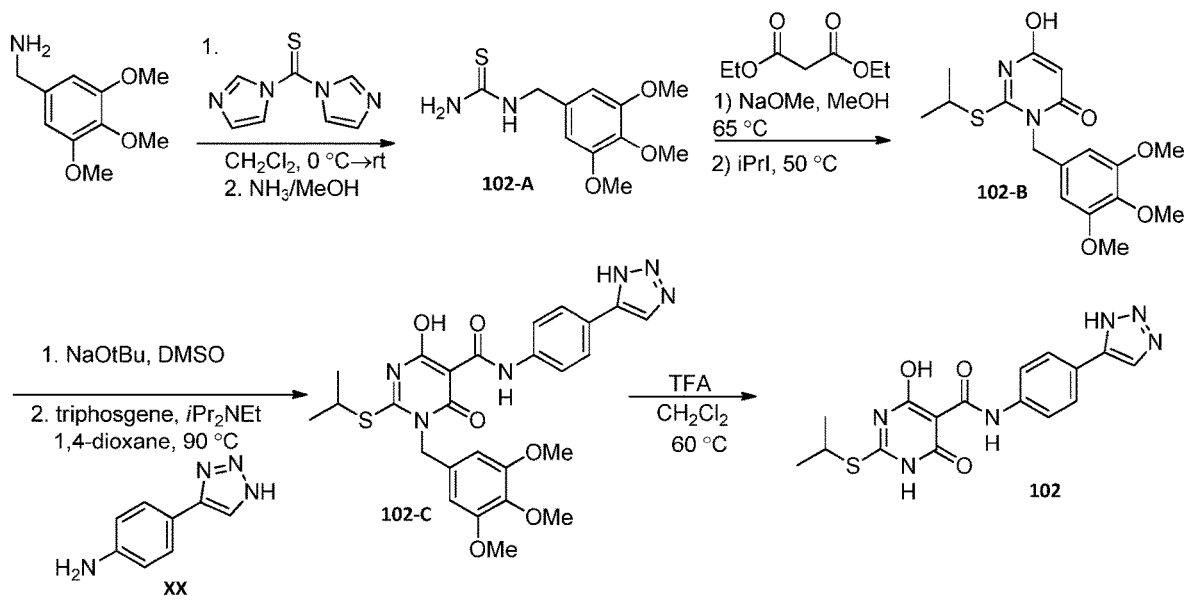
FIG. 10 illustrates the synthesis scheme described in Example 2.

Preparation of N-(4-(1H-1,2,3-triazol-5-yl)phenyl)-4-hydroxy-2-(isopropylthio)-6-oxo-1,6-dihydropyrimidine-5-carboxamide (102). (102, Formula (II$_i$), with Reference to FIG. 10)

Step One. 1-(3,4,5-trimethoxybenzyl)thiourea (102-A): (3,4,5-Trimethoxyphenyl)methanamine (2.5 mL, 14.6 mmol) was added dropwise to a solution of 1,1'-thiocarbonyl diimidazole (3.91 g, 22.0 mmol) dissolved in dichloromethane (36.5 mL) at 0° C. The reaction mixture was then allowed to warm up to rt over 2 h. After complete consumption of the starting material was observed via LCMS, a solution of ammonia in methanol (7.5 mL, 52.6 mmol, 7.0 M in MeOH) was added, then stirred for an additional 20 h. The reaction mixture was concentrated under reduced pressure, dichloromethane was added, the precipitate was isolated and washed with additional CH$_2$Cl$_2$, then dried under high vacuum to yield the product as a light pink solid (2.83 g, 76% yield).

LCMS: m/z [M+1]$^+$=257.07; R$_T$=1.06 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 6-hydroxy-2-(isopropylthio)-3-(3,4,5-trimethoxybenzyl)pyrimidin-4(3H)-one (102-B): A mixture of 102-A (781 mg, 3.05 mmol), diethyl malonate (465 µL, 3.05 mmol), and NaOMe (1.4 mL, 6.10 mmol, 4.4 M in MeOH) in methanol (2.4 mL) was heated to reflux for 3 h. The reaction was then cooled to ~50° C., isopropyl iodide (3.5 mL, 30.5 mmol) was then added in one-portion. The reaction was stirred for an additional 30 min at 50° C. The reaction mixture was then cooled to rt, then concentrated under reduced pressure. The crude product was purified via reverse-phase chromatography (gradient eluent from 0 to 100% acetonitrile in water with an ammonium formate buffer 10 mM over 15 CV) to yield the product as a white solid (433 mg, 97.7% purity, 38% yield), after lyophilization.

LCMS: m/z [M+1]$^+$=367.02; R$_T$=1.41 min; purity=97.7%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. N-(4-(1H-1,2,3-triazol-5-yl)phenyl)-4-hydroxy-2-(isopropylthio)-6-oxo-1-(3,4,5-trimethoxybenzyl)-1,6-dihydropyrimidine-5-carboxamide (102-C): 102-C was synthesized following general procedure 2. 102-B (97 mg, 0.265 mmol) was added to a stirring solution of sodium tert-butoxide (25 mg, 0.265 mmol) dissolved in DMSO (870 µL) at rt for 5 min. In a separate flask, aniline XX was dissolved in 1,4-dioxane (220 µL), to this solution was added triphosgene (17 mg, 0.0578 mmol) in one-portion. The suspension was stirred vigorously for 2 min at rt, then iPr$_2$NEt (60 µL) was added. The suspension was stirred vigorously at rt for 2 min. Freshly prepared solution of sodium 6-hydroxy-2-(isopropylthio)-3-(3,4,5-trimethoxybenzyl)pyrimidin-4(3H)-olate in DMSO was added to the suspension in one-portion. The reaction was stirred at 90° C. for 30 min, until complete consumption of starting material observed via LCMS. The reaction mixture was loaded directly on C18 column and purified via reverse-phase chromatography (gradient eluent from 30 to 100% acetonitrile in water with an ammonium formate buffer 10 mM over 15 CV) to yield the product as brown solid (31.2 mg, 80.2% purity, 26% yield), after lyophilization.

LCMS: m/z [M+1]$^+$=552.9; R$_T$=1.80 min; purity=80.2%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. N-(4-(1H-1,2,3-triazol-5-yl)phenyl)-4-hydroxy-2-(isopropylthio)-6-oxo-1,6-dihydropyrimidine-5- carboxamide (102): A solution of 102-C (31.2 mg, 0.0452 mmol, 80% purity) in dichloromethane (1.5 mL) was added trifluoroacetic acid (270 µL). The resulting reaction mixture was sealed in a pressure vessel then heated to 60° C. for 20 h. The reaction mixture was allowed to cool to rt, then concentrated under reduced pressure. The crude product was co-evaporated several times with methanol (3×), then purified via reverse-phase chromatography (C18, gradient eluent from 30 to 100% acetonitrile in water with an ammonium formate buffer 10 mM over 20 CV) to yield the product as an off-white solid (6.0 mg, 98.6% purity, 35% yield), after lyophilization.

$^1$H NMR (400 MHz, DMSO-d6+AcOD) δ 8.23 (s, 1H), 7.87 (d, J=8.2 Hz, 2H), 7.68 (d, J=8.2 Hz, 2H), 3.92 (dt, J=13.7, 6.9 Hz, 1H), 1.36 (d, J=6.9 Hz, 6H).

LCMS: m/z [M+1]$^+$=373.1; R$_T$=1.49 min; purity=98.6%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 3

Figure 11:
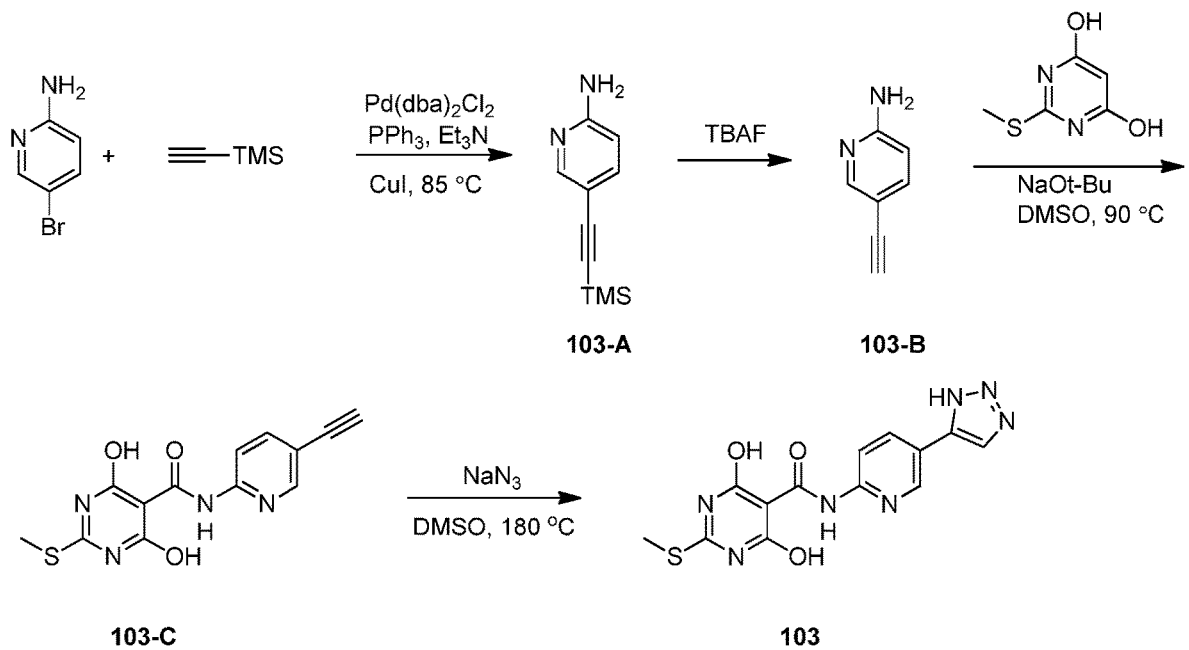
FIG. 11 illustrates the synthesis scheme described in Example 3.

Preparation of N-(5-(1H-1,2,3-triazol-5-yl)pyridin-2-yl)-4,6-dihydroxy-2-(methylthio)pyrimidine-5-carboxamide (103, Formula (II$_{jj}$), with Reference to FIG. 11)

Step One. 5-((Trimethylsilyl)ethynyl)pyridin-2-amine (103-A): To a sealed tube was added 2-amino-5-bromopyridine (1.00 g, 5.8 mmol), Pd(dba)$_2$Cl$_2$ (202 mg, 0.29 mmol), PPh$_3$ (151 mg, 0.58 mmol), CuI (110 mg, 0.578 mmol), Et$_3$N (10 mL) and TMS-acetylene (963 mg, 9.8 mmol) sequentially. The mixture was degassed and heated at 85° C. for 2 h. After complete consumption of starting material was observed via LCMS, the solvent was removed in vacuo and the crude was purified over silica (gradient eluent from 0 to 100% ethyl acetate in hexanes). 103-A was obtained as beige solid (812 mg, 74% yield).

LCMS: m/z [M+1]$^+$=191.3; R$_T$=1.55 min

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. N-(5-Ethynylpyridin-2-amine (103-B): 103-A (500 mg, 2.6 mmol) was dissolved in THF (5 mL) and to this solution was added TBAF (5 mL, 1 M in THF). The reaction was stirred at rt for 10 min and THF was removed in vacuo. The crude was dissolved in EtOAc and this solution was passed through a pad of silica and washed with EtOAc. The filtrate was concentrated to yield 103-B as a beige solid (256 mg, 82% yield).

LCMS: m/z [M+1]$^+$=118.8; R$_T$=0.41 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. N-(5-Ethynylpyridin-2-yl)-4,6-dihydroxy-2-(methylthio)pyrimidine-5-carboxamide (103-C): t-BuONa (136 mg, 1.4 mmol) was dissolved in DMSO (2 mL) and to this solution was added 2-(methylthio)pyrimidine-4,6-diol (224 mg, 1.4 mmol). The solution was stirred at rt for 5 min and left aside for the second step. At the same time, 103-B (84 mg, 0.71 mmol) was dissolved in DCE (1 mL) and to the solution was added CDI (115 mg, 0.71 mmol) in one-portion. The suspension was stirred vigorously for 2 min at rt and iPr$_2$NEt (250 uL, 1.4 mmol) was added. The solution was stirred at rt vigorously for 2 min. Freshly prepared solution of sodium 6-hydroxy-2-(methylthio)pyrimidin-4-olate in DMSO was added to the suspension. The reaction was stirred at 90° C. for 30 min. DCE solvent was removed in vacuo and the product was isolated by ISCO (120 g C18 column, gradient eluent from 0 to 50% acetonitrile in water with an ammonium bicarbonate buffer 10 mM over 20 CV). Product elutes at 35% MeCN in water. The product was isolated as a beige solid (62 mg, 29% yield), after lyophilization.

LCMS: m/z [M+1]$^+$=303.0; R$_T$=1.59 min

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. N-(5-(1H-1,2,3-triazol-5-yl)pyridin-2-yl)-4,6-dihydroxy-2-(methylthio)pyrimidine-5-carboxamide (103). 103-C (62 mg, 0.21 mmol) was dissolved in DMSO (2 mL) and to this solution was added NaN$_3$ (67 mg, 1.0 mmol). The mixture was stirred at 180° C. for 30 min. The product was purified by ISCO (60 g C18 column, gradient eluent from 0 to 50% acetonitrile in water with an ammonium bicarbonate buffer 10 mM over 20 CV, product elutes at 22% MeCN in water). The product was isolated as an off-white solid (25 mg, 35% yield), after lyophilization.

1HNMR (500 MHz, DMSO-d6, DCl in D$_2$O) δ 12.11 (s, 1H), 8.88 (dd, J=2.4, 0.8 Hz, 1H), 8.45 (s, 1H), 8.33 (dd, J=8.6, 2.4 Hz, 1H), 8.22 (dd, J=8.7, 0.8 Hz, 1H), 2.56 (s, 3H).

LCMS: m/z [M−1]$^-$=346.0; R$_T$=1.29 min; purity=94.4%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 4

Figure 12:
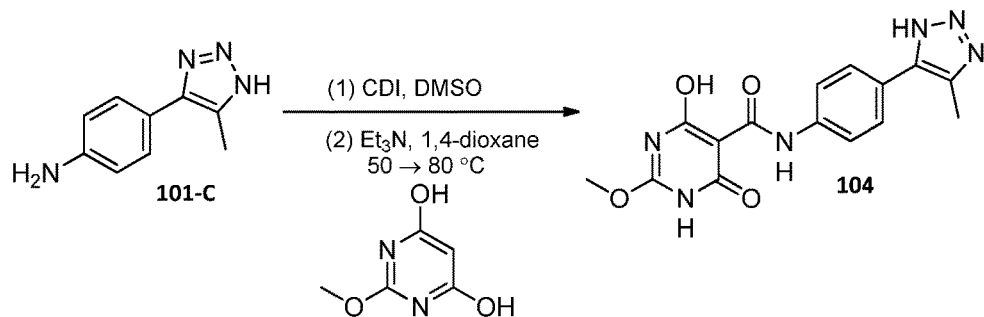
FIG. 12 illustrates the synthesis scheme described in Example 4.

Preparation of 4-hydroxy-2-methoxy-N-(4-(4-methyl-1H-1,2,3-triazol-5-yl)phenyl)-6-oxo-1,6-dihydropyrimidine-5-carboxamide (104, Formula (II$_{gg}$), with reference to FIG. 12). 104 was synthesized following general procedure 1. To a stirring solution of 101-C (23 mg, 0.132 mmol) in anhydrous DMSO (130 µL) was added 1,1'carbonyldiimidazole (33 mg, 0.198 mmol) was added at rt, under inert atmosphere. The resulting solution was stirred for 20 min at rt. In a separate flask containing 2-methoxypyrimidine-4,6-diol (21 mg, 0.145 mmol) was added anhydrous 1,4-dioxane (440 µL), then heated to 50° C. Et$_3$N (29 µL, 0.211 mmol) was added and stirred for 15 min at 50° C. The isocyanate generated from the amine in DMSO was added to the stirring suspension, then heated to 80° C. until complete consumption of the starting materials were observed via LCMS (30 min). The reaction mixture was cooled to rt, then acidified with 6M HCl (aq), the reaction mixture was directly loaded onto a C18 column and purified via ISCO (gradient eluent from 0 to 50% acetonitrile in water with an ammonium bicarbonate buffer 10 mM over 20 CV) to yield the product as an off-white solid (1.6 mg, 97.0% purity, 4% yield), after lyophilization.

$^1$H NMR (400 MHz, DMSO-d6) δ 8.14 (s, 1H), 7.69 (s, 4H), 3.79 (s, 3H), 2.44 (s, 3H).

LCMS: m/z [M+1]$^+$=342.7; R$_T$=1.24 min; purity=97.0%.

HPLC conditions: Column: XBridge C18, 3.5 µm, 4.6×30 mm; Gradient: 5% B for 0.2 min, 5% to 100% B in 1.8 min;

100% B for 1 min; 3 mL/min. Eluent A: Milli-Q H$_2$O+10 mM ammonium formate pH: 3.8; Eluent B: Acetonitrile.

Example 5

Figure 13:
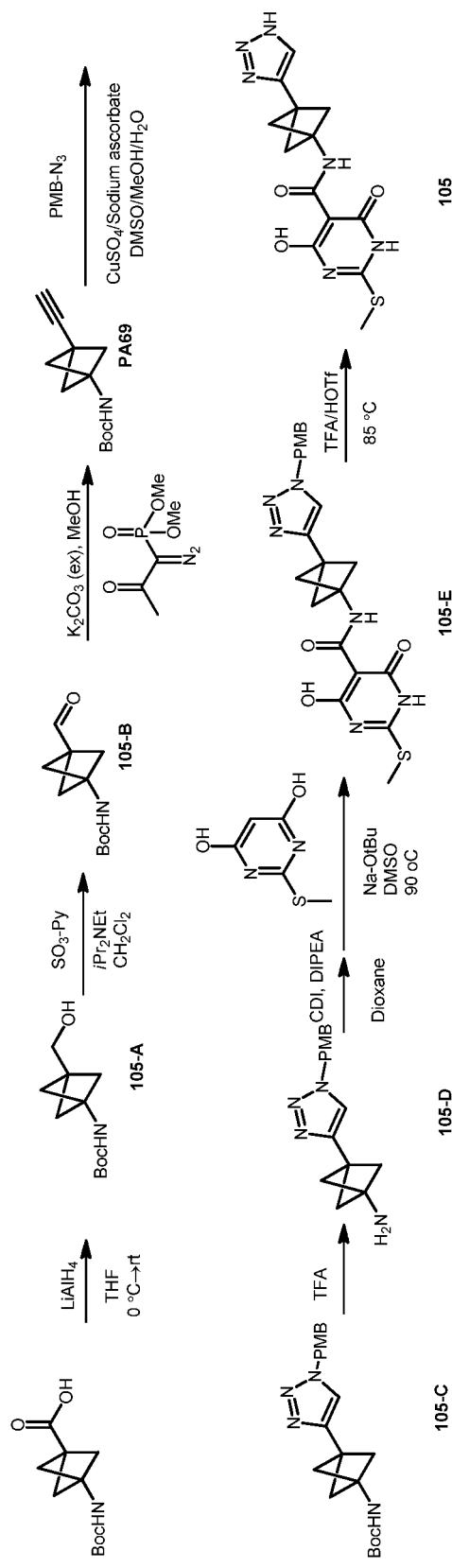
FIG. 13 illustrates the synthesis scheme described in Example 5.

Preparation of N-(3-(1H-1,2,3-triazol-4-yl)bicyclo[1.1.1]pentan-1-yl)-2,4-dihydroxy-6-oxo-1,6-dihydropyrimidine-5-carboxamide (105, Formula (II$_{hh}$), with Reference to FIG. 13)

Step One. tert-Butyl (3-(hydroxymethyl)bicyclo[1.1.1]pentan-1-yl)carbamate (105-A). 3-((Tert-butoxycarbonyl)amino)bicyclo[1.1.1]pentane-1-carboxylic acid (600 mg, 2.6 mmol) was added to THF (25 mL). The solution was cooled to 0° C. under N$_2$. To the solution was added LiAH$_4$ (401 mg, 10.6 mmol) under N$_2$. The reaction was warmed up to rt and stirred for 1 h. Na$_2$SO$_4$ decahydrate (500 mg) was added slowly to the reaction and the reaction was diluted with EtOAc (30 mL). The precipitate was filtered and the filtrate was concentrated in vacuo to yield crude PA67 (420 mg, 75% yield), which was used without purification.

1HNMR (500 MHz, CDCl$_3$) δ 3.7 (s, 2H), 1.94 (s, 6H), 1.44 (s, 9H).

Step Two. tert-Butyl (3-formylbicyclo[1.1.1]pentan-1-yl)carbamate (105-B). SO$_3$—Pyridine (500 mg, 3.1 mmol) was added portion wise (small exotherm) to a solution of DMSO (1.2 g, 15 mmol), 105-A (335 mg, 1.6 mmol) and iPr$_2$Net (811 mg, 6.3 mmol) in CH$_2$Cl$_2$ (6 mL) at rt. The reaction was stirred for 20 min at rt. The reaction mixture was diluted with CH$_2$Cl$_2$ (30 mL). The reaction was then washed with sat. NaHCO$_3$ (10 mL), brine (10 mL) and dried over MgSO$_4$ and concentrated in vacuo. The crude 105-B was used in the next step, without further purification.

1HNMR (500 MHz, CDCl$_3$) δ 9.66 (s, 1H), 2.29 (s, 6H), 1.44 (s, 9H).

Step Three. tert-butyl (3-ethynylbicyclo[1.1.1]pentan-1-yl)carbamate (105-C). 105-B (80 mg, 0.38 mmol) was dissolved in dry MeOH/THF (2 mL, 1:1 v/v, dried over MgSO$_4$ overnight). To the solution was added K$_2$CO$_3$ (105 mg, 0.76 mmol) and dimethyl diazo-2-oxopropylphosphonate (95 mg, 0.49 mmol). The mixture was stirred overnight. ISCO purification was performed (dry loading with silica, gradient 1HNMR (500 MHz, CDCl$_3$) δ 2.29 (s, 6H), 2.10 (s, 1H), 1.25 (s, 9H). t eluent from 0 to 50% ethyl acetate in hexanes) to yield the desired product, 105-C (42 mg, 53% yield).

Step Four. tert-butyl (3-(1-(4-methoxybenzyl)-1H-1,2,3-triazol-4-yl)bicyclo[1.1.1]pentan-1-yl)carbamate (105-D). CuSO$_4$ (263 mg in 3 mL water, 1.6 mmol) was added to sodium ascorbate (390 mg in 3 mL water, 2.0 mmol). The solution was stirred at rt for 1 min and DMSO (8 mL) was added to the mixture. The suspension was added to 105-C (70 mg, 0.33 mmol) and PMB-N$_3$ (161 mg, 0.99 mmol) mixture in 4 mL MeOH. The resulting mixture was stirred at rt for 30 min. The precipitate was filtered by Celite and washed with methanol. The filtrate was concentrated to remove MeOH and the product was extracted with EtOAc/H$_2$O (40 mL/20 mL). The organic layer was washed with brine and dried over MgSO$_4$, then concentrated in vacuo to give the crude product. The crude product was purified by silica pad, (30% ethyl acetate in hexanes to remove the excess azide. The product was flushed out by 1/1 MeOH/DCM) to yield the desired product (115 mg, 95% yield).

LCMS: m/z [M+1]$^+$=371.1; R$_T$=1.61 min

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Five. 3-(1-(4-methoxybenzyl)-1H-1,2,3-triazol-4-yl)bicyclo[1.1.1]pentan-1-amine (105-E). 105-D (80 mg, 0.22 mol) was dissolved in TFA (4 mL) and the reaction was stirred at rt for 30 min. Removal of the solvent in vacuo and the crude was dissolved in EtOAc (30 mL). The organic layer was washed with sat. aqueous Na$_2$CO$_3$ (10 mL) and brine (10 mL). The organic layer was then dried over MgSO$_4$ and the solvent was removed in vacuo to yield the crude product (58 mg, 99% yield).

LCMS: m/z [M+1]$^+$=271.0; R$_T$=1.08 min

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Six. 4-Hydroxy-N-(3-(1-(4-methoxybenzyl)-1H-1,2,3-triazol-4-yl)bicyclo[1.1.1]pentan-1-yl)-2-(methylthio)-6-oxo-1,6-dihydropyrimidine-5-carboxamide (105-F). 105-E (57 mg, 0.21 mmol) was dissolved in dioxane (0.3 mL). To this solution was added CDI (45 mg, 0.27 mmol), the reaction was stirred at rt for 3 min and iPr$_2$NEt (82 mg, 0.63 mmol) was added. The solution was stirred at rt for 10 min. To this solution was added freshly prepared 2-(methylthio)pyrimidine-4,6-diol (100 mg, 0.63 mmol) with NaOt-Bu (61 mg, 0.63 mmol) in DMSO (1 mL). The mixture was heated up to 90° C. for 1 h until complete consumption of the starting material was observed by LCMS. The crude product was then purified by ISCO (gradient eluent from 0 to 100% acetonitrile in water with an ammonium bicarbonate buffer 10 mM, product eluted at 35% MeCN in water) to yield the product (42 mg, 44% yield), after lyophilization.

LCMS: m/z [M+1]$^+$=455.1; R$_T$=1.54 min

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Seven. N-(3-(1H-1,2,3-Triazol-4-yl)bicyclo[1.1.1]pentan-1-yl)-2,4-dihydroxy-6-oxo-1,6-dihydropyrimidine-5-carboxamide (105) . . . 106-F (20 mg, 0.044 mmol) was dissolved in TFA (4 mL) and TfOH (0.2 mL) was added. The reaction mixture was heated at 85° C. for 4 h. To the reaction was added 0.3 mL iPr$_2$NEt (To prevent decomposition caused by TfOH) and the reaction was concentrated in vacuo. The crude product was purified by ISCO (gradient eluent from 0 to 100% acetonitrile in water with an ammonium bicarbonate buffer 10 mM over 15 CV) to yield the product as a white solid (27 mg, 87% yield).

1HNMR (500 MHz, DMSO-d6+TFA) δ 9.91 (s, 1H), 7.74 (s, 1H), 2.55 (s, 3H), 2.45 (s, 6H).

LCMS: m/z [M+1]$^+$=334.9; R$_T$=1.23 min; purity=97.0%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 6

Figure 14:
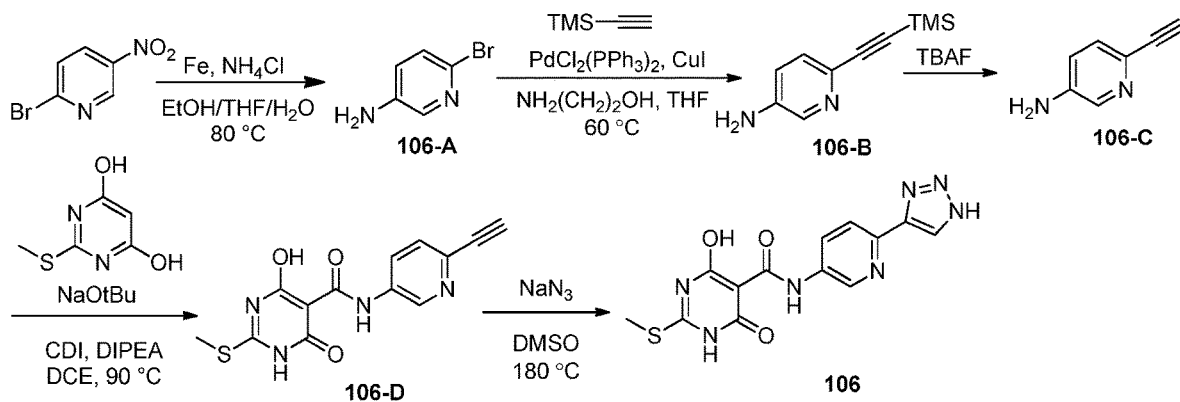
FIG. 14 illustrates the synthesis scheme described in Example 6.

Preparation of N-(6-(1H-1,2,3-triazol-4-yl)pyridin-3-yl)-4-hydroxy-2-(methylthio)-6-oxo-1,6-dihydropyrimidine-5-carboxamide (106, Formula (II$_{ii}$), with Reference to FIG. 14)

Step One. 6-Bromopyridin-3-amine (106-A). To a solution of 2-bromo-5-nitropyridine (502 mg, 2.47 mmol) in a mixture of EtOH/THF/H$_2$O/NH$_4$Cl (sat.) (5.0 mL, 4:4:1:1 v/v) was added Fe powder (1.40 g, 25.1 mmol) and the mixture was heated to 80° C. overnight. The reaction mixture was filtered through a small pad of Celite/MgSO$_4$ mixture (1:1) using EtOAc. The crude product was concentrated and subjected to purification via ISCO (SiO$_2$, 0-50% ethyl acetate in hexanes) to afford the product as a brown solid (411 mg, 96.1% yield).

1H NMR (400 MHz, CDCl$_3$) δ 7.84 (dd, J=3.1, 0.5 Hz, 1H), 7.21 (dd, J=8.5, 0.6 Hz, 1H), 6.87 (dd, J=8.5, 3.1 Hz, 1H), 3.73 (br s, 2H).

13C NMR (101 MHz, CDCl$_3$) δ 142.1, 137.1, 129.6, 127.8, 124.7.

LCMS: m/z [M+2H]$^+$=175.2, R$_T$=0.92 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 6-((Trimethylsilyl)ethynyl)pyridin-3-amine (106-B). To a dry 15 mL round bottom flask was added PdCl$_2$(PPh$_3$)$_2$ (25 mg, 0.0360 mmol), CuI (4.9 mg, 0.0260 mmol) and 6-bromopyridin-3-amine 106-A (200 mg, 1.16 mmol) was added THF (4 mL) and the solution was degassed by bubbling with N$_2$. The solution mixture was treated with 2-ethanolamine (140 μL, 2.32 mmol) and ethynyltrimethylsilane (200 μL, 1.42 mmol) and the reaction was stirred overnight at 60° C. The reaction mixture was filtered through a pad of Celite using EtOAc. The crude product was concentrated and subjected to purification via ISCO (SiO$_2$, 0-25% ethyl acetate in hexanes) to afford a brown solid (179 mg, 81.4% yield).

1H NMR (400 MHz, CDCl$_3$) δ 8.02 (dd, J=2.9, 0.5 Hz, 1H), 7.28-7.22 (m, 1H), 6.87 (dd, J=8.4, 2.8 Hz, 1H), 3.86 (s, 2H), 0.24 (s, 9H).

LCMS: m/z [M+H]$^+$=191.3, R$_T$=1.52 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. 6-Ethynylpyridin-3-amine (106-C). To a solution of 106-B (529 mg, 2.78 mmol) in THF (14 mL) was added TBAF (3.0 mL 3.00 mmol, 1 M in THF) and the resulting black solution was stirred at room temperature. After 30 min., the reaction mixture was washed with water (20 mL) and extracted with CH$_2$Cl$_2$ (3×10 mL). The organic phase was washed with brine (10 mL), dried over MgSO$_4$ and then concentrated. The crude solid was subjected to purification via ISCO (10-100% ethyl acetate in hexanes) to afford 106-C as a brown solid (310 mg, 94.5% yield).

1H NMR (400 MHz, CDCl$_3$) δ 8.04 (dd, J=2.9, 0.7 Hz, 1H), 7.28 (dd, J=8.4, 0.7 Hz, 1H), 6.90 (dd, J=8.4, 2.9 Hz, 1H), 3.88 (brs, 2H), 3.02 (s, 1H).

LCMS: m/z [M+H]$^+$=119.4, R$_T$=0.50 min; 98% purity.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. N-(6-Ethynylpyridin-3-yl)-4-hydroxy-2-(methylthio)-6-oxo-1,6-dihydropyrimidine-5-carboxamide (106-D). To a solution of t-BuONa (163 mg, 1.69 mmol) in DMSO (2.4 mL) was added 4,6-dihydroxy-2-methylmercaptopyrimidine (268 mg, 1.69 mmol) and the solution was stirred at rt for 5 min. At the same time, the 106-C (100 mg, 0.846 mmol) was dissolved in DCE (1.2 mL) and to the solution was added CDI (251 mg, 0.846 mmol). The suspension was stirred vigorously for 2 min at rt and iPr$_2$NEt (300 μL) was added. The solution was stirred vigorously for 2 min. Then the prepared DMSO solution was added to the suspension at once and the reaction was stirred at 90° C. for 30 min. Afterwards, DCE was removed in vacuo and the crude product was subject to purification by ISCO (C18 column, 0-50% acetonitrile in water with an ammonium formate buffer 10 mM). Product precipitated in column, column was flushed with 100% DMSO. The solvent was removed to yield the 106-D as a red solid (67.2 mg, 13.1% yield).

LCMS: m/z [M+H]$^+$=303.0, R$_T$=1.36 min; 94% purity.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Five. 4-Hydroxy-N-(4-(5-hydroxy-1H-pyrazol-3-yl)phenyl)-2-(methylthio)-6-oxo-1,6-dihydropyrimidine-5-carboxamide (106). The 106-D (67.2 mg, 0.220 mmol) and sodium azide (72.3 mg, 1.11 mmol) were dissolved in DMSO (2.2 mL). The solution was stirred at 180° C. and the consumption of the starting material was monitored via LCMS. After 2 h, the crude product was subjected to purification by ISCO (C18 column, 0-40% acetonitrile in water with an ammonium bicarbonate buffer 10 mM) and was lyophilized to afford a white solid (7.4 mg, 9.7% yield).

1H NMR (400 MHz, DMSO-d6, DCl in D$_2$O) δ 9.18 (d, J=2.2 Hz, 1H), 9.04 (s, 1H), 8.63 (dd, J=8.9, 2.3 Hz, 1H), 8.47 (app d, J=8.9 Hz, 1H), 2.54-2.53 (m, J=4.7 Hz, 3H).

1H NMR (400 MHz, CD$_3$OD, DCl in D$_2$O) δ 9.44 (d, J=2.1 Hz, 1H), 8.84 (s, 1H), 8.69 (dd, J=8.9, 2.1 Hz, 1H), 8.56 (d, J=8.9 Hz, 1H), 2.64 (s, 3H).

LCMS: m/z [M+H]$^+$=346.1, R$_T$=1.19 min; 99% purity.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 7

Figure 15:
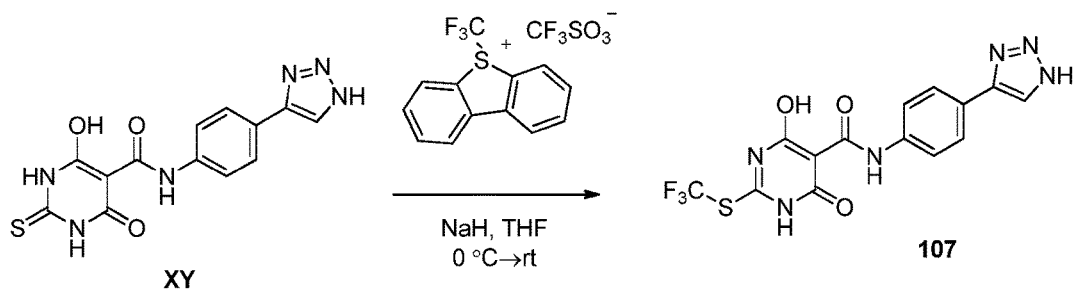
FIG. 15 illustrates the synthesis scheme described in Example 7.

Preparation of 4-hydroxy-N-(4-(5-hydroxy-1H-pyrazol-3-yl)phenyl)-2-(methylthio)-6-oxo-1,6-dihydropyrimidine-5-carboxamide (107, Formula (II$_j$), with Reference to FIG. 15)

NaH (2.4 mg, 0.0615 mmol) was added to XY (19.6 mg, 0.056 mmol) in THF (280 μL) at 0° C., and stirred for 30 min at 0° C. 5-(Trifluoromethyl)-5H-dibenzo[b,d]thiophen-5-ium trifluoromethanesulfonate (27 mg, 0.067 mmol) was then added in one-portion, and the resulting reaction mixture was warmed up to rt over 72 h. The reaction was quenched with methanol (5 mL) then concentrated under reduced pressure. The crude product was purified via reverse-phase chromatography (C18, gradient eluent from 30 to 100% acetonitrile in water with an ammonium formate buffer 10 mM over 15 CV) to yield the product 107, after lyophillization, as a white solid (2.0 mg, 9% yield).

$^1$H NMR (400 MHz, DMSO-d6+AcOD) δ 8.09 (s, 5H).

LCMS: m/z [M+1]$^+$=399.1; R$_T$=2.01 min; purity=99.2%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 8

Figure 16:
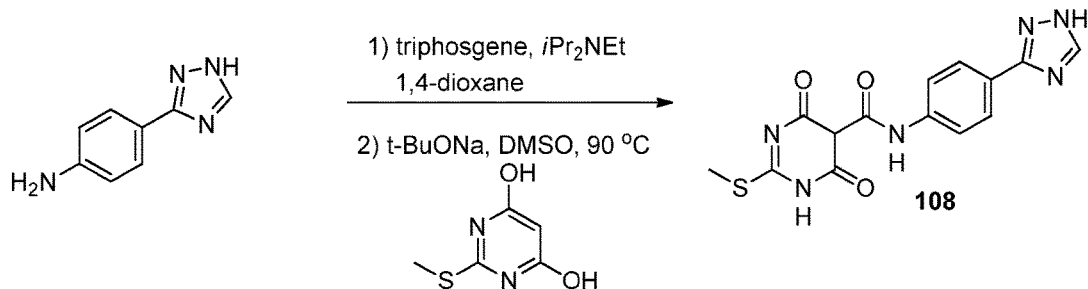
FIG. 16 illustrates the synthesis scheme described in Example 8.

Preparation of N-(4-(1H-1,2,4-Triazol-3-yl)phenyl)-2-(methylthio)-4,6-dioxo-1,4,5,6-tetrahydropyrimidine-5-carboxamide (108, Formula (II$_k$), with Reference to FIG. 16)

2-(Methylthio)pyrimidine-4,6-diol (300 mg, 1.90 mmol) was added to a stirring solution of sodium tert-butoxide (182 mg, 1.90 mmol) dissolved in DMSO (4.8 mL) at rt for 5 min. In a separate flask, 4-(4H-1,2,4-triazol-3-yl)aniline (160 mg, 0.95 mmol, 95% purity) was dissolved in 1,4-dioxane (1.2 mL), to this solution was added triphosgene (93 mg, 0.314 mmol) in one-portion. The suspension was stirred vigorously for 2 min at rt, then iPr$_2$NEt (330 μL, 1.90) was added. The suspension was stirred vigorously at rt for 2 min. Freshly prepared solution of sodium 6-hydroxy-2-(methylthio)pyrimidin-4-olate in DMSO was added to the suspension in one-portion. The reaction was stirred at 90° C. for 30 min, until complete consumption of starting material observed via LCMS. The reaction mixture was loaded directly on C18 column and purified via reverse-phase chromatography (C18, gradient eluent from 5 to 100% acetonitrile in water with an ammonium bicarbonate buffer 10 mM over 20 CV) to yield the product 108, after lyophillization, as a beige solid (23.5 mg, 7.0% yield).

$^1$H NMR (400 MHz, DMSO-d6+AcOD) δ 8.07 (s, 1H), 7.99 (d, J=8.8 Hz, 2H), 7.69 (d, J=8.7 Hz, 2H), 2.50 (s, 3H).

LCMS: m/z [M+1]$^+$=345.2; R$_T$=1.21 min; purity=95.2%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 9

Figure 17:
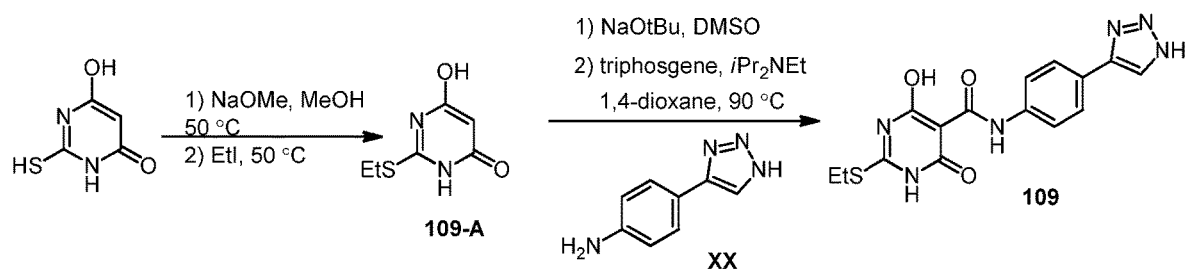
FIG. 17 illustrates the synthesis scheme described in Example 9.

Preparation of N-(4-(1H-1,2,3-triazol-4-yl)phenyl)-2-(ethylthio)-4-hydroxy-6-oxo-1,6-dihydropyrimidine-5-carboxamide (109, Formula (II), with Reference to FIG. 17)

Step One. 2-(Ethylthio)-6-hydroxypyrimidin-4(3H)-one (109-A). A mixture of 6-hydroxy-2-mercaptopyrimidin-4 (3H)-one (250 mg, 1.73 mmol) and NaOMe (400 μL, 1.76 mmol, 4.4 M in MeOH) in methanol (1.5 mL) was heated to 50° C. for 30 min. Iodoethane (140 μL, 1.74 mmol) was added dropwise to the reaction mixture and the reaction was stirred overnight at 50° C. Afterwards, the reaction mixture was filtered, and then washed with methanol. The filtrate was concentrated to afford the crude product as a white solid. The crude product was triturated with ethyl acetate to afford 109-A as a white solid (270 mg, 90.5% yield).

LCMS: m/z [M+1]$^+$=173.4; R$_T$=0.78 min; purity=92.5%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. N-(4-(1H-1,2,3-triazol-4-yl)phenyl)-2-(ethylthio)-4-hydroxy-6-oxo-1,6-dihydropyrimidine-5-carboxamide (109). Compound 109 was synthesized in accordance in General Procedure 1. The reaction mixture was loaded directly on C18 column and purified via reverse-phase chromatography (C18, gradient eluent from 5 to 75% acetonitrile in water with an ammonium bicarbonate buffer 10 mM over 20 CV) to yield impure product 109 after concentration. The impure product was purified via reverse-phase chromatography (C18, gradient eluent from 0 to 50% acetonitrile in water with an ammonium bicarbonate buffer 10 mM over 20 CV) to partially purified product 109. Further purification via trituration was performed using the centrifuge. The solid was washed with water, the supernatant was removed, the sequence was repeated three additional times, and then washed with acetonitrile two times. The resulting solid was collected and lyophilized to yield the pure product 109 as an off-white solid (11.2 mg, 2% yield).

$^1$H NMR (400 MHz, CDCl$_3$+TFA) δ 8.58 (s, 1H), 7.87 (d, J=8.7 Hz, 2H), 7.81 (d, J=8.7 Hz, 2H), 3.47 (q, J=7.5 Hz, 2H), 1.53 (t, J=7.4 Hz, 3H).

LCMS: m/z [M+1]$^+$=359.2; R$_T$=1.42 min; purity=95.2%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 10

Figure 18:
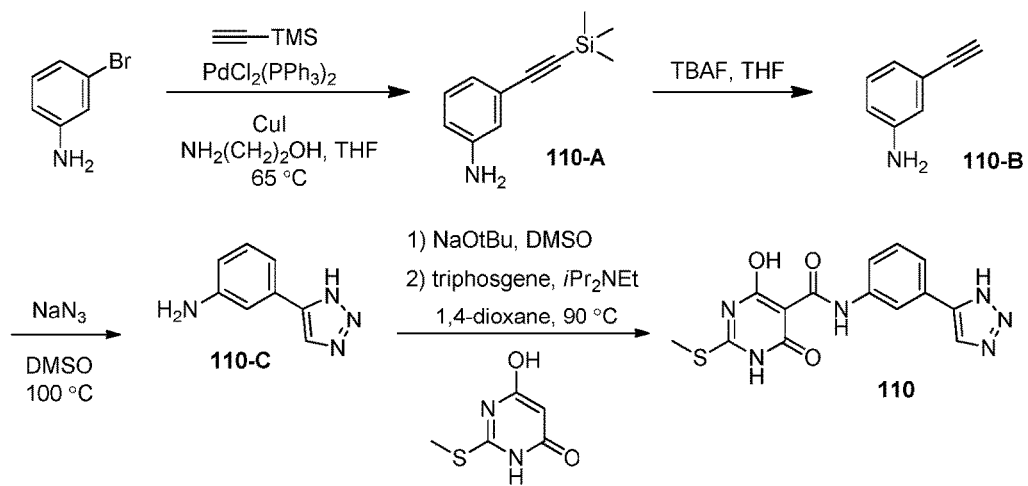
FIG. 18 illustrates the synthesis scheme described in Example 10.

Preparation of N-(3-(1H-1,2,3-triazol-5-yl)phenyl)-4-hydroxy-2-(methylthio)-6-oxo-1,6-dihydropyrimidine-5-carboxamide (110, Formula (II$_m$), with Reference to FIG. 18)

Step One. 3-((Trimethylsilyl)ethynyl)aniline (110-A). To a solution of PdCl$_2$(PPh$_3$)$_2$ (124 mg, 0.176 mmol), CuI (22 mg, 0.118 mmol) and 3-bromoaniline (320 μL, 2.94 mmol) was added THF (10 mL) and the solution was degassed by bubbling with N$_2$. The solution mixture was treated with 2-ethanolamine (360 μL, 5.88 mmol) and ethynyltrimethylsilane (620 μL, 4.41 mmol) and the reaction was stirred for 2 days at 65° C. The reaction mixture was filtered through a pad of Celite using ethyl acetate. The crude product was concentrated and carried onto the subsequent reaction without further purification.

LCMS: m/z [M+1]$^+$=190.3; R$_T$=1.82 min; purity=66%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 3-Ethynylaniline (110-B). To a solution of 110-A (556 g, 2.94 mmol) in THF (15 mL) was added TBAF (1 M in THF, 4.40 mL, 4.40 mmol) and the resulting black solution was stirred at room temperature. After 1 h, the reaction mixture was washed with water (40 mL) and extracted with CH$_2$Cl$_2$ (3×10 mL). The organic phase was washed with brine (10 mL), dried over MgSO$_4$, and then concentrated. The crude product was subjected to purification via ISCO (SiO$_2$, 10 to 50% ethyl acetate in hexanes) to afford 110-B as a dark brown oil (320 mg, 93.2% yield).

1H NMR (400 MHz, CDCl$_3$) δ 7.10 (ddd, J=8.1, 7.6, 0.5 Hz, 1H), 6.92-6.88 (m, 1H), 6.83-6.79 (m, 1H), 6.67 (ddd, J=8.1, 2.4, 1.0 Hz, 1H), 3.68 (brs, 2H), 3.01 (s, 1H).

LCMS: m/z [M+1]$^+$=118.4; R$_T$=1.22 min; purity=97%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. 3-(1H-1,2,3-Triazol-5-yl)aniline (110-C). A solution of 3-ethynylaniline 110-B (300 mg, 2.56 mmol), CuI (24.4 mg, 0.128 mmol) and trimethylsilyl azide (510 μL, 3.84 mmol) in anhydrous MeOH/DMF solution (12.0 mL, 1:23 v/v) was heated overnight at 100° C. The reaction mixture was washed with water (20 mL) and extracted with EtOAc (3×10 mL). The organic phase was washed with saturated NH$_4$Cl (10 mL), brine (10 mL), dried over MgSO$_4$ and then concentrated. The crude product was subjected to purification via ISCO (10-100% ethyl acetate in hexanes) to afford the product as a pink solid (205 mg, 50% yield).

LCMS: m/z [M+1]$^+$=161.4; R$_T$=0.79 min; purity=98%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. N-(3-(1H-1,2,3-triazol-5-yl)phenyl)-4-hydroxy-2-(methylthio)-6-oxo-1,6-dihydropyrimidine-5-carboxamide (110). To a solution of t-BuONa (120 mg, 1.25 mmol) in DMSO (3.1 mL) was added 4,6-dihydroxy-2-methylmercaptopyrimidine (198 mg, 1.25 mmol) and the solution was stirred at rt for 5 min. At the same time, 110-C (100 mg, 0.624 mmol) was dissolved in 1,4-dioxane (0.800 mL) and to the solution was added triphosgene (61.0 mg, 0.206 mmol). The suspension was stirred vigorously for 2 min at rt and iPr$_2$NEt (220 µL, 1.25 mmol) was added. The solution was stirred vigorously for 2 min. Then the prepared DMSO solution was added to the suspension at once and the reaction was stirred at 90° C. for 30 min. Afterwards, water (2 mL) was added to the reaction mixture and the crude solution was transferred into a flask using MeOH. The crude mixture was concentrated and the crude product was subject to purification by ISCO (30 g, C18 column, 10 mM AmF in water/MeCN). The C18 column was flushed with DMSO and was evaporated with air drying to afford the crude product. The product was subject to purification by ISCO (30 g, C18 column, 0 to 50% acetonitrile in water with an ammonium bicarbonate buffer 10 mM) to afford the product (22.8 mg, 5.3% yield).

1H NMR (400 MHz, CDCl$_3$+TFA) δ 8.59 (s, 1H), 8.11 (s, 1H), 7.68 (s, 3H), 2.85 (s, 3H).

LCMS: m/z [M+1]$^+$=345.1; R$_T$=1.33 min; purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 11

Figure 19:
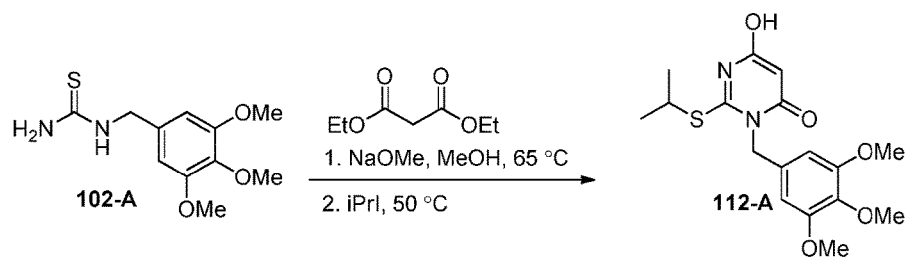
FIG. 19 illustrates the synthesis scheme described in Example 11.
Figure 19:
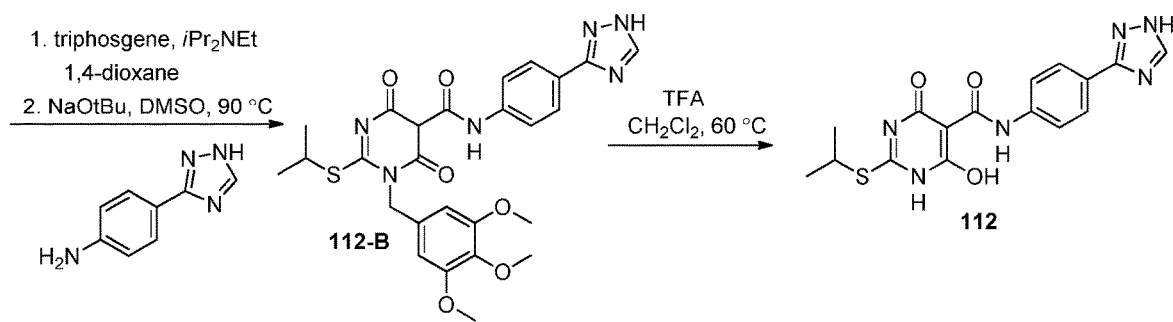

Preparation of N-(4-(1H-1,2,4-triazol-3-yl)phenyl)-6-hydroxy-2-(isopropylthio)-4-oxo-1,4-dihydropyrimidine-5-carboxamide (112, Formula (II$_n$), with Reference to FIG. 19)

Step One. 6-Hydroxy-2-(isopropylthio)-3-(3,4,5-trimethoxybenzyl)pyrimidin-4(3H)-one (112-A). A mixture of 102-A (1.00 g, 3.91 mmol), diethyl malonate (600 µL, 3.91 mmol), and NaOMe (1.8 mL, 7.82 mmol, 4.4 M in MeOH) in methanol (4.4 mL) was heated to reflux for 3 h. The reaction was then cooled to ~50° C., isopropyl iodide (4.4 mL, 39.1 mmol) was then added in one-portion. The reaction was stirred for an additional 30 min at 50° C. The reaction mixture was then cooled to rt, then concentrated under reduced pressure. The crude product was purified via reverse-phase chromatography (gradient eluent from 0 to 100% acetonitrile in water with an ammonium formate buffer 10 mM over 15 CV) to yield the product as a white solid (695 mg, 49% yield), after lyophilization.

LCMS: m/z [M+1]$^+$=367.02; R$_T$=1.42 min; purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. N-(4-(1H-1,2,4-Triazol-3-yl)phenyl)-2-(isopropylthio)-4,6-dioxo-1-(3,4,5-trimethoxybenzyl)-1,4,5,6-tetrahydropyrimidine-5-carboxamide (112-B). 112-A (354 mg, 0.924 mmol) was added to a stirring solution of sodium tert-butoxide (87 mg, 0.924 mmol) dissolved in DMSO (4.2 mL) at rt for 5 min. In a separate flask, 4-(1H-1,2,4-triazol-5-yl)aniline (141 mg 0.840 mmol, 95% purity) was dissolved in 1,4-dioxane (1.1 mL), to this solution was added triphosgene (82 mg, 0.277 mmol) in one-portion. The suspension was stirred vigorously for 2 min at rt, then iPr$_2$NEt (290 µL, 1.68) was added. The suspension was stirred vigorously at rt for 2 min. Freshly prepared solution of sodium 6-hydroxy-2-(methylthio)pyrimidin-4-olate in DMSO was added to the suspension in one-portion. The reaction was stirred at 90° C. for 30 min, until complete consumption of starting material observed via LCMS. The reaction mixture was loaded directly on C18 column and purified via reverse-phase chromatography (C18, gradient eluent from 10 to 75% acetonitrile in water with an ammonium bicarbonate buffer 10 mM over 20 CV) to yield the product 112-C, after lyophillization, as a white solid (34 mg, 6% yield).

LCMS: m/z [M+1]$^+$=553.4; R$_T$=1.73 min; purity=85.3%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. N-(4-(1H-1,2,4-triazol-3-yl)phenyl)-6-hydroxy-2-(isopropylthio)-4-oxo-1,4-dihydropyrimidine-5-carboxamide (112). Solution of 112-B (31.2 mg, 0.0452 mmol) in dichloromethane (1.5 mL) was added trifluoroacetic acid (270 µL), the reaction was sealed in a high-pressure vessel and heated to 60° C. After 20 h, the reaction mixture was concentrated and co-evaporated with methanol (3×). The crude product was purified via reverse-phase chromatography (C18, gradient eluent from 0 to 60% acetonitrile in water with an ammonium bicarbonate buffer 10 mM over 20 CV) to yield the product 7, after lyophillization, as a white solid. Further purification via trituration was performed using the centrifuge. The solid was washed with water, the supernatant was removed, the sequence was repeated three additional times, and then washed with acetonitrile two times. The resulting solid was collected and lyophilized to yield the pure product 112 as an off-white solid (13.0 mg, 64% yield).

$^1$H NMR (400 MHz, CDCl$_3$+TFA) δ 9.49 (s, 1H), 8.15-8.08 (m, 2H), 7.88-7.80 (m, 2H), 4.28-4.16 (m, 1H), 1.59 (d, J=6.5 Hz, 6H).

LCMS: m/z [M+1]$^+$=373.1; R$_T$=1.07 min; purity=98.9%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium bicarbonate; Eluent B: Acetonitrile.

Example 12

Figure 20:
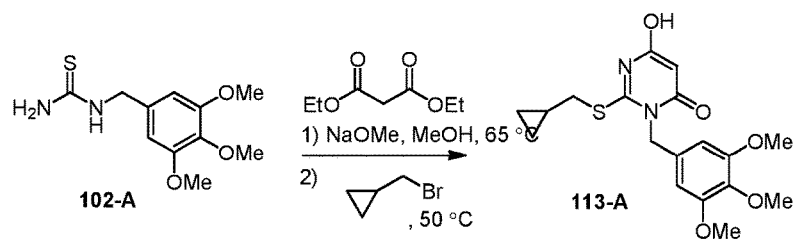
FIG. 20 illustrates the synthesis scheme described in Example 12.
Figure 20:
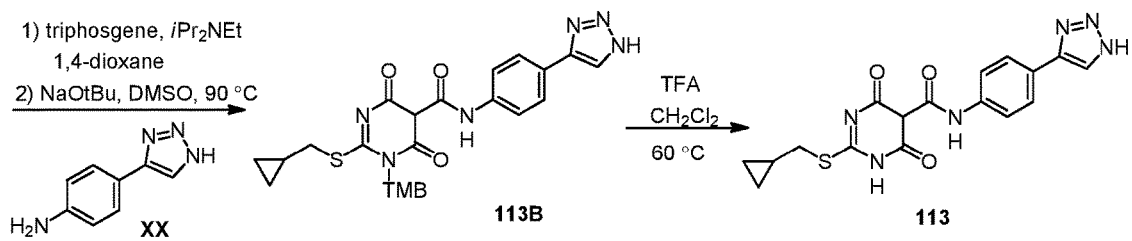

Preparation of N-(4-(1H-1,2,3-triazol-4-yl)phenyl)-2-((cyclopropylmethyl)thio)-4,6-dioxo-1,4,5,6-tetrahydropyrimidine-5-carboxamide (113, Formula (II$_o$), with Reference to FIG. 20)

Step One. 2-((Cyclopropylmethyl)thio)-1-(3,4,5-trimethoxybenzyl)pyrimidine-4,6(1H,5H)-dione (113-A). To a mixture of 102-A (697 mg, 2.71 mmol, 99.4% purity), diethyl malonate (940 mL, 6.13 mmol, and NaOMe (2.8 mL, 12.3 mmol, 4.4 M in MeOH) in methanol (4.9 mL). The reaction was heated to reflux for 2 h, the reaction was then cooled to 50° C., (bromomethyl)cyclopropane (290 µL, 2.98 mmol) was added stirred for an additional 12 h at 50° C., incomplete conversion was observed. An additional NaOMe solution (0.5 mL, 2.71 mmol, 4.4 M in MeOH) was added to the reaction mixture, followed by the addition of (bromomethyl)cyclopropane (300 µL, 3.09 mmol). The resulting reaction mixture was stirred for 30 min, complete conversion was observed via LCMS, the reaction mixture was then concentrated. Ethyl acetate (~10 mL) was added, the precipitate was filtered and washed with isopropanol (~10 mL), then washed with ethyl acetate. The product was isolated as a white solid (715 mg, 67% yield).

LCMS: m/z [M+1]$^+$=379.4; m/z [M−1]$^-$=377.5; $R_T$=1.45 min; purity=96.5%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. N-(4-(1H-1,2,3-triazol-4-yl)phenyl)-2-((cyclopropylmethyl)thio)-4,6-dioxo-1-(3,4,5-trimethoxybenzyl)-1,4,5,6-tetrahydropyrimidine-5-carboxamide (113B). Compound 113B was synthesized following General Procedure 1. Crude 113A was purified via reverse-phase chromatography (C18, gradient eluent from 0 to 70% acetonitrile in water with an ammonium bicarbonate buffer 10 mM over 20 CV) to yield the partially purified product 113A, after lyophillization, as a yellow solid (255 mg, 16% yield).

LCMS: m/z [M+1]$^+$=565.5; $R_T$=1.82 min; purity=50.0%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. N-(4-(1H-1,2,3-triazol-4-yl)phenyl)-2-((cyclopropylmethyl)thio)-4,6-dioxo-1,4,5,6-tetrahydropyrimidine-5-carboxamide (113). Solution of 113-B (225 mg, 0.199 mmol) in dichloromethane (6.6 mL) was added trifluoroacetic acid (1.2 mL), the reaction was sealed in a high-pressure vessel and heated to 60° C. After 20 h, the reaction mixture was concentrated and co-evaporated with methanol (3×). The crude product 113 was purified via reverse-phase chromatography (C18, gradient eluent from 0 to 40% acetonitrile in water with an ammonium bicarbonate buffer 10 mM over 20 CV); fractions containing the product was collected, and then concentrated under reduced pressure. The residue was added water with ammonium bicarbonate buffer 10 mM (~20 mL), then sonicated. The precipitate was filtered off and the filtrate was concentrated. The residue was purified via reverse-phase chromatography (C18, gradient eluent from 0 to 50% acetonitrile in water with an ammonium bicarbonate buffer 10 mM over 20 CV) to yield partially pure product, which was purified again via reverse-phase chromatography (C18, gradient eluent from 0 to 30% acetonitrile in water with an ammonium bicarbonate buffer 10 mM over 20 CV) to yield partially pure product as a white solid, after concentration. The white solid was triturated with deionized water, then the filtrate was lyophilized. Further purification via trituration was performed using the centrifuge. The solid was washed with water, the supernatant was removed, the sequence was repeated three additional times, and then washed with acetonitrile two times. The resulting solid was collected and dried under high vacuum to yield the pure product 113 as an off-white solid (3.0 mg, 4% yield).

$^1$H NMR (400 MHz, CDCl$_3$+TFA) δ 8.61-8.58 (m, 1H), 7.89 (d, J=5.6 Hz, 2H), 7.83-7.78 (m, 2H), 2.40-2.19 (m, 2H), 1.32 (br s, 4H), 0.49 (dd, J=10.3, 4.6 Hz, 1H).

LCMS: m/z [M+1]$^+$=385.2; $R_T$=1.54 min; purity=96.4%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium bicarbonate; Eluent B: Acetonitrile.

Example 13

Figure 21:
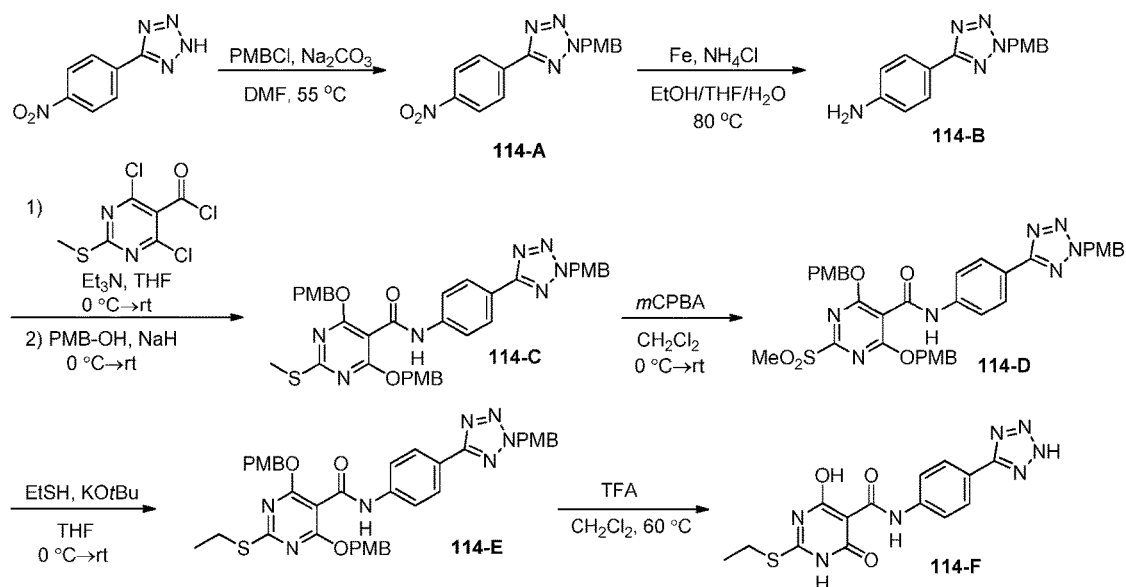
FIG. 21 illustrates the synthesis scheme described in Example 13.

Preparation of N-(4-(1H-tetrazol-5-yl)phenyl)-2-(ethylthio)-4-hydroxy-6-oxo-1,6-dihydropyrimidine-5-carboxamide (114, Formula (II$_p$), with Reference to FIG. 21)

Step One. 2-(4-methoxybenzyl)-5-(4-nitrophenyl)-2H-tetrazole (114-A). To a solution of 5-(4-nitrophenyl)-1H-tetrazole (1.00 g, 5.23 mmol) and K$_2$CO$_3$ (1.33 g, 5.76 mmol) in DMF (3.5 mL) was added p-methoxybenzyl chloride (901 mg, 5.76 mmol). The reaction mixture was stirred at 55° C. for 18 h. The mixture cooled to rt and was diluted with sat. aq. NH$_4$Cl (50 mL) and extracted with EtOAc (3×25 mL). The combined organic extracts were pooled together and washed with brine (50 mL), dried over MgSO$_4$, and then concentrated. The crude product was precipitated upon addition of ethyl acetate followed by filtration. The filtrate was concentrated and this method was repeated until the newly formed precipitate was greater than 90% purity. No further purification was performed.

1H NMR (400 MHz, CDCl$_3$) δ 8.31 (s, 4H), 7.43-7.38 (m, 2H), 6.94-6.88 (m, 2H), 5.76 (s, 2H), 3.80 (s, 3H).

LCMS: m/z [M+1]$^+$=312.2; $R_T$=1.79 min; purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium bicarbonate; Eluent B: Acetonitrile.

Step Two. 4-(2-(4-methoxybenzyl)-2H-tetrazol-5-yl)aniline (114-B). To a solution of the 114-A (1.09 g, 3.52 mmol) in a mixture of EtOH/THF/H$_2$O/NH$_4$Cl (sat.) (7 mL, 4:4:1:1 v/v) was added Fe powder (1.98 g, 35.5 mmol) and the mixture was heated to 80° C. overnight. The reaction mixture was filtered through a small pad of Celite/MgSO$_4$ mixture (1:1) using EtOAc. The crude product obtained after filtration was concentrated in vacuo. The product was not purified any further to afford an off-white solid (1.04 g, quant. yield).

LCMS: m/z [M+1]$^+$=282.3; $R_T$=1.51 min; purity=97.1%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium bicarbonate; Eluent B: Acetonitrile.

Step Three. N-(4-(2-(4-methoxybenzyl)-2H-tetrazol-5-yl)phenyl)-4,6-bis((4-methoxybenzyl)oxy)-2-(methylthio)pyrimidine-5-carboxamide (114-C). To a cooled solution (0° C.) of 2-(methylthio)pyrimidine-5-carbonyl chloride (183 mg, 0.711 mmol) in THF (2.5 mL) was added Et$_3$N (109 µL, 0.782 mmol), followed by the corresponding aniline intermediate 114-B (200 mg, 0.711 mmol) dissolved in THF (2.5 mL). The reaction mixture was warmed to rt and stirred for 1.5 h. Once the starting material was fully consumed, the solution was cooled to 0° C. and treated with PMBOH (333 µL, 2.84 mmol) followed by NaH (114 mg, 2.84 mmol, 60% dispersed in oil). The solution was stirred at 0° C. for 10 min and then warmed to rt. After 1.5 h, the solution was cooled to 0° C. and treated with water. The solution was concentrated then washed with water and filtered. The precipitate was then washed with MTBE to afford the desired product as a white solid (362 mg, 72% yield). The product was used without additional purification.

LCMS: m/z [M+1]$^+$=706.5; $R_T$=2.11 min; purity=94.1%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium bicarbonate; Eluent B: Acetonitrile.

Step Four. N-(4-(2-(4-methoxybenzyl)-2H-tetrazol-5-yl)phenyl)-4,6-bis((4-methoxybenzyl)oxy)-2-(methylsulfonyl)pyrimidine-5-carboxamide (114-D). To a solution of the methythioether substrate (362 mg, 0.512 mmol) in CH$_2$Cl$_2$ (10.2 mL) was added mCPBA (241 mg, 1.08 mmol) at 0° C. and open to air. After 10 min, the reaction was warmed to rt and stirred for 3.5 h. The reaction mixture was treated with NaHCO$_3$(sat) (50 mL) and stirred for 30 min. The organic fraction was washed with NaHCO$_3$(sat) (3×10 mL), brine (10 mL), dried (MgSO$_4$), filtered and then concentrated.

Based on LC-MS, traces of mCBA was in the crude product and so the sample was dissolved in $CH_2Cl_2$ (20 mL) and once more subjected to the previous workup to afford a yellow solid (320 mg, 85% yield), which was used without any additional purification.

LCMS: m/z $[M+1]^+$=738.4; $R_T$=1.91 min; purity=88.6%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium bicarbonate; Eluent B: Acetonitrile.

Step Five. 2-(Ethylthio)-N-(4-(2-(4-methoxybenzyl)-2H-tetrazol-5-yl)phenyl)-4,6-bis((4-methoxybenzyl)oxy)pyrimidine-5-carboxamide (114-E). To a solution of the 114-D (320 mg, 0.434 mmol) in THF (8.7 mL) at 0° C. was added ethanethiol (160 μL, 2.17 mmol) followed by dropwise addition of KOtBu (2.60 mL, 2.60 mmol, 1 M in THF). The resulting solution was stirred at 0° C. for 10 min. Afterwards, the reaction mixture was warmed to rt and stirred for 2 h. The solution was treated with $H_2O$ (20 mL) and extracted with EtOAc (3×10 mL). The organic fraction was washed with brine (20 mL), dried ($MgSO_4$), filtered and concentrated to afford the product as an off-white solid (257 mg, 82% yield), which was used without any additional purification.

LCMS: m/z $[M+1]^+$=720.1; $R_T$=2.14 min; purity=81.1%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium bicarbonate; Eluent B: Acetonitrile.

Step Six. N-(4-(2H-Tetrazol-5-yl)phenyl)-2-(ethylthio)-4-hydroxy-6-oxo-1,6-dihydropyrimidine-5-carboxamide (114). To a solution of the 114-E (257 mg, 0.356 mmol) in $CH_2Cl_2$ (11.9 mL) at rt was added TFA (2.1 mL). The reaction vessel was sealed and heated at 60° C. After 48 h, the mixture was concentrated, using MeOH to co-evaporate any residual TFA. The crude product was subjected to purification via to ISCO (60 g, C18 column, from 0 to 50% acetonitrile in water with an ammonium bicarbonate buffer 10 mM) to afford the product as a white solid (87 mg, 68% yield).

1H NMR (400 MHz, $CDCl_3$+TFA) δ 8.08 (d, J=8.6 Hz, 2H), 7.83 (d, J=8.7 Hz, 2H), 3.43 (q, J=7.4 Hz, 2H), 1.52 (t, J=7.4 Hz, 3H).

LCMS: m/z $[M+1]^+$=360.3; $R_T$=1.35 min; purity=>99%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium bicarbonate; Eluent B: Acetonitrile.

Example 14

Figure 22:
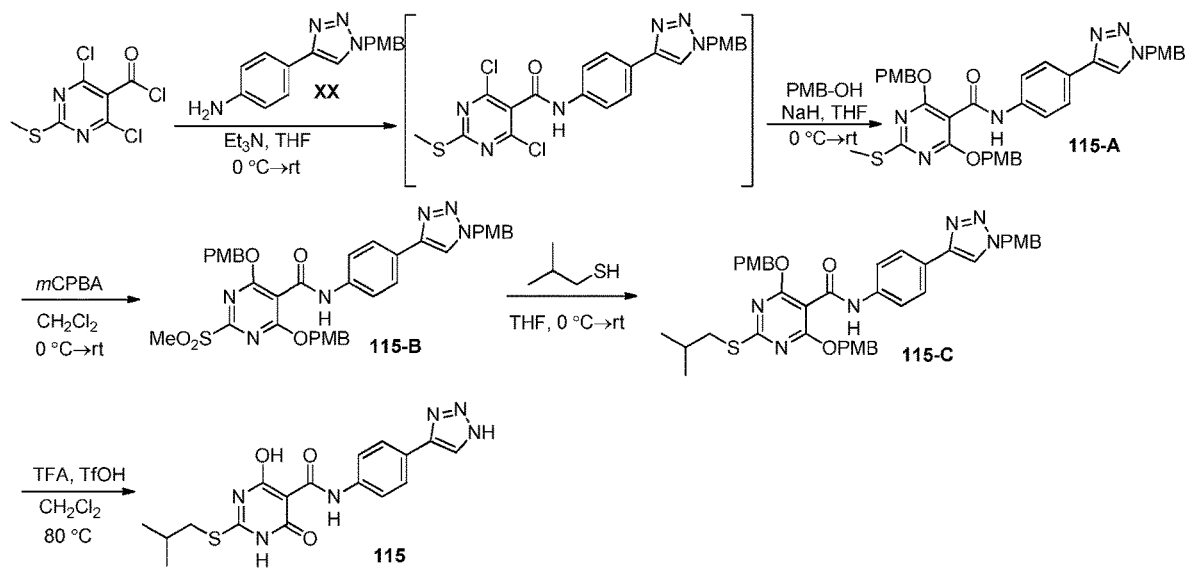
FIG. 22 illustrates the synthesis scheme described in Example 14.

Preparation of N-(4-(1H-1,2,3-triazol-4-yl)phenyl)-4-hydroxy-2-(isobutylthio)-6-oxo-1,6-dihydropyrimidine-5-carboxamide (115, Formula ($II_q$), with Reference to FIG. 22)

Step One. N-(4-(1-(4-methoxybenzyl)-1H-1,2,3-triazol-4-yl)phenyl)-4,6-bis((4-methoxybenzyl)oxy)-2-(methylthio)pyrimidine-5-carboxamide (115-A). To a stirring solution of 4,6-dichloro-2-(methylthio)-5-pyrimidinecarbonyl chloride (227 mg, 0.881 mmol) and triethylamine (98 mg, 0.97 mmol) in anhydrous THF (6.3 mL) was added amine XX (247 mg, 280 mmol) at 0° C. The reaction was warmed up to rt over 1 h, then cooled to 0° C. again. para-Methoxylbenzylamine (220 μL, 1.76 mmol) was added, followed by portion-wise addition of sodium hydride (109 mg, 2.73 mmol, 60% dispersed in mineral oil). The reaction was allowed to stir at 0° C. for 5 min, and then warmed up to rt overnight. Additional sodium hydride (50 mg) was added, then stirred for an additional 1 h; when complete conversion was observed via LCMS, the reaction was quenched with methanol (~10 mL). tert-Butyl methyl ether (~20 mL) was added, and then sonicated. The precipitate was filtered and washed with MeOH and TBME, the precipitate was collected. The product was isolated as an off-white solid (550 mg, 80% yield).

LCMS: m/z $[M+1]^+$=705.5; $R_T$=2.02 min; purity=90.6%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Two. N-(4-(1-(4-methoxybenzyl)-1H-1,2,3-triazol-4-yl)phenyl)-4,6-bis((4-methoxybenzyl)oxy)-2-(methylsulfonyl)pyrimidine-5-carboxamide (115-B). 115-A (550 mg, 0.707 mmol) was dissolved in dichloromethane (3.5 mL) and cooled to 0° C. meta-Chloroperoxybenzoic acid (332 mg, 1.48 mmol, 77% in water) was added and the resulting reaction mixture was warmed up to rt overnight. The reaction was quenched with sat. $NaHCO_3$ aq. solution and stirred vigorously for 30 min. The organic phase was extracted, and washed with sat. $NaHCO_3$ aq. solution (3×), and then brine (1×). The resulting organic extract was dried over $MgSO_4$ then concentrated to yield the crude product as an orange solid (440 mg, 70% yield). No further purification required.

LCMS: m/z $[M+1]^+$=737.5; $R_T$=1.84 min; purity=83.4%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Three. N-(4-(1H-1,2,3-triazol-4-yl)phenyl)-4-hydroxy-2-(isobutylthio)-6-oxo-1,6-dihydropyrimidine-5-carboxamide (115). To a stirring solution of 115-B (105 mg, 0.119 mmol) and 2-methylpropane-1-thiol (64 μL, 0.594 mmol) in anhydrous THF (2.4 mL) at 0° C., was added KOtBu (714 mL, 0.714 mmol, 1.0 M in THF), under inert atmosphere. The resulting reaction mixture was warmed up to rt over 30 min, after complete consumption of the starting material was observed via LCMS, the reaction was quenched with deionized water (~5 mL). The reaction mixture was extracted with EtOAc (3×), the combined organic extracts was dried over $MgSO_4$, and then concentrated. The crude product 115-C was used without further purification. The crude product 115-C was isolated as an off-white solid.

Crude 115-C was suspended in dichloromethane (2.4 mL), TFA (700 μL) was added, followed by TfOH (100 μL), the resulting reaction mixture was sealed in a high pressure vessel and heated to 80° C. After 20 h, the reaction mixture was added methanol, and then co-evaporated with methanol (3×) under reduced pressure. The crude product was purified via reverse-phase chromatography (C18, gradient eluent from 5 to 25% acetonitrile in water with an ammonium bicarbonate buffer 10 mM over 20 CV) to yield impure product 115 after lyophilization. Further purification via trituration was performed using the centrifuge. The solid was washed with water, the supernatant was removed, the sequence was repeated three additional times, and then washed with acetonitrile two times. The resulting solid was collected and lyophilized to yield the pure product 115 as an off-white solid (25.4 mg, 55% yield).

1H NMR (400 MHz, $CDCl_3$+TFA) δ 8.61 (s, 1H), 7.90 (d, J=7.6 Hz, 2H), 7.81 (d, J=8.5 Hz, 2H), 3.37 (d, J=6.7 Hz, 2H), 2.14 (d, J=6.9 Hz, 1H), 1.17 (d, J=6.6 Hz, 6H).

LCMS: m/z [M+1]$^+$=387.0; R$_T$=1.60 min; purity=98.6%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium bicarbonate; Eluent B: Acetonitrile.

Example 15

Figure 23:
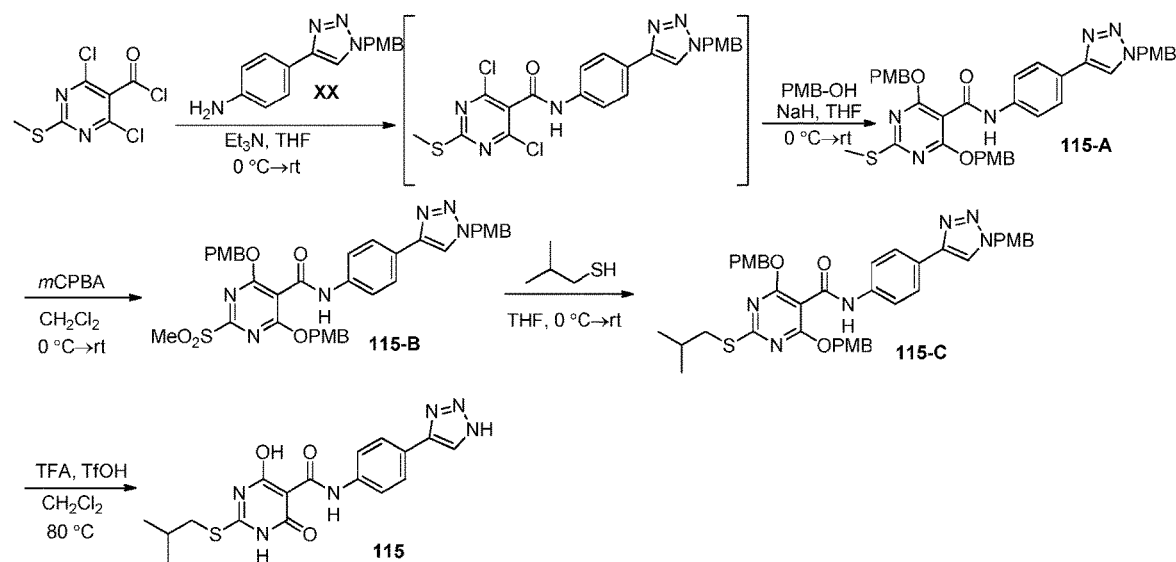
FIG. 23 illustrates the synthesis scheme described in Example 15.

Preparation N-(3-Fluoro-4-(1H-1,2,3-triazol-4-yl)phenyl)-4-hydroxy-2-(methylthio)-6-oxo-1,6-dihydropyrimidine-5-carboxamide (116, Formula (II$_r$), with reference to FIG. 23).

Step One. 3-Fluoro-4-((trimethylsilyl)ethynyl)aniline (116-A). A round bottom flask containing 4-bromo-2-fluoroaniline (380 mg, 2.0 mmol), PdCl$_2$(PPh$_3$)$_2$ (84 mg, 0.12 mmol), and CuI (15 mg, 0.08 mmol) was purged with nitrogen for 15 min. Anhydrous THF (6.7 mL) was added, followed by trimethylsilylacetylene (560 uL, 4.0 mmol) and ethanolamine (240 uL, 4.0 mmol). The reaction mixture was sealed and heated to 65° C. for 20 h. The reaction mixture was cooled to rt, filtered through a small pad of Celite. The filtrate was concentrated and used without further purification.

LCMS: R$_T$=1.86 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Two. 4-Ethynyl-3-fluoroaniline (116-B). To a solution of crude 116-A (2.0 mmol) dissolved in methanol (2.0 mL) was added potassium carbonate (553 mg, 4.00 mmol) at rt. The resulting reaction mixture was stirred at rt for 2 h, or until complete consumption of the starting material was observed. The reaction mixture was filtered, and the filtrate was concentrated. The crude product 116-B was used without further purification.

LCMS: m/z [M+1]$^+$=136.1; R$_T$=1.34 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Three. 3-Fluoro-4-(1-(3,4,5-trimethoxybenzyl)-1H-1,2,3-triazol-4-yl)aniline (116-C). To a solution of crude 116-B (2.0 mmol) was dissolved in a mixture of anhydrous MeOH/DMF (10.0 mL, 1:9, v/v), under inert atmosphere. At room temperature, CuI (38 mg, 0.20 mmol) was added, followed by the addition of 5-(azidomethyl)-1,2,3-trimethoxybenzene (487 mg, 2.14 mmol), the reaction mixture was sealed in a high pressure vessel and heated to 100° C. for 2 h, the reaction was then cooled to rt, then concentration. The crude product was purified via ISCO (SiO$_2$, gradient eluent from 0 to 40% ethyl acetate in hexanes over 20 CV) to yield the product as a brown oil (374 mg, 37% yield over 3 steps).

LCMS: m/z [M+1]$^+$=359.3; R$_T$=1.39 min; purity=70%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Four. N-(3-Fluoro-4-(1-(3,4,5-trimethoxybenzyl)-1H-1,2,3-triazol-4-yl)phenyl)-4,6-bis((4-methoxybenzyl)oxy)-2-(methylthio)pyrimidine-5-carboxamide (116-D). To a stirring solution of 116-C (374 mg, 0.731 mmol, 70% purity) in anhydrous THF (5.2 mL) at 0° C., under inert atmosphere was added Et$_3$N (110 μL, 0.804 mmol), followed by the addition of 4,6-dichloro-2-(methylthio)pyrimidine-5-carbonyl chloride (188 mg, 0.731 mmol). The resulting reaction mixture was warmed up to rt over 60 min, until complete consumption of the starting materials were observed via LCMS. The reaction mixture was then cooled to 0° C., then p-methoxybenzyl alcohol (180 μL, 1.46 mmol) was added, followed by careful addition of NaH (91 mg, 2.27 mmol, 60% dispersed in oil). The reaction was kept at 0° C. for 5 min, then warmed up to rt over 20 h; the progress of the reaction was monitored by LCMS. Methanol (~1 mL) was added to quench the reaction, then TBME (20 mL) was added and the resulting suspension was sonicated for 10 min. The suspension was then filtered, and the solid was washed with TBME, the brown solid (308 mg, 54% yield) was collected.

LCMS: m/z [M+1]$^+$=784.3; R$_T$=2.03 min; purity=92.9%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Five. N-(3-Fluoro-4-(1H-1,2,3-triazol-4-yl)phenyl)-4-hydroxy-2-(methylthio)-6-oxo-1,6-dihydropyrimidine-5-carboxamide (116). 116-D (308 mg, 0.365 mmol) dissolved in CH$_2$Cl$_2$ (7.3 mL) was added TFA (2.1 mL) and sealed in a pressure vessel, heated to 60° C. for 20 h. Reaction was cooled to rt, then TfOH (50 μL) was added, sealed and heated to 60° C. for 20 h. The reaction mixture was cooled to rt, then co-evaporated with MeOH (3×). TBME and deionized water (~10 mL, 1:1 v/v) was added; the suspension was sonicated. The solid was filtered and washed with water and washed with TBME. The green solid was collected (302 mg, quantitative yield, 69.6% purity) as the TMB-protected intermediate The TMB-protected intermediate (288 mg, 0.256 mmol) was added CH$_2$Cl$_2$ (1.3 mL), TfOH (640 μL), the resulting reaction mixture was sealed in a microwave vessel and heated to 80° C. for 20 h. The reaction was then cooled to rt, then co-evaporated with methanol (3×). The crude product was purified via reverse-phase chromatography (C18, gradient eluent from 0 to 30% acetonitrile in water with an ammonium bicarbonate buffer 10 mM over 20 CV) to yield impure product 116 after lyophilization. Further purification via trituration was performed using the centrifuge. The solid was washed with water, the supernatant was removed, the sequence was repeated three additional times, and then washed with acetonitrile two times. The resulting solid was collected and lyophilized to yield the pure product 116 as an off-white solid (12.9 mg, 14% yield).

$^1$H NMR (400 MHz, CDCl$_3$+TFA) δ 8.66 (s, 1H), 7.92 (t, J=8.2 Hz, 1H), 7.84 (dd, J=12.3, 2.0 Hz, 1H), 7.52 (dd, J=8.6, 1.9 Hz, 1H), 2.86 (s, 3H).

LCMS: m/z [M+1]$^+$=363.1; m/z [M−1]$^−$=361.3; R$_T$=1.38 min; purity=98.6%. HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 16

Figure 24:
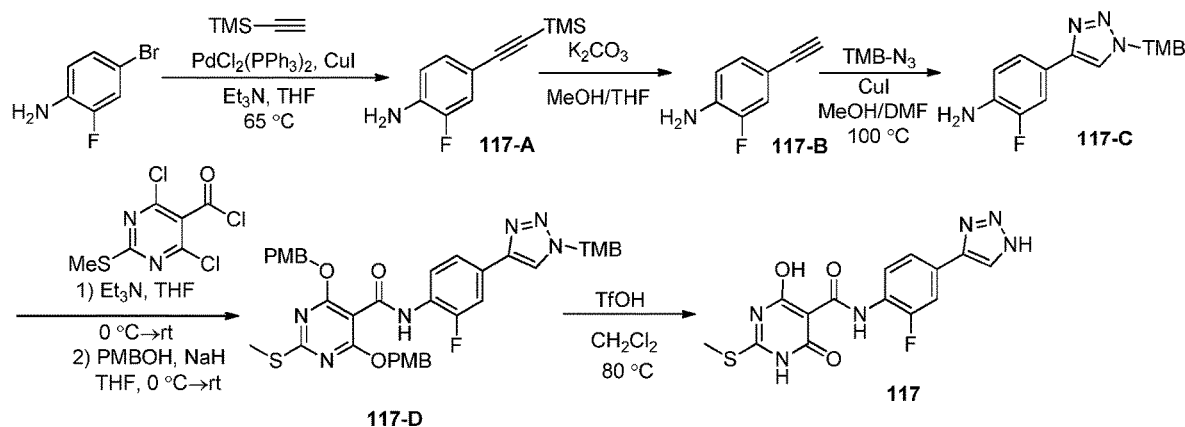
FIG. 24 illustrates the synthesis scheme described in Example 16.

Preparation of N-(2-Fluoro-4-(1H-1,2,3-triazol-4-yl)phenyl)-4-hydroxy-2-(methylthio)-6-oxo-1,6-dihydropyrimidine-5-carboxamide (117, Formula (II$_s$), with Reference to FIG. 24)

Step One. 2-Fluoro-4-((trimethylsilyl)ethynyl)aniline (117-A). A round bottom flask containing 4-bromo-2-fluoroaniline (380 mg, 2.0 mmol), PdCl$_2$(PPh$_3$)$_2$ (84 mg, 0.12 mmol), and CuI (15 mg, 0.08 mmol) was purged with nitrogen for 15 min. Anhydrous THF (6.7 mL) was added, followed by trimethylsilylacetylene (560 μL, 4.0 mmol) and ethanolamine (240 μL, 4.0 mmol). The reaction mixture was sealed and heated to 65° C. for 20 h. The reaction mixture was cooled to rt, filtered through a small pad of Celite. The filtrate was concentrated and used without further purification.

LCMS: $R_T$=1.91 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Two. 4-Ethynyl-2-fluoroaniline (117-B). To a solution of crude 116-A (2.0 mmol) dissolved in methanol (2.0 mL) was added potassium carbonate (553 mg, 4.00 mmol) at rt. The resulting reaction mixture was stirred at rt for 2 h, or until complete consumption of the starting material was observed. The reaction mixture was filtered, and the filtrate was concentrated. The crude product 117-B was used without further purification.

LCMS: $R_T$=1.37 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Three. 2-Fluoro-4-(1-(3,4,5-trimethoxybenzyl)-1H-1,2,3-triazol-4-yl)aniline (117-C). To a solution of crude 117-B (2.0 mmol) was dissolved in a mixture of anhydrous MeOH/DMF (10.0 mL, 1:9, v/v), under inert atmosphere. At room temperature, CuI (38 mg, 0.20 mmol) was added, followed by the addition of 5-(azidomethyl)-1,2,3-trimethoxybenzene (487 mg, 2.14 mmol), the reaction mixture was sealed in a high pressure vessel and heated to 100° C. for 2 h, the reaction was then cooled to rt, then concentration. The crude product was purified via ISCO ($SiO_2$, gradient eluent from 0 to 35% ethyl acetate in hexanes over 20 CV) to yield the product as a brown oil (566 mg, 70% yield over 3 steps).

LCMS: m/z [M+1]$^+$=359.2; $R_T$=1.36 min; purity=89.9%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Four. N-(2-Fluoro-4-(1-(3,4,5-trimethoxybenzyl)-1H-1,2,3-triazol-4-yl)phenyl)-4,6-bis((4-methoxybenzyl)oxy)-2-(methylthio)pyrimidine-5-carboxamide (117-D). To a stirring solution of 117-C (285 mg, 0.715 mmol, 89.8% purity) in anhydrous THF (5.1 mL) at 0° C., under inert atmosphere was added $Et_3N$ (110 μL, 0.804 mmol), followed by the addition of 4,6-dichloro-2-(methylthio)pyrimidine-5-carbonyl chloride (184 mg, 0.731 mmol). The resulting reaction mixture was warmed up to rt over 60 min, until complete consumption of the starting materials were observed via LCMS. The reaction mixture was then cooled to 0° C., then p-methoxylbenzyl alcohol (180 μL, 1.43 mmol) was added, followed by careful addition of NaH (89 mg, 2.22 mmol, 60% dispersed in oil). The reaction was kept at 0° C. for 5 min, then warmed up to rt over 20 h; the progress of the reaction was monitored by LCMS. Methanol (~1 mL) was added to quench the reaction, then TBME (20 mL) was added and the resulting suspension was sonicated for 10 min. The suspension was then filtered, and the solid was washed with TBME, the brown solid (461 mg, 74% yield) was collected.

LCMS: m/z [M+1]$^+$=783.6; $R_T$=2.05 min; purity=90.0%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Five. N-(2-Fluoro-4-(1H-1,2,3-triazol-4-yl)phenyl)-4-hydroxy-2-(methylthio)-6-oxo-1,6-dihydropyrimidine-5-carboxamide (117). 117-D (461 mg, 0.530 mmol, 90.0% purity) dissolved in $CH_2Cl_2$ (5.3 mL) was added TFA (3.8 mL) and sealed in a pressure vessel, heated to 60° C. for 20 h. Reaction was cooled to rt, then TfOH (50 μL) was added, sealed and heated to 60° C. for 20 h. The reaction mixture was cooled to rt, then co-evaporated with MeOH (3×). TBME and deionized water (~10 mL, 1:1 v/v) was added; the suspension was sonicated. The solid was filtered and washed with water and washed with TBME. The green solid was collected (100 mg, 27% yield, 77.4% purity) as the TMB-protected intermediate.

The TMB-protected intermediate (100 mg, 0.0989 mmol, 77.4% purity) was added $CH_2Cl_2$ (1.3 mL), TfOH (640 μL), the resulting reaction mixture was sealed in a microwave vessel and heated to 80° C. for 20 h. The reaction was then cooled to rt, then co-evaporated with methanol (3×). The crude product was purified via reverse-phase chromatography (C18, gradient eluent from 0 to 30% acetonitrile in water with an ammonium bicarbonate buffer 10 mM over 20 CV) to yield impure product 117 after lyophilization. Further purification via trituration was performed using the centrifuge. The solid was washed with water, the supernatant was removed, the sequence was repeated three additional times, and then washed with acetonitrile two times. The resulting solid was collected and lyophilized to yield the pure product 117 as an off-white solid (13.0 mg, 35% yield).

$^1$H NMR (400 MHz, $CDCl_3$+TFA) δ 8.61 (s, 1H), 8.41-8.32 (m, 1H), 7.70 (t, J=7.9 Hz, 2H), 2.90 (s, 3H).

LCMS: m/z [M+1]$^+$=362.8; $R_T$=0.92 min; purity=97.2%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium bicarbonate; Eluent B: Acetonitrile.

Example 17

Figure 25:
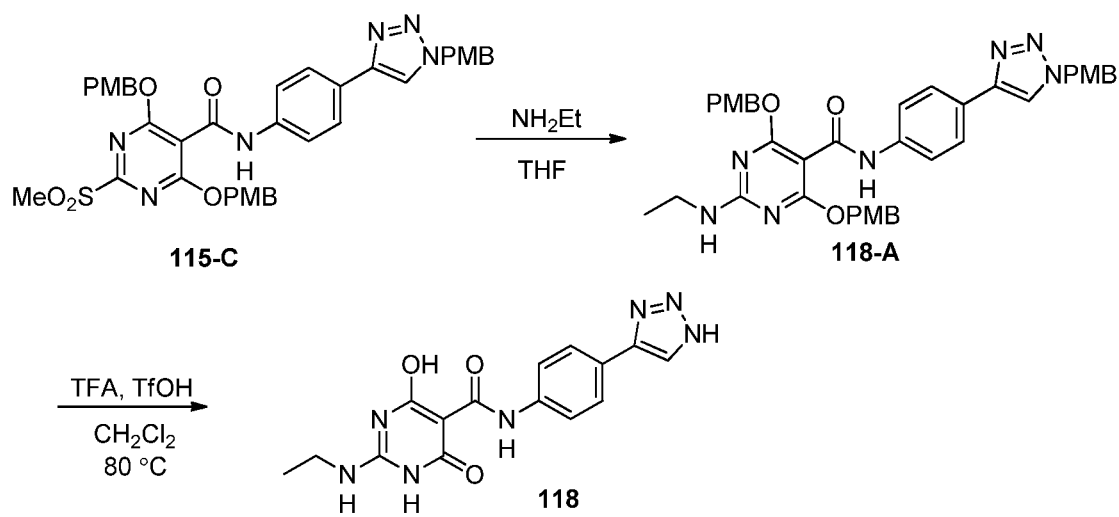
FIG. 25 illustrates the synthesis scheme described in Example 17.

Preparation of N-(4-(1H-1,2,3-triazol-4-yl)phenyl)-2-(ethylamino)-4-hydroxy-6-oxo-1,6-dihydropyrimidine-5-carboxamide (118, Formula ($II_{II}$), with Reference to FIG. 25)

Step One. 2-(Ethylamino)-N-(4-(1-(4-methoxybenzyl)-1H-1,2,3-triazol-4-yl)phenyl)-4,6-bis((4-methoxybenzyl)oxy)pyrimidine-5-carboxamide (118-A). 115-C (138 mg, 0.167 mmol, 89% purity) dissolved in anhydrous THF (3.3 mL) at rt, under inert atmosphere was added N-ethylamine (330 μL, 0.668 mmol, 2.0 M in THF). The reaction was allowed to stir at rt for 30 min, until complete consumption of starting material was observed. The reaction mixture was concentrated under reduced pressure. The crude product was used without further purification.

LCMS: m/z [M+1]$^+$=702.6; $R_T$=1.96 min; purity=88.1%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Two. N-(4-(1H-1,2,3-triazol-4-yl)phenyl)-2-(ethylamino)-4-hydroxy-6-oxo-1,6-dihydropyrimidine-5-carboxamide (118). TfOH (50 μL) was added to a solution of 118-A (0.167 mmol) in TFA (980 μL) and $CH_2Cl_2$ (3.3 mL). The reaction was heated at 80° C. for 72 h. After complete consumption of starting material was observed via LCMS, the reaction was then cooled to rt, then co-evaporated with methanol (3×). The crude product was purified via reverse-phase chromatography (C18, gradient eluent from 0 to 25% acetonitrile in water with an ammonium bicarbonate buffer 10 mM over 30 CV) to yield product 118 after lyophilization as a white solid (22.8 mg, 40% yield).

$^1$H NMR (400 MHz, CDCl$_3$+TFA) δ 8.57 (s, 1H), 7.88 (d, J=8.8 Hz, 2H), 7.77 (d, J=8.8 Hz, 2H), 3.66-3.58 (m, 2H), 1.41 (t, J=7.3 Hz, 3H).

LCMS: m/z [M+1]$^+$=342.2; R$_T$=1.24 min; purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 18

Figure 26:
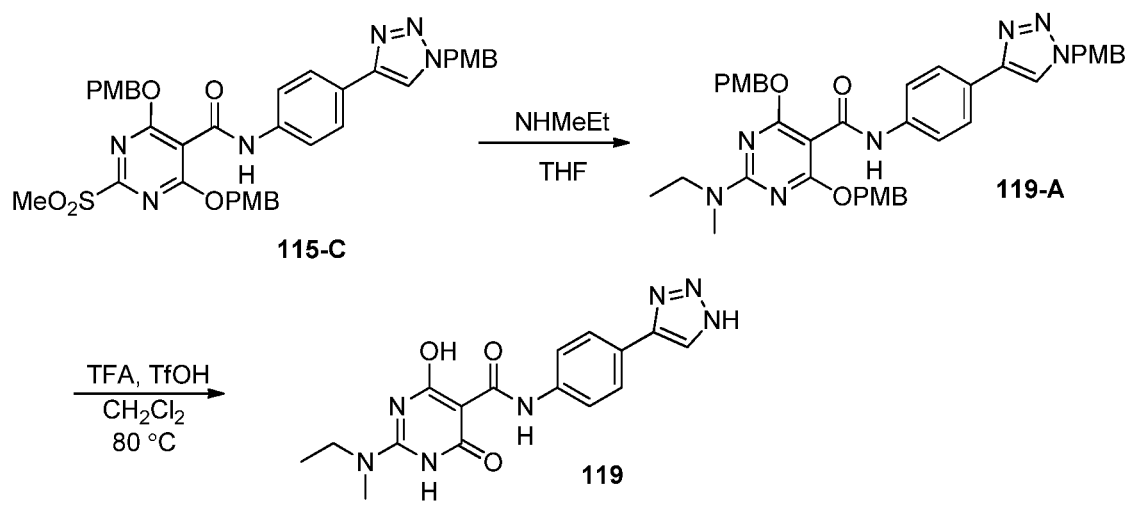
FIG. 26 illustrates the synthesis scheme described in Example 18.

Preparation of N-(4-(1H-1,2,3-Triazol-4-yl)phenyl)-2-(ethyl(methyl)amino)-4-hydroxy-6-oxo-1,6-dihydropyrimidine-5-carboxamide (119, Formula (II$_{mm}$), with Reference to FIG. 26)

115-C (146 mg, 0.188 mmol) dissolved in anhydrous THF (3.8 mL) at rt, under inert atmosphere was added N-ethylmethylamine (64 µL, 0.750 mmol). The reaction was allowed to stir at rt for 30 min, until complete consumption of starting material was observed. The reaction mixture was concentrated under reduced pressure. The crude product was used without further purification. The crude product was dissolved in CH$_2$Cl$_2$ (3.8 mL), TFA (1.1 mL) was added at rt, followed by the addition of TfOH (70 µL). The resulting reaction was sealed in a pressure vessel and heated to 80° C. for 72 h. The reaction was cooled, and then co-evaporated with methanol (3×) concentrated under reduced pressure. The crude product was purified via reverse-phase chromatography (C18, gradient eluent from 0 to 25% acetonitrile in water with an ammonium bicarbonate buffer 10 mM over 30 CV) to yield impure product 119 after lyophilization. Further purification via trituration was performed using the centrifuge. The solid was washed with water, the supernatant was removed, the sequence was repeated three additional times, then washed with acetonitrile two times. The resulting solid was collected and lyophilized to yield the pure product 119 as a white solid (28.5 mg, 42% yield).

$^1$H NMR (400 MHz, CDCl$_3$+TFA) δ 8.64 (s, 1H), 7.92 (d, J=8.7 Hz, 2H), 7.80 (d, J=8.8 Hz, 2H), 3.83 (d, J=7.5 Hz, 2H), 3.49 (s, 3H), 1.46 (t, J=7.3 Hz, 3H).

LCMS: m/z [M+1]$^+$=356.2; R$_T$=1.33 min; purity=99.5%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 19

Figure 27:
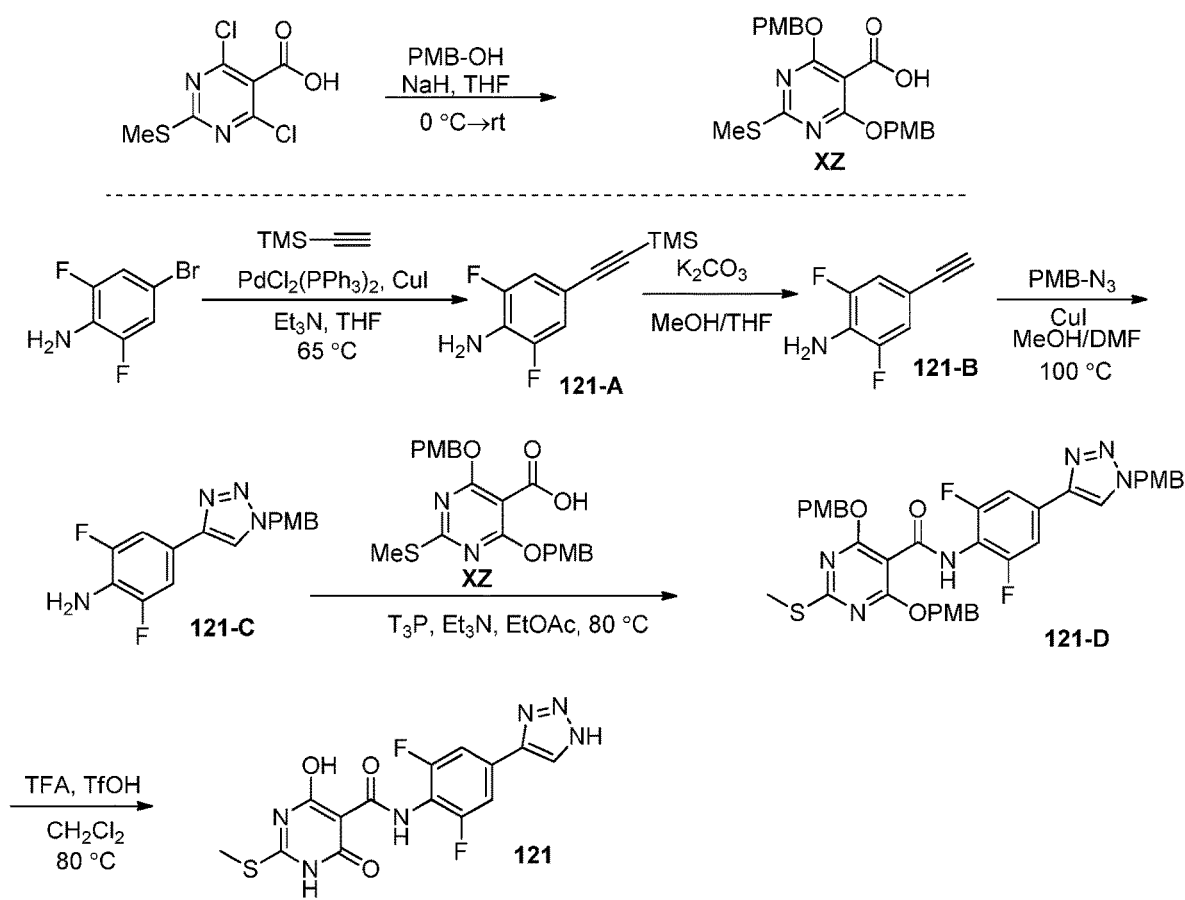
FIG. 27 illustrates the synthesis scheme described in Example 19.

Preparation of N-(4-(1H-1,2,3-triazol-5-yl)phenyl)-2-((cyclopropylmethyl)thio)-4-hydroxy-6-oxo-1,6-dihydropyrimidine-5-carboxamide (121, Formula (II$_t$), with Reference to FIG. 27)

Step One. 4,6-Bis((4-methoxybenzyl)oxy)-2-(methylthio)pyrimidine-5-carboxylic acid (XZ). A flask containing 4,6-dichloro-2-(methylthio)pyrimidine-5-carboxylic acid (1.099 g, 4.46 mmol) was dissolved in anhydrous THF (32 mL, under inert atmosphere. The solution was cooled to 0° C., then p-methoxylbenzyl alcohol (1.10 mL, 8.92 mmol) was added, followed by careful addition of NaH (535 mg, 13.4 mmol, 60% dispersed in oil). The reaction was kept at 0° C. for 5 min, then warmed up to rt over 20 h; the progress of the reaction was monitored by LCMS. Methanol (~1 mL) was added to quench the reaction; the reaction mixture was concentrated under reduced pressure. The residue was added CH$_3$CN and sonicated. The suspension was then filtered, and the solid was washed with CH$_3$CN, the off-white solid (1.234 g, 58% yield) was collected.

LCMS: m/z [M+1]$^+$=442.9; R$_T$=1.86 min; purity=90.0%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Two. 2,6-Difluoro-4-((trimethylsilyl)ethynyl)aniline (121-A). A round bottom flask containing 4-bromo-2,6-difluoroaniline (1.00 g, 4.80 mmol), PdCl$_2$(PPh$_3$)$_2$ (202 mg, 0.288 mmol), and CuI (37 mg, 0.1.92 mmol) was purged with nitrogen for 15 min. Anhydrous THF (16.0 mL) was added, followed by trimethylsilylacetylene (1.40 mL, 9.62 mmol) and ethanolamine (580 µL, 9.62 mmol). The reaction mixture was sealed and heated to 65° C. for 20 h. The reaction mixture was cooled to rt, filtered through a small pad of Celite. The filtrate was concentrated and used without further purification.

LCMS: m/z [M+1]$^+$=226.0; R$_T$=2.01 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Three. 4-Ethynyl-2,6-difluoroaniline (121-B). To a solution of crude 121-A (4.80 mmol) dissolved in methanol (4.8 mL) was added potassium carbonate (1.33 mg, 9.60 mmol) at rt. The resulting reaction mixture was stirred at rt for 2 h, or until complete consumption of the starting material was observed. The reaction mixture was filtered, and the filtrate was concentrated. The crude product 121-B was used without further purification.

LCMS: R$_T$=1.49 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Four. 2,6-Difluoro-4-(1-(4-methoxybenzyl)-1H-1,2,3-triazol-4-yl)aniline (121-C). To a solution of crude 121-B (4.80 mmol) was dissolved in a mixture of anhydrous MeOH/DMF (2.4 mL, 1:9, v/v), under inert atmosphere. At room temperature, CuI (91 mg, 0.480 mmol) was added, followed by the addition of p-methoxybenzyl azide (838 mg, 5.14 mmol), the reaction mixture was sealed in a high pressure vessel and heated to 100° C. for 48 h, the reaction was then cooled to rt, then concentration. The crude product was purified via ISCO (SiO$_2$, gradient eluent from 0 to 50% ethyl acetate in hexanes over 20 CV) to yield the product as a brown solid (1.057 g, 61% yield over 3 steps).

LCMS: m/z [M+1]$^+$=317.1; R$_T$=1.55 min; purity=87.3%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Five. N-(2,6-Difluoro-4-(1-(4-methoxybenzyl)-1H-1,2,3-triazol-4-yl)phenyl)-4,6-bis((4-methoxybenzyl)oxy)-2-(methylthio)pyrimidine-5-carboxamide (121-D). T$_3$P (920 µL, 1.55 mmol, 50% in EtOAc) was added to a mixture of 121-C (93 mg, 0.258 mmol), triethyl amine (490 µL, 3.48 mmol) and XZ (178 mg, 0.387 mmol) in EtOAc (1.3 mL). The reaction was heated at 80° C. overnight. After complete consumption of starting material was observed via LCMS, the mixture was concentrated. MeOH/H$_2$O (~10 mL, 1:1 v/v) was added to the residue, and sonicated to yield the title compound (108 mg, 23% yield) as a brown solid.

LCMS: m/z [M+1]$^+$=741.4; R$_T$=2.07 min; purity=60.7%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Six. N-(2,6-Difluoro-4-(1H-1,2,3-triazol-4-yl)phenyl)-4-hydroxy-2-(methylthio)-6-oxo-1,6-dihydropyrimidine-5-carboxamide (121). TfOH (35 μL) was added to a solution of 121-C (114 mg, 0.0935 mmol) in TFA (550 μL) and CH$_2$Cl$_2$ (1.9 mL). The reaction was heated at 80° C. for 20 h. After complete consumption of starting material was observed via LCMS, MeOH 10 mL was added to the mixture. The resulting mixture was concentrated to remove CH$_2$Cl$_2$ and TFA. Add MeOH 10 mL two more times to co-evaporate with CH$_2$Cl$_2$ and TFA. The crude product was purified via reverse-phase chromatography (C18, gradient eluent from 0 to 25% acetonitrile in water with an ammonium bicarbonate buffer 10 mM over 30 CV) to yield impure product 121 after lyophilization. Further purification via trituration was performed using the centrifuge. The solid was washed with water, the supernatant was removed, the sequence was repeated, then washed with acetonitrile. The resulting solid was collected and lyophilized to yield the pure product 121 as a white solid (6.4 mg, 18% yield).

$^1$H NMR (400 MHz, CDCl$_3$+TFA) δ 8.54 (s, 1H), 7.52 (s, 2H), 2.79 (s, 3H).

LCMS: m/z [M+1]$^+$=381.1; R$_T$=1.36 min; purity=98.6%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 20

Figure 28:
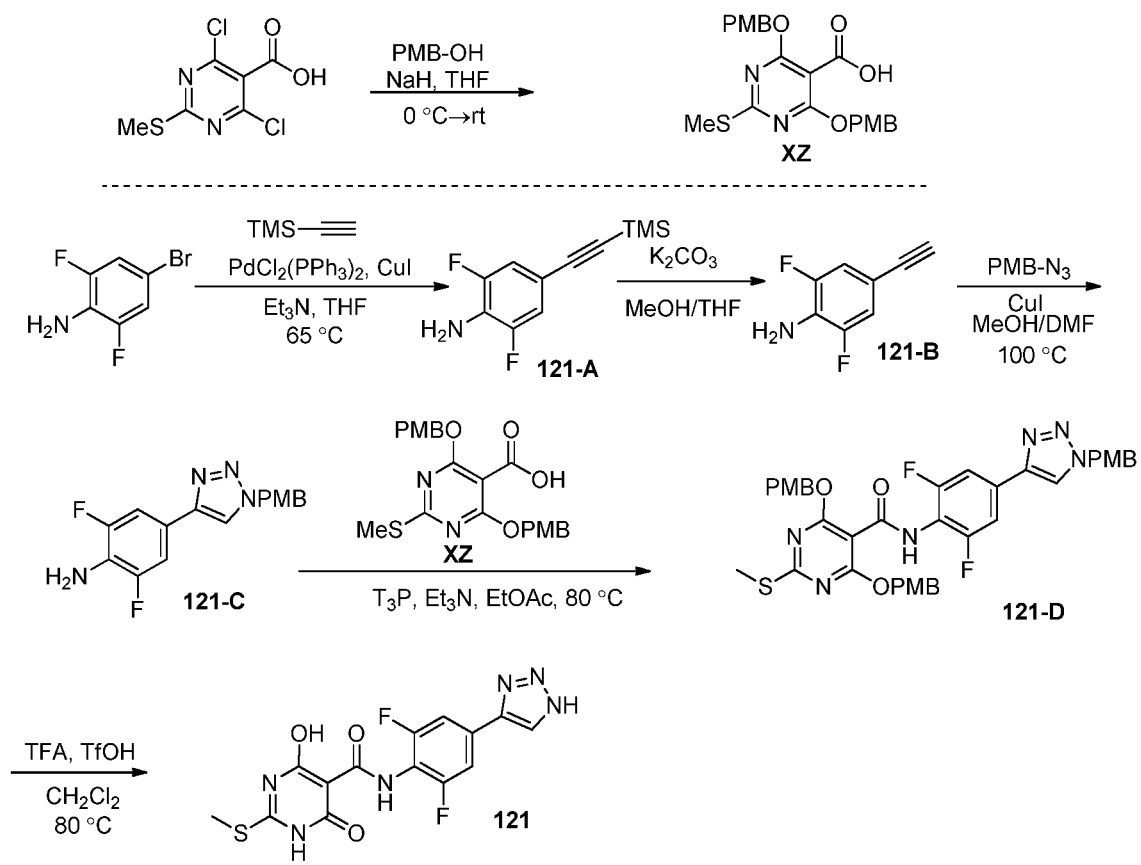
FIG. 28 illustrates the synthesis scheme described in Example 20.

Preparation of N-(3,5-difluoro-4-(1H-1,2,3-triazol-4-yl)phenyl)-4-hydroxy-2-(methylthio)-6-oxo-1,6-dihydropyrimidine-5-carboxamide (122, Formula (II$_u$), with Reference to FIG. 28)

Step One. 3,5-difluoro-4-((trimethylsilyl)ethynyl)aniline. To a mixture of PdCl$_2$(PPh$_3$)$_2$ (168 mg, 0.24 mmol), CuI (30 mg, 0.16 mmol) and 3,5-difluoro-4-iodoaniline (1.02 g, 4.0 mmol), was added THF 14.0 mL, followed by ethanolamine (489 mg, 8.0 mmol) and TMS-acetylene (786 mg, 8.0 mmol). The reaction was heated at 65° C. for 20 h. After complete consumption of starting material was observed via LCMS, the mixture was filtered through Celite, washed by ethyl acetate (3×10 mL). The filtrate was concentrated to yield the desired product, which was used as crude without further purification.

LCMS: m/z [M+1]$^+$=226.1; R$_T$=1.81 min; purity=>87%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 4-ethynyl-3,5-difluoroaniline. To a solution of 3,5-difluoro-4-((trimethylsilyl)ethynyl)aniline (1.1 g, 4.0 mmol) in MeOH (4.0 mL), was added K$_2$CO$_3$ (1.11 g, 8.0 mmol). The reaction was stirred at rt for 2 h. After complete consumption of starting material was observed via LCMS, the mixture was filtered through Celite, washed by MeOH (3×5 mL). The concentrated to further yield the desired product, which was used without further purification (product were to be used right away to avoid decomposition).

LCMS: m/z [M+1]$^+$=154.3; R$_T$=1.43 min; purity=>90%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. 3,5-difluoro-4-(1-(4-methoxybenzyl)-1H-1,2,3-triazol-4-yl)aniline. To a suspension of 4-ethynyl-3,5-difluoroaniline (306 mg, 2.0 mmol) and CuI (38 mg, 0.20 mmol) in MeOH/DMF (1.0 mL, 1:9, v/v), was added PMB-N$_3$ (359 mg, 2.2 mmol). The reaction tube was sealed and heated at 100° C. for 2 h. After complete consumption of starting material was observed via LCMS, the mixture was concentrated, and the residue was purified by ISCO (25 g SiO$_2$, 0-80% ethyl acetate in hexanes), yielding the title compound as a yellow solid (265 mg, 42% yield).

LCMS: m/z [M+1]$^+$=317.0; R$_T$=1.46 min; purity=>99%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. N-(3,5-difluoro-4-(1-(4-methoxybenzyl)-1H-1,2,3-triazol-4-yl)phenyl)-4,6-bis((4-methoxybenzyl)oxy)-2-(methylthio)pyrimidine-5-carboxamide. T$_3$P (636.36 mg, 2 mmol) was added to a mixture of 3,5-difluoro-4-(1-(4-methoxybenzyl)-1H-1,2,3-triazol-4-yl)aniline (158 mg, 0.50 mmol), triethylamine (455 mg, 4.5 mmol) and 4,6-bis((4-methoxybenzyl)oxy)-2-(methylthio)pyrimidine-5-carboxylic acid (331 mg, 0.75 mmol) in EtOAc 2.5 mL. The reaction was heated at 100° C. overnight. After complete consumption of starting material was observed via LCMS, the mixture was concentrated. MeOH (10 mL) was added to the residue, and sonicated to yield the title compound as a light yellow solid (406 mg, quantitative yield).

LCMS: m/z [M+1]$^+$=741.2; R$_T$=2.06 min; purity=>90%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Five. N-(3,5-difluoro-4-(1H-1,2,3-triazol-4-yl)phenyl)-4-hydroxy-2-(methylthio)-6-oxo-1,6-dihydropyrimidine-5-carboxamide (122). TfOH (100 μL) was added to a solution of N-(3,5-difluoro-4-(1-(4-methoxybenzyl)-1H-1,2,3-triazol-4-yl)phenyl)-4,6-bis((4-methoxybenzyl)oxy)-2-(methylthio)pyrimidine-5-carboxamide (200 mg, 0.27 mmol) in TFA 1.6 mL and CH$_2$Cl$_2$ (5.0 mL). The reaction was heated at 80° C. for 2 days. After complete consumption of starting material was observed via LCMS, MeOH (10 mL) was added to the mixture. The resulting mixture was concentrated to remove CH$_2$Cl$_2$ and TFA. MeOH (10 mL) was added two more times to co-evaporate with TFA. MeOH (5 mL) was added, and the mixture was filtered, the precipitate collected was washed with acetonitrile (2×5 mL), water (1×5 mL), and acetone (1×5 mL) to yield the title compound as light yellow solid (74.1 mg, 72% yield).

LCMS: m/z [M+1]$^+$=380.9; R$_T$=1.39 min; purity=> 96.3%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

$^1$H NMR (400 MHz, CDCl$_3$+TFA) δ 8.68 (s, 1H), 7.59 (d, J=11.0 Hz, 2H), 2.77 (s, 3H).

Example 21

Figure 29:
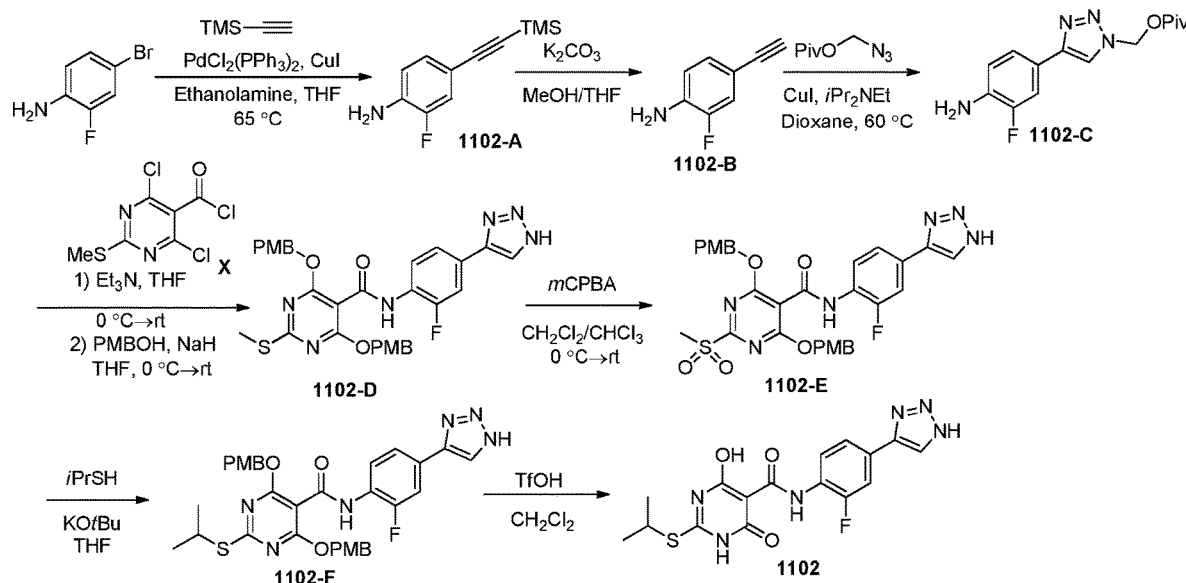
FIG. 29 illustrates the synthesis scheme described in Example 21.

Preparation of N-(4-(1H-1,2,3-triazol-4-yl) benzyl)-4,6-dihydroxy-2-(methylthio) pyrimidine-5-carboxamide (1102, Formula (II$_v$), with Reference to FIG. 29)

Step One. 2-Fluoro-4-((trimethylsilyl)ethynyl) aniline (1102-A). A round bottom flask containing 4-bromo-2- fluoroaniline (1.00 g, 5.26 mmol), PdCl$_2$(PPh$_3$)$_2$ (222 mg, 0.316 mmol), and CuI (40 mg, 0.21 mmol) was purged with nitrogen for 15 min. Anhydrous THF (17.5 mL) was added, followed by trimethylsilyl acetylene (1.5 mL, 10.5 mmol) and ethanolamine (634 uL, 10.5 mmol). The reaction mixture was sealed and heated to 65° C. for 20 h. The reaction mixture was cooled to rt, filtered through a small pad of Celite. The filtrate was concentrated and the crude product was used without further purification.

LCMS: R$_T$=1.91 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Two. 4-Ethynyl-2-fluoroaniline (1102-B). To a solution of crude 1102-A (5.26 mmol) dissolved in methanol (5.3 mL) was added potassium carbonate (1.45 g, 10.5 mmol) at rt. The resulting reaction mixture was stirred at rt until complete consumption of the starting material was observed. The reaction mixture was filtered, and the filtrate was concentrated. The crude product was purified via ISCO (0 to 30% ethyl acetate in hexanes, over 20 CV) to yield the product as a yellow oil (543 mg, 72% yield over 2 steps, 93.9% purity).

LCMS: R$_T$=1.37 min; purity=93.9%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Three. (4-(4-Amino-3-fluorophenyl)-1H-1,2,3-triazol-1-yl) methyl pivalate (1102-C). To a solution of 1102-B (543 mg, 3.78 mmol) was dissolved in anhydrous 1,4-dioxane (7.6 mL). CuI (72 mg, 0.378 mmol) was added, followed by the addition of iPr$_2$NEt (660 µL, 3.78 mmol) and azidomethyl pivalate (7.6 mL, 3.78 mmol, 0.5 M in 2-methoxypropane). The resulting reaction mixture was heated to 60° C. for 8 h. The reaction mixture was then cooled to rt and then concentrated under reduced pressure. The crude product was purified via ISCO (0 to 60% ethyl acetate in hexanes, over 15 CV) to yield the product as a yellow solid (823 mg, 72% yield, 97.3% purity).

LCMS: m/z [M+1]$^+$=293.2; R$_T$=1.51 min; purity=97.3%

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Four. N-(2-Fluoro-4-(1H-1,2,3-triazol-4-yl) phenyl)-4,6-bis((4-methoxybenzyl) oxy)-2-(methylthio) pyrimidine-5-carboxamide (1102-D). To a solution of 1102-C (412 mg, 1.37 mmol) dissolved in anhydrous THF (9.8 mL), under inert atmosphere was cooled to 0° C. Et$_3$N (210 µL, 1.51 mmol) was added followed by the addition of 4,6-dichloro-2-(methylthio) pyrimidine-5-carbonyl chloride X (352 mg, 1.37 mmol). The resulting reaction mixture was warmed up to rt over 18 h. The reaction mixture was cooled to 0° C., p-methoxybenzyl alcohol (510 µL, 4.11 mmol), followed by the addition of NaH (219 mg, 5.48 mmol, 60% dispersed in oil). The reaction was stirred at 0° C. for 5 min, then warmed up to rt over 20 h. Methanol (~10 mL) was added, followed by TBME (~10 mL), the resulting suspension was sonicated and the precipitate was filtered and collected to yield the product as a brown solid (722 mg, 63% yield, 72.0% purity).

LCMS: m/z [M+1]$^+$=603.2; R$_T$=1.97 min; purity=72.0%

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Five. N-(2-Fluoro-4-(1H-1,2,3-triazol-4-yl) phenyl)-4,6-bis((4-methoxybenzyl) oxy)-2-(methyl sulfonyl) pyrimidine-5-carboxamide (1102-E). To a solution of 1102-D (364 mg, 0.435 mmol, 72.0% purity) dissolved in CH$_2$Cl$_2$ (2.2 mL) and CHCl$_3$ (2.0 mL) was added mCPBA (158 mg, 0.914 mmol, 77% in H$_2$O) at 0° C. The reaction was warmed up to rt over 20 h with vigorous stirring. After complete conversion was observed via LCMS, the reaction mixture was loaded onto a 6 g Si-TMA acetate column. Acid impurities were retained on the column and the product was eluted with methanol. The crude product was used without further purification.

LCMS: m/z [M+1]$^+$=635.4; R$_T$=1.71 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Six. N-(2-Fluoro-4-(1H-1,2,3-triazol-4-yl) phenyl)-2-(isopropylthio)-4,6-bis((4-methoxybenzyl) oxy) pyrimidine-5-carboxamide (1102-F). To a solution of crude 1102-D (0.435 mmol) and iPrSH (200 µL, 2.18 mmol) in anhydrous THF (8.7 mL) was added KOtBu (2.6 mL, 0.261 mmol, 1.0 M in THF) at 0° C. The reaction mixture was then warmed up to rt over 30 min, H$_2$O (10 mL) was added then extracted with EtOAc (3×~10 mL). The combined organic extracts were dried over MgSO$_4$, and then concentrated under reduced pressure to yield the crude product as a brown solid, used without further purification.

LCMS: m/z [M+1]$^+$=631.2; R$_T$=2.11 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Seven. N-(2-Fluoro-4-(1H-1,2,3-triazol-4-yl) phenyl)-4-hydroxy-2-(isopropylthio)-6-oxo-1,6-dihydropyrimidine-5-carboxamide (1102). Crude 1102-F (0.435 mmol) in dichloromethane (8.7 mL) was added trifluoroacetic acid (2.6 mL) at rt. The reaction was stirred for 1 h, and then co-evaporated with MeOH (3× ~20 mL). The crude product was purified via reverse-phase chromatography (C18, gradient eluent from 0 to 30% acetonitrile in water with an ammonium bicarbonate buffer 10 mM over 20 CV) to yield 1102 as an off-white solid (12.3 mg, 3% yield over 3 steps, 97.2% purity), after lyophilization.

$^1$H NMR (400 MHz, DMSO-d6+Acetone+TFA) δ 8.70 (s, 1H), 8.56 (s, 1H), 7.78 (dd, J=17.0, 10.3 Hz, 2H), 4.11-4.00 (m, 1H), 1.41 (d, J=6.9 Hz, 6H).

LCMS: m/z [M+1]$^+$=391.2; R$_T$=1.55 min; purity=97.2%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 22

Figure 30:
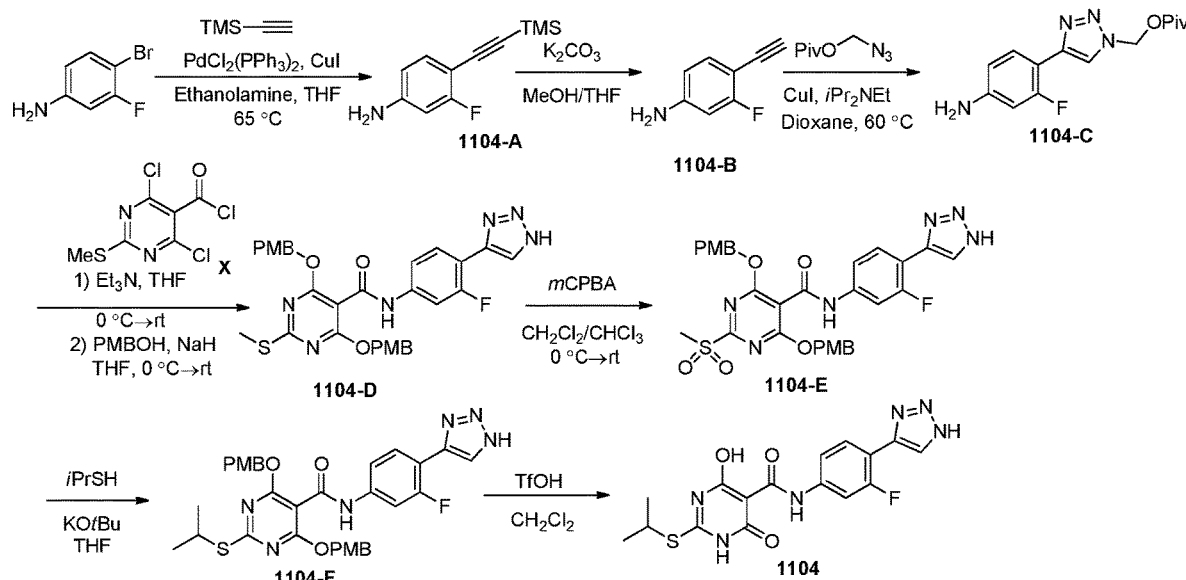
FIG. 30 illustrates the synthesis scheme described in Example 22.

Preparation of N-(3-Fluoro-4-(1H-1,2,3-triazol-4-yl) phenyl)-4-hydroxy-2-(isopropylthio)-6-oxo-1,6-dihydropyrimidine-5-carboxamide (1104, Formula (II$_w$), with Reference to FIG. 30)

Step One. 3-Fluoro-4-((trimethylsilyl)ethynyl) aniline (1104-A). A round bottom flask containing 4-bromo-3-fluoroaniline (2.00 g, 10.5 mmol), PdCl$_2$(PPh$_3$)$_2$ (442 mg, 0.63 mmol), and CuI (80 mg, 0.42 mmol) was purged with nitrogen for 15 min. Anhydrous THF (35 mL) was added, followed by trimethylsilyl acetylene (2.9 mL, 21.0 mmol) and ethanolamine (1.3 mL, 21.0 mmol). The reaction mixture was sealed and heated to 65° C. for 20 h. The reaction mixture was cooled to rt, filtered through a small pad of Celite. The filtrate was concentrated and the crude product was used without further purification.

LCMS: $R_T$=1.86 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Two. 4-Ethynyl-3-fluoroaniline (1104-B). To a solution of crude 1104-A (10.5 mmol) dissolved in methanol (21 mL) was added potassium carbonate (2.90 g, 21.0 mmol) at rt. The resulting reaction mixture was stirred at rt until complete consumption of the starting material was observed. The reaction mixture was filtered, and the filtrate was concentrated. The crude product was purified via ISCO (0 to 30% ethyl acetate in hexanes, over 20 CV) to yield the product as a brown oil (1.70 g, 90% yield, 75.2% purity).

LCMS: $R_T$=1.43 min (75.2% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Three. (4-(4-Amino-3-fluorophenyl)-1H-1,2,3-triazol-1-yl) methyl pivalate (1104-C). To a solution of 1104-B (1.033 g, 5.75 mmol, 75.2% purity) was dissolved in anhydrous 1,4-dioxane (11.5 mL). CuI (110 mg, 0.575 mmol) was added, followed by the addition of iPr$_2$NEt (1.0 mL, 5.75 mmol) and azidomethyl pivalate (995 mg, 6.33 mmol). The resulting reaction mixture was heated to 60° C. for 20 h. The reaction mixture was then cooled to rt and then concentrated under reduced pressure. The crude product was purified via ISCO (0 to 60% ethyl acetate in hexanes, over 15 CV) to yield the product as a orangish-yellow solid (605 mg, 35% yield, 95.9% purity).

LCMS: m/z [M+1]$^+$=293.0; $R_T$=1.54 min (95.9% purity)

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Four. N-(3-fluoro-4-(1H-1,2,3-triazol-4-yl) phenyl)-4,6-bis((4-methoxybenzyl) oxy)-2-(methylthio) pyrimidine-5-carboxamide (1104-D). To a solution of 1104-C (512 mg, 1.99 mmol) dissolved in anhydrous THF (14.2 mL), under inert atmosphere was cooled to 0° C. Et$_3$N (305 μL, 2.19 mmol) was added followed by the addition of 4,6-dichloro-2-(methyl thio) pyrimidine-5-carbonyl chloride X (512 mg, 1.99 mmol). The resulting reaction mixture was warmed up to rt over 20 h. The reaction mixture was cooled to 0° C., p-methoxybenzyl alcohol (740 μL, 5.97 mmol), followed by the addition of NaH (318 mg, 7.96 mmol, 60% dispersed in oil). The reaction was stirred at 0° C. for 5 min, then warmed up to rt over 20 h, then concentrated under reduced pressure. The crude product was purified via reverse-phase chromatography (C18, gradient eluent from 20 to 100% acetonitrile in water with an ammonium formate buffer 10 mM over 20 CV) to yield the product as an off-white solid (351 mg, 25% yield, 89.8% purity), after lyophilization.

LCMS: m/z [M+1]$^+$=603.1; $R_T$=1.88 min (89.8% purity)

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Five. N-(3-fluoro-4-(1H-1,2,3-triazol-4-yl) phenyl)-4,6-bis((4-methoxybenzyl) oxy)-2-(methyl sulfonyl) pyrimidine-5-carboxamide (1104-E). To a solution of 1104-D (250 mg, 0.373 mmol, 89.8% purity) dissolved in CH$_2$Cl$_2$ (1.9 mL) and CHCl$_3$ (1.9 mL) was added mCPBA (176 mg, 0.783 mmol, 77% in $H_2O$) at 0° C. The reaction was warmed up to rt over 20 h with vigorous stirring. After complete conversion was observed via LCMS, the reaction mixture was loaded onto a 6 g Si-TMA acetate column. Acid impurities were retained on the column and the product was eluted with methanol. The crude product was used without further purification.

LCMS: m/z [M+1]$^+$=635.1; $R_T$=1.67 min (75.5% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Six. N-(3-fluoro-4-(1H-1,2,3-triazol-4-yl) phenyl)-2-(isopropylthio)-4,6-bis((4-methoxybenzyl) oxy) pyrimidine-5-carboxamide (1104-F). To a solution of crude 1104-D (0.373 mmol) and iPrSH (170 μL, 1.87 mmol) in anhydrous THF (7.5 mL) was added KOtBu (2.2 mL, 2.24 mmol, 1.0 M in THF) at 0° C. The reaction mixture was then warmed up to rt over 30 min, $H_2O$ (10 mL) was added then extracted with EtOAc (3×~10 mL). The combined organic extracts were dried over MgSO$_4$, and then concentrated under reduced pressure; the crude product was used without further purification.

LCMS: m/z [M+1]$^+$=631.2; $R_T$=2.02 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Seven. N-(3-fluoro-4-(1H-1,2,3-triazol-4-yl) phenyl)-4-hydroxy-2-(isopropylthio)-6-oxo-1,6-dihydropyrimidine-5-carboxamide (1104). Crude 1104-F (0.373 mmol) in dichloromethane (7.5 mL) was added trifluoroacetic acid (2.2 mL) at rt. The reaction was stirred for 1 h, and then co-evaporated with MeOH (3×~20 mL). The crude product was purified via reverse-phase chromatography (C18, gradient eluent from 0 to 25% acetonitrile in water with an ammonium bicarbonate buffer 10 mM over 20 CV) to yield the product 1104 as a white solid (25.8 mg, 18% yield over 3 steps, 99.1% purity), after lyophilization.

$^1$H NMR (400 MHz, CHCl$_3$+TFA) δ 8.66 (s, 1H), 7.92 (s, 1H), 7.85 (d, J=12.9 Hz, 1H), 7.53 (s, 1H), 4.22 (d, J=6.4 Hz, 1H), 1.55 (d, J=6.8 Hz, 6H).

LCMS: m/z [M+1]$^+$=391.0; $R_T$=1.60 min (99.1% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate pH: 3.8; Eluent B: Acetonitrile.

Example 23

Figure 31:
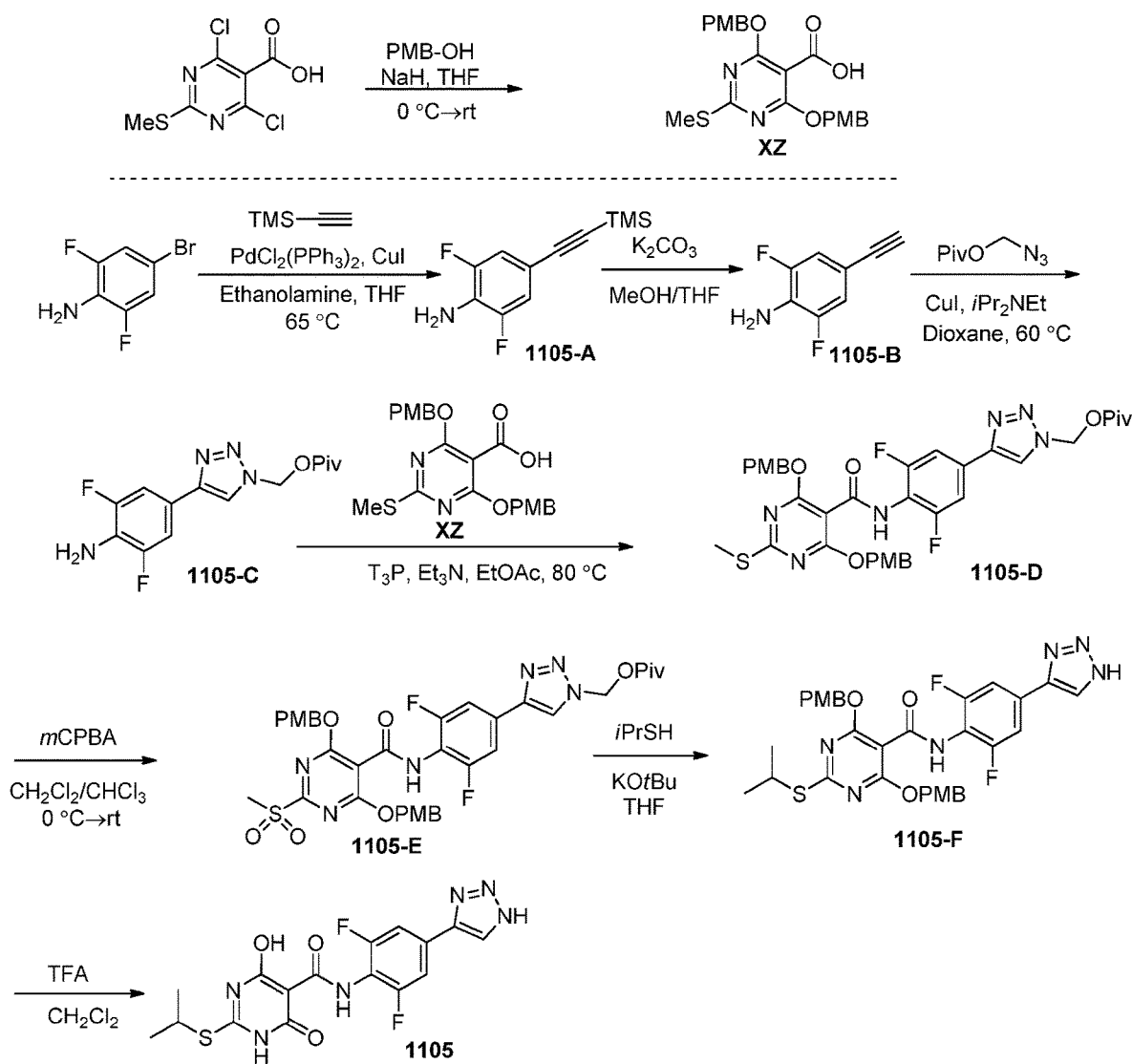
FIG. 31 illustrates the synthesis scheme described in Example 23.

Preparation of N-(2,6-Difluoro-4-(1H-1,2,3-triazol-4-yl) phenyl)-4-hydroxy-2-(isopropylthio)-6-oxo-1,6-dihydropyrimidine-5-carboxamide (1105, Formula (II$_x$), with Reference to FIG. 31)

Step One. 4,6-Bis((4-methoxybenzyl) oxy)-2-(methylthio) pyrimidine-5-carboxylic acid (XZ). A flask containing 4,6-dichloro-2-(methylthio) pyrimidine-5-carboxylic acid (1.099 g, 4.46 mmol) was dissolved in anhydrous THF (32 mL, under inert atmosphere. The solution was cooled to 0° C., then p-methoxybenzyl alcohol (1.10 mL, 8.92 mmol) was added, followed by careful addition of NaH (535 mg, 13.4 mmol, 60% dispersed in oil). The reaction was kept at 0° C. for 5 min, then warmed up to rt over 20 h; the progress of the reaction was monitored by LCMS. Methanol (~1 mL) was added to quench the reaction; the reaction mixture was concentrated under reduced pressure. The residue was added $CH_3CN$ and sonicated. The suspension was then filtered, and the solid was washed with $CH_3CN$, the off-white solid (1.234 g, 58% yield) was collected.

LCMS: m/z $[M+1]^+$=442.9; $R_T$=1.86 min; (90.0% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Two. 2,6-Difluoro-4-((trimethylsilyl)ethynyl) aniline (1105-A). A round bottom flask containing 4-bromo-2,6-difluoroaniline (3.94 g, 18.9 mmol), $PdCl_2(PPh_3)_2$ (798 mg, 1.14 mmol), and CuI (144 mg, 0.0758 mmol) was purged with nitrogen for 15 min. Anhydrous THF (38 mL) was added, followed by trimethylsilyl acetylene (5.3 mL, 37.9 mmol) and ethanolamine (2.3 mL, 37.9 mmol). The reaction mixture was sealed and heated to 65° C. for 20 h. The reaction mixture was cooled to rt, filtered through a small pad of Celite. The filtrate was concentrated and used without further purification.

LCMS: $R_T$=1.98 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Three. 4-Ethynyl-2,6-difluoroaniline (1105-B). To a solution of crude 1105-A (9.47 mmol) dissolved in methanol (9.5 mL) was added potassium carbonate (2.61 g, 18.9 mmol) at rt. The resulting reaction mixture was stirred at rt for 20 h, or until complete consumption of the starting material was observed. The reaction mixture was filtered, and the filtrate was concentrated. The crude product was purified via ISCO (0 to 10% ethyl acetate in hexanes, over 20 CV to yield the product as a yellow solid (508 mg, 35% yield over 2 steps)

LCMS: $R_T$=1.46 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Four. (4-(4-Amino-3,5-difluorophenyl)-1H-1,2,3-triazol-1-yl) methyl pivalate (1105-C). To a solution of 1104-B (508 mg, 3.32 mmol) was dissolved in anhydrous 1,4-dioxane (6.6 mL). CuI (63 mg, 0.332 mmol) was added, followed by the addition of $iPr_2NEt$ (580 µL, 3.32 mmol) and azidomethyl pivalate (6.6 mL, 3.32 mmol, 0.5 M in 2-methoxypropane). The resulting reaction mixture was heated to 60° C. for 20 h. The reaction mixture was then cooled to rt and then concentrated. The crude reaction mixture was sonicated with a mixture of $H_2O$/MeOH (1:1 v/v), the precipitate was filtered and washed with $H_2O$, MeOH, and then TBME to yield as a solid (817 mg, 78% yield, 97.7% purity).

LCMS: m/z $[M+I]^+$=311.0; $R_T$=1.68 min (97.7% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Five. (4-(4-(4,6-bis((4-methoxybenzyl) oxy)-2-(methylthio) pyrimidine-5-carboxamido)-3,5-difluorophenyl)-1H-1,2,3-triazol-1-yl) methyl pivalate (1105-D). Fluoro-N, N, N', N'-bis(tetramethylene) formamidinium hexafluorophosphate, BTFFH (270 mg, 0.853 mmol) and XY (330 mg, 0.711 mmol) in anhydrous dichloromethane (2.4 mL) was added $iPr_2Net$ (370 µL, 2.13 mmol), the resulting reaction was stirred for 30 min at rt. 1105-C (150 mg, 0.474 mmol, 97.7% purity) was added then sealed in a pressure vessel heated to 80° C. for 24 h. The reaction mixture was cooled to rt, then extracted with EtOAc (3×), the organic extracts were combined and washed with brine, then dried over $MgSO_4$ and concentrated under reduced pressure. The crude product was purified via ISCO (0 to 60% ethyl acetate in hexanes, over 20 CV) to yield the product as an off-white solid (176 mg, 51% yield, >99% purity).

LCMS: m/z $[M+1]^+$=735.3; $R_T$=2.08 min (99% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate pH: 3.8; Eluent B: Acetonitrile.

Step Six. (4-(4-(4,6-Bis((4-methoxybenzyl) oxy)-2-(methyl sulfonyl) pyrimidine-5-carboxamido)-3,5-difluorophenyl)-1H-1,2,3-triazol-1-yl) methyl pivalate (1105-E). To a solution of 1105-D (176 mg, 0.239 mmol) dissolved in $CH_2Cl_2$ (1.2 mL) was added mCPBA (113 mg, 0.503 mmol, 77% in $H_2O$) at 0° C. The reaction was warmed up to rt over 20 h with vigorous stirring. After complete conversion was observed via LCMS, the reaction mixture was quenched with sat. $NaHCO_3$, then stirred vigorously for 30 min, the organic layer was separated and washed with sat. $NaHCO_3$ (aq) (3×), until all mCBA and mCPBA impurities were removed from organic phase. The resulting organic extract was dried over $MgSO_4$, and then concentrated under reduced pressure. The crude product was used without further purification.

LCMS: m/z $[M+1]^+$=767.4; $R_T$=1.89 min(67.5% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Seven. N-(2,6-difluoro-4-(1H-1,2,3-triazol-4-yl) phenyl)-2-(isopropylthio)-4,6-bis((4-methoxybenzyl) oxy) pyrimidine-5-carboxamide (1105-F). To a solution of crude 1105-E (120 mg, 0.106 mmol, 67.5% purity) and iPrSH (50 µL, 0.530 mmol) in anhydrous THF (2.1 mL) was added KOtBu (740 µL, 0.742 mmol, 1.0 M in THF) at 0° C. The reaction mixture was then warmed up to rt over 30 min, $H_2O$ (10 mL) was added then extracted with EtOAc (3×~10 mL). The combined organic extracts were dried over $MgSO_4$, and then concentrated under reduced pressure; the crude product was used without further purification.

LCMS: m/z $[M+1]^+$=769.3; $R_T$=1.99 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate; Eluent B: Acetonitrile.

Step Eight. N-(2,6-Difluoro-4-(1H-1,2,3-triazol-4-yl) phenyl)-4-hydroxy-2-(isopropylthio)-6-oxo-1,6-dihydropyrimidine-5-carboxamide (1105). TFA (630 µL) was added to a solution of 1105-F (0.1.06 mmol) $CH_2Cl_2$ (2.1 mL). The reaction was stirred at rt for 0.5 h. After complete consumption of starting material was observed via LCMS, MeOH 10 mL was added to the mixture. The resulting mixture was concentrated to remove $CH_2Cl_2$ and TFA. Add MeOH 10 mL two more times to co-evaporate with $CH_2Cl_2$ and TFA. The crude product was purified via reverse-phase chromatography (C18, gradient eluent from 0 to 35% acetonitrile in water with an ammonium bicarbonate buffer 10 mM over 30 CV) to yield impure product 1105 after lyophilization. Further purification via trituration was performed using the centrifuge. The solid was washed with water, the supernatant was removed, the sequence was repeated, then washed with acetonitrile. The resulting solid was collected and lyophilized to yield the pure product 1105 as a white solid (1.1 mg, 2% yield over 3 steps, >99% purity).

$^1$H NMR (400 MHz, CDCl$_3$+TFA) δ 8.63 (s, 1H), 7.53 (s, 2H), 4.28-4.15 (m, 1H), 1.55 (d, J=6.7 Hz, 6H).

LCMS: m/z [M+1]$^+$=409.2; R$_T$=1.51 min (99.1% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 24

Figure 32:
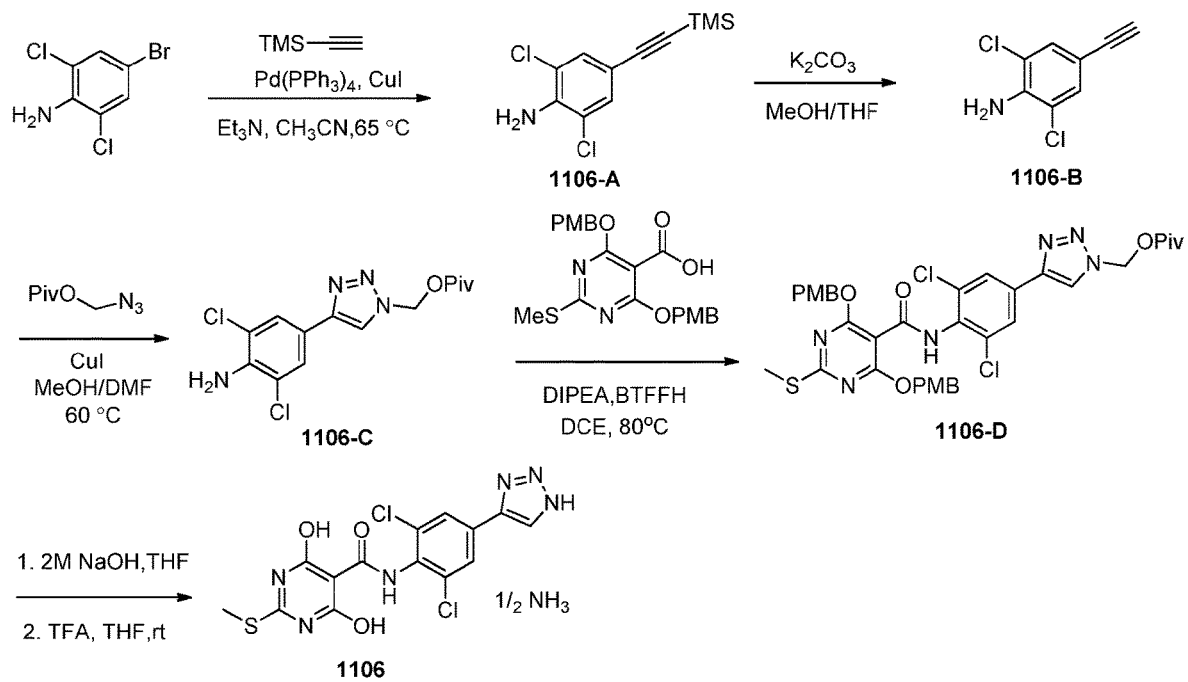
FIG. 32 illustrates the synthesis scheme described in Example 24.

Preparation of N-(2,6-dichloro-4-(1H-1,2,3-triazol-4-yl) phenyl)-4,6-dihydroxy-2-(methylthio) pyrimidine-5-carboxamide (1106, Formula (II$_y$), with Reference to FIG. 32)

Step One. 2,6-dichloro-4-((trimethylsilyl)ethynyl) aniline (1106-A). A round bottom flask containing 4-bromo-2,6-dichloroaniline (1.2 g, 5.0 mmol), Pd(PPh$_3$)$_4$ (115 mg, 0.1 mmol), and CuI (38 mg, 0.2 mmol) was purged with nitrogen for 15 min. Anhydrous CH$_3$CN (10.0 mL) was added, followed by trimethylsilyl acetylene (0.8 mL, 5.5 mmol) and triethylamine (2.1 mL, 15.0 mmol). The reaction mixture was heated to 65° C. for 12 h. After completion reaction mixture was cooled to rt, filtered through a small pad of Celite. The filtrate was concentrated and used in next step without further purification.

LCMS: R$_T$=2.18 min (98% Purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Two. 2,6-dichloro-4-ethynylaniline (1106-B). To a solution of crude 1106-A (1.28 g, 5.0 mmol) dissolved in methanol (20.0 mL) was added potassium carbonate (1.38 g, 10.0 mmol) at rt. The resulting reaction mixture was stirred at rt until complete consumption of the starting material was observed. The reaction mixture was filtered, and the filtrate was concentrated. The crude product was purified via ISCO (0 to 30% ethyl acetate in hexanes, over 20 CV) to yield the product as a yellow solid (721 mg, 78% yield over 2 steps).

LCMS: R$_T$=1.72 min (99.5% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Three. (4-(4-amino-3,5-dichlorophenyl)-1H-1,2,3-triazol-1-yl) methyl pivalate (1106-C). To a solution of 1106-B (372 mg, 2.0 mmol) dissolved in anhydrous 1,4-dioxane (5.0 mL). CuI (38 mg, 0.2 mmol) was added, followed by the addition of DIPEA (0.7 mL, 4.0 mmol) and azidomethyl pivalate (377 mg, 2.4 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 1106-C as an off-white solid (610 mg, 89% yield).

LCMS: m/z [M+1]$^+$=343.0; R$_T$=1.76 min (98.8% purity)

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Four. (4-(4-(4,6-bis((4-methoxybenzyl) oxy)-2-(methylthio) pyrimidine-5-carboxamido)-3,5-dichlorophenyl)-1H-1,2,3-triazol-1-yl) methyl pivalate (1106-D). Fluoro-N, N, N', N'-bis (tetramethylene) formamidinium hexafluorophosphate, BTFFH (427 mg, 1.35 mmol) and XY (403 mg, 1.5 mmol) in anhydrous 1,2 dichloroethane (4.0 mL) was added DIPEA (0.42 mL, 2.4 mmol), the resulting reaction was stirred for 30 min at rt. 1106-C (200 mg, 0.6 mmol, 87.7% purity) was added then sealed tube and heated to 80° C. for 16 h. The reaction mixture was cooled to rt, and then concentrated under reduced pressure. The crude product was purified via ISCO (0 to 40% ethyl acetate in hexanes, over 20 CV) to yield the product as white solid (55 mg, 12% yield).

LCMS: m/z [M+1]$^+$=768.1; R$_T$=2.13 min (99.5% purity)

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Five. N-(2,6-dichloro-4-(1H-1,2,3-triazol-4-yl) phenyl)-4,6-dihydroxy-2-(methylthio) pyrimidine-5-carboxamide (1106). 2.0 M aqueous solution of NaOH (1.0 mL) was added to 1106-D (50 mg, 0.07 mmol) in THF (1.0 mL) at rt. The reaction mixture was stirred for 1 h, and then concentrated and evaporated with MeOH to obtained intermediate crude product which was dissolved in THF (2.0 mL), followed by the addition of TFA (2.0 mL) at rt. The reaction was stirred at rt for 2 h. After complete consumption of starting material was observed via LCMS, MeOH 10 mL was added to the mixture. The resulting mixture was concentrated to get crude product. The crude product was purified via reverse-phase chromatography (C18, gradient eluent from 0 to 35% acetonitrile in water with an ammonium bicarbonate buffer 10 mM over 30 CV) followed by lypholization to yield ammonium salt of 1106 as white solid (8.0 mg, 30% yield).

$^1$H NMR (400 MHz, CDCl3+TFA): δ 10.86 (s, 1H), 8.45 (s, 1H), 7.85 (s, 2H), 6.81-6.39 (m, 2H), 2.92 (s, 1H), 2.74 (s, 3H).

LCMS: m/z [M+1]$^+$=414.9; R$_T$=1.37 min (97.3% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 25

Figure 33:
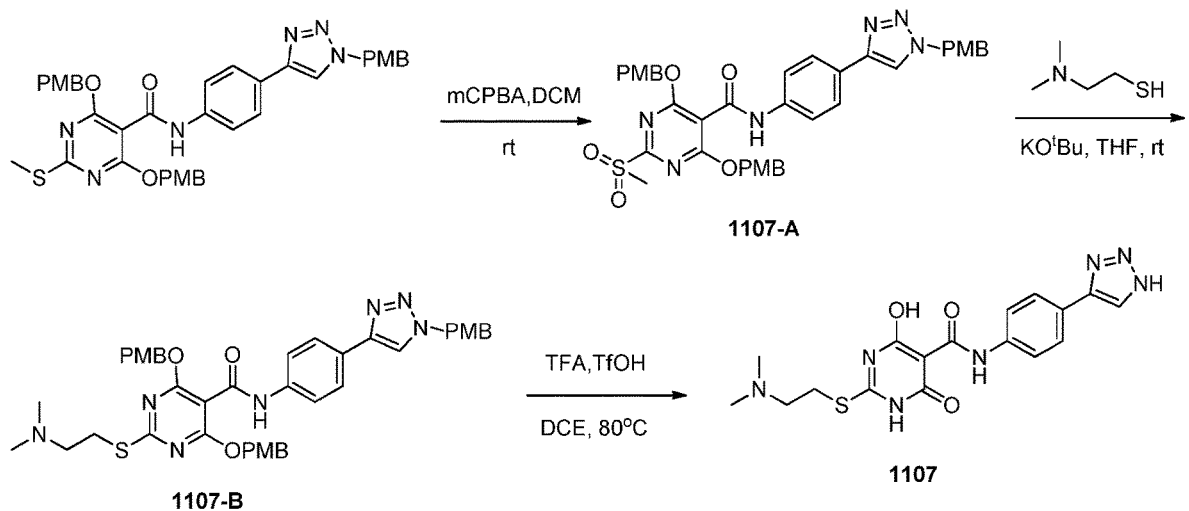
FIG. 33 illustrates the synthesis scheme described in Example 25.

Preparation of N-(4-(1H-1,2,3-triazol-4-yl) phenyl)-2-((2-(dimethyl amino) ethyl) thio)-4-hydroxy-6-oxo-1,6-dihydropyrimidine-5-carboxamide (1107, Formula (II$_z$), with Reference to FIG. 33)

Step one. N-(4-(1-(4-methoxybenzyl)-1H-1,2,3-triazol-4-yl) phenyl)-4,6-bis((4-methoxybenzyl) oxy)-2-(methyl sulfonyl) pyrimidine-5-carboxamide (1107-A). To a solution of N-(4-(1-(4-methoxybenzyl)-1H-1,2,3-triazol-4-yl) phenyl)-4,6-bis ((4-methoxy benzyl) oxy)-2-(methylthio) pyrimidine-5-carboxamide (71 mg, 0.1 mmol) dissolved in CH$_2$Cl$_2$ (10.0 mL) was added mCPBA (67 mg, 0.22 mmol, 77% in H$_2$O) at 0° C. The reaction was warmed up to rt over 2 h with vigorous stirring. After complete conversion was observed via LCMS, the reaction mixture was quenched with sat. NaHCO$_3$, then stirred vigorously for 30 min, the organic layer was separated and washed with sat. NaHCO$_3$ (aq) (3×), until all mCPBA and mCPBA impurities were removed from organic phase. The resulting organic extract was dried over MgSO4, and then concentrated under reduced pressure. The crude product 1107-A (68 mg, 92% yield) was used in next step without further purification.

LCMS: m/z [M+1]$^+$=737.2; R$_T$=1.80 min (92.7% purity)

HPLC conditions: Column: XBridge C18, 3.5 µm, 4.6×30 mm; Gradient: 5% B for 0.2 min, 5% to 100% B in 1.8 min;

100% B for 1 min; 3 mL/min. Eluent A: Milli-Q H$_2$O+10 mM ammonium formate; Eluent B: Acetonitrile.

Step two. 2-((2-(dimethylamino) ethyl) thio)-N-(4-(1-(4-methoxybenzyl)-1H-1,2,3-triazol-4-yl) phenyl)-4,6-bis((4-methoxybenzyl) oxy) pyrimidine-5-carboxamide (1107-B). To a solution of crude 1107-A (68 mg, 0.092 mmol, 92.7% purity) and dimethylamino ethane thiol (65 mg, 0.46 mmol) in anhydrous THF (3.0 mL) was added KOtBu (0.65 mL, 0.65 mmol, 1.0 M in THF) at 0° C. The reaction mixture was then warmed up to rt over 30 min, H$_2$O (10 mL) was added then extracted with EtOAc (3×~10 mL). The combined organic extracts were dried over MgSO4, and concentrated under reduced pressure; the crude product 1107-B was used in next step without further purification.

LCMS: m/z [M+1]$^+$=762.3; R$_T$=1.72 min (68% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Three. N-(4-(1H-1,2,3-triazol-4-yl) phenyl)-2-((2-(dimethylamino) ethyl) thio)-4-hydroxy-6-oxo-1,6-dihydropyrimidine-5-carboxamide (1107). To a microwave vial TFA (2.0 mL) was added to a solution of 1107-B (0.092 mmol) in CH$_2$Cl$_2$ (2.0 mL) followed by addition of TfOH (0.1 mL). The reaction was sealed and heated at 80° C. for 48 h. After complete consumption of starting material was observed via LCMS, it was cooled to rt, MeOH 10 mL was added to the reaction mixture and concentrated to remove excess of TFA. Add MeOH 10 mL two more times to co-evaporate with CH$_2$Cl$_2$ and TFA. The crude product was purified via reverse-phase chromatography (C18, gradient eluent from 0 to 35% acetonitrile in water with an ammonium bicarbonate buffer 10 mM over 30 CV) to yield impure product 1107 after lyophilization. Further purification via trituration was performed using the centrifuge. The solid was washed with water, the supernatant was removed, the sequence was repeated, then washed with acetonitrile. The resulting solid was collected and lyophilized to yield the pure product 1107 as a white solid (5.5 mg, 15% yield over 2 steps).

$^1$H NMR (400 MHz, DMSO+DCl in D$_2$O) δ 8.63 (s, 1H), 7.79 (d, J=8.2 Hz, 2H), 7.55 (d, J=8.3 Hz, 2H) 3.32 (dd, J=8.0 Hz, 4H), 2.70 (s, 6H).

LCMS: m/z [M+1]$^+$=402.1; R$_T$=1.04 min (98.2% purity)

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 26

Figure 34:
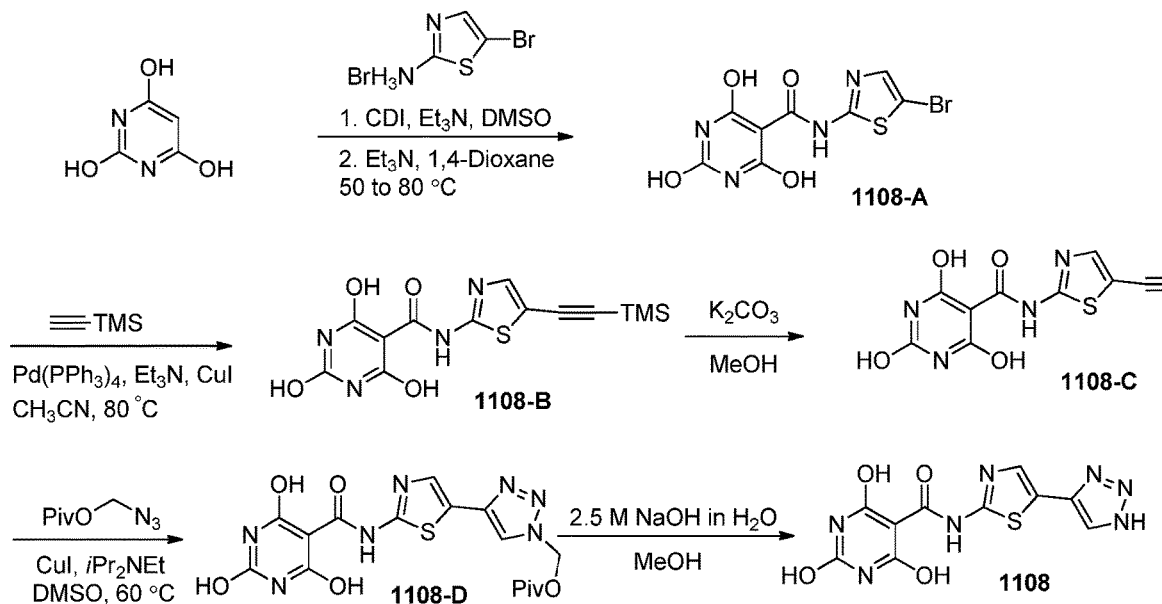
FIG. 34 illustrates the synthesis scheme described in Example 26.

Preparation of N-(5-(1H-1,2,3-Triazol-4-yl) thiazol-2-yl)-2,4,6-trihydroxypyrimidine-5-carboxamide (1108, Formula (I$_o$), with Reference to FIG. 34)

Step One. N-(5-Bromothiazol-2-yl)-2,4,6-trihydroxypyrimidine-5-carboxamide (1108-A). To a solution of 2-amino-5-bromothiazole monohydrobromide (938 mg, 3.61 mmol) in dry DMSO (3.6 mL), under inert atmosphere was added triethylamine (1.0 mL, 7.22 mmol) and CDI (1.17 g, 7.22 mmol) in one portion at room temperature. The resulting reaction mixture was stirred for 20 h to generate the corresponding isocyanate.

In a separate flask, to a suspension of barbituric acid (462 mg, 3.61 mmole) in anhydrous 1,4-dioxane (12.0 mL) at 55° C. was added triethylamine (810 μL, 7.22 mmol) and reaction mixture stirred at 55° C. for 30 minutes, then the isocyanate generated from the previous step was added. The resulting reaction mixture was heated at 80° C. for 4 h 30 min. Reaction mixture cooled to rt, then acidified with 6 M HCl, the precipitate formed was filtered and washed with H$_2$O, and MeOH to yield the product as a brown solid (899 mg, 75% yield, >99% purity).

LCMS: m/z [M+1]$^+$=333.1/335.1; R$_T$=0.99 min

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 2, 4, 6-Trihydroxy-N-(5-((trimethylsilyl) ethynyl) thiazol-2-yl) pyrimidine-5-carboxamide (1108-B). A round bottom flask containing 1108-A (899 mg, 2.71 mmol), PdCl$_2$(PPh$_3$)$_2$ (114 mg, 0.163 mmol), and CuI (21 mg, 0.108 mmol) was purged with nitrogen for 15 min. Anhydrous DMF (5.4 mL) was added, followed by trimethylsilylacetylene (760 μL, 5.42 mmol) and triethylamine (760 μL, 5.42 mmol). The reaction mixture was sealed and heated to 65° C. for 20 h. The reaction mixture was cooled to rt, filtered through a small pad of Celite. The filtrate was concentrated and purified via reverse-phase chromatography (C18, gradient eluent from 0 to 100% acetonitrile in water with an ammonium formate buffer 10 mM over 20 CV) to yield impure 1108-B as a brown solid, after lyophilization. Further purification via trituration was performed, the solid was washed with ethyl acetate and methanol. The resulting solid was collected and lyophilized to yield the pure product 1108-B as a brown solid (182 mg, 20% yield, 87.9% purity).

LCMS: m/z [M+1]$^+$=351.2; R$_T$=1.33 min (87.9% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. N-(5-Ethynylthiazol-2-yl)-2,4,6-trihydroxypyrimidine-5-carboxamide (1108-C). To a solution of crude 1108-B (182 mg, 0.457 mmol) dissolved in methanol (2.3 mL) was added potassium carbonate (12.6 mg, 0.914 mmol) at rt. The resulting reaction mixture was stirred at rt for 20 h, or until complete consumption of the starting material was observed. The reaction mixture was filtered, and the filtrate was concentrated. The crude product was used without further purification.

LCMS: m/z [M+1]$^+$=278.8; R$_T$=0.96 min (97.7% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. (4-(2-(2,4,6-trihydroxypyrimidine-5-carboxamido) thiazol-5-yl)-1H-1,2,3-triazol-1-yl) methyl pivalate (1108-D). To a solution of crude 1108-C (125 mg, 0.450 mmol) was dissolved in anhydrous DMSO (900 μL). CuI (9 mg, 0.045 mmol) was added, followed by the addition of iPr$_2$NEt (80 μL, 457 mmol) and azidomethyl pivalate (78 mg, 0.503 mmol). The resulting reaction mixture was heated to 60° C. for 20 h. The reaction mixture was then cooled to rt and then concentrated. The crude reaction mixture was triturated with ethyl acetate, the precipitate was filtered and washed with H$_2$O, MeOH, and then TBME to yield as a solid (148 mg, 67% yield over 2 steps, 88.9% purity).

LCMS: m/z [M+1]$^+$=436.0; R$_T$=1.18 min (88.9% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Five. N-(5-(1H-1,2,3-Triazol-4-yl) thiazol-2-yl)-2,4,6-trihydroxypyrimidine-5-carboxamide (1108). 2.5 M aqueous solution of NaOH (610 μL) was added to 1108-D (148 mg, 0.302 mmol, 88.9% purity) in MeOH (6.1 mL) at rt. The reaction was stirred for 10 min, and then acidified with 6 M HCl, then concentrated under reduced pressure. The crude product was purified via reverse-phase chromatography (C18, gradient eluent from 0 to 30% acetonitrile in water with an ammonium bicarbonate buffer 10 mM over 20 CV) to yield the product 1108 as a brown solid, after lyophilization (6.5 mg, 6% yield, 96.0% purity).

$^1$H NMR (400 MHz, DMSO+TFA) δ 8.85 (s, 1H), 8.60 (s, 1H).

LCMS: m/z [M+1]$^+$=321.8; R$_T$=0.82 min (96.0% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 27

Figure 35:
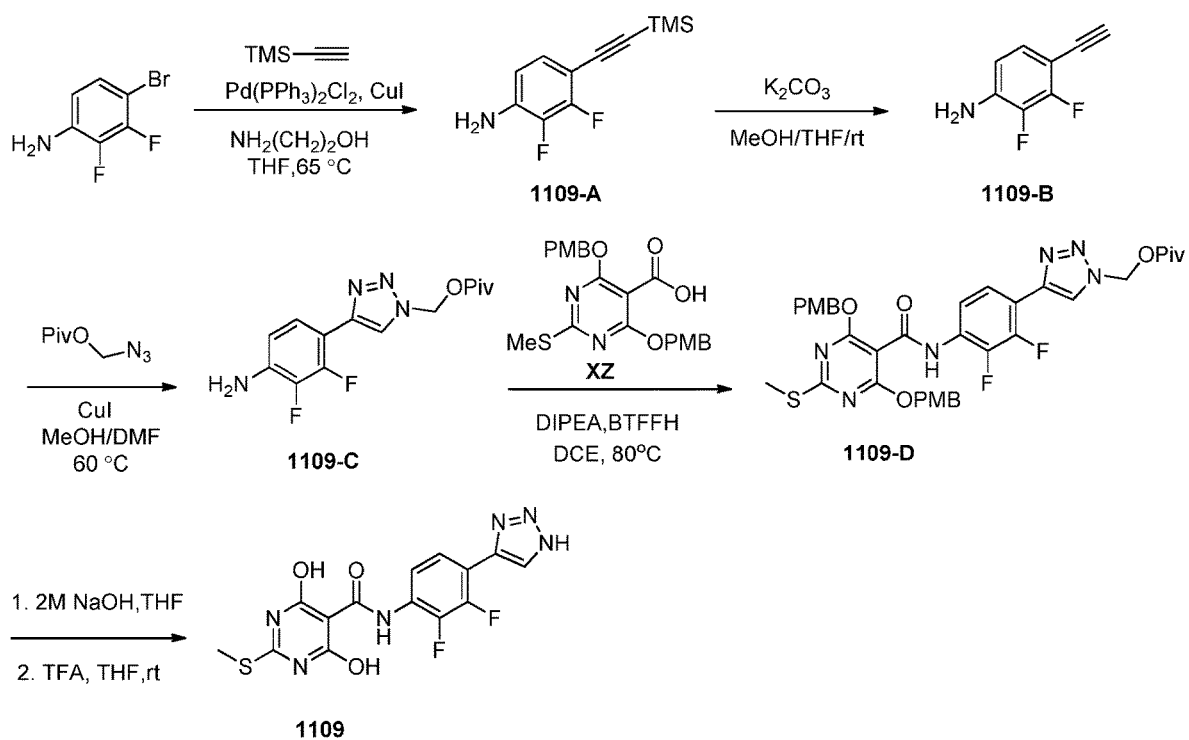
FIG. 35 illustrates the synthesis scheme described in Example 27.

Preparation of N-(2,3-difluoro-4-(1H-1,2,3-triazol-4-yl) phenyl)-4,6-dihydroxy-2-(methylthio) pyrimidine-5-carboxamide (1109, Formula (II$_{aa}$), with Reference to FIG. 35)

Step One. 2,3-difluoro-4-((trimethylsilyl)ethynyl) aniline (1109-A). A round bottom flask containing 4-bromo-2,3-difluoroaniline (1.04 g, 5.0 mmol), PdCl$_2$(PPh$_3$)$_2$ (210 mg, 0.3 mmol), and CuI (38 mg, 0.2 mmol) was purged with nitrogen for 15 min. Anhydrous THF (10.0 mL) was added, followed by trimethylsilyl acetylene (1.4 mL, 10.0 mmol) and ethanolamine (0.6 mL, 10.0 mmol). The reaction mixture was heated to 65° C. for 12 h. After completion reaction mixture was cooled to rt, filtered through a small pad of Celite. The filtrate was concentrated and used in next step without further purification.

LCMS: R$_T$=1.90 min (90% Purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Two. 4-ethynyl-2,3-difluoroaniline (1109-B). To a solution of crude 1109-A (1.1 g, 4.9 mmol) dissolved in methanol (20.0 mL) was added potassium carbonate (1.35 g, 9.8 mmol) at rt. The resulting reaction mixture was stirred at rt until complete consumption of the starting material was observed. The reaction mixture was filtered, and the filtrate was concentrated. The crude product was purified via ISCO (0 to 30% ethyl acetate in hexanes, over 20 CV) to yield the product as a yellow solid (207 mg, 77% purity).

LCMS: R$_T$=1.43 min (77.0% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Three. (4-(4-amino-2,3-difluorophenyl)-1H-1,2,3-triazol-1-yl) methyl pivalate (1109-C). To a solution of crude 1109-B (200 mg, 1.3 mmol) dissolved in anhydrous 1,4-dioxane (3.0 mL). CuI (25 mg, 0.13 mmol) was added, followed by the addition of DIPEA (0.5 mL, 2.6 mmol) and azidomethyl pivalate (250 mg, 1.56 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 1109-C as an off-white solid (208 mg, 14% yield over three steps).

LCMS: m/z [M+1]$^+$=311.1; R$_T$=1.61 min (98.2% purity)

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Four. (4-(4-(4,6-bis((4-methoxybenzyl) oxy)-2-(methylthio) pyrimidine-5-carboxamido)-2,3-difluorophenyl)-1H-1,2,3-triazol-1-yl) methyl pivalate (1109-D). Fluoro-N, N, N', N'-bis (tetramethylene) formamidinium hexafluorophosphate, BTFFH (435 mg, 1.4 mmol) and XY (383 mg, 0.825 mmol) in anhydrous 1,2 dichloroethane (5.0 mL) was added DIPEA (0.5 mL, 2.75 mmol), the resulting reaction was stirred for 30 min at rt. 1109-C (170 mg, 0.55 mmol, 98.2% purity) was added and reaction was heated to 80° C. for 16 h. After completion it was cooled to rt, and then concentrated under reduced pressure. The crude product was purified via ISCO (0 to 40% ethyl acetate in hexanes, over 20 CV) to yield the product as white solid (290 mg, 74.2% yield).

LCMS: m/z [M+1]$^+$=735.4; RT=2.18 min (98.5% purity)

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate pH: 3.8; Eluent B: Acetonitrile.

Step Five. N-(2,3-difluoro-4-(1H-1,2,3-triazol-4-yl) phenyl)-4,6-dihydroxy-2-(methylthio) pyrimidine-5-carboxamide (1109). 2.0 M aqueous solution of NaOH (3.0 mL) was added to 1109-D (290 mg, 0.4 mmol) in THF: MeOH (6.0 mL) at rt. The reaction mixture was stirred for 1 h, and then concentrated and co-evaporated with MeOH to obtained intermediate crude product which was re-dissolved in THF (2.0 mL), followed by the addition of TFA (2.0 mL) at rt and allowed to stir for 2 h. After complete consumption of starting material was observed via LCMS, MeOH 10 mL was added to the mixture. The resulting mixture was concentrated to get crude product. The crude product was purified via reverse-phase chromatography (C18, gradient eluent from 0 to 35% acetonitrile in water with an ammonium bicarbonate buffer 10 mM over 30 CV) followed by lypholization to yield 1109 as white solid (21.0 mg, 14% yield).

$^1$H NMR (400 MHz, CDCl3+TFA): δ 8.63 (s, 1H), 8.28 (t, J=7.3 Hz, 1H), 7.69 (t, J=8.4 Hz, 1H), 2.80 (s, 3H).

LCMS: m/z [M+1]+=381.0; RT=0.89 min (99.07% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium bicarbonate; Eluent B: Acetonitrile.

Example 28

Figure 36:
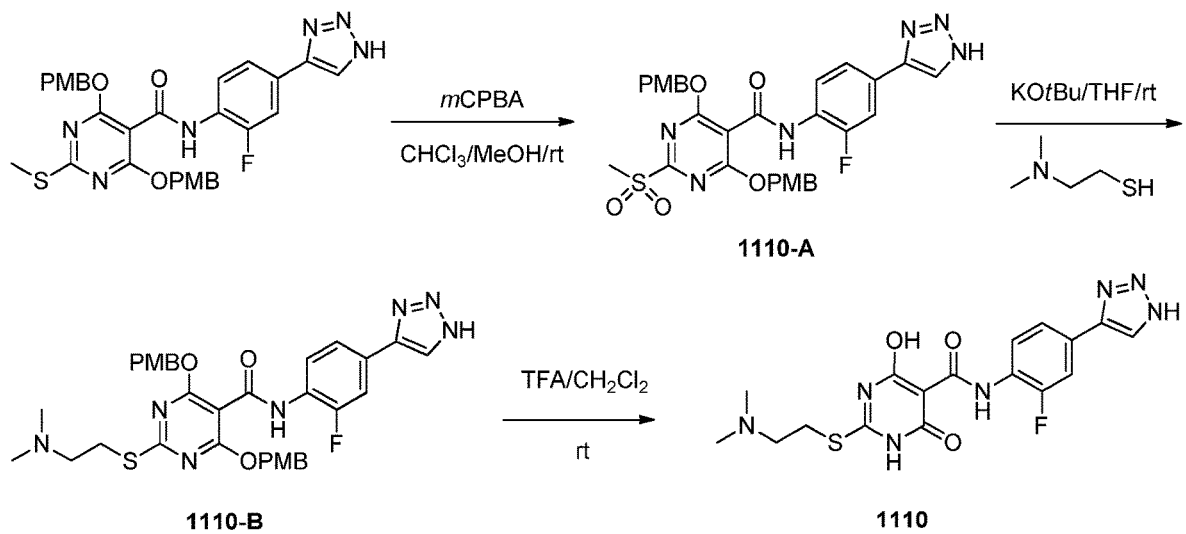
FIG. 36 illustrates the synthesis scheme described in Example 28.

Preparation of 2-((2-(dimethylamino) ethyl) thio)-N-(2-fluoro-4-(1H-1,2,3-triazol-4-yl) phenyl) 4-hydroxy-6-oxo-1,6-dihydropyrimidine-5-carboxamide (1110, Formula (II$_{bb}$), with Reference to FIG. 36)

Step one. N-(2-fluoro-4-(1H-1,2,3-triazol-4-yl) phenyl)-4,6-bis((4-methoxybenzyl) oxy)-2-(methylsulfonyl) pyrimidine-5-carboxamide (1110-A). To a solution of N-(2-fluoro-4-(1H-1,2,3-triazol-4-yl) phenyl)-4,6-bis((4-methoxybenzyl) oxy)-2-(methylthio) pyrimidine-5-carboxamide (182 mg, 0.217 mmol, 67% purity) dissolved in CHCl$_3$ (7.0 mL) was added mCPBA (158 mg, 0.912 mmol, 77% in H2O) at 0° C. The reaction was warmed up to rt over 20 h with vigorous stirring. After complete conversion was observed via LCMS, the reaction mixture was quenched with sat. NaHCO$_3$, then stirred vigorously for 30 min, the organic layer was separated and washed with sat. NaHCO$_3$ (aq) (3×), until all mCPBA and mCPBA impurities were removed from organic phase. The resulting organic extract was dried over MgSO4, and then concentrated under reduced pressure. The crude product 1110-A was used in next step without further purification.

LCMS: m/z [M+1]+=635.2; $R_T$=1.64 min (62% purity)

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step two. 2-((2-(dimethylamino) ethyl) thio)-N-(2-fluoro-4-(1H-1,2,3-triazol-4-yl) phenyl)-4,6-bis((4-methoxybenzyl) oxy) pyrimidine-5-carboxamide (1110-B). To a solution of crude 1110-A (258 mg, 0.4 mmol, 60% purity) and dimethylamino ethane thiol (283 mg, 2.0 mmol) in anhydrous THF (5.0 mL) was added KOtBu (2.8 mL, 2.8 mmol, 1.0 M in THF) at 0° C. The reaction mixture was then warmed up to rt over 40 min, H$_2$O (10 mL) was added then extracted with EtOAc (3×~10 mL). The combined organic extracts were dried over MgSO4, and concentrated under reduced pressure; the crude product 1110-B was used in next step without further purification.

LCMS: m/z [M+1]$^+$=660.2; $R_T$=1.46 min (68% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. 2-((2-(dimethylamino) ethyl) thio)-N-(2-fluoro-4-(1H-1,2,3-triazol-4-yl) phenyl)-4-hydroxy-6-oxo-1,6-dihydropyrimidine-5-carboxamide (1110). TFA (2.0 mL) was added to a solution of 1110-B (0.4 mmol) in CH$_2$Cl$_2$ (2.0 mL) and the reaction was stirred at rt for 3 h. After complete consumption of starting material was observed via LCMS, MeOH 10 mL was added to the reaction mixture and concentrated to remove excess of TFA. Add MeOH 10 mL two more times to co-evaporate CH$_2$Cl$_2$ and TFA. The crude product was purified via reverse-phase chromatography (C18, gradient eluent from 0 to 35% acetonitrile in water with an ammonium bicarbonate buffer 10 mM over 30 CV) to yield impure product 1110 after lyophilization. Further purification via trituration was performed using the centrifuge. The solid was washed with water, the supernatant was removed, the sequence was repeated, then washed with acetonitrile. The resulting solid was collected and lyophilized to yield the pure product 1110 as a white solid (12.0 mg, 12% yield over 3 steps).

1H NMR (400 MHz, DMSO+TFA): δ 9.56 (s, 1H), 8.37 (s, 1H) 8.31 (t, J=8.5 Hz, 1H), 7.80 (d, J=11.6 Hz, 1H), 7.73 (d, J=8.5 Hz, 1H) 3.47 (m, 4H), 2.84 (s, 6H).

LCMS: m/z [M+1]+=420.0; $R_T$=1.09 min (95.6% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Example 29

Figure 37:
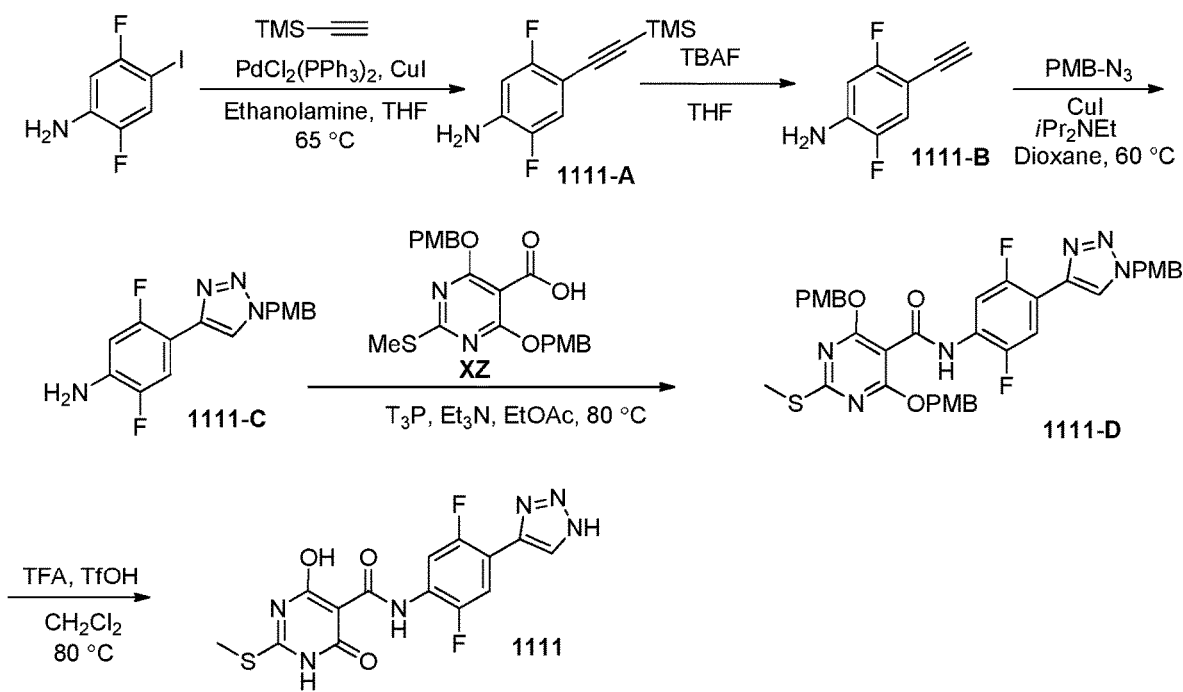
FIG. 37 illustrates the synthesis scheme described in Example 29.

Preparation of N-(2,5-Difluoro-4-(1H-1,2,3-triazol-4-yl) phenyl)-4-hydroxy-2-(methylthio)-6-oxo-1,6-dihydropyrimidine-5-carboxamide (1111, Formula (II$_{cc}$), with Reference to FIG. 37)

Step One. 2,5-Difluoro-4-((trimethylsilyl)ethynyl) aniline (1111-A). A round bottom flask containing 2,5-difluoro-4-iodoaniline (1.20 g, 4.61 mmol), PdCl$_2$(PPh$_3$)$_2$ (194 mg, 0.277 mmol), and CuI (35 mg, 0.184 mmol) was purged with nitrogen for 15 min. Anhydrous THF (9.2 mL) was added, followed by trimethylsilyl acetylene (1.3 mL, 9.22 mmol) and ethanolamine (556 µL, 9.22 mmol). The reaction mixture was sealed and heated to 65° C. for 2 h. The reaction mixture was cooled to rt, filtered through a small pad of Celite. The filtrate was concentrated and used without further purification.

LCMS: m/z [M+1]$^+$=226.2; $R_T$=1.87 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Two. 4-Ethynyl-2,5-difluoroaniline (1111-B). Crude 1111-A (2.31 mmol) was dissolved in THF (4.6 mL) and to this solution was added TBAF (4.6 mL, 1 M in THF). The reaction was stirred at rt for 10 min and THF was removed in vacuo. The crude was dissolved in EtOAc and this solution was passed through a pad of silica and washed with EtOAc. The filtrate was concentrated and the crude product was used without further purification.

LCMS: $R_T$=1.43 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Three. 2,5-difluoro-4-(1-(4-methoxybenzyl)-1H-1,2,3-triazol-4-yl) aniline (1111-C). To a solution of crude 1111-B (2.31 mmol) was dissolved in anhydrous 1,4-dioxane (4.6 mL). CuI (44 mg, 0.231 mmol) was added, followed by the addition of iPr$_2$NEt (400 V L, 2.31 mmol) and p-methoxylbenzyl pivalate (377 mg, 2.31 mmol). The resulting reaction mixture was heated to 60° C. for 20 h. The reaction mixture was then cooled to rt and then concentrated. The crude reaction mixture was purified via ISCO (SiO2, 0 to 50% ethyl acetate in hexanes, over 20 CV) to yield the product as an orange foam (352 mg, 43% yield over 3 steps, 89.3% purity).

LCMS: m/z [M+1]$^+$=317.3; $R_T$=1.50 min (89.3% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Four. N-(2,5-Difluoro-4-(1-(4-methoxybenzyl)-1H-1,2,3-triazol-4-yl) phenyl)-4,6-bis((4-methoxybenzyl) oxy)-2-(methylthio) pyrimidine-5-carboxamide (1111-D). T$_3$P (3.4 mL, 5.70 mmol, 50% in EtOAc) was added to a mixture of 1111-C (336 mg, 0.950 mmol), triethylamine (1.2 mL, 8.55 mmol) and XZ (594 mg, 1.24 mmol) in EtOAc (4.8 mL). The reaction was heated at 80° C. overnight. After complete consumption of starting material was observed via LCMS, the mixture was concentrated. TBME was added to the residue, and sonicated, the solid was filtered and washed with H$_2$O and TBME to yield the title compound as a light brown solid (575 mg, 40% yield, 82.1% purity).

LCMS: m/z [M+1]$^+$=741.1; $R_T$=2.13 min (82.1% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Five. N-(2,5-difluoro-4-(1H-1,2,3-triazol-4-yl) phenyl)-4-hydroxy-2-(methylthio)-6-oxo-1,6-dihydropyrimidine-5-carboxamide (1111). TfOH (90 µL) was added to a solution of 1111-D (210 mg, 0.252 mmol) in TFA (1.5 mL) and 1,2-dichloroethane (5.0 mL). The reaction was heated at 80° C. for 20 h in a sealed pressure vessel. After complete consumption of starting material was observed via LCMS, MeOH 10 mL was added to the mixture. The resulting mixture was concentrated to remove CH$_2$Cl$_2$ and TFA. Add MeOH 10 mL two more times to co-evaporate with CH$_2$Cl$_2$ and TFA. The crude product was purified via reverse-phase chromatography (C18, gradient eluent from 0 to 30% acetonitrile in water with an ammonium bicarbonate buffer 10 mM over 30 CV) to yield the product 1111 as a white solid (25.4 mg, 26% yield, 96.7% purity) after lyophilization.

$^1$H NMR (400 MHz, CDCl$_3$+TFA) δ 8.63 (s, 1H), 8.50-8.41 (m, 1H), 7.72 (s, 1H), 2.77 (s, 3H).

LCMS: m/z [M+1]$^+$=381.0; R$_T$=1.46 min (96.7% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 30

Figure 38:
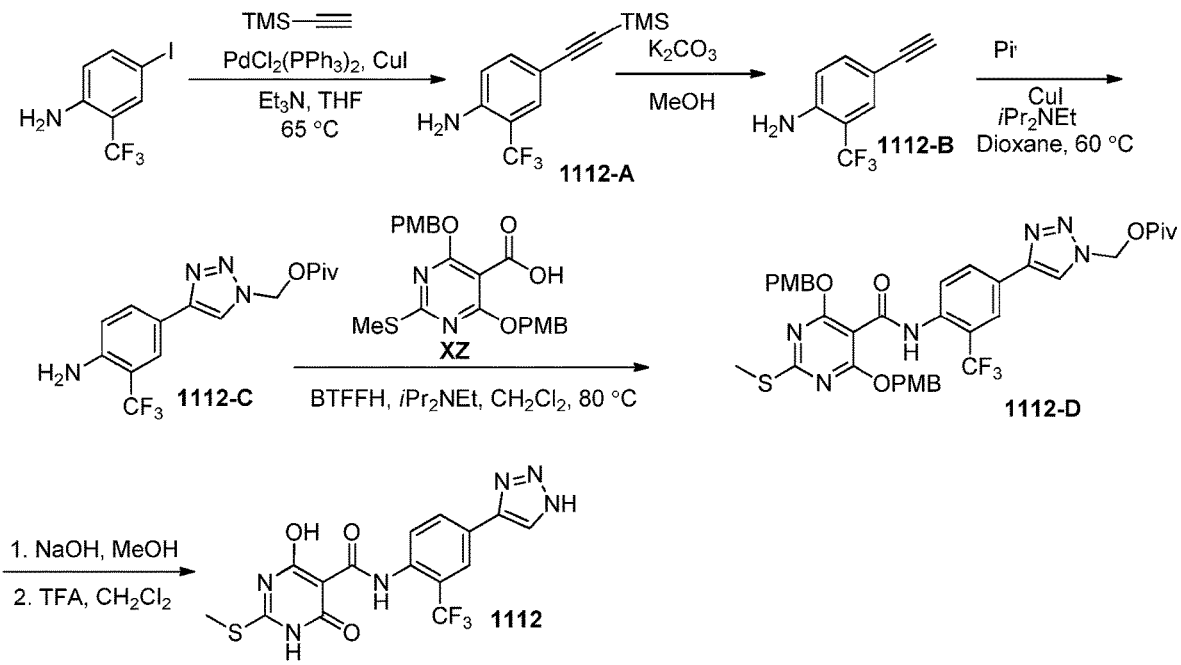
FIG. 38 illustrates the synthesis scheme described in Example 30.

Preparation of N-(4-(1H-1,2,3-triazol-4-yl)-2-(trifluoromethyl) phenyl)-4-hydroxy-2-(methyl thio)-6-oxo-1,6-dihydropyrimidine-5-carboxamide (1112, Formula (II$_{dd}$), with Reference to FIG. 38)

Step One. 2-(Trifluoromethyl)-4-((trimethylsilyl)ethynyl) aniline (1112-A). A round bottom flask containing 4-iodo-2-(trifluoromethyl) aniline (280 mg, 2.02 mmol), PdCl$_2$ (PPh$_3$)$_2$ (84 mg, 0.12 mmol), and CuI (30 mg, 0.16 mmol) was purged with nitrogen for 15 min. Anhydrous THF (4.0 mL) was added, followed by trimethylsilyl acetylene (570 μL, 4.04 mmol) and triethylamine (560 μL, 4.04 mmol). The reaction mixture was sealed and heated to 65° C. for 20 h. The reaction mixture was cooled to rt, filtered through a small pad of Celite. The filtrate was concentrated and used without further purification.

LCMS: R$_T$=2.08 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Two. 4-Ethynyl-2-(trifluoromethyl) aniline (1112-B). To a solution of crude 1112-A (2.02 mmol) dissolved in methanol (4.0 mL) was added potassium carbonate (558 mg, 4.04 mmol) at rt. The resulting reaction mixture was stirred at rt until complete consumption of the starting material was observed. The reaction mixture was filtered, and the filtrate was concentrated. The crude product was purified via ISCO (0 to 30% ethyl acetate in hexanes, over 20 CV) to yield the product as a yellow solid (280 mg, 74% yield over 2 steps, 98.6% purity).

LCMS: R$_T$=1.64 min (98.6% Purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Three. (4-(4-Amino-3-(trifluoromethyl) phenyl)-1H-1,2,3-triazol-1-yl) methyl pivalate (1112-C). To a solution of 1111-B (280 mg, 1.51 mmol) was dissolved in anhydrous 1,4-dioxane (3.0 mL). CuI (29 mg, 0.151 mmol) was added, followed by the addition of iPr$_2$NEt (260 μL, 1.51 mmol) and azidomethyl pivalate (261 mg, 1.66 mmol). The resulting reaction mixture was heated to 60° C. for 20 h. The reaction mixture was then cooled to rt and then concentrated. The crude product was purified via ISCO (SiO$_2$, 0 to 50% ethyl acetate in hexanes over 20 CV) to yield the product as an off-white solid (370 mg, 70% yield, 97.0% purity).

LCMS: m/z [M+1]$^+$=343.2; R$_T$=1.70 min (97.0% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Four. (4-(4-(4,6-Bis ((4-methoxy benzyl) oxy)-2-(methylthio) pyrimidine-5-carboxamido)-3-(trifluoromethyl) phenyl)-1H-1,2,3-triazol-1-yl) methyl pivalate (1112-D). Fluoro-N, N, N', N'-bis (tetramethylene) formamidinium hexafluorophosphate, BTFFH (85 mg, 0.270 mmol) and XY (111 mg, 0.230 mmol) in anhydrous dichloromethane (1.5 mL) was added iPr$_2$Net (120 μL, 0.88 mmol), the resulting reaction was stirred for 30 min at rt. 1112-C (50 mg, 0.150 mmol, 97.0% purity) was added then sealed in a pressure vessel heated to 80° C. for 24 h. The reaction mixture was cooled to rt, and then concentrated under reduced pressure. The crude product was purified via ISCO (0 to 40% ethyl acetate in hexanes, over 20 CV) to yield the product as an off-white solid (62 mg, 46% yield, 84.8% purity).

LCMS: m/z [M+1]$^+$=767.3; R$_T$=2.19 min(84.8% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Five. (4-(4-(4,6-Bis ((4-methoxy benzyl) oxy)-2-(methylthio) pyrimidine-5-carboxamido)-3-(trifluoromethyl) phenyl)-1H-1,2,3-triazol-1-yl) methyl pivalate (1112). 2.5 M Aqueous solution of NaOH (690 μL) was added to 1112-D (62 mg, 0.0686 mmol, 84.8% purity) in THF (1.4 mL) at rt. The reaction was stirred for 20 h, and then co-evaporated with ethyl acetate. The crude product was sonicated with ethyl acetate, and then filtered, the precipitate was washed with EtOAc, then collected.

The intermediate was added CH$_2$Cl$_2$ (1.4 mL), followed by the addition of TFA (400 μL) at rt. The reaction was stirred at rt for 15 min. After complete consumption of starting material was observed via LCMS, MeOH 10 mL was added to the mixture. The resulting mixture was concentrated to remove CH$_2$Cl$_2$ and TFA. Add MeOH 10 mL two more times to co-evaporate with CH$_2$Cl$_2$ and TFA. The crude product was purified via trituration was performed using the centrifuge. The solid was washed with water, the supernatant was removed, and the sequence was repeated, and then washed with acetonitrile. The resulting solid was collected and lyophilized to yield the pure product 1112 as an off-white solid (18.4 mg, 63% yield over 2 steps, 95.4% purity).

$^1$H NMR (400 MHz, CDCl$_3$+TFA) δ 8.65 (d, J=1.1 Hz, 1H), 8.36 (d, J=8.6 Hz, 1H), 8.17 (s, 1H), 8.07 (d, J=8.9 Hz, 1H), 2.83 (s, 3H).

LCMS: m/z [M+1]$^+$=413.2; R$_T$=1.41 min(95.4% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Example 31

Figure 39:
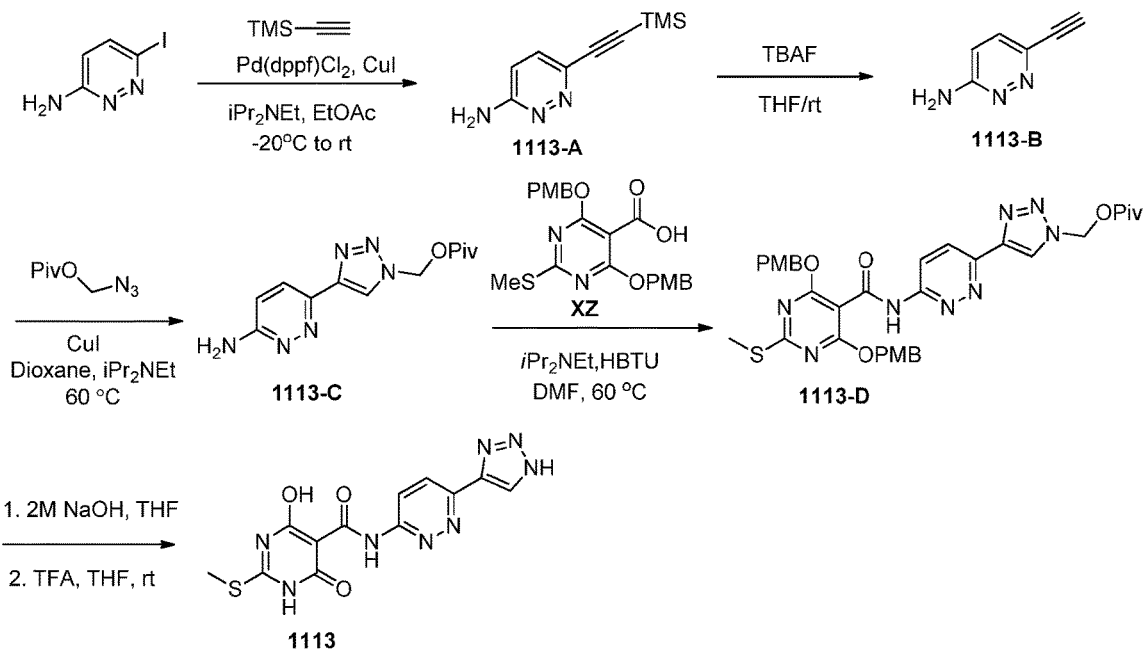
FIG. 39 illustrates the synthesis scheme described in Example 31.

Preparation of N-(6-(1H-1,2,3-triazol-4-yl) pyridazin-3-yl)-4-hydroxy-2-(methylthio)-6-oxo-1,6-dihydropyrimidine-5-carboxamide (1113, Formula (II$_{kk}$), with Reference to FIG. 39)

Step One. 6-((trimethylsilyl)ethynyl) pyridazin-3-amine (1113-A). A round bottom flask containing 6-iodopyridazin-3-amine (1.1 g, 5.0 mmol), trimethylsilyl acetylene (3.58 mL, 25.0 mmol) and CuI (380 mg, 2.0 mmol) was dissolved in EtOAc (30.0 mL) and purged with nitrogen for 15 min. Reaction mixture was then cooled at −20° C. and PdCl$_2$ (dppf) (732 mg, 1 mmol), DIPEA (1.75 mL, 10.0 mmol) was added. After 10 min The reaction mixture was brought to rt and stirred for 12 h. After completion reaction mixture was filtered through a small pad of Celite. The filtrate was concentrated and Purified via silica gel column chromatography using 0 to 5% MeOH in DCM as eluent to obtained 1113-A as off-white solid (680 mg, 70% Yield).

LCMS: m/z [M+1]+=192.0; $R_T$=1.41 min (95.1% Purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 6-ethynylpyridazin-3-amine (1113-B). To a solution of 1113-A (680 mg, 3.6 mmol) dissolved in THF (15.0 mL) was added TBAF (7.2 mL, 7.2 mmol, 1M In THF) at rt. The resulting reaction mixture was stirred at rt until complete consumption of the starting material was observed. The reaction mixture was concentrated. The crude product was purified via ISCO (0 to 30% MeOH in DCM, over 20 CV) to yield the product as a brown solid (380 mg, 89.8% yield).

LCMS: m/z [M+1]+=120.4; $R_T$=0.31 min (99.2% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. (4-(6-aminopyridazin-3-yl)-1H-1,2,3-triazol-1-yl) methyl pivalate (1113-C). To a solution of 1113-B (198 mg, 1.7 mmol) dissolved in anhydrous 1,4-dioxane (5.0 mL). CuI (33 mg, 0.17 mmol) was added, followed by the addition of DIPEA (0.6 mL, 3.4 mmol) and azidomethyl pivalate (321 mg, 2.0 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 1113-C as brown solid (328 mg, 71% yield).

LCMS: m/z [M+1]+=277.3; $R_T$=1.18 min (95.2% purity)

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Four. (4-(6-(4,6-bis((4-methoxybenzyl) oxy)-2-(methylthio) pyrimidine-5-carboxamido) pyridazin-3-yl)-1H-1,2,3-triazol-1-yl) methyl pivalate (1113-D). To a stirred solution of HBTU (380 mg, 1.0 mmol) and XY (443 mg, 1.0 mmol) dissolved in anhydrous DMF (5.0 mL) was added DIPEA (0.49 mL, 2.8 mmol), the resulting reaction was stirred for 30 min at rt. 1113-C (138 mg, 0.5 mmol) was added then reaction mixture was heated to 60° C. for 16 h. reaction mixture was cooled to rt, and then concentrated under reduced pressure. The crude product was purified via ISCO (0 to 40% ethyl acetate in hexanes, over 20 CV) to yield the product as white solid (60 mg, 78% purity).

LCMS: m/z [M+1]+=701.3; $R_T$=2.07 min(78.0% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate pH: 3.8; Eluent B: Acetonitrile.

Step Five. N-(6-(1H-1,2,3-triazol-4-yl) pyridazin-3-yl)-4-hydroxy-2-(methylthio)-6-oxo-1,6-dihydropyrimidine-5-carboxamide (1113). 2.0 M Aqueous solution of NaOH (2.0 mL) was added to 1113-D (60 mg, 0.06 mmol, 78.0% purity) in THF: MeOH (3.0 mL, 1:1) at rt. The reaction mixture was stirred for 1 h, and then concentrated and evaporated with MeOH to obtained intermediate crude product which was dissolved in CH2Cl2 (3.0 mL), followed by the addition of TFA (2.0 mL) at rt. The reaction was stirred at rt for 30 min.

After complete consumption of starting material was observed via LCMS, MeOH 10 mL was added to the mixture. The resulting mixture was concentrated to remove CH2Cl2 and TFA. Add MeOH 10 mL two more times to co-evaporate CH2Cl2 and TFA. The crude product was purified via trituration using the centrifuge. The solid was washed with water, the supernatant was removed, and the sequence was repeated, and then washed with acetonitrile. The resulting solid was collected and lyophilized to yield the pure product 1113 as an off-white solid (4.8 mg, 22% yield over 2 steps).

1H NMR (400 MHz, 1M K2CO3 in D2O): δ 8.28 (d, J=9.6 Hz, 1H), 8.01 (s, 1H), 7.91 (d, J=9.0 Hz, 1H), 2.18 (s, 3H).

LCMS: m/z [M+1]+=347.0; $R_T$=1.20 min (97.8% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Example 32

Figure 40:
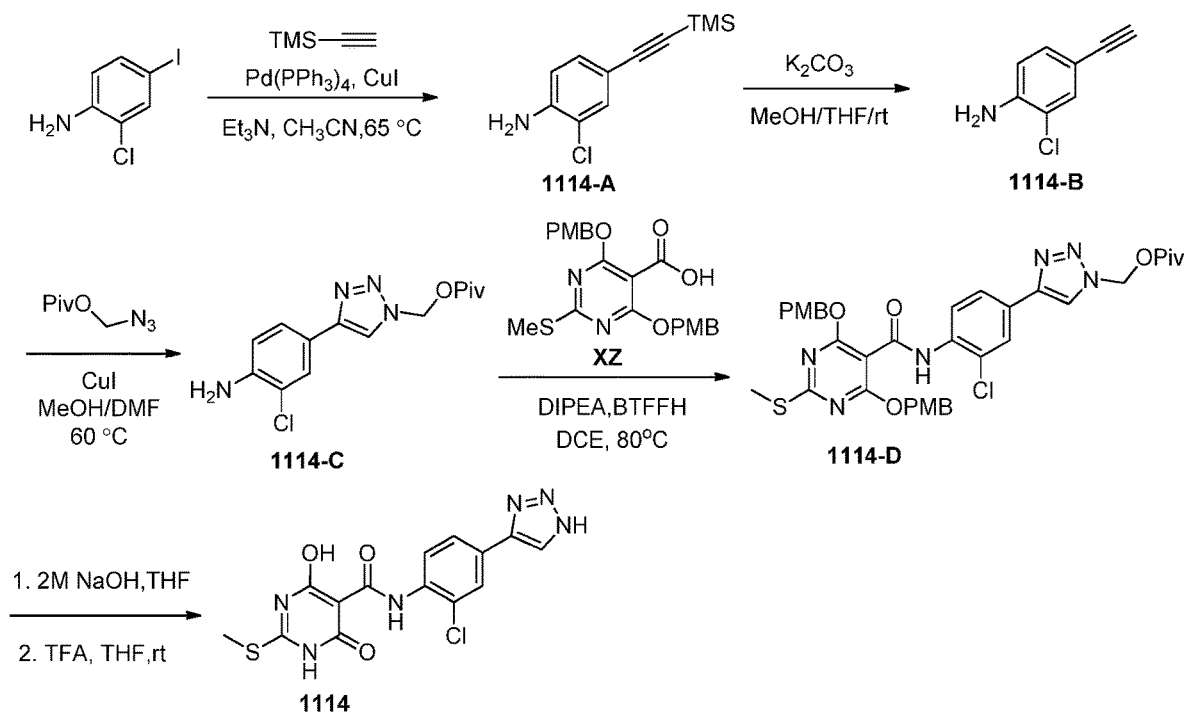
FIG. 40 illustrates the synthesis scheme described in Example 32.

Preparation of N-(2-chloro-4-(1H-1,2,3-triazol-4-yl) phenyl)-4-hydroxy-2-(methylthio)-6-oxo-1,6-dihydropyrimidine-5-carboxamide (1114, Formula (II$_{ee}$), with Reference to FIG. 40)

Step One. 2-chloro-4-((trimethylsilyl)ethynyl) aniline (1114-A). A round bottom flask containing 2-chloro-4-iodoaniline (1.27 g, 5.0 mmol), Pd(PPh3)4 (115 mg, 0.1 mmol), and CuI (38 mg, 0.2 mmol) was purged with nitrogen for 15 min. Anhydrous CH3CN (10.0 mL) was added, followed by trimethylsilyl acetylene (0.8 mL, 5.5 mmol) and triethylamine (2.1 mL, 15.0 mmol). The reaction mixture was heated to 65° C. for 12 h. After completion reaction mixture was cooled to rt, filtered through a small pad of Celite. The filtrate was concentrated and used in next step without further purification.

LCMS: $R_T$=2.02 min (97.7% Purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 2-chloro-4-ethynylaniline (1114-B). To a solution of crude 1114-A (1.32 g, 5.9 mmol) dissolved in methanol (20.0 mL) was added potassium carbonate (1.63 g, 11.8 mmol) at rt. The resulting reaction mixture was stirred at rt until complete consumption of the starting material was observed. The reaction mixture was filtered, and the filtrate was concentrated. The crude product was purified via ISCO (0 to 30% ethyl acetate in hexanes, over 20 CV) to yield the product as a yellow solid (580 mg, 77% yield over 2 steps).

LCMS: $R_T$=1.55 min (97.9% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. (4-(4-amino-3-chlorophenyl)-1H-1,2,3-triazol-1-yl) methyl pivalate (1114-C). To a solution of 1114-B (303 mg, 2.0 mmol) dissolved in anhydrous 1,4-dioxane (5.0 mL). CuI (38 mg, 0.2 mmol) was added, followed by the addition of DIPEA (0.7 mL, 4.0 mmol) and azidomethyl pivalate (377 mg, 2.4 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 1114-C as an off-white solid (521 mg, 84% yield). LCMS: m/z [M+1]$^+$=309.2; $R_T$=1.62 min (87.7% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Four. (4-(4-(4,6-bis((4-methoxybenzyl) oxy)-2-(methyl thio) pyrimidine-5-carboxamido)-3-chlorophenyl)-1H-1,2,3-triazol-1-yl) methyl pivalate (1114-D). Fluoro-N, N, N', N'-bis (tetramethylene) formamidinium hexafluorophosphate, BTFFH (316 mg, 1.0 mmol) and XY (443 mg, 1.0 mmol) in anhydrous 1,2 dichloroethane (4.0 mL) was added DIPEA (0.49 mL, 2.8 mmol), the resulting reaction was stirred for 30 min at rt. 1114-C (206 mg, 0.7 mmol, 87.7% purity) was added then sealed tube and heated to 80° C. for 16 h. The reaction mixture was cooled to rt, and then concentrated under reduced pressure. The crude product was purified via ISCO (0 to 40% ethyl acetate in hexanes, over 20 CV) to yield the product as an off-white solid (100 mg, 21% yield, 85% purity).

LCMS: m/z [M+1]$^+$=734.3; $R_T$=2.19 min(85.0% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate pH: 3.8; Eluent B: Acetonitrile.

Step Five. N-(2-chloro-4-(1H-1,2,3-triazol-4-yl) phenyl)-4-hydroxy-2-(methylthio)-6-oxo-1,6-dihydropyrimidine-5-carboxamide (1114). 2.0 M Aqueous solution of NaOH (2.0 mL) was added to 1114-D (100 mg, 0.12 mmol, 85.0% purity) in THF: MeOH (3.0 mL, 1:1) at rt. The reaction mixture was stirred for 1 h, and then concentrated and evaporated with MeOH to obtained intermediate crude product which was dissolved in CH$_2$Cl$_2$ (3.0 mL), followed by the addition of TFA (2.0 mL) at rt. The reaction was stirred at rt for 30 min. After complete consumption of starting material was observed via LCMS, MeOH 10 mL was added to the mixture. The resulting mixture was concentrated to remove CH$_2$Cl$_2$ and TFA. Add MeOH 10 mL two more times to co-evaporate CH$_2$Cl$_2$ and TFA. The crude product was purified via trituration using the centrifuge. The solid was washed with water, the supernatant was removed, and the sequence was repeated, and then washed with acetonitrile. The resulting solid was collected and lyophilized to yield the pure product 1114 as an off-white solid (7.0 mg, 16% yield over 2 steps, 95.2% purity). 1H NMR (400 MHz, 1M K$_2$CO$_3$ in D$_2$O): δ 7.97 (d, J=8.8 Hz, 1H), 7.75 (s, 1H), 7.66 (s, 1H), 7.47 (d, J=9.1 Hz, 1H), 2.18 (s, 3H).

LCMS: m/z [M+1]$^+$=379.2; $R_T$=1.20 min (95.2% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Example 33

Figure 45:
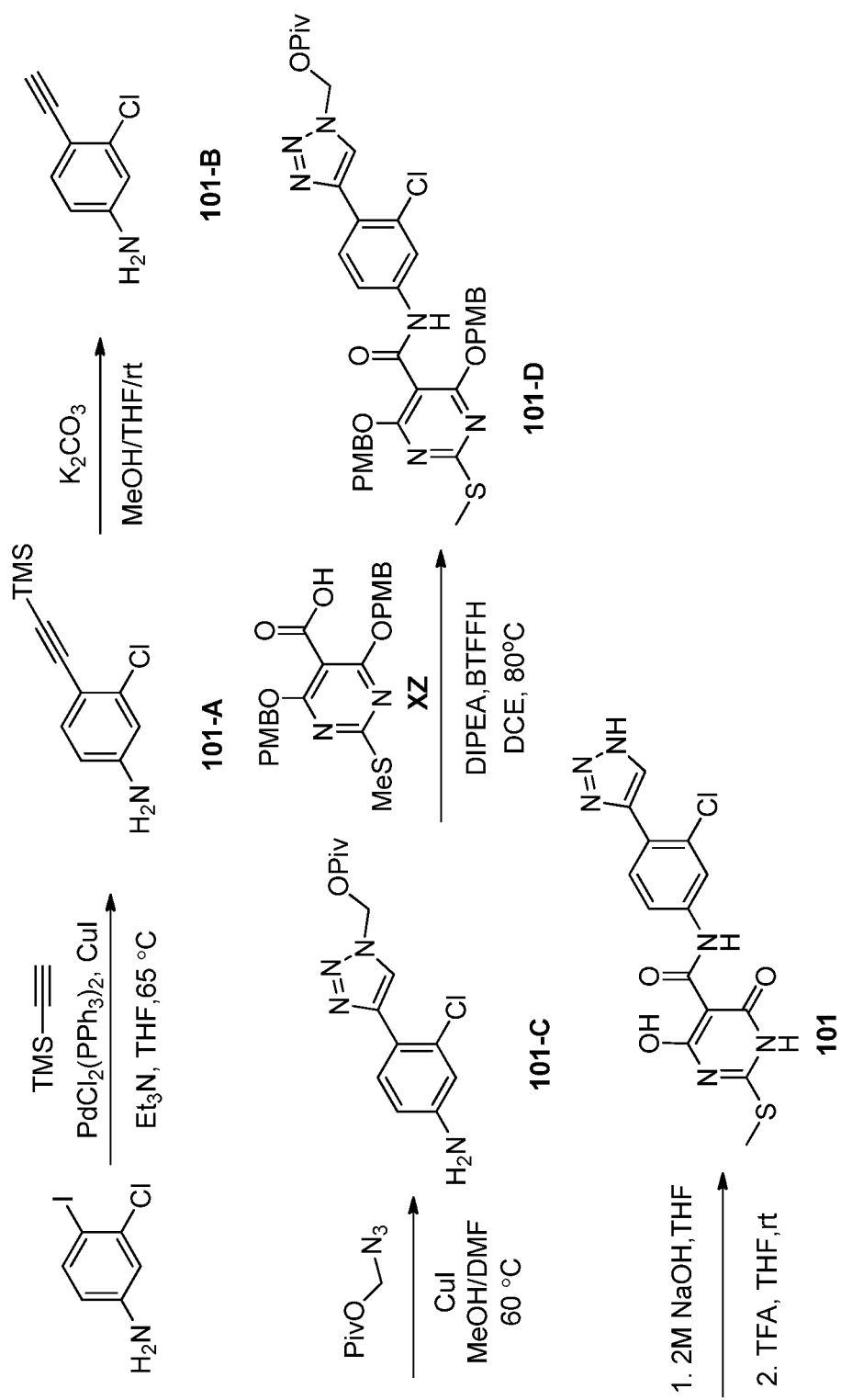
FIG. 45 illustrates the synthesis scheme described in Example 33.

Preparation of N-(3-chloro-4-(1H-1,2,3-triazol-4-yl) phenyl)-4-hydroxy-2-(methylthio)-6-oxo-1,6-dihydropyrimidine-5-carboxamide (101) (a Compound Having a Structure Represented by Formula II$_2$, with Reference to Synthesis Illustrated in FIG. 45)

Step One. 3-chloro-4-((trimethylsilyl)ethynyl) aniline (101-A): A round bottom flask containing 3-chloro-4-iodoaniline (1.27 g, 5.0 mmol), PdCl$_2$(PPh$_3$)$_2$ (175 mg, 0.1 mmol), and CuI (38 mg, 0.2 mmol) was purged with nitrogen for 15 min. Anhydrous THF (10.0 mL) was added, followed by trimethylsilyl acetylene (1.4 mL, 10.0 mmol) and triethylamine (1.4 mL, 10.0 mmol). The reaction mixture was heated to 65° C. for 12 h. After completion reaction mixture was cooled to rt, filtered through a small pad of Celite. The filtrate was concentrated to get crude product which was purified by using column chromatography using hexane: EtOAc (0 to 100% gradient) to yield (1.01 g, 90%) of product 101-A.

LCMS: $R_T$=1.95 min (98% Purity). HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 3-chloro-4-ethynylaniline (101-B): To a solution of 101-A (0.446 g, 2.0 mmol) dissolved in THF (3.0 mL) was added 1M solution of TBAF (3.0 ml, 3.0 mmol) at rt. The resulting reaction mixture was stirred at rt until complete consumption of the starting material was observed. The reaction mixture was quenched with water and extracted with EtOAc and then concentrated. The crude product was used in next step without any purification.

LCMS: m/z [M+1]$^+$=152.1; $R_T$=1.40 min (97.9% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. (4-(4-amino-2-chlorophenyl)-1H-1,2,3-triazol-1-yl) methyl pivalate (101-C): To a solution of 101-B (303 mg, 2.0 mmol) dissolved in anhydrous 1,4-dioxane (5.0 mL). CuI (38 mg, 0.2 mmol) was added, followed by the addition of DIPEA (0.7 mL, 4.0 mmol) and azidomethyl pivalate (377 mg, 2.4 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 101-C as an off-white solid (210 mg, 34% yield over two steps).

LCMS: m/z [M+1]$^+$=309.2; $R_T$=1.60 min (91% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Four. (4-(4-(4,6-bis((4-methoxybenzyl) oxy)-2-(methylthio) pyrimidine-5-carboxamido)-2-chlorophenyl)-1H-1,2,3-triazol-1-yl) methyl pivalate (101-D): Fluoro-N, N, N', N'-bis (tetramethylene) formamidinium hexafluorophosphate, BTFFH (400 mg, 1.25 mmol) and XY (350 mg, 0.75 mmol) in anhydrous 1,2 dichloromethane (3.0 mL) was added DIPEA (0.4 mL, 2.5 mmol), the resulting reaction was stirred for 30 min at rt. 101-C (160 mg, 0.5 mmol, 91% purity) was added in a sealed tube and heated to 80° C. for 16 h. The reaction mixture was cooled to rt, and then concentrated under reduced pressure. The crude product was purified via ISCO (0 to 40% ethyl acetate in hexanes, over 20 CV) to yield 101-D as an off-white solid (138 mg, 35% yield).

LCMS: m/z [M]$^+$=733.5; $R_T$=2.16 min (95.2% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate pH: 3.8; Eluent B: Acetonitrile.

Step Five. N-(2-chloro-4-(1H-1,2,3-triazol-4-yl) phenyl)-4-hydroxy-2-(methylthio)-6-oxo-1,6-dihydropyrimidine-5-carboxamide (101): 2.0 M Aqueous solution of NaOH (0.75 mL) was added to 101-D (108 mg, 0.15 mmol, 91.0% purity) in MeOH (2.0 mL) at rt. The reaction mixture was stirred for 1 h, and then concentrated and evaporated with MeOH to obtained intermediate crude product which was dissolved in $CH_2Cl_2$ (3.0 mL), followed by the addition of TFA (2.0 mL) at rt. The reaction was stirred at rt for 30 min. After complete consumption of starting material was observed via LCMS, MeOH 10 mL was added to the mixture. The resulting mixture was concentrated to remove $CH_2Cl_2$ and TFA. Add MeOH 10 mL two more times to co-evaporate $CH_2Cl_2$ and TFA. The crude product was purified via trituration using the centrifuge. The solid was washed with water, the supernatant was removed, and the sequence was repeated, and then washed with acetonitrile. The resulting solid was collected and lyophilized to yield the pure product 101 as an off-white solid (7.0 mg, 12.5% yield, 96.8% purity).

1H NMR (400 MHz, $CDCl_3$+TFA): δ 8.67 (s, 1H), 8.02 (d, J=1.4 Hz, 1H), 7.74 (d, J=8.5 Hz, 1H), 7.67 (dd, J=8.8, 1.7 Hz, 1H), 2.79 (s, 3H).

LCMS: m/z [M+1]+=379.2; $R_T$=1.44 min (96.8% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Example 34

Figure 46:
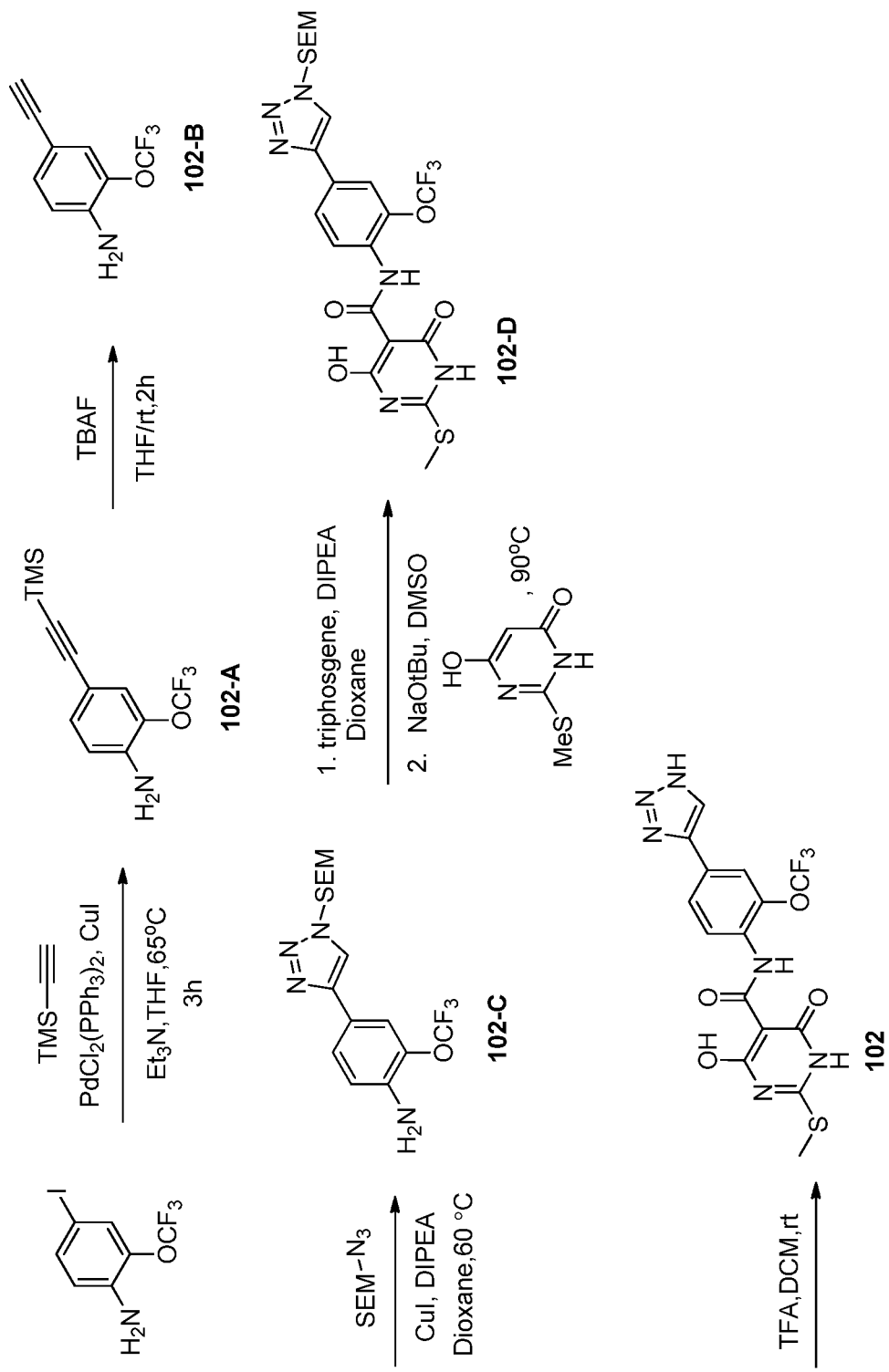
FIG. 46 illustrates the synthesis scheme described in Example 34.

Preparation of N-(4-(1H-1,2,3-triazol-4-yl)-2-(trifluoromethoxy) phenyl)-4-hydroxy-2-(methylthio)-6-oxo-1,6-dihydropyrimidine-5-carboxamide (102) (a Compound Having a Structure Represented by Formula $II_3$, with Reference to Synthesis Illustrated in FIG. 46)

Step One. 2-(trifluoromethoxy)-4-((trimethylsilyl)ethynyl) aniline (102-A): A round bottom flask containing 4-iodo-2-(trifluoromethoxy) aniline (1.52 g, 5.0 mmol), $PdCl_2(PPh_3)_2$ (175 mg, 0.1 mmol), and CuI (38 mg, 0.2 mmol) was purged with nitrogen for 15 min. Anhydrous THF (10.0 mL) was added, followed by trimethylsilyl acetylene (1.4 mL, 10.0 mmol) and triethylamine (1.4 mL, 10.0 mmol). The reaction mixture was heated to 65° C. for 12 h. After completion reaction mixture was cooled to rt, filtered through a small pad of Celite. The filtrate was concentrated to get crude product which was purified by using column chromatography using hexane: EtOAc (0 to 100% gradient) to yield (1.21 g, 88%) of product 102-A.

LCMS: $R_T$=2.09 min (99.1% Purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 4-ethynyl-2-(trifluoromethoxy) aniline (102-B): To a solution of 102-A (0.546 g, 2.0 mmol) dissolved in THF (3.0 mL) was added 1M solution of TBAF (3.0 ml, 3.0 mmol) at rt. The resulting reaction mixture was stirred at rt until complete consumption of the starting material was observed. The reaction mixture was quenched with water and extracted with EtOAc and then concentrated. The crude product was used in next step without any purification.

LCMS: $R_T$=1.65 min (98% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. 2-(trifluoromethoxy)-4-(1-((2-(trimethylsilyl) ethoxy) methyl)-1H-1,2,3-triazol-4-yl) aniline (102-C): To a solution of 102-B (402 mg, 2.0 mmol) dissolved in anhydrous 1,4-dioxane: MeOH (1:1, 5.0 mL). CuI (38 mg, 0.2 mmol) was added, followed by the addition of DIPEA (0.7 mL, 4.0 mmol) and SEM-azide (416 mg, 2.4 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 102-C as an off-white solid (520 mg, 70% yield over two steps).

LCMS: m/z [M+1]+=375.2; $R_T$=1.89 min (97% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step four. 4-hydroxy-2-(methylthio)-6-oxo-N-(2-(trifluoromethoxy)-4-(1-((2-(trimethylsilyl) ethoxy) methyl)-1H-1,2,3-triazol-4-yl) phenyl)-1,6-dihydropyrimidine-5-carboxamide (102-D): 6-hydroxy-2-(methylthio) pyrimidin-4(3H)-one (316 mg, 2.0 mmol) was added to a stirring solution of sodium tert-butoxide (192 mg, 2.0 mmol) dissolved in DMSO (2.0 mL) at rt for 5 min. In a separate flask, aniline 102-C (374 mg, 1.0 mmol) was dissolved in 1,4-dioxane (2.0 mL), to this solution was added triphosgene (98 mg, 0.33 mmol) in one-portion. The suspension was stirred vigorously for 2 min at rt, then $iPr_2NEt$ (0.35 mL) was added. The suspension was stirred vigorously at rt for 2 min. Freshly prepared solution of sodium 6-hydroxy-2-(methylthio)-3-(3,4,5-trimethoxybenzyl) pyrimidin-4(3H)-olate in DMSO was added to the suspension in one-portion. The reaction was stirred at 90° C. for 30 min, until complete consumption of starting material observed via LCMS. Reaction mixture was then cooled at rt; Methanol was added to get clear solution followed by addition of 1M HCl to precipitate; which was filtered and dried and used in next step without any further purification.

LCMS: m/z [M+1]+=559.2; $R_T$=2.01 min (90% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step five. N-(4-(1H-1,2,3-triazol-4-yl)-2-(trifluoromethoxy) phenyl)-4-hydroxy-2-(methylthio)-6-oxo-1,6-dihydropyrimidine-5-carboxamide (102): A solution of crude 102-D (90% purity) in dichloromethane (2.0 mL) was added trifluoroacetic acid (2.0 mL). The resulting reaction mixture was stirred at rt for 20 h. The reaction mixture was then concentrated under reduced pressure. The crude product was co-evaporated several times with methanol (3×), then purified via reverse-phase chromatography (C18, gradient eluent from 0 to 20% acetonitrile in water with an ammonium bicarbonate buffer 10 mM over 20 CV) to yield the product as an off-white solid (107 mg, 25% yield over two steps), after lyophilization.

$^1$H NMR (400 MHz, 1M $K_2CO_3$ in $D_2O$) δ 8.07 (d, J=8.2 Hz, 1H), 7.79 (s, 1H) 7.58 (s, 1H), 7.53 (d, J=8.9 Hz, 1H), 2.21 (s, 3H).

LCMS: m/z [M+1]+=429.7; $R_T$=1.50 min (98.9% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium formate pH: 3.8; Eluent B: Acetonitrile.

Example 35

Figure 47:
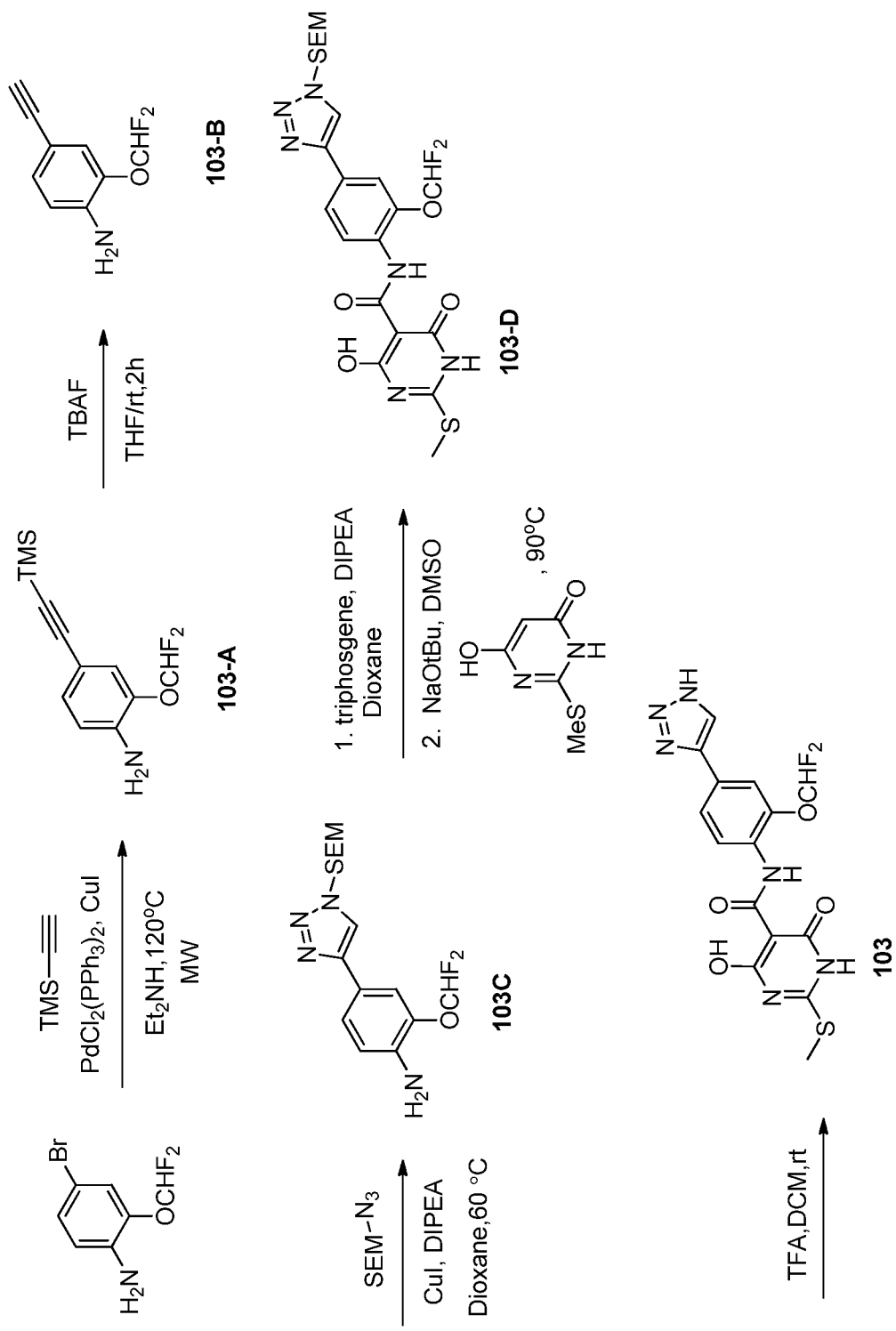
FIG. 47 illustrates the synthesis scheme described in Example 35.

Preparation of N-(2-(difluoromethoxy)-4-(1H-1,2,3-triazol-4-yl) phenyl)-4-hydroxy-2-(methylthio)-6-oxo-1,6-dihydropyrimidine-5-carboxamide (103) (a Compound Having a Structure Represented by Formula ($II_4$), with Reference to Synthesis Illustrated in FIG. 47)

Step One. 2-(difluoromethoxy)-4-((trimethylsilyl)ethynyl) aniline (103-A): A microwave vial containing 4-bromo- 2-(difluoromethoxy) aniline (1.19 g, 5.0 mmol), PdCl$_2$(PPh$_3$)$_2$ (702 mg, 1.0 mmol), and CuI (190 mg, 1 mmol) was purged with nitrogen for 15 min. diethyl amine (20.0 mL) was added, followed by trimethylsilyl acetylene (1.4 mL, 10.0 mmol) and vial was sealed. The reaction mixture was heated to 120° C. for 30 min in microwave. After completion reaction mixture was cooled to rt, filtered through a small pad of Celite. The filtrate was washed with EtOAc and concentrated to get crude product which was purified by using column chromatography using hexane: EtOAc (0 to 100% gradient) to yield (0.825 g, 65%) of product 103-A LCMS: R$_T$=1.96 min (98% Purity). HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 2-(difluoromethoxy)-4-ethynylaniline (103-B): To a solution of 103-A (0.77 g, 3.0 mmol) dissolved in THF (4.0 mL) was added 1M solution of TBAF (6.0 ml, 6.0 mmol) at rt. The resulting reaction mixture was stirred at rt until complete consumption of the starting material was observed. The reaction mixture was quenched with water and extracted with EtOAc and then concentrated. The crude product was used in next step without any purification LCMS: R$_T$=1.51 min (97% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. 2-(difluoromethoxy)-4-(1-((2-(trimethylsilyl) ethoxy) methyl)-1H-1,2,3-triazol-4-yl) aniline (103-C): To a solution of 103-B (550 mg, 3.0 mmol) dissolved in anhydrous 1,4-dioxane (5.0 mL). CuI (57 mg, 0.3 mmol) was added, followed by the addition of DIPEA (1.05 mL, 6.0 mmol) and SEM-azide (630 mg, 3.6 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 103-C as an off-white solid (720 mg, 67% yield over two steps).

LCMS: m/z [M+1]$^+$=357.2; R$_T$=1.80 min (96% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step four. N-(2-(difluoromethoxy)-4-(1-((2-(trimethylsilyl) ethoxy) methyl)-1H-1,2,3-triazol-4-yl) phenyl)-4-hydroxy-2-(methylthio)-6-oxo-1,6-dihydropyrimidine-5-carboxamide (103-D): 6-hydroxy-2-(methylthio) pyrimidin-4(3H)-one (95 mg, 0.6 mmol) was added to a stirring solution of sodium tert-butoxide (58 mg, 0.6 mmol) dissolved in DMSO (1.0 mL) at rt for 5 min. In a separate flask, aniline 103-C (107 mg, 0.3 mmol) was dissolved in 1,4-dioxane (0.5 mL), to this solution was added triphosgene (30 mg, 0.1 mmol) in one-portion. The suspension was stirred vigorously for 2 min at rt, then iPr$_2$NEt (0.1 mL) was added. The suspension was stirred vigorously at rt for 2 min. Freshly prepared solution of sodium 6-hydroxy-2-(methylthio)-3-(3,4,5-trimethoxybenzyl) pyrimidin-4(3H)-olate in DMSO was added to the suspension in one-portion. The reaction was stirred at 90° C. for 30 min, until complete consumption of starting material observed via LCMS. Reaction mixture was then cooled at rt; Methanol was added to get clear solution followed by addition of 1M HCl to precipitate; which was filtered and dried and used in next step without any further purification.

LCMS: m/z [M+1]$^+$=541.3; R$_T$=1.94 min (88% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step five. N-(4-(1H-1,2,3-triazol-4-yl)-2-(trifluoromethoxy) phenyl)-4-hydroxy-2-(methylthio)-6-oxo-1,6-dihydropyrimidine-5-carboxamide (103): A solution of crude 103-D (88% purity) in dichloromethane (1.0 mL) was added trifluoroacetic acid (10 mL). The resulting reaction mixture was stirred at rt for 20 h. The reaction mixture was then concentrated under reduced pressure. The crude product was co-evaporated several times with methanol (3×), then purified via reverse-phase chromatography (C18, gradient eluent from 0 to 20% acetonitrile in water with an ammonium bicarbonate buffer 10 mM over 20 CV) to yield the product 103 as white solid (14 mg, 13% yield over two steps), after lyophilization as an ammonium salt.

$^1$H NMR (500 MHz, DMSO+TFA) δ 12.15 (s, 1H), 8.43 (d, J=8.6 Hz, 1H), 8.32 (s, 1H) 7.78 (s, 1H), 7.75 (dd, J=8.5, 1.8 Hz, 1H), 7.20 (dt, J=91.7, 62.3 Hz, 3H) 2.54 (s, 1H), 2.53 (s, 3H).

LCMS: m/z [M−1]$^+$=409.1; R$_T$=1.42 min (97.8% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 36

Figure 48:
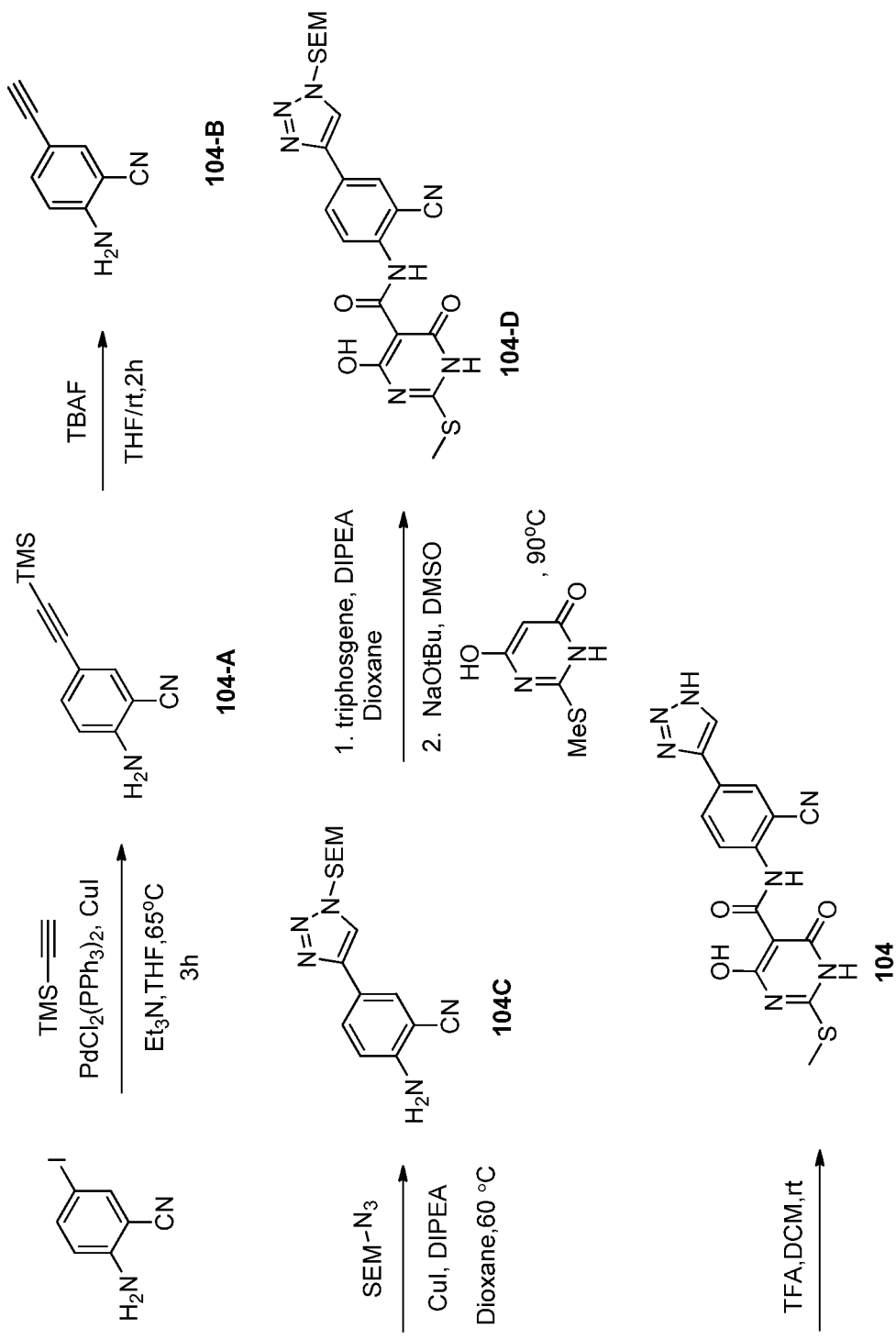
FIG. 48 illustrates the synthesis scheme described in Example 36.

Preparation of N-(2-cyano-4-(1H-1,2,3-triazol-4-yl) phenyl)-4-hydroxy-2-(methylthio)-6-oxo-1,6-dihydropyrimidine-5-carboxamide (104) (a Compound Having a Structure Represented by Formula (II$_5$), with Reference to the Synthesis Illustrated in FIG. 48)

Step One. 2-amino-5-((trimethylsilyl)ethynyl) benzonitrile (104-A): A round bottom flask containing 2-amino-5-iodobenzonitrile (1.22 g, 5.0 mmol), PdCl$_2$(PPh$_3$)$_2$ (175 mg, 0.1 mmol), and CuI (38 mg, 0.2 mmol) was purged with nitrogen for 15 min. Anhydrous THF (10.0 mL) was added, followed by trimethylsilyl acetylene (1.4 mL, 10.0 mmol) and triethylamine (1.4 mL, 10.0 mmol). The reaction mixture was heated to 65° C. for 12 h. After completion reaction mixture was cooled to rt, filtered through a small pad of Celite. The filtrate was concentrated to get crude product which was purified by using column chromatography using hexane: EtOAc (0 to 100% gradient) to yield (0.98 g, 92%) of product 104-A.

LCMS: R$_T$=1.88 min (97% Purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 2-amino-5-ethynylbenzonitrile (104-B): To a solution of 104-A (0.856 g, 4.0 mmol) dissolved in THF (2.0 mL) was added 1M solution of TBAF (8.0 ml, 8.0 mmol) at rt. The resulting reaction mixture was stirred at rt until complete consumption of the starting material was observed. The reaction mixture was quenched with water and extracted with EtOAc and then concentrated. The crude product was used in next step without any purification.

LCMS: R$_T$=1.38 min (96% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. 2-amino-5-(1-((2-(trimethylsilyl) ethoxy) methyl)-1H-1,2,3-triazol-4-yl) benzonitrile (104-C): To a solution of 104-B (426 mg, 3.0 mmol) dissolved in anhydrous 1,4-dioxane (5.0 mL). CuI (38 mg, 0.3 mmol) was added, followed by the addition of DIPEA (1.05 mL, 6.0 mmol) and SEM-azide 630 mg, 3.6 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 104-C as an off-white solid (520 mg, 70% yield over two steps).

LCMS: m/z [M+1]$^+$=316.2; R$_T$=1.72 min (95% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile Step four. 4-hydroxy-2-(methylthio)-6-oxo-N-(2-(trifluoromethoxy)-4-(1-((2-(trimethylsilyl) ethoxy) methyl)-1H-1,2,3-triazol-4-yl) phenyl)-1,6-dihydropyrimidine-5-carboxamide (104-D): 6-hydroxy-2-(methylthio) pyrimidin-4(3H)-one (95 mg, 0.6 mmol) was added to a stirring solution of sodium tert-butoxide (58 mg, 0.6 mmol) dissolved in DMSO (1.0 mL) at rt for 5 min. In a separate flask, aniline 104-C (95 mg, 0.3 mmol) was dissolved in 1,4-dioxane (2.0 mL), to this solution was added triphosgene (30 mg, 0.1 mmol) in one-portion. The suspension was stirred vigorously for 2 min at rt, then iPr$_2$NEt (0.1 mL) was added. The suspension was stirred vigorously at rt for 2 min. Freshly prepared solution of sodium 6-hydroxy-2-(methylthio)-3-(3,4,5-trimethoxybenzyl) pyrimidin-4(3H)-olate in DMSO was added to the suspension in one-portion. The reaction was stirred at 90° C. for 30 min, until complete consumption of starting material observed via LCMS. Reaction mixture was then cooled at rt; Methanol was added to get clear solution followed by addition of 1M HCl to precipitate; which was filtered and dried and used in next step without any further purification.

LCMS: m/z [M+1]$^+$=500.3; R$_T$=1.91 min (80% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step five. N-(4-(1H-1,2,3-triazol-4-yl)-2-(trifluoromethoxy) phenyl)-4-hydroxy-2-(methylthio)-6-oxo-1,6-dihydropyrimidine-5-carboxamide (104): A solution of crude 104-D (80% purity) in dichloromethane (1.0 mL) was added trifluoroacetic acid (1.0 mL). The resulting reaction mixture was stirred at rt for 20 h. The reaction mixture was then concentrated under reduced pressure. The crude product was co-evaporated several times with methanol (3×), then purified via reverse-phase chromatography (C18, gradient eluent from 0 to 20% acetonitrile in water with an ammonium bicarbonate buffer 10 mM over 20 CV) to yield the product 104 as an off-white solid (11 mg, 10% yield over two steps), after lyophilization as an ammonium salt.

$^1$H NMR (500 MHz, DMSO+TFA) δ 12.28 (s, 1H), 8.39 (s, 1H), 8.34 (d, J=8.8 Hz, 1H), 8.27 (d, J=2.0 Hz, 1H), 8.16 (dd, J=8.8, 2.0 Hz, 1H), 7.20-6.90 (t, 1.5H ammonia peak), 2.51 (s, 3H).

LCMS: m/z [M−1]$^+$=368.3; R$_T$=1.35 min (96.5% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 37

Figure 49:
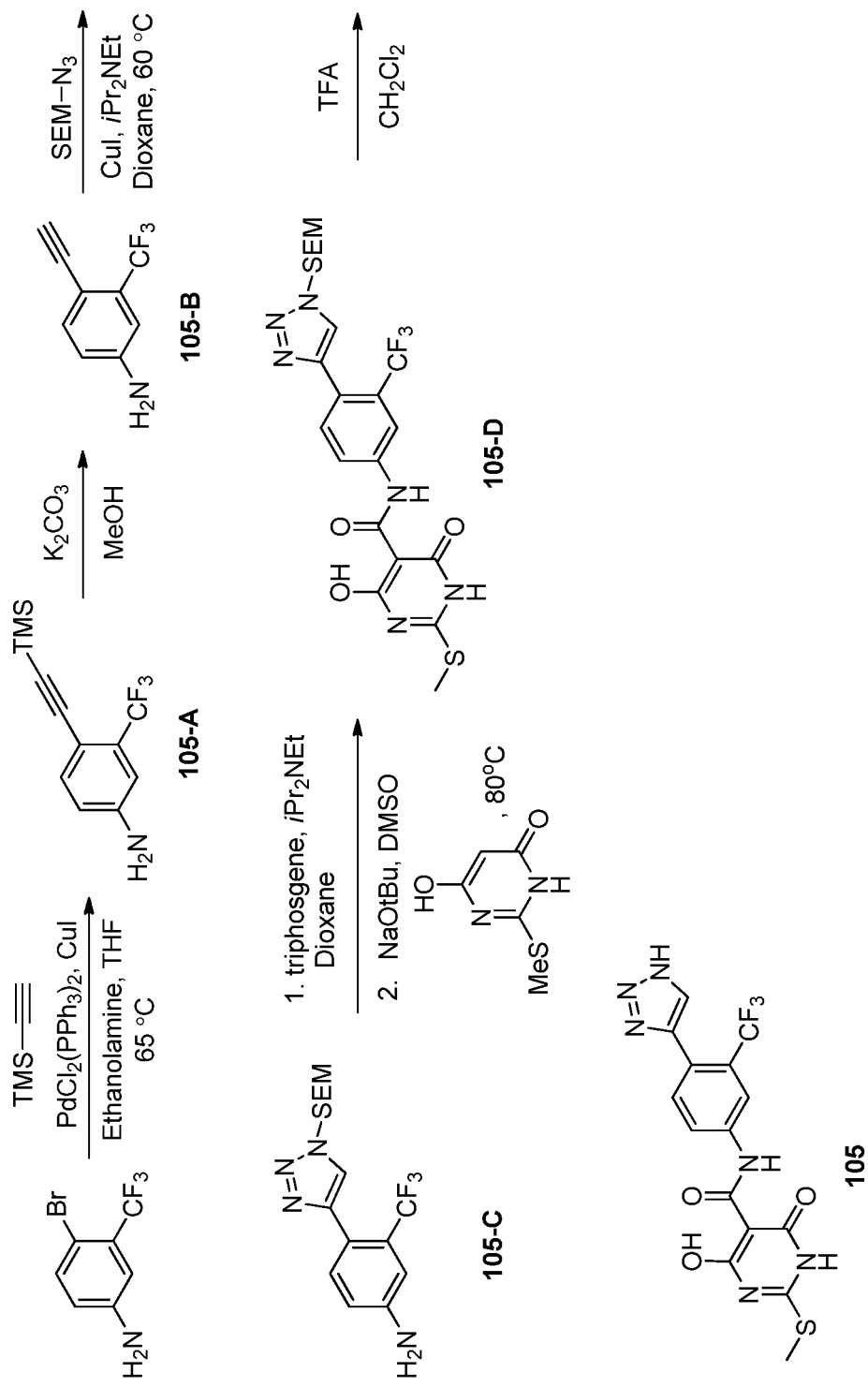
FIG. 49 illustrates the synthesis scheme described in Example 37.

Preparation of N-(4-(1H-1,2,3-Triazol-4-yl)-3-(trifluoromethyl)phenyl)-4-hydroxy-2-(methyl-thio)-6-oxo-1,6-dihydropyrimidine-5-carboxamide (105) (a Compound Having a Structure Represented by Formula (II$_6$), with Reference to the Synthesis Illustrated in FIG. 49)

Step One. 3-(Trifluoromethyl)-4-((trimethylsilyl)ethynyl) aniline (105-A): A round bottom flask containing 4-bromo-3-(trifluoromethyl)aniline (2.17 g, 9.04 mmol), PdCl$_2$(PPh$_3$)$_2$ (381 mg, 0.543 mmol), and CuI (69 mg, 0.36 mmol) was purged with nitrogen for 15 min. Anhydrous THF (40 mL) was added, followed by trimethylsilyl acetylene (2.60 mL, 18.4 mmol) and ethanolamine (1.09 mL, 18.1 mmol). The reaction mixture was sealed and heated to 65° C. for 16 h. The reaction mixture was cooled to rt, filtered through a small pad of Celite. The filtrate was concentrated and the crude product was used without further purification.

LCMS: R$_T$=1.97 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Two. 4-Ethynyl-3-(trifluoromethyl)aniline (105-B): To a solution of crude 105-A (9.04 mmol) dissolved in methanol (18.0 mL) was added potassium carbonate (2.50 g, 18.1 mmol) at rt. The resulting reaction mixture was stirred at rt for 2 h. The reaction mixture was filtered, and the filtrate was concentrated. The crude product was purified via ISCO (0 to 50% ethyl acetate in hexanes, over 20 CV) to yield the product as a brown oil (1.46 g, purity=18%; contaminated with 4-bromo-3-(trifluoromethyl)aniline (82%)).

LCMS: R$_T$=1.55 min; purity=18%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate; Eluent B: Acetonitrile.

Step Three. 3-(Trifluoromethyl)-4-(1-((2-(trimethylsilyl)ethoxy)methyl)-1H-1,2,3-triazol-4-yl)aniline (105-C): 105-B (1.26 g, 6.81 mmol, purity=18%) was dissolved in anhydrous 1,4-dioxane (13.5 mL). CuI (65 mg, 0.34 mmol) was added, followed by the addition of iPr$_2$NEt (590 µL, 3.39 mmol) and (2-(2-azidoethoxy)ethyl)trimethylsilane (590 mg, 3.40 mmol). The resulting reaction mixture was heated to 60° C. for 16 h. The reaction mixture was then cooled to rt and then concentrated under reduced pressure. The crude product was purified via ISCO (0 to 40% ethyl acetate in hexanes, over 20 CV) to yield the product as orange oil (118 mg, 5% yield over three steps, >99% purity).

Step Three. 3-(Trifluoromethyl)-4-(1-((2-(trimethylsilyl)ethoxy)methyl)-1H-1,2,3-triazol-4-yl)aniline (105-C): 105-B (1.26 g, 6.81 mmol, purity=18%) was dissolved in anhydrous 1,4-dioxane (13.5 mL). CuI (65 mg, 0.34 mmol) was added, followed by the addition of iPr$_2$NEt (590 µL, 3.39 mmol) and (2-(2-azidoethoxy)ethyl)trimethylsilane (590 mg, 3.40 mmol). The resulting reaction mixture was heated to 60° C. for 16 h. The reaction mixture was then cooled to rt and then concentrated under reduced pressure. The crude product was purified via ISCO (0 to 40% ethyl acetate in hexanes, over 20 CV) to yield the product as orange oil (118 mg, 5% yield over three steps, >99% purity).

LCMS: m/z [M+1]$^+$=359.3; R$_T$=1.79 min; purity=>99%.

HPLC conditions: Column: XBridge C18, 3.5 µm, 4.6×30 mm; Gradient: 5% B for 0.2 min, 5% to 100% B in 1.8 min;

100% B for 1 min; 3 mL/min. Eluent A: Milli-Q H₂O+10 mM ammonium formate; Eluent B: Acetonitrile.

Step Four. 4-Hydroxy-2-(methylthio)-6-oxo-N-(3-(trifluoromethyl)-4-(1-((2-(trimethylsilyl)-ethoxy)methyl)-1H-1,2,3-triazol-4-yl)phenyl)-1,6-dihydropyrimidine-5-carboxamide (105-D): 6-Hydroxy-2-(methylthio)pyrimidin-4(3H)-one (84 mg, 0.53 mmol) was added to a stirring solution of sodium tert-butoxide (51 mg, 0.53 mmol) dissolved in DMSO (0.90 mL) at room temperature for 5 min. In a separate flask, aniline 105-C (95 mg, 0.265 mmol) was dissolved in 1,4-dioxane (0.65 mL). To this solution was added triphosgene (26 mg, 0.088 mmol) in one-portion. The suspension was stirred vigorously for 2 min at room temperature, then iPr₂NEt (92 µL, 0.53 mmol) was added. The suspension was stirred vigorously at room temperature for 2 min. The previous solution prepared in DMSO was added to this suspension in one-portion. The reaction was then stirred at 80° C. for 45 min. Reaction mixture was then cooled to room temperature and diluted with $CH_2Cl_2$. The solution was washed with water (1×) and with brine (1×) then dried over $MgSO_4$, filtered, and concentrated under reduced pressure. The crude product was purified via ISCO (0 to 10% methanol in dichloromethane, over 30 CV) to yield the product as orange oil (39 mg, 27% yield, 84% purity).

LCMS: m/z $[M+1]^+$=543.2; $R_T$=1.95 min (84% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate; Eluent B: Acetonitrile.

Step Five. N-(4-(1H-1,2,3-Triazol-4-yl)-3-(trifluoromethyl)phenyl)-4-hydroxy-2-(methylthio)-6-oxo-1,6-dihydropyrimidine-5-carboxamide (105): Trifluoroacetic acid (0.70 mL) was added to 105-D (37 mg, 0.068 mmol) in dichloromethane (0.70 mL). The reaction mixture was stirred at room temperature for 3 h, and then co-evaporated with MeOH (3× ~5 mL). The crude product was purified via reverse-phase chromatography (C18, gradient eluent from 0 to 30% acetonitrile in water with an ammonium bicarbonate buffer 10 mM over 30 CV) to yield 105 as a white solid (8.2 mg, 29% yield, >99.9% purity), after lyophilization.

¹H NMR (500 MHz, CDCl₃:TFA (10:1)) δ 8.34 (s, 1H), 8.22 (d, J=2.1 Hz, 1H), 7.97 (dd, J=8.3, 2.2 Hz, 1H), 7.66 (d, J=8.5 Hz, 1H), 2.74 (s, 3H).

LCMS: m/z $[M+1]^+$=413.2; $R_T$=1.44 min; purity=>99.9%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Example 38

Figure 50:
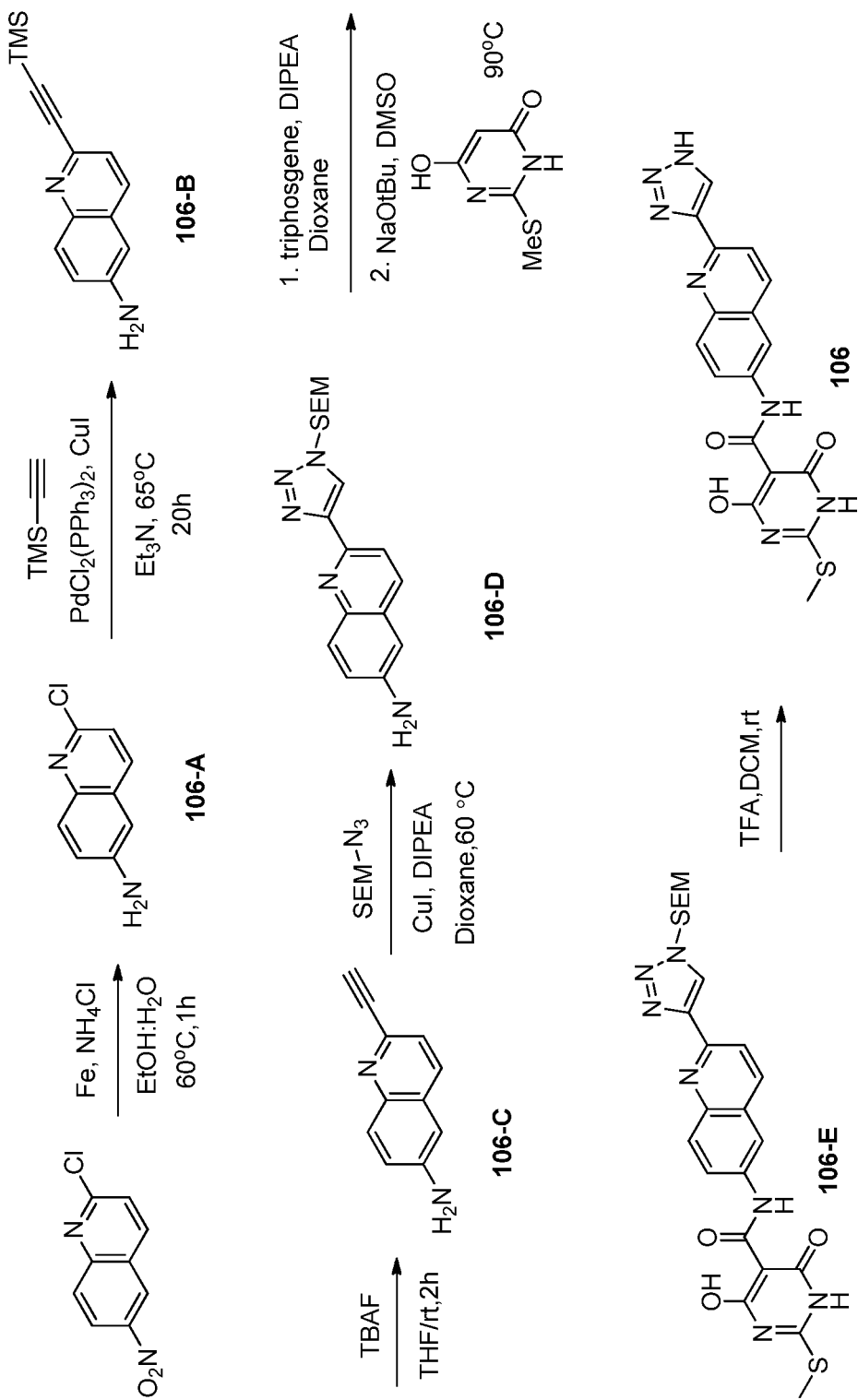
FIG. 50 illustrates the synthesis scheme described in Example 38.

Preparation of N-(2-(1H-1,2,3-triazol-4-yl) quinolin-6-yl)-4-hydroxy-2-(methylthio)-6-oxo-1,6-dihydropyrimidine-5-carboxamide (106) (a Compound Having a Structure Represented by Formula ($II_{10}$), with Reference to the Synthesis Illustrated in FIG. 50)

Step One. 2-Chloroquinolin-6-amine (106-A): To 2-chloro-6-nitroquinoline (418 mg, 2.0 mmol) and NH₄Cl (535 mg, 10.0 mmol) was added EtOH (20 mL) and water (0.4 mL). The reaction mixture was heated to 600° C. and Fe (335 mg, 6.0 mmol) was added in several portions. The reaction mixture was stirred for 2 h maintaining the temperature at 60° C. The mixture was cooled to room temperature and the ethanol was removed under reduced pressure. The aqueous mixture was diluted with 100 mL of EtOAc and solids were removed by filtration. The filtrate was concentrated under reduced pressure to yield the desired product, 339 mg (95%), as a yellow solid.

LCMS: m/z $[M+1]^+$=179.2; $R_T$=1.26 min (99% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 2-((trimethylsilyl)ethynyl)quinolin-6-amine (106-B): A round bottom flask containing 2-chloro-6-aminoquinoline (356 mg, 2.0 mmol), PdCl₂(PPh₃)₂ (281 mg, 0.4 mmol), and CuI (152 mg, 0.8 mmol) was purged with nitrogen for 15 min. triethylamine (10.0 ml) was added, followed by trimethylsilyl acetylene (1.4 mL, 10.0 mmol). The reaction mixture was heated to 65° C. for 16 h. After completion reaction mixture was cooled to rt, filtered through a small pad of Celite. The filtrate was concentrated to get crude product which was purified by using column chromatography using hexane: EtOAc (0 to 100% gradient) to yield (425 mg, 88%) of product 106-B.

LCMS: m/z $[M+1]^+$=241.2; $R_T$=1.75 min (96% Purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. 2-ethynylquinolin-6-amine (106-C): To a solution of 106-B (480 mg, 2.0 mmol) dissolved in THF (2.0 mL) was added 1M solution of TBAF (4.0 ml, 4.0 mmol) at rt. The resulting reaction mixture was stirred at rt until complete consumption of the starting material was observed. The reaction mixture was quenched with water and extracted with EtOAc and then concentrated. The crude product 106-C was used in next step without any purification.

LCMS: m/z $[M+1]^+$=169.3; $R_T$=1.43 min (95% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Four. 2-(1-((2-(trimethylsilyl) ethoxy) methyl)-1H-1,2,3-triazol-4-yl) quinolin-6-amine (106-D): To a solution of 106-C (336 mg, 2.0 mmol) dissolved in methanol (3.0 mL). CuI (38 mg, 0.3 mmol) was added, followed by the addition of DIPEA (0.7 mL, 4.0 mmol) and SEM-azide (416 mg, 2.4 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 106-D as an off-white solid (550 mg, 81% yield over two steps).

LCMS: m/z $[M+1]^+$=342.6; $R_T$=1.68 min (99.5% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Five. 4-hydroxy-2-(methylthio)-6-oxo-N-(2-(1-((2-(trimethylsilyl) ethoxy) methyl)-1H-1,2,3-triazol-4-yl) quinolin-6-yl)-1,6-dihydropyrimidine-5-carboxamide (106-E): 6-hydroxy-2-(methylthio) pyrimidin-4(3H)-one (158 mg, 1.0 mmol) was added to a stirring solution of sodium tert-butoxide (96 mg, 1.0 mmol) dissolved in DMSO (1.0 mL) at rt for 5 min. In a separate flask, aniline 106-D (171 mg, 0.5 mmol) was dissolved in 1,4-dioxane (2.0 mL), to this solution was added triphosgene (82 mg, 0.275 mmol) in one-portion. The suspension was stirred vigorously for 2 min at rt, then iPr₂NEt (0.2 mL) was added. The suspension was stirred vigorously at rt for 2 min. Freshly prepared solution of sodium 6-hydroxy-2-(methylthio)-3-(3,4,5-trimethoxybenzyl) pyrimidin-4(3H)-olate in DMSO was added to the suspension in one-portion. The reaction was stirred at 90° C. for 30 min, until complete consumption of starting material observed via LCMS. Reaction mixture was then cooled at rt; concentrated under vacuum. Purification was done by reverse phase column chromatography using 10 mM ammonium bicarbonate buffer (PH=10.0) and acetonitrile. Pure fraction was lyophilized to get desired product 106-E LCMS: m/z [M+1]$^+$=526.3; R$_T$=2.10 min (98% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Six. N-(2-(1H-1,2,3-triazol-4-yl) quinolin-6-yl)-4-hydroxy-2-(methylthio)-6-oxo-1,6-dihydropyrimidine-5-carboxamide (106): A solution of 106-E (80 mg, 0.15 mmol) in dichloromethane (2.0 mL) was added trifluoroacetic acid (2.0 mL). The resulting reaction mixture was stirred at rt for 2 h. The reaction mixture was then concentrated under reduced pressure. The crude product was co-evaporated several times with methanol (3×), then purified via reverse-phase chromatography (C18, gradient eluent from 0 to 20% acetonitrile in water with an ammonium bicarbonate buffer 10 mM over 20 CV) to yield the product 106 as white solid (36 mg, 60% yield), after lyophilization.

$^1$H NMR (500 MHz, DMSO+TFA) δ 12.02 (s, 1H), 8.78 (s, 1H), 8.72 (d, J=8.7 Hz, 1H), 8.47 (d, J=1.9 Hz, 1H), 8.29 (d, J=8.7 Hz, 1H), 8.21 (d, J=9.0 Hz, 1H), 8.04 (dd, J=9.1, 2.2 Hz, 1H), 2.55 (s, 3H).

LCMS: m/z [M+1]$^+$=396.1; R$_T$=0.93 min (99.0% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium bicarbonate pH: 10.0; Eluent B: Acetonitrile.

Example 39

Figure 51:
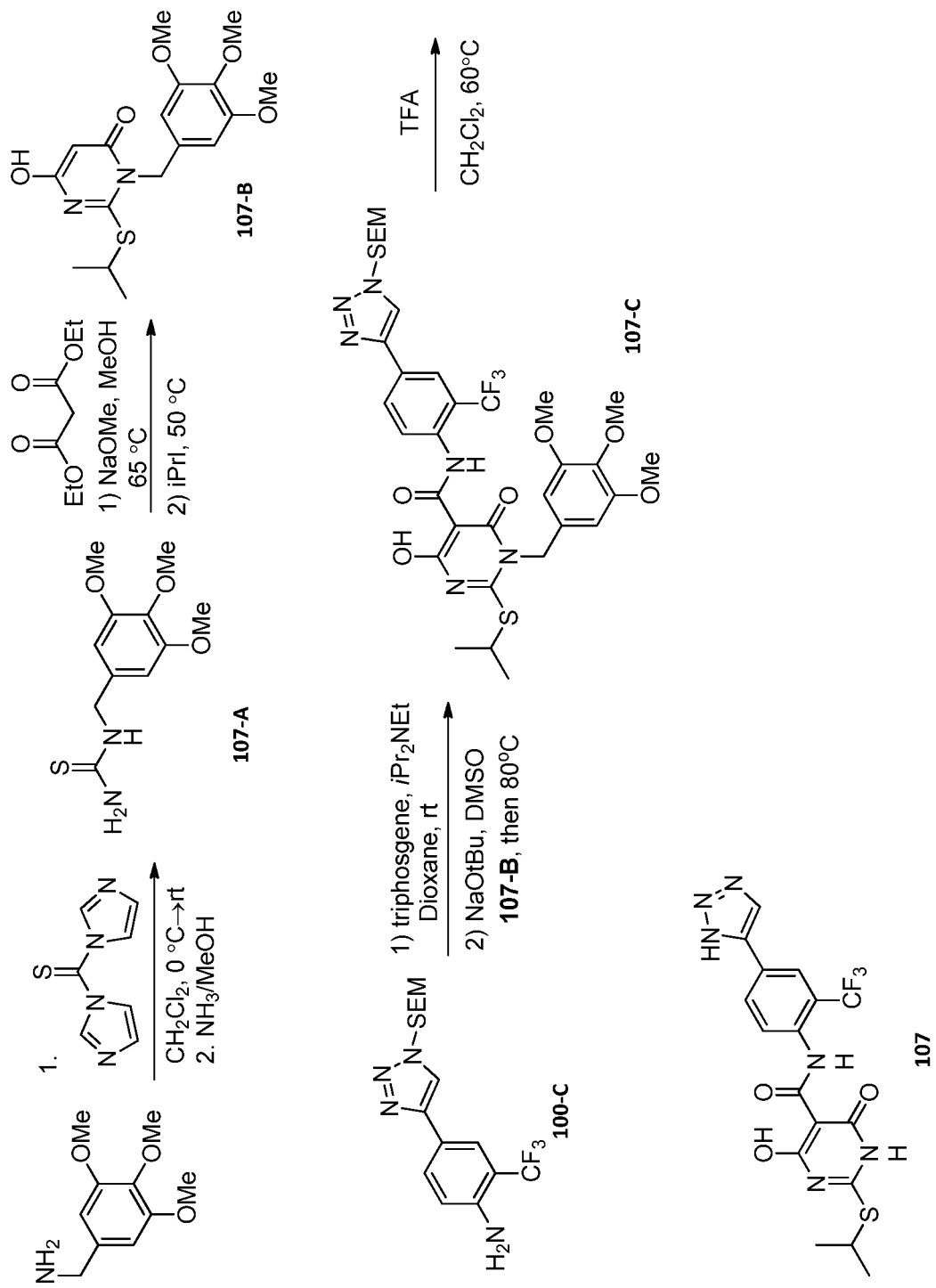
FIG. 51 illustrates the synthesis scheme described in Example 39.

Preparation of N-(4-(1H-1,2,3-Triazol-5-yl)-2-(trifluoromethyl)phenyl)-4-hydroxy-2-(isopropyl-thio)-6-oxo-1,6-dihydropyrimidine-5-carboxamide (107) (a Compound Having a Structure Represented by Formula (II$_7$), with Reference to the Synthesis Illustrated in FIG. 51)

Step One. 1-(3,4,5-Trimethoxybenzyl)thiourea (107-A): (3,4,5-Trimethoxyphenyl)methanamine (2.5 mL, 14.6 mmol) was added dropwise to a solution of 1,1'-thiocarbonyl diimidazole (3.91 g, 22.0 mmol) dissolved in dichloromethane (36.5 mL) at 0° C. The reaction mixture was then allowed to warm up to rt over 2 h. After complete consumption of the starting material was observed via LCMS, a solution of ammonia in methanol (7.5 mL, 52.6 mmol, 7.0 M in MeOH) was added, then stirred for an additional 20 h. The reaction mixture was concentrated under reduced pressure, dichloromethane was added, the precipitate was isolated and washed with additional CH$_2$Cl$_2$, then dried under high vacuum to yield the product as a light pink solid (2.83 g, 76% yield).

LCMS: m/z [M+1]$^+$=257.07; R$_T$=1.06 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 6-Hydroxy-2-(isopropylthio)-3-(3,4,5-trimethoxybenzyl) pyrimidin-4(3H)-one (107-B): A mixture of 107-A (781 mg, 3.05 mmol), diethyl malonate (465 μL, 3.05 mmol), and NaOMe (1.4 mL, 6.10 mmol, 4.4 M in MeOH) in methanol (2.4 mL) was heated to reflux for 3 h. The reaction was then cooled to ~50° C., isopropyl iodide (3.5 mL, 30.5 mmol) was then added in one-portion. The reaction was stirred for an additional 30 min at 50° C. The reaction mixture was then cooled to rt, then concentrated under reduced pressure. The crude product was purified via reverse-phase chromatography (gradient eluent from 0 to 100% acetonitrile in water with an ammonium formate buffer 10 mM over 15 CV) to yield the product as a white solid (433 mg, 97.7% purity, 38% yield), after lyophilization.

LCMS: m/z [M+1]$^+$=367.02; R$_T$=1.41 min; purity=97.7%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. 4-Hydroxy-2-(isopropylthio)-6-oxo-N-(2-(trifluoromethyl)-4-(1-((2-(trimethylsilyl)-ethoxy)methyl)-1H-1,2,3-triazol-4-yl)phenyl)-1-(3,4,5-trimethoxybenzyl)-1,6-dihydropyrimi-dine-5-carboxamide (107-C): 107-B (159 mg, 0.434 mmol) was added to a stirring solution of sodium tert-butoxide (42 mg, 0.437 mmol) dissolved in DMSO (1.50 mL) at room temperature for 5 min. In a separate flask, aniline 100-C (78 mg, 0.22 mmol) was dissolved in 1,4-dioxane (1.10 mL). To this solution was added triphosgene (21 mg, 0.071 mmol) in one-portion. The suspension was stirred vigorously for 2 min at room temperature, then iPr$_2$NEt (76 μL, 0.44 mmol) was added. The suspension was stirred vigorously at room temperature for 2 min. The previous solution prepared in DMSO was added to this suspension in one-portion. The reaction was then stirred at 80° C. for 45 min. Reaction mixture was then cooled to room temperature and water was added. The mixture was extracted with 2-methyl-THF (3×). Combined organic layers were washed with brine (1×) then dried over MgSO$_4$, filtered, and concentrated under reduced pressure. The crude product was purified via ISCO (0 to 5% methanol in dichloromethane, over 25 CV) to yield the product as an off-white solid (146 mg, 90% yield, 81% purity).

LCMS: m/z [M+1]$^+$=751.6; R$_T$=2.29 min; purity=81%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. N-(4-(1H-1,2,3-Triazol-5-yl)-2-(trifluoromethyl)phenyl)-4-hydroxy-2-(isopropyl-thio)-6-oxo-1,6-dihydropyrimidine-5-carboxamide (107): Trifluoroacetic acid (1.20 mL) was added to a solution of 107-C (146 mg, 0.194 mmol) in dichloromethane (6.5 mL). The resulting reaction mixture was sealed in a pressure vessel then heated to 60° C. for 16 h. The reaction mixture was allowed to cool to rt, then concentrated under reduced pressure. The crude product was co-evaporated several times with methanol (3×5 mL), then purified via reverse-phase chromatography (C18, gradient eluent from 0 to 30% acetonitrile in water with an ammonium bicarbonate buffer 10 mM over 25 CV). A second purification via reverse-phase chromatography (C18, gradient eluent from 20 to 60% acetonitrile in water with an ammonium formate buffer 10 mM over 24 CV) was done to yield the product 107 as a white solid (9.2 mg, >99.9% purity, 11% yield), after lyophilization.

¹H NMR (500 MHz, CDCl₃:TFA (10:1)) δ 8.54 (s, 1H), 8.43 (d, J=8.6 Hz, 1H), 8.10 (s, 1H), 7.99 (d, J=8.5 Hz, 1H), 4.19-4.13 (m, 1H), 1.51 (d, J=6.8 Hz, 6H).

LCMS: m/z [M+1]$^+$=441.1; R$_T$=1.60 min; purity=>99.9%. HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Example 40

Figure 52:
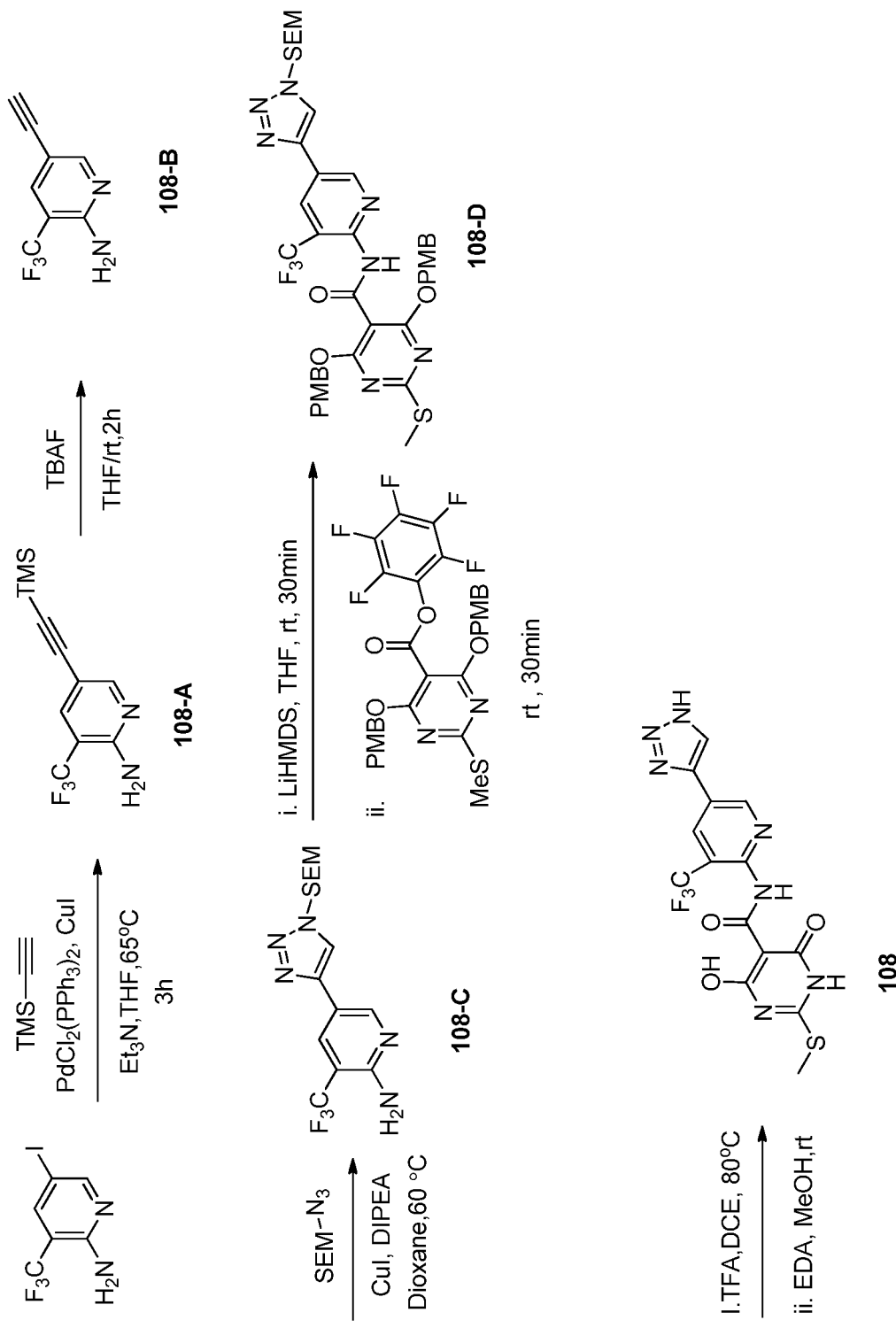
FIG. 52 illustrates the synthesis scheme described in Example 40.

Preparation of N-(5-(1H-1,2,3-triazol-4-yl)-3-(trifluoromethyl) pyridin-2-yl)-4-hydroxy-2-(methylthio)-6-oxo-1,6-dihydropyrimidine-5-carboxamide (108) (a Compound Having a Structure Represented by Formula (II₈), with Reference to the Synthesis Illustrated in FIG. 52)

Step One. 3-(trifluoromethyl)-5-((trimethylsilyl)ethynyl) pyridin-2-amine (108-A): A round bottom flask containing 5-iodo-3-(trifluoromethyl) pyridin-2-amine (1.0 g, 3.5 mmol), PdCl₂(PPh₃)₂ (25 mg, 0.035 mmol), and CuI (7 mg, 0.035 mmol) was purged with nitrogen for 15 min. Anhydrous THF (15.0 mL) was added, followed by trimethylsilyl acetylene (0.6 mL, 4.2 mmol) and triethylamine (4.9 mL, 35.0 mmol). The reaction mixture was heated to 65° C. for 3 h. After completion reaction mixture was cooled to rt, filtered through a small pad of Celite. The filtrate was concentrated to get crude product which was purified by using column chromatography using hexane: EtOAc (0 to 100% gradient) to yield (0.452 g, 50%) of product 108-A.

LCMS: m/z [M+1]+=259.2; R$_T$=1.95 min (94% Purity). HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 5-ethynyl-3-(trifluoromethyl) pyridin-2-amine (108-B): To a solution of 108-A (0.452 g, 1.75 mmol) dissolved in THF (2.0 mL) was added 1M solution of TBAF (3.5 ml, 3.5 mmol) at rt. The resulting reaction mixture was stirred at rt until complete consumption of the starting material was observed. The reaction mixture was quenched with water and extracted with EtOAc and then concentrated. The crude product was purified by using column chromatography with hexane: EtOAc (0 to 100% gradient) to yield (0.228 g, 70%) of product 108-B.

LCMS: m/z [M+1]$^+$=187.2; R$_T$=1.43 min (98% purity). HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. 3-(trifluoromethyl)-5-(1-((2-(trimethylsilyl) ethoxy) methyl)-1H-1, 2, 3-triazol-4-yl) pyridin-2-amine (108-C): To a solution of 108-B (228 mg, 1.23 mmol) dissolved in MeOH (5.0 mL). CuI (24 mg, 0.123 mmol) was added, followed by the addition of DIPEA (0.65 mL, 3.7 mmol) and SEM-azide (255 mg, 1.47 mmol). The resulting reaction mixture was heated to 60° C. for 12 h. The reaction mixture was then cooled to rt and concentrated. The crude product was purified via ISCO (SiO2, 0 to 50% ethyl acetate in hexanes over 20 CV) to yield 108-C as an off-white solid (243 mg, 55% yield).

LCMS: m/z [M+1]$^+$=360.3; R$_T$=1.78 min (95% purity). HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step four. 4,6-bis((4-methoxybenzyl) oxy)-2-(methylthio)-N-(3-(trifluoromethyl)-5-(1-((2-(trimethylsilyl) ethoxy) methyl)-1H-1,2,3-triazol-4-yl) pyridin-2-yl) pyrimidine-5-carboxamide (108-D):

To a stirred solution of 108-C (180 mg, 0.5 mmol) in THF under N₂ atmosphere at rt was added 1M LiHMDS solution in THF (0.5 ml, 0.5 mmol). The reaction mixture was allowed to stir for 30 min at rt. After 30 min, perfluorophenyl 4,6-bis((4-methoxybenzyl) oxy)-2-(methylthio) pyrimidine-5-carboxylate (300 mg, 0.5 mmol) dissolved in THF (2.0 ml) was added slowly to the reaction mixture. After stirring reaction mixture for another 30 min at rt it was quenched with water; extracted with ethyl acetate. The combined ethyl acetate layer was washed with brine, dried over sodium sulfate and concentrated under vacuum to get crude product (312 mg; 80% Yield) which was used in next step without any further purification.

LCMS: m/z [M+1]$^+$=784.5; R$_T$=2.22 min (98% purity). HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step five. N-(5-(1H-1,2,3-triazol-4-yl)-3-(trifluoromethyl) pyridin-2-yl)-4-hydroxy-2-(methylthio)-6-oxo-1,6-dihydropyrimidine-5-carboxamide (108):

A solution of crude 108-D (156 mg, 0.2 mmol) in dichloromethane (2.0 mL) was added trifluoroacetic acid (1.0 mL). The resulting reaction mixture was stirred at rt for 1 h then heated at 80° C. for 6 h. Reaction mixture was cooled at rt and concentrated to get crude product which was co-evaporated 2-3 times with methanol. The resulting reside was re-dissolved in MeOH (2.0 ml) and ethylenediamine (0.4 ml, 6 mmol, 30 eq) and reaction mixture was stirred for another 12 h it was then concentrated under vacuum to get crude product. Finally, crude product was purified via reverse-phase chromatography (C18, gradient eluent from 0 to 100% acetonitrile in water with an ammonium formate buffer 10 mM over 22 CV) to yield the product 108 as an off-white solid (18 mg, 23% yield), after lyophilization as an ammonium salt.

¹H NMR (500 MHz, DMSO+DCl in D₂O) δ 9.30 (d, J=2.1 Hz, 1H), 8.81 (s, 1H), 8.76 (d, J=2.1 Hz, 1H), 8.23 (s, 1H, —HCOOH peak), 2.60 (s, 3H).

LCMS: m/z [M−1]$^+$=412.3; R$_T$=1.26 min (99.2% purity). HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Example 41

Figure 53:
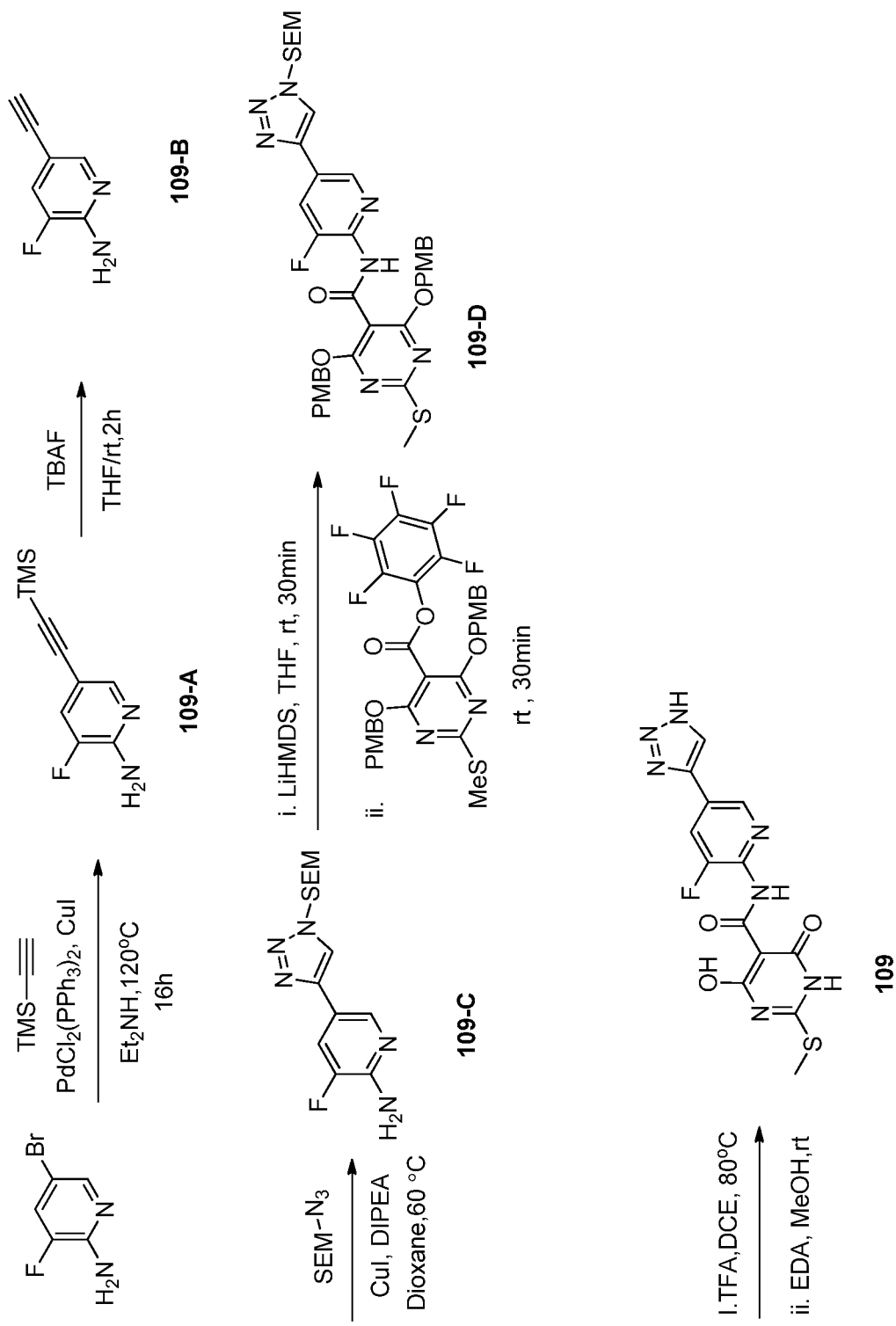
FIG. 53 illustrates the synthesis scheme described in Example 41.

Preparation of N-(3-fluoro-5-(1H-1,2,3-triazol-4-yl) pyridin-2-yl)-4-hydroxy-2-(methylthio)-6-oxo-1,6-dihydropyrimidine-5-carboxamide (109) (a Compound Having a Structure Represented by Formula (II₉), with Reference to the Synthesis Illustrated in FIG. 53)

Step One. 3-(fluoro)-5-((trimethylsilyl)ethynyl) pyridin-2-amine (109-A): In a microwave vial containing 5-bromo-3-fluoropyridin-2-amine (0.955 g, 5.0 mmol), PdCl₂(PPh₃)₂ (702 mg, 1.0 mmol), and CuI (380 mg, 2.0 mmol) was purged with nitrogen for 15 min. Diethylamine (20.0 mL) was added, followed by trimethylsilyl acetylene (3.5 mL, 25.0 mmol). Microwave vial was sealed and heated to 120°

C. for 2 h in microwave. After completion reaction mixture was cooled to rt, filtered through a small pad of Celite. The filtrate was concentrated to get crude product which was purified by using column chromatography in hexane: EtOAc (0 to 100% gradient) to yield (0.75 g, 72%) of product 109-A.

LCMS: m/z [M+1]$^+$=209.3; R$_T$=1.77 min (95% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 5-ethynyl-3-fluoropyridin-2-amine (109-B): To a solution of 109-A (0.75 g, 3.6 mmol) dissolved in THF (5.0 mL) was added 1M solution of TBAF (7.2 ml, 7.2 mmol) at rt. The resulting reaction mixture was stirred at rt until complete consumption of the starting material was observed. The reaction mixture was quenched with water and extracted with EtOAc and then concentrated. The crude product was used in next step without any purification.

LCMS: m/z [M+1]$^+$=137.2; R$_T$=1.11 min (96% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. 3-fluoro-5-(1-((2-(trimethylsilyl) ethoxy) methyl)-1H-1,2,3-triazol-4-yl) pyridin-2-amine (109-C): To a solution of 109-B (490 mg, 3.6 mmol) dissolved in MeOH (5.0 mL). CuI (69 mg, 0.36 mmol) was added, followed by the addition of DIPEA (1.25 mL, 7.2 mmol) and SEM-azide (748 mg, 4.32 mmol). The resulting reaction mixture was heated to 60° C. for 12 h then cooled to rt and concentrated. The crude product was purified via ISCO (SiO2, 0 to 50% ethyl acetate in hexanes over 20 CV) to yield 109-C as an off-white solid (835 mg, 75% yield).

LCMS: m/z [M+1]$^+$=310.2; R$_T$=1.61 min (97% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step four. N-(3-fluoro-5-(1-((2-(trimethylsilyl) ethoxy) methyl)-1H-1,2,3-triazol-4-yl) pyridin-2-yl)-4,6-bis((4-methoxybenzyl) oxy)-2-(methylthio) pyrimidine-5-carboxamide (109-D): To a stirred solution of 109-C (150 mg, 0.5 mmol) in THF under N$_2$ atmosphere at rt was added 1M LiHMDS solution in THF (0.5 ml, 0.5 mmol). The reaction mixture was allowed to stir for 30 min at rt. After 30 min, perfluorophenyl 4,6-bis((4-methoxybenzyl) oxy)-2-(methylthio) pyrimidine-5-carboxylate (300 mg, 0.5 mmol) dissolved in THF (2.0 ml) was added slowly to the reaction mixture. After stirring reaction mixture for another 30 min at rt it was quenched with water; extracted with ethyl acetate. The combined ethyl acetate layer was washed with brine, dried over sodium sulfate and concentrated under vacuum to get crude product (265 mg; 72% Yield) which was used in next step without any further purification.

LCMS: m/z [M+1]$^+$=734.6; R$_T$=2.15 min (97% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step five. N-(3-fluoro-5-(1H-1,2,3-triazol-4-yl) pyridin-2-yl)-4-hydroxy-2-(methylthio)-6-oxo-1,6-dihydropyrimidine-5-carboxamide (109): A solution of crude 109-D (265 mg, 0.36 mmol) in dichloromethane (2.0 mL) was added trifluoroacetic acid (1.0 mL). The resulting reaction mixture was stirred at rt for 1 h then heated at 80° C. for 6 h. Reaction mixture was cooled at rt and concentrated to get crude product which was co-evaporated 2-3 times with methanol. The resulting reside was re-dissolved in MeOH (2.0 ml) and ethylenediamine (0.7 ml, 10.8 mmol, 30 eq) and reaction mixture was stirred for another 12 h it was then concentrated under vacuum to get crude product. Finally, crude product was purified via reverse-phase chromatography (C18, gradient eluent from 0 to 100% acetonitrile in water with an ammonium formate buffer 10 mM over 22 CV) to yield the product 109 as an off-white solid (28 mg, 22% yield), after lyophilization.

$^1$H NMR (500 MHz, DMSO+TFA) δ 8.68 (d, J=1.8 Hz, 1H), 8.56 (s, 1H), 8.51 (d, J=10.5 Hz, 1H), 2.41 (s, 3H).

LCMS: m/z [M+1]$^+$=364.1; R$_T$=1.17 min (96.0% purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 42

Figure 54:
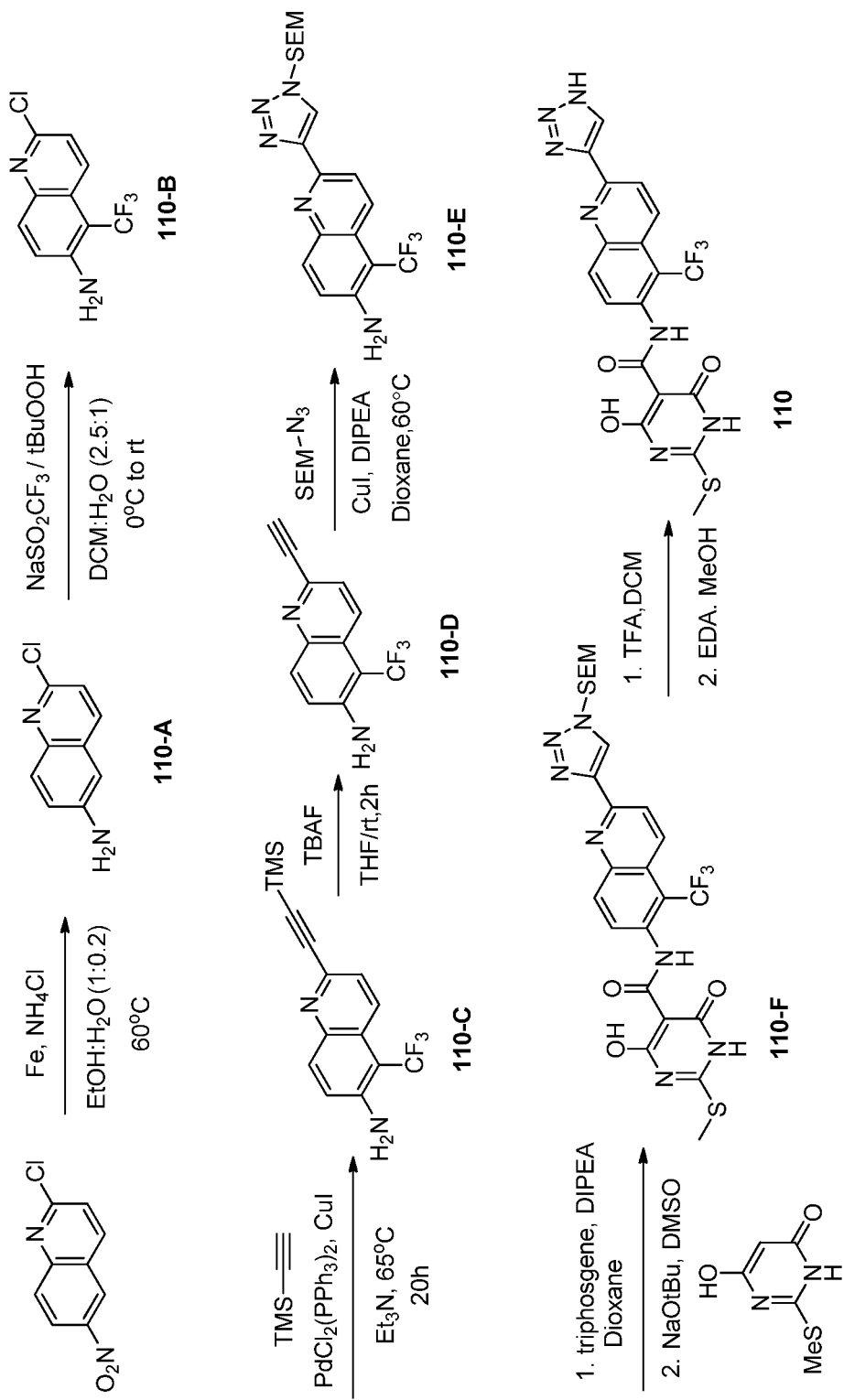
FIG. 54 illustrates the synthesis scheme described in Example 42.

Preparation of N-(2-(1H-1,2,3-triazol-4-yl)-5-(trifluoromethyl) quinolin-6-yl)-4-hydroxy-2-(methylthio)-6-oxo-1,6-dihydropyrimidine-5-carboxamide (110) (a Compound Having a Structure Represented by Formula (II$_{11}$), with Reference to the Synthesis Illustrated in FIG. 54)

Step One. 2-Chloroquinolin-6-amine (110-A): To 2-chloro-6-nitroquinoline (2.08 g, 10.0 mmol) and NH$_4$Cl (2.68 g, 50.0 mmol) was added EtOH (100 mL) and water (2.0 mL). The reaction mixture was heated to 60° C. and Fe (1.68 g, 30.0 mmol) was added in several portions. The reaction mixture was stirred for 2 h maintaining the temperature at 600° C. The mixture was cooled to room temperature and the ethanol was removed under reduced pressure. The aqueous mixture was diluted with 500 mL of EtOAc and solids were removed by filtration. The filtrate was concentrated under reduced pressure to yield the desired product, 1.64 g (92%), as a yellow solid.

LCMS: m/z [M+1]$^+$=179.2; R$_T$=1.25 min (98% Purity).

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Two. 2-chloro-5-(trifluoromethyl) quinolin-6-amine (110-B): To a solution of 110-A (890 mg, 5.0 mmol, 1.0 equiv) and sodium trifluoromethylsulfinate (2.34 g, 15.0 mmol, 3.0 equiv) in dichloromethane (18.0 mL) and water (7.0 mL) at 0° C. was slowly added tert-butylhydroperoxide (70% solution in water, 2.26 g, 25 mmol, 5.0 equiv) with vigorous stirring. The reaction was allowed to warm to room temperature and monitored by LCMS until completion. Reaction does not go to completion in 20 h, a second addition of sodium trifluoromethylsulfinate (3.0 equiv) and tert-butylhydroperoxide (5.0 equiv) was added to drive the reaction towards completion. Upon consumption of starting material, the reaction was partitioned between dichloromethane (100 mL) and saturated sodium bicarbonate (50 mL). The organic layer was separated, and the aqueous layer was extracted with dichloromethane (3×50 mL). The organic layers were dried with sodium sulfate, concentrated, and purified by column chromatography on silica gel to get 110-B (308 mg, 25% Yield).

$^1$H NMR (500 MHz, DMSO) δ 8.21-8.10 (m, 1H), 7.81 (d, J=9.3 Hz, 1H), 7.53 (d, J=9.1 Hz, 1H), 7.35 (d, J=9.4 Hz, 1H), 6.49 (s, 2H).

LCMS: m/z [M+1]$^+$=247.1; R$_T$=1.68 min (99.5% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Three. 5-(trifluoromethyl)-2-((trimethylsilyl)ethynyl) quinolin-6-amine (110-C): A round bottom flask containing 110-B (330 mg, 1.34 mmol), $PdCl_2(PPh_3)_2$ (190 mg, 0.27 mmol), and CuI (103 mg, 0.54 mmol) was purged with nitrogen for 15 min. triethylamine (4.5 ml) was added, followed by trimethylsilyl acetylene (0.94 mL, 6.7 mmol). The reaction mixture was heated to 65° C. for 16 h. After completion reaction mixture was cooled to rt, filtered through a small pad of Celite. The filtrate was concentrated to get crude product which was purified by using column chromatography using hexane: EtOAc (0 to 100% gradient) to yield (315 mg, 76%) of product 110-C.

LCMS: m/z $[M+1]^+$=309.1; $R_T$=2.04 min (95% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Four. 2-ethynyl-5-(trifluoromethyl) quinolin-6-amine (110-D): To a solution of 110-C (308 mg, 1.0 mmol) dissolved in THF (2.0 mL) was added 1M solution of TBAF (2.0 ml, 2.0 mmol) at rt. The resulting reaction mixture was stirred at rt until complete consumption of the starting material was observed. The reaction mixture was quenched with water and extracted with EtOAc and then concentrated. The crude product 110-D was used in next step without any purification.

LCMS: m/z $[M+1]^+$=237.1; $R_T$=1.54 min (90% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Five. 5-(trifluoromethyl)-2-(1-((2-(trimethylsilyl) ethoxy) methyl)-1H-1,2,3-triazol-4-yl) quinolin-6-amine (110-E): To a solution of 110-D (236 mg, 1.0 mmol) dissolved in methanol (5.0 mL). CuI (20 mg, 0.1 mmol) was added, followed by the addition of DIPEA (0.35 mL, 2.0 mmol) and SEM-azide (208 mg, 1.2 mmol). The resulting reaction mixture was heated to 65° C. for 12 h. The reaction mixture was then cooled to rt and concentrated. The crude product was purified via ISCO (SiO2, 0 to 50% ethyl acetate in hexanes over 20 CV) to yield 110-E as an off-white solid (180 mg, 45% yield over two steps).

LCMS: m/z [M+1]+=410.3; $R_T$=1.94 min (99.0% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Six. 4-hydroxy-2-(methylthio)-6-oxo-N-(5-(trifluoromethyl)-2-(1-((2-(trimethylsilyl) ethoxy) methyl)-1H-1,2, 3-triazol-4-yl) quinolin-6-yl)-1,6-dihydropyrimidine-5-carboxamide (110-F): 6-hydroxy-2-(methylthio) pyrimidin-4 (3H)-one (127 mg, 0.8 mmol) was added to a stirring solution of sodium tert-butoxide (77 mg, 0.8 mmol) dissolved in DMSO (2.0 mL) at rt for 5 min. In a separate flask, aniline 110-E (164 mg, 0.4 mmol) was dissolved in 1,4-dioxane (2.0 mL), to this solution was added triphosgene (40 mg, 0.132 mmol) in one-portion. The suspension was stirred vigorously for 2 min at rt, then iPr₂NEt (0.14 mL) was added. The suspension was stirred vigorously at rt for 2 min. Freshly prepared solution of sodium 6-hydroxy-2-(methylthio)-3-(3,4,5-trimethoxybenzyl) pyrimidin-4(3H)-olate in DMSO was added to the suspension in one-portion. The reaction was stirred at rt for 30 min, until complete consumption of starting material observed via LCMS. Reaction mixture was then cooled at rt; concentrated under vacuum. Purification was done by reverse phase column chromatography using 10 mM ammonium bicarbonate buffer (PH=10.0) and acetonitrile. Pure fraction was lyophilized to get desired product 110-F (170 mg, 70%).

LCMS: m/z $[M+1]^+$=594.3; $R_T$=2.01 min (98% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H2O+10 mM ammonium formate; Eluent B: Acetonitrile.

Step Seven. N-(2-(1H-1,2,3-triazol-4-yl)-5-(trifluoromethyl) quinolin-6-yl)-4-hydroxy-2-(methylthio)-6-oxo-1,6-dihydropyrimidine-5-carboxamide (110): A solution of crude 110-F (170 mg, 0.29 mmol) in dichloromethane (1.5 mL) was added trifluoroacetic acid (0.5 mL). The resulting reaction mixture was stirred at rt for 6 h. Reaction mixture was concentrated to get crude product which was co-evaporated 2-3 times with methanol. The resulting reside was re-dissolved in MeOH (2.0 ml) and ethylenediamine (1.0 ml, 14.5 mmol, 50 eq) and reaction mixture was stirred for another 12 h it was then concentrated under vacuum to get crude product. Finally, crude product was purified via reverse-phase chromatography (C18, gradient eluent from 0 to 100% acetonitrile in water with an ammonium formate buffer 10 mM over 22 CV) to yield the product 110 as an off-white solid (80 mg, 60% yield), after lyophilisation.

$^1$H NMR (500 MHz, DMSO+TFA) δ 12.00 (s, 1H), 8.70-8.65 (m, 1H), 8.64 (s, 1H), 8.35 (d, J=9.2 Hz, 1H), 8.32 (d, J=9.3 Hz, 1H), 8.20 (d, J=9.3 Hz, 1H), 2.56 (s, 3H). LCMS: m/z $[M+1]^+$=464.1; $R_T$=1.11 min (99.0% purity).

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q $H_2O$+10 mM ammonium bicarbonate pH: 10.0; Eluent B: Acetonitrile.

Example 43: Bioactivity Assays

The biological activities of compounds having structures represented by Formulae (I) and Formula (II) were evaluated in two assays: xanthine oxidase activity and URAT1 activity.

Xanthine oxidase inhibition was determined using a standard fluorescence-based assay for xanthine oxidase activity (McHale A, Grimes H, Coughlan M P: Int J Biochem. 10:317-9, 1979) with minor variations. The procedure was internally standardized using allopurinol and DPI as controls for all experiments after determination of their optimal inhibitory concentrations. Experiments on test compounds were performed in triplicate in multi-well plates using 10 concentrations of each compound that ranged over a 3-fold dilution.

URAT1 (SLC22A12) activity was evaluated in a cellular uptake assay using a 96-well plate with stably transfected URAT-1/CHO cells. $^3$H-orotate was used as the test transport agent, which was measured in a liquid scintillation counter, using benzbromarone as a positive control, and DMSO and non-transfected CHO cells as negative controls (Solvo Biotechnology, Boston, Mass.). Generally determined over 7 concentrations (range, 0.01 to 150 µM), a semi-log plot (percent relative transport of oratate vs. time) was generated to determine the concentration at which 50% inhibition was observed (i.e., the IC50).

The results of these assays for the exemplary compounds according to Formula (I) and Formula (II) are shown in Table 1:

TABLE 1

| Compound | URAT1 IC50 (µM) | Xanthine Oxidase IC50 (nM) |
|---|---|---|
| Formula ($II_{ff}$) | | 2.92 |
| Formula ($II_i$) | 1.077 | <0.02 |
| Formula ($II_{jj}$) | >9.4 | 0.02 |
| Formula ($II_{gg}$) | | 1.73 |
| Formula ($II_{hh}$) | | 211.45 |
| Formula ($II_{ii}$) | >40 | 0.377 |
| Formula ($II_j$) | | >300 |
| Formula ($II_k$) | 10.2 | 0.28 |
| Formula ($II_l$) | 2.43 | <0.02 |
| Formula ($II_m$) | | 8.64 |
| Formula ($II_n$) | | 3.57 |
| Formula ($II_o$) | | 1.14 |
| Formula ($II_p$) | >50 | 0.20 |
| Formula ($II_q$) | 14.16 | 0.04 |
| Formula ($II_r$) | 1.85 | 0.21 |
| Formula ($II_s$) | >3.5 | 0.12 |
| Formula ($II_{ll}$) | | 1.02 |
| Formula ($II_{mm}$) | | 2.86 |
| Formula ($II_t$) | 19.88 | 0.18 |
| Formula ($II_u$) | | 4.30 |
| Formula ($II_v$) | 18.53 | 0.10 |
| Formula ($II_w$) | >30 | 0.66 |
| Formula ($II_x$) | ≥30 | |
| Formula ($II_y$) | | 0.33 |
| Formula ($II_z$) | | 0.015 |
| Formula ($I_o$) | | 5.297 |
| Formula ($II_{aa}$) | >90 | 0.103 |
| Formula ($II_{bb}$) | >90 | 0.206 |
| Formula ($II_{cc}$) | | 0.519 |
| Formula ($II_{dd}$) | | 0.064 |
| Formula ($II_{kk}$) | | 0.315 |
| Formula ($II_{ee}$) | | 0.029 |
| Allopurinol | >300† | 2.0 to 5.0 |
| Lesinurad | 18.61* | >300† |
| | 52.5 ± 5.9†* | |

†Presentation estimate; Proc. EULAR Abstract #THU0357, 2008
*URAT1 assay as described herein The results of bioactivity assays for additional exemplary compounds according to Formula (II) are shown in Table 2:

TABLE 2

| Compound | URAT1 IC50 (µM) | Xanthine Oxidase IC50 (nM) |
|---|---|---|
| Formula ($II_2$) | — | 0.53 |
| Formula ($II_3$) | 4.9 | 0.06 |
| Formula ($II_4$) | 2.3 | 0.06 |
| Formula ($II_5$) | 7.5 | 0.04 |
| Formula ($II_6$) | — | >10.0 |
| Formula ($II_7$) | >100 | 0.07 |
| Formula ($II_8$) | 19.9 | 0.06 |
| Formula ($II_9$) | — | 0.52 |
| Formula ($II_{10}$) | >100 | 0.19 |
| Formula ($II_{11}$) | — | 0.22 |
| Allopurinol | >300† | 2.0 to 5.0 |
| Lesinurad | 18.61* | >300† |
| | 52.5 ± 5.9†* | |

†Presentation estimate; Proc. EULAR Abstract #THU0357, 2008
*URAT1 assay as described herein Among the compounds listed in Table 1, Formulae ($II_i$), ($II_{jj}$), ($II_{ii}$), ($II_k$), ($II_l$), ($II_p$), ($II_q$), ($II_r$), ($II_s$), and ($II_t$) are particularly potent inhibitors of xanthine oxidase compared to allopurinol. Several of the compounds also effectively inhibit URAT1 (e.g., Formulae ($II_i$), ($II_k$), ($II_l$), ($II_q$), ($II_r$), ($II_s$)), although not all of them were tested. These are the most promising bifunctional inhibitors. Two representative examples of a particularly effective bifunctional inhibitors are Formulae ($II_r$) and ($II_s$).

Of the compounds listed in Table 2, all are particularly potent inhibitors of xanthine oxidase compared to allopurinol, with the exception of Formula ($II_6$). Formula ($II_3$), Formula ($II_4$), and Formula ($II_5$) were also found to be particularly potent inhibitors of URAT1 compared to lesinurad.

While many compounds were potent inhibitors, the extent of inhibition of each enzyme/channel was different. Such variability allows the intelligent selection of a pharmaceutically acceptable product that exhibits greater or lesser inhibition of one or the other enzyme target. For example, greater inhibition of XO might be deemed preferable for a patient whose primary metabolic defect was over-production of uric acid. Conversely, greater inhibition of URAT1 might be deemed preferable for a patient whose primary metabolic defect was under-excretion of uric acid. However, it should be noted that almost all patients with hyperuricemia or a disorder associated with excess uric acid will benefit from reduction in serum uric acid, and bifunctional compounds can be expected to exert a beneficial effect in such patients. The practitioner, guided by the present disclosure, will be able to select particular compounds as appropriate for a specific use based on the level of skill in the art.

By way of comparison, allopurinol has an IC50 for XO ranging from about 2.0 to about 5.0 µM and an IC50 for URAT1 of >300 µM. Lesinurad has an IC50 for XO of >300 µM and an IC50 for URAT1 ranging from 18 to 53 µM. Thus, neither of these compounds is considered bifunctional, since both are selective inhibitors of only one enzyme that affects either production or excretion of uric acid. In contrast, certain of the compounds described herein are not only bifunctional, several are substantially more potent inhibitors of either or both XO and URAT1.

While in many clinical situations it is desirable to treat hyperuricemia with a drug that is highly potent against both XO and URAT1, it is also contemplated that selection of a particular compound of the invention for treatment of hyperuricemia or a disorder associated with excess uric acid may be based on the phenotype of the patient being treated (i.e., the relative contributions of over-production of uric acid and under-excretion of uric acid to the patient's specific disease). Where over-production of uric acid predominates, use of compounds according to the invention that are substantially more potent against XO than URAT1 may be appropriate. Where under-excretion of uric acid predominates, use of compounds according to the invention that are substantially more potent against URAT1 than XO may be appropriate. Although the genetics of these two pathways are not completely understood, chemical testing to determine the extent to which each contributes to the hyperuricemia of a particular patient has been published, and may be useful to clarify the patient's disease phenotype for selection of an appropriate drug that balances these respective activities, as can be appropriately determined by those skilled in the art.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A compound selected from the group consisting of
   a) compounds having a structure represented by Formula (II):

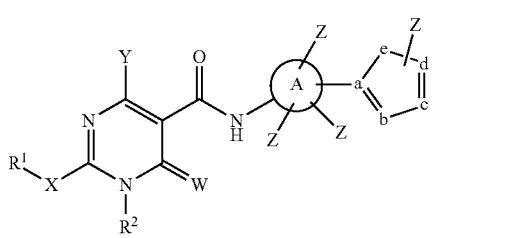

Formula (II)

wherein
W is O, Y is selected from OH and $N(R^2)_2$, X is selected from O, S, and $NR^2$;
A is phenyl, heteroaryl, C5-C10 branched or unbranched cycloalkyl, C6-C10 bicycloalkyl or C5-C10 spirocycloalkyl;
each Z is independently present or absent and, if present, is independently selected from one or more halogen atoms, —CN, —$CF_3$, —$OCF_3$, —$OCHF_2$, —$OR^2$, —$C(O)R^2$, $SR^2$, —$S(O)_gR^3$ where g is 1 or 2, —$N(R^2)_2$, —$NO_2$, —$CO_2R^2$, —$OCO_2R^3$, $OC(O)R^2$, —$CON(R^2)_2$, —$NR^2C(O)R^2$, —$SO_2N(R^2)_2$, —$NR^2SO_2R^3$, $NR^2SO_2N(R^2)_2$ or -$NR^2C(O)N(R^2)_2$, —$C(O)NHOR^2$, alkyl, aryl, alkenyl, alkynyl and cycloalkyl;
wherein each $R^1$ is C1-C8 branched or unbranched alkyl, optionally substituted with Z;
wherein each $R^2$ is H;
wherein each $R^3$ is independently alkyl or aryl, optionally substituted with one or more halogen atoms or $OR^2$; and
wherein a, b, c, d, and e are each independently carbon or nitrogen, or four of a, b, c, d, and e are each independently carbon or nitrogen and one of a, b, c, d, and e is O, with the proviso that at least three of a, b, c, d and e are nitrogen, and Z is not connected directly to nitrogen or oxygen; and
   b) tautomers of any of the foregoing compounds.

2. The compound according to claim 1, wherein three of a, b, c, d, and e are nitrogen.

3. The compound according to claim 1, wherein $R^1$ is —$CH(CH_3)_2$.

4. The compound according to claim 3, wherein —$XR^1$ is —$SCH(CH_3)_2$.

5. The compound according to claim 4, wherein A is substituted phenyl.

6. The compound according to claim 5, wherein A is selected from the group consisting of —$CF_3$ substituted phenyl, —CN substituted phenyl, and —$OCHF_2$ substituted phenyl.

7. The compound according to claim 6, which has a structure represented by Formula ($II_7$)

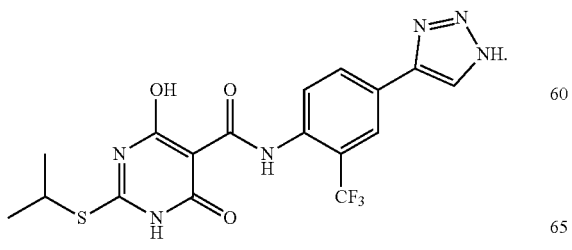

8. The compound according to claim 1, which is selected from the group consisting of compounds having a structure represented by

Formula ($II_i$)

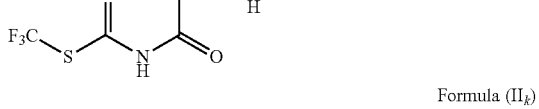

Formula ($II_j$)

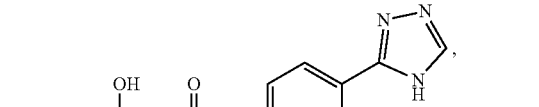

Formula ($II_k$)

Formula ($II_l$)

Formula ($II_m$)

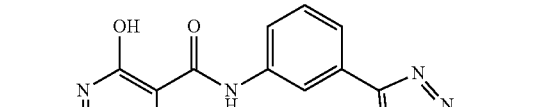

Formula ($II_n$)

Formula (II_o)
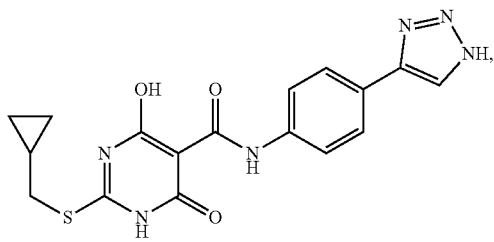
Formula (II_p)
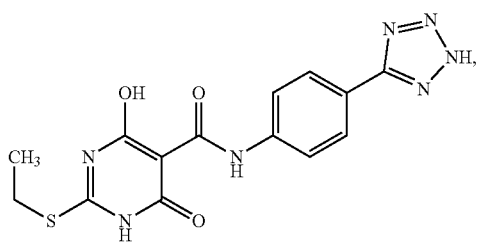
Formula (II_q)
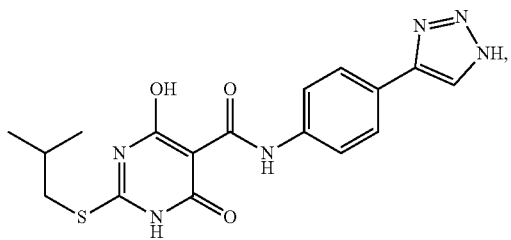
Formula (II_r)
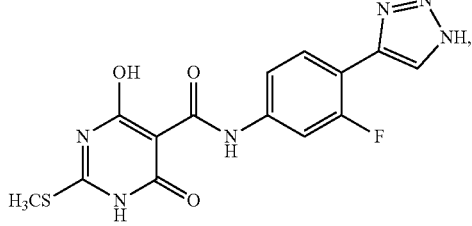
Formula (II_s)
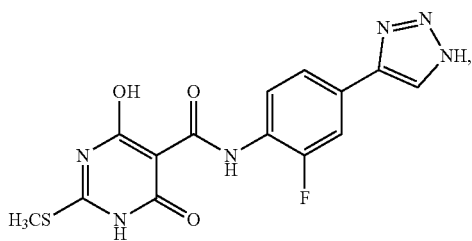
Formula (II_t)
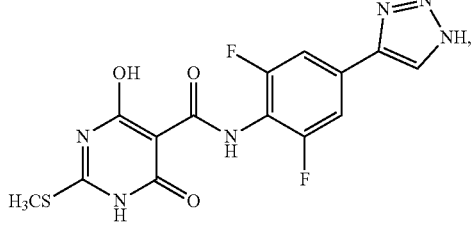
Formula (II_u)
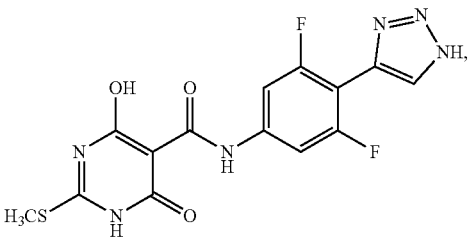
Formula (II_v)
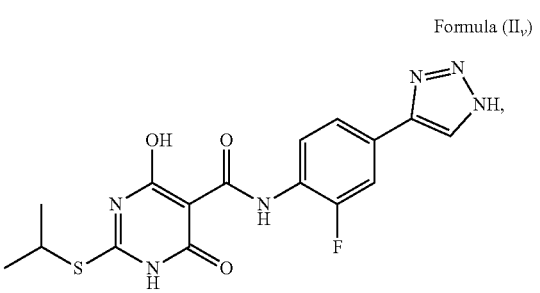
Formula (II_w)
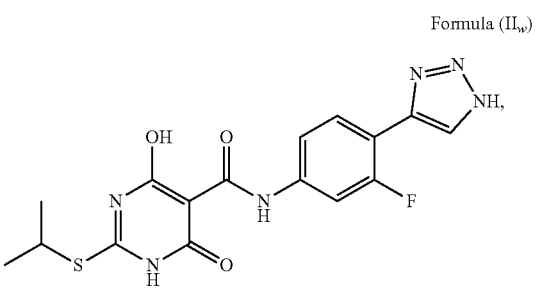
Formula (II_x)
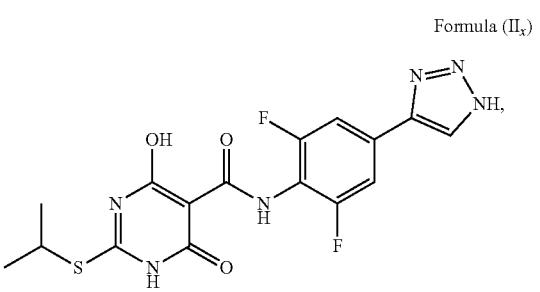
Formula (II_y)
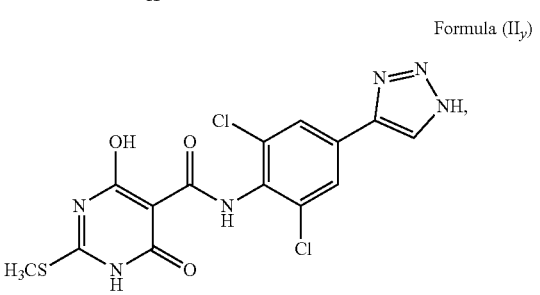
Formula (II_z)
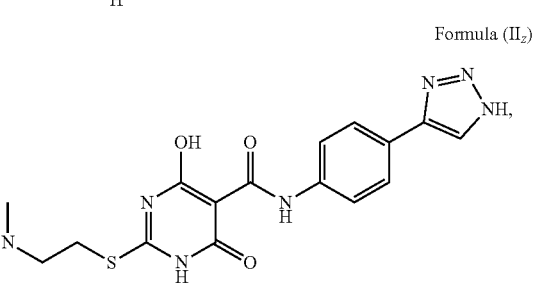

-continued

Formula (II<sub>aa</sub>)
Formula (II<sub>bb</sub>)
Formula (II<sub>cc</sub>)
Formula (II<sub>dd</sub>)
Formula (II<sub>ee</sub>)
Formula (II<sub>ff</sub>)

-continued

Formula (II<sub>gg</sub>)
Formula (II<sub>hh</sub>)
Formula (II<sub>ii</sub>)
Formula (II<sub>jj</sub>)
Formula (II<sub>kk</sub>)
Formula (II<sub>ll</sub>)

Formula (II$_{mm}$)
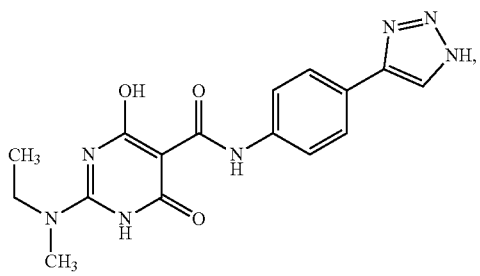

Formula (II$_2$)
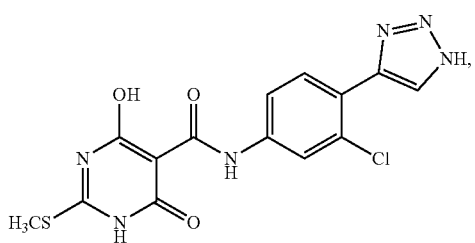

Formula (II$_3$)
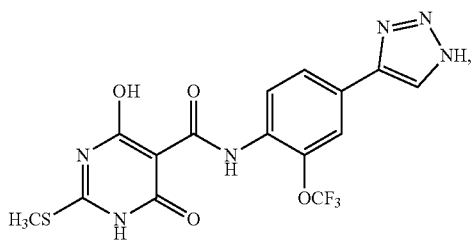

Formula (II$_4$)
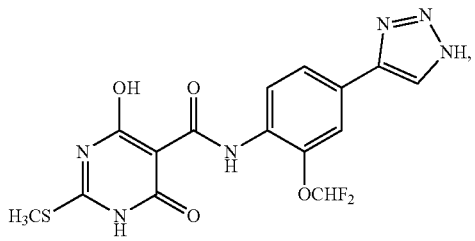

Formula (II$_5$)
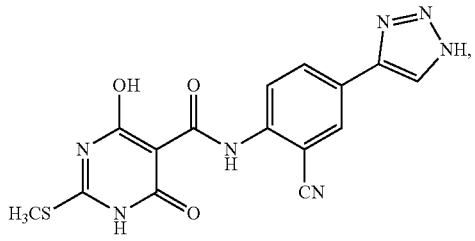

Formula (II$_6$)
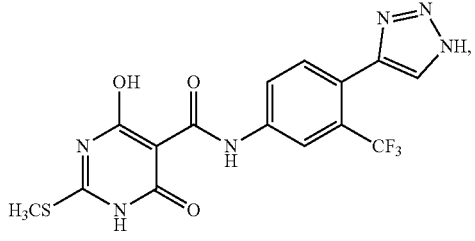

Formula (II$_7$)
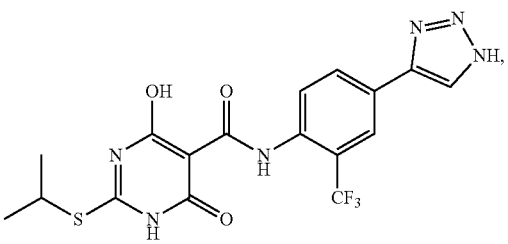

Formula (II$_8$)
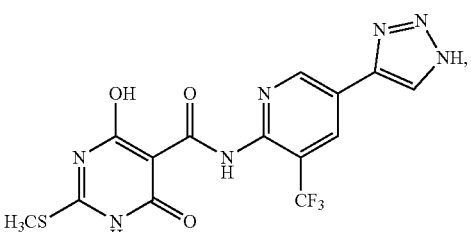

Formula (II$_9$)
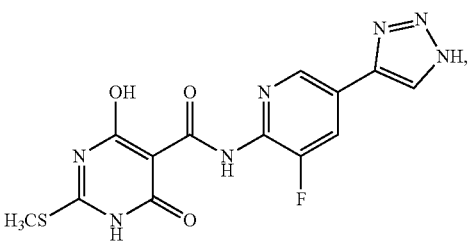

Formula II$_{10}$)
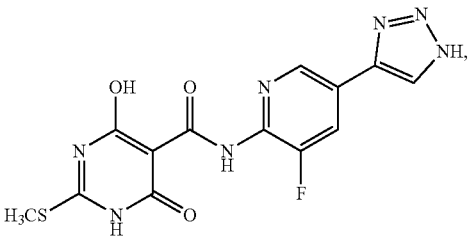

Formula (II$_{11}$)
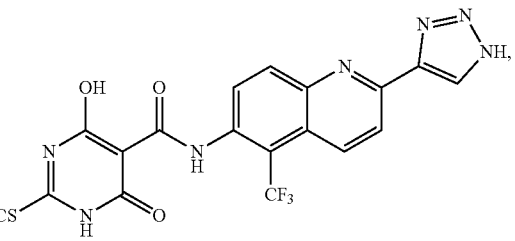

and tautomers thereof.

9. A pharmaceutical composition comprising the compound, tautomer, or combination thereof of claim 1, and a pharmaceutically acceptable carrier.

10. The pharmaceutical composition according to claim 9, which comprises a compound having a structure represented by Formula (II$_7$) or a tautomer thereof.

\* \* \* \* \*